(12) United States Patent
Gunde et al.

(10) Patent No.: US 12,077,588 B2
(45) Date of Patent: *Sep. 3, 2024

(54) ANTIBODIES TARGETING PDL1 AND METHODS OF USE THEREOF

(71) Applicant: Numab Therapeutics AG, Wädenswil (CH)

(72) Inventors: Tea Gunde, Zurich (CH); Matthias Brock, Aesch (CH); Christian Hess, Zurich (CH); Alexandre Simonin, Rosenau (FR)

(73) Assignee: Numab Therapeutics AG, Horgen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/753,876

(22) PCT Filed: Oct. 9, 2018

(86) PCT No.: PCT/EP2018/077511
§ 371 (c)(1),
(2) Date: Apr. 6, 2020

(87) PCT Pub. No.: WO2019/072869
PCT Pub. Date: Apr. 18, 2019

(65) Prior Publication Data
US 2020/0283528 A1    Sep. 10, 2020

(30) Foreign Application Priority Data

Oct. 10, 2017  (EP) .................................... 17195781
Apr. 12, 2018  (EP) .................................... 18167094
Jun. 29, 2018  (EP) .................................... 18180816

(51) Int. Cl.
*A61K 39/395*    (2006.01)
*A61P 35/00*    (2006.01)
(Continued)

(52) U.S. Cl.
CPC .......... *C07K 16/2827* (2013.01); *A61P 35/00* (2018.01); *C07K 16/2878* (2013.01);
(Continued)

(58) Field of Classification Search
None
See application file for complete search history.

(56) References Cited

FOREIGN PATENT DOCUMENTS

JP     2013511959 A    4/2013
JP     2017507650 A    3/2017
(Continued)

OTHER PUBLICATIONS

Ewert et al., Biophysical properties of human antibody variable domains, J. Mol. Biol. 325:531-553, 2003.*
(Continued)

*Primary Examiner* — Claire Kaufman
(74) *Attorney, Agent, or Firm* — Prismatic Law Group, PLLC; Ronald J. Kamis

(57) ABSTRACT

The present invention relates to an isolated antibody which specifically binds human PDL 1, and pharmaceutical compositions and methods of use thereof. The present invention further relates to a nucleic acid encoding said antibody, a vector comprising said nucleic acid, a host cell comprising said nucleic acid or said vector, and a method of producing said antibody.

28 Claims, 15 Drawing Sheets
Specification includes a Sequence Listing.

(51) Int. Cl.
*C07K 16/28* (2006.01)
*A61K 39/00* (2006.01)

(52) U.S. Cl.
CPC .... *A61K 2039/505* (2013.01); *C07K 2317/24* (2013.01); *C07K 2317/31* (2013.01); *C07K 2317/622* (2013.01); *C07K 2317/76* (2013.01); *C07K 2317/92* (2013.01)

(56) References Cited

FOREIGN PATENT DOCUMENTS

| WO | 2011066389 A1 | 6/2011 |
| WO | 2013/079174 A1 | 6/2013 |
| WO | 2015112805 A1 | 7/2016 |
| WO | 2017/118321 A1 | 7/2017 |
| WO | 2017/123650 A2 | 7/2017 |

OTHER PUBLICATIONS

Hosse et al., A new generation of protein display scaffolds for molecular recognition, Prot. Sci, 15:14-27, 2006.*
Sela-Culang et al., The structural basis of antibody-antigen recognition, Frontiers Immuno. 4, article 302, pp. 1-13, 2013.*
MacCallum et al., Antibody-antigen interactions: contact analysis and binding site topography, J. Mol. Biol. 262:732-745, 1996.*
Narional Cancer Institute Dictionary, Molecule, Retrieved from: <URL:https://www.cancer.gov/publications/dictionaries/cancer-terms/def/molecule> {retrieved on Aug. 23, 2022], 2022.*
Grievink et al., Stimulation of the PD-1 Pathway Decreases Atherosclerotic Lesion Development in Ldlr Deficient Mice, Front. Cardiovasc. Med. 8:740531, doi: 10.3389/fcvm.2021.740531, 12 pages, Nov. 2021.*
Ohaegbulam et al., Human cancer immunotherapy with antibodies to the PD-1 and PD-L1 pathway, Trends Molec. Med. 21(1):24-33, Jan. 2015.*
International Search Report and Written Opinion, International Application No. PCT/EP2018/077511.

* cited by examiner

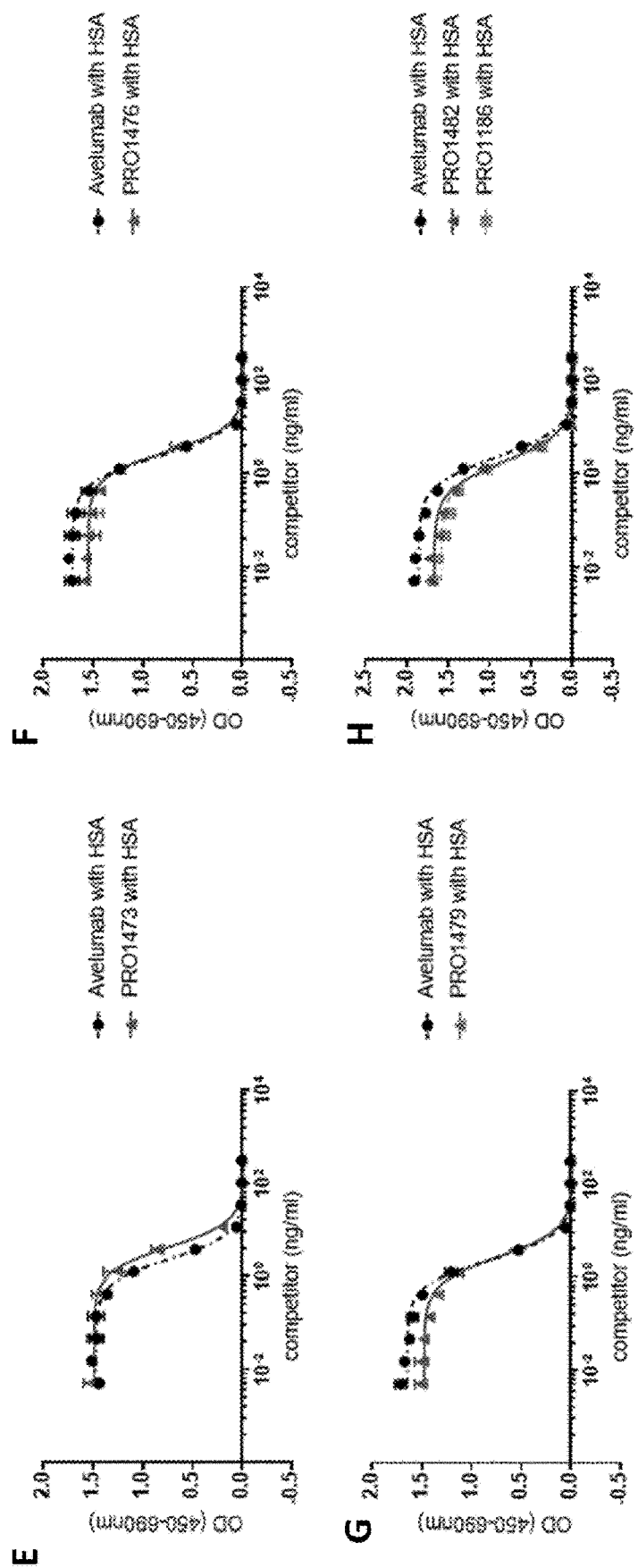
Figures 7 (contd.):

Figures 7 (contd.):
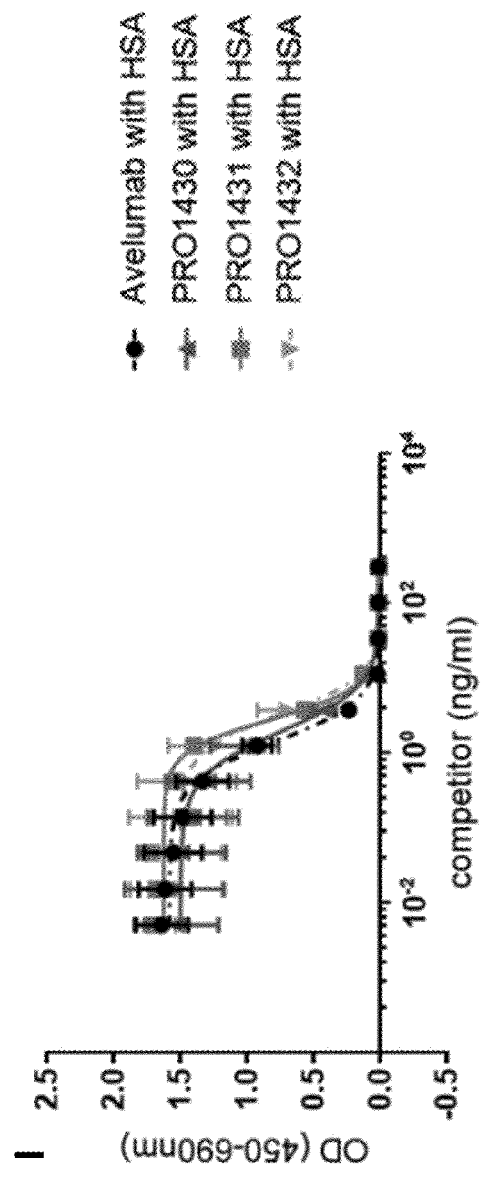

Figures 8 (contd.):
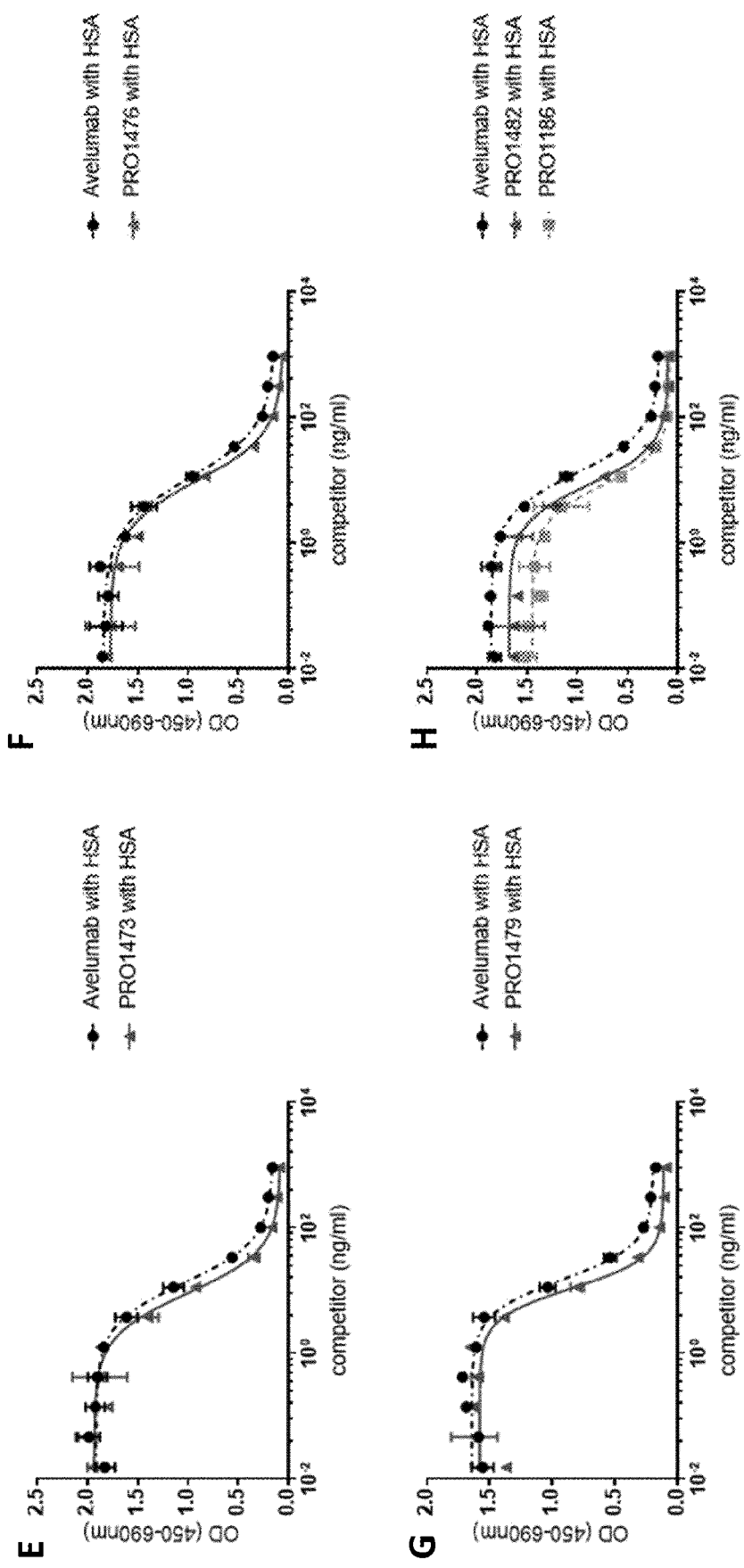

ANTIBODIES TARGETING PDL1 AND METHODS OF USE THEREOF

CROSS-REFERENCE TO RELATED APPLICATIONS

This application is a 371 National Phase of International Patent Application No. PCT/EP2018/077511 filed on Oct. 9, 2018, which claims priority to EP 17195781.4 filed on Oct. 10, 2017, EP 18167094.4 filed on Apr. 12, 2018 and EP 18180816.3 filed on Jun. 29, 2018, the content of each of which applications is incorporated herein by reference.

INCORPORATION OF SEQUENCE LISTING

This application contains a sequence listing submitted electronically via EFS-web, which serves as both the paper copy and the computer readable form (CRF) and consists of a file entitled "WRN15NP_seqlist2", which was created on Jun. 30, 2022, which is 143,414 bytes in size, and which is herein incorporated by reference in its entirety.

FIELD OF THE INVENTION

The present invention relates to an isolated antibody which specifically binds human PDL1, and pharmaceutical compositions and methods of use thereof. The present invention further relates to a nucleic acid encoding said antibody, a vector comprising said nucleic acid, a host cell comprising said nucleic acid or said vector, and a method of producing said antibody.

BACKGROUND OF THE INVENTION

PDL1 (CD274, B7-H1) is a 40 kDa type I transmembrane protein. PDL1 is a surface glycoprotein ligand for PD-1, a key immune checkpoint receptor expressed by activated T and B cells, and mediates immunosuppression. PDL1 is implicated in the suppression of immune system responses during chronic infections, pregnancy, tissue allografts, autoimmune diseases, and cancer. PDL1 is found on both antigen-presenting cells and human cancer cells, such as squamous cell carcinoma of the head and neck, melanoma, and brain tumor, thyroid, thymus, esophagus, lung, breast, gastrointestinal tract, colorectum, liver, pancreas, kidney, adrenal cortex, bladder, urothelium, ovary, and skin (Katsuya Y, et al., Lung Cancer. 88(2):154-159 (2015); Nakanishi J, et al., Cancer Immunol Immunother. 56(8):1173-1182 (2007); Nomi T, et al., Clin Cancer Res. 13(7):2151-2157 (2007); Fay A P, et al., J Immunother Cancer. 3:3 (2015); Strome S E, et al., Cancer Res. 63(19):6501-6505 (2003); Jacobs J F, et al. Neuro Oncol. 11(4):394-402 (2009); Wilmotte R, et al. Neuroreport. 16(10):1081-1085 (2005)). PDL1 is rarely expressed on normal tissues but inducibly expressed on tumor site (Dong H, et al., Nat Med. 8(8):793-800 (2002); Wang et al., Onco Targets Ther. 9: 5023-5039 (2016)). PDL1 downregulates T cell activation and cytokine secretion by binding to PD-1 (Freeman et al., 2000; Latchman et al, 2001). PD-1, activated by PDL1, potentially provides an immune-tolerant environment for tumor development and growth. PDL1 also negatively regulates T-cell function through interaction with another receptor, B7.1 (B7-1, CD80).

Inhibition of the PDL1/PD-1 interaction allows for potent anti-tumor activity. Various antibodies against PDL1 are already known (see, for example, WO 2013/079174 and WO 2017/118321), and a number of antibodies that disrupt the PD-1 signaling have entered clinical development. These antibodies belong to the following two main categories: those that target PD-1 (nivolumab, Bristol-Myers Squibb; pembrolizumab, Merck, Whitehouse Station, NJ; pidilizumab, CureTech, Yavne, Israel) and those that target PDL1 (MPDL3280A, Genentech, South San Francisco, CA; MEDI4736, MedImmune/AstraZeneca; BMS-936559, Bristol-Myers Squibb; MSB0010718C, EMD Serono, Rockland, MA) (for review see Postow M A et al., J Clin Oncol. June 10; 33(17):1974-82 (2015)). Targeting PDL1 versus targeting PD-1 may result in different biologic effects. PD-1 antibodies prevent interaction of PD-1 with both its ligands, PDL1 and PDL2. PDL1 antibodies do not prevent PD-1 from interacting with PDL2, although the effect of this interaction remains unknown. PDL1 antibodies however prevent interaction of PDL1 with not only PD-1, but also B7-1 (Butte M J, et al., Immunity 27:111-122, (2007)), which is believed to exert negative signals on T cells. Blocking PDL1 has demonstrated promising early data, and currently, four clinical anti-PDL1 mAbs are in the testing: atezolizumab and MEDI4736 (both are Fc null variants of human IgG1), MSB001078C (IgG1), and BMS-936559 (IgG4) (Chester C., et al., Cancer Immunol Immunother October; 65(10):1243-8 (2016)).

To date, no satisfactory approach has been proven to induce potent immune responses in cancer patients. There is a need in the field to generate improved therapeutic modulators of the PDL1/PD-1 interaction and methods to overcome the immunosuppressive mechanisms observed in cancer patients.

SUMMARY OF THE INVENTION

It is an object of the present invention to provide antibodies that specifically bind to human PDL1 protein, and which have beneficial properties for use in therapies, such as higher affinity, improved efficacy and improved biophysical properties, such as solubility, developability, and stability.

In one aspect, the present invention relates to a novel PDL1 antibody.

In one aspect, the present invention relates to a pharmaceutical composition comprising the antibody of the invention, and a pharmaceutically acceptable carrier.

In another aspect, the present invention relates to the antibody of the invention, or the composition of the invention for use as a medicament In one aspect, the present invention relates to the antibody of the invention, or the composition of the invention for use in the treatment of a cancer in a subject in need thereof.

In one aspect, the present invention relates to use of the antibody of the invention, or the composition of the invention in the manufacture of a medicament for the treatment of a cancer in a subject in need thereof.

In another aspect, the present invention relates to a method of treating a cancer in a subject in need thereof comprising administering to the subject a therapeutically effective amount of the antibody of the invention, or the composition of the invention.

In yet another aspect, the present invention relates to a nucleic acid encoding the antibody of the invention. In a further aspect, the present invention relates to a vector comprising said nucleic acid. In a further aspect, the present invention relates to a host cell comprising said nucleic acid or said vector.

In another aspect, the present invention relates to a method of producing the antibody of the invention, the method comprising the step of culturing a host cell comprising the nucleic acid or the vector of the invention.

The aspects, advantageous features and preferred embodiments of the present invention, summarized in the following items, respectively alone or in combination, further contribute to solving the object of the invention:

1. An isolated antibody having a binding specificity for human PDL1, which comprises: (a) a heavy chain variable region CDR1 comprising, preferably consisting of, an amino acid sequence selected from any one of SEQ ID NOs: 1, 4, 5, 8, 11, 32, 35, 36, 39 and 42, preferably SEQ ID NO: 1 or 32, more preferably SEQ ID NO: 1; (b) a heavy chain variable region CDR2 comprising, preferably consisting of, an amino acid sequence selected from any of SEQ ID NOs: 2, 6, 9, 12, 33, 37, 40 and 43, preferably SEQ ID NO: 2 or 33, more preferably SEQ ID NO: 2; (c) a heavy chain variable region CDR3 comprising, preferably consisting of, an amino acid sequence selected from any of SEQ ID NOs: 3, 7, 10, 13, 34, 38, 41 and 44, preferably SEQ ID NO: 3 or 34, more preferably SEQ ID NO: 3; (d) a light chain variable region CDR1 comprising, preferably consisting of, an amino acid sequence selected from any of SEQ ID NOs: 17, 20, 23, 48, 51 and 54, preferably SEQ ID NO: 17 or 48, more preferably SEQ ID NO: 17; (e) a light chain variable region CDR2 comprising, preferably consisting of, an amino acid sequence selected from any of SEQ ID NOs: 18, 21, 24, 49, 52 and 55, preferably SEQ ID NO: 18 or 49, more preferably SEQ ID NO: 18; and (f) a light chain variable region CDR3 comprising, preferably consisting of, an amino acid sequence selected from any of SEQ ID NOs: 19, 22, 25, 50, 53 and 56, preferably SEQ ID NO: 19 or 50, more preferably SEQ ID NO: 19.
2. The antibody of item 1, wherein the antibody comprises: (a) HCDR1, HCDR2, and HCDR3 sequences of SEQ ID NOs: 1, 2 and 3, respectively, and LCDR1, LCDR2, and LCDR3 sequences of SEQ ID NOs: 17, 18 and 19, respectively; (b) HCDR1, HCDR2, and HCDR3 sequences of SEQ ID NOs: 4, 6, and 7, respectively, and LCDR1, LCDR2, and LCDR3 sequences of SEQ ID NOs: 20, 21, and 22, respectively; (c) HCDR1, HCDR2, and HCDR3 sequences of SEQ ID NOs: 5, 6, and 7, respectively, and LCDR1, LCDR2, and LCDR3 sequences of SEQ ID NOs: 20, 21, and 22, respectively; (d) HCDR1, HCDR2, and HCDR3 sequences of SEQ ID NOs: 8, 9, and 10, respectively, and LCDR1, LCDR2, and LCDR3 sequences of SEQ ID NOs: 17, 18, and 19, respectively; (e) HCDR1, HCDR2, and HCDR3 sequences of SEQ ID NOs: 11, 12, and 13, respectively, and LCDR1, LCDR2, and LCDR3 sequences of SEQ ID NOs: 23, 24, and 25, respectively; (f) HCDR1, HCDR2, and HCDR3 sequences of SEQ ID NOs: 32, 33 and 34, respectively, and LCDR1, LCDR2, and LCDR3 sequences of SEQ ID NOs: 48, 49 and 50, respectively; (g) HCDR1, HCDR2, and HCDR3 sequences of SEQ ID NOs: 35, 37, and 38, respectively, and LCDR1, LCDR2, and LCDR3 sequences of SEQ ID NOs: 51, 52, and 53, respectively; (h) HCDR1, HCDR2, and HCDR3 sequences of SEQ ID NOs: 36, 37, and 38, respectively, and LCDR1, LCDR2, and LCDR3 sequences of SEQ ID NOs: 51, 52, and 53, respectively; (i) HCDR1, HCDR2, and HCDR3 sequences of SEQ ID NOs: 39, 40, and 41, respectively, and LCDR1, LCDR2, and LCDR3 sequences of SEQ ID NOs: 48, 49, and 50, respectively; (j) HCDR1, HCDR2, and HCDR3 sequences of SEQ ID NOs: 42, 43, and 44, respectively, and LCDR1, LCDR2, and LCDR3 sequences of SEQ ID NOs: 54, 55, and 56, respectively.
3. The antibody of item 1, comprising: (a) an HCDR1 comprising, preferably consisting of, the amino acid sequence of SEQ ID NO: 1; (b) an HCDR2 comprising, preferably consisting of, the amino acid sequence of SEQ ID NO: 2; (c) an HCDR3 comprising, preferably consisting of, the amino acid sequence of SEQ ID NO: 3; (d) an LCDR1 comprising, preferably consisting of, the amino acid sequence of SEQ ID NOs: 17; (e) an LCDR2 comprising, preferably consisting of, the amino acid sequence of SEQ ID NOs: 18; and (f) an LCDR3 comprising, preferably consisting of, the amino acid sequence of SEQ ID NO: 19.
4. The antibody of item 1, comprising: (a) an HCDR1 comprising, preferably consisting of, the amino acid sequence of SEQ ID NO: 4 or SEQ ID NO: 5; (b) an HCDR2 comprising, preferably consisting of, the amino acid sequence of SEQ ID NO: 6; (c) an HCDR3 comprising, preferably consisting of, the amino acid sequence of SEQ ID NO: 7; (d) an LCDR1 comprising, preferably consisting of, the amino acid sequence of SEQ ID NOs: 20; (e) an LCDR2 comprising, preferably consisting of, the amino acid sequence of SEQ ID NOs: 21; and (f) an LCDR3 comprising, preferably consisting of, the amino acid sequence of SEQ ID NO: 22.
5. The antibody of item 1, comprising: (a) an HCDR1 comprising, preferably consisting of, the amino acid sequence of SEQ ID NO: 32; (b) an HCDR2 comprising, preferably consisting of, the amino acid sequence of SEQ ID NO: 33; (c) an HCDR3 comprising, preferably consisting of, the amino acid sequence of SEQ ID NO: 34; (d) an LCDR1 comprising, preferably consisting of, the amino acid sequence of SEQ ID NOs: 48; (e) an LCDR2 comprising, preferably consisting of, the amino acid sequence of SEQ ID NOs: 49; and (f) an LCDR3 comprising, preferably consisting of, the amino acid sequence of SEQ ID NO: 50.
6. The antibody of item 1, comprising: (a) an HCDR1 comprising, preferably consisting of, the amino acid sequence of SEQ ID NO: 35 or SEQ ID NO: 36; (b) an HCDR2 comprising, preferably consisting of, the amino acid sequence of SEQ ID NO: 37; (c) an HCDR3 comprising, preferably consisting of, the amino acid sequence of SEQ ID NO: 38; (d) an LCDR1 comprising, preferably consisting of, the amino acid sequence of SEQ ID NOs: 51; (e) an LCDR2 comprising, preferably consisting of, the amino acid sequence of SEQ ID NOs: 52; and (f) an LCDR3 comprising, preferably consisting of, the amino acid sequence of SEQ ID NO: 53.
7. The antibody of any one of the preceding items, wherein the antibody comprises a heavy chain variable region (VH), wherein said VH is VH1, VH3 or VH4, preferably VH3 or VH4, more preferably VH3.
8. The antibody of any one of the preceding items, wherein the antibody comprises a light chain variable region (VL), wherein said VL comprises Vκ frameworks FR1, FR2 and FR3, particularly Vκ1 or Vκ3 FR1 to FR3, preferably Vκ1 FR1 to FR3, and a framework FR4, which is selected from a VK FR4, particularly Vκ1 FR4, Vκ3 FR4, and Vλ FR4, particularly Vλ FR4 comprising the amino acid sequence having at least 60, 70, 80, 90 percent identity to an amino acid sequence selected from any of SEQ ID NO:

64 to SEQ ID NO: 70, preferably Vλ FR4 as set forth in any of SEQ ID NO: 64 to SEQ ID NO: 70, preferably Vλ FR4 as set forth in SEQ ID NO: 64 or 65, more preferably Vλ FR4 as set forth in SEQ ID NO: 64.

9. The antibody of any one of the preceding items, wherein the antibody comprises a heavy chain variable region comprising an amino acid sequence that is at least 90 percent identical to the amino acid sequence selected from the group consisting of SEQ ID NOs: 14, 15, 16, 45, 46 and 47, preferably SEQ ID NO: 14 or 16, more preferably SEQ ID NO: 16; and a light chain variable region comprising an amino acid sequence that is at least 90 percent identical to the amino acid sequence selected from the group consisting of SEQ ID NOs: 26, 27, 57 and 58, preferably SEQ ID NO: 26 or 27, more preferably SEQ ID NO: 27.

10. The antibody of any one of the preceding items, wherein the antibody comprises: (a) a heavy chain variable region comprising an amino acid sequence that is at least 90 percent identical to the amino acid sequence SEQ ID NO: 14 and a light chain variable region comprising an amino acid sequence that is at least 90 percent identical to the amino acid sequence SEQ ID NO: 26; (b) a heavy chain variable region comprising an amino acid sequence that is at least 90 percent identical to the amino acid sequence SEQ ID NO: 15 and a light chain variable region comprising an amino acid sequence that is at least 90 percent identical to the amino acid sequence SEQ ID NO: 26; (c) a heavy chain variable region comprising an amino acid sequence that is at least 90 percent identical to the amino acid sequence SEQ ID NO: 16 and a light chain variable region comprising an amino acid sequence that is at least 90 percent identical to the amino acid sequence SEQ ID NO: 27; (d) a heavy chain variable region comprising an amino acid sequence that is at least 90 percent identical to the amino acid sequence SEQ ID NO: 45 and a light chain variable region comprising an amino acid sequence that is at least 90 percent identical to the amino acid sequence SEQ ID NO: 57; (f) a heavy chain variable region comprising an amino acid sequence that is at least 90 percent identical to the amino acid sequence SEQ ID NO: 46 and a light chain variable region comprising an amino acid sequence that is at least 90 percent identical to the amino acid sequence SEQ ID NO: 58; (g) a heavy chain variable region comprising an amino acid sequence that is at least 90 percent identical to the amino acid sequence SEQ ID NO: 47 and a light chain variable region comprising an amino acid sequence that is at least 90 percent identical to the amino acid sequence SEQ ID NO: 57.

11. The antibody of any one of the preceding items, wherein the antibody comprises: a heavy chain variable region comprising an amino acid sequence selected from any of SEQ ID NOs: 14, 15, 16, 45, 46 and 47, preferably SEQ ID NO: 14 or 16, more preferably SEQ ID NO: 16; and a light chain variable region comprising an amino acid sequence selected from any of SEQ ID NOs: 26, 27, 57 and 58, preferably SEQ ID NO: 26 or 27, more preferably SEQ ID NO: 27.

12. The antibody of any one of the preceding items, comprising: (a) a VH sequence of SEQ ID NO: 14 and a VL sequence of SEQ ID NO: 26; (b) a VH sequence of SEQ ID NO: 15 and a VL sequence of SEQ ID NO: 26; (c) a VH sequence of SEQ ID NO: 16 and a VL sequence of SEQ ID NO: 27; (d) a VH sequence of SEQ ID NO: 45 and a VL sequence of SEQ ID NO: 57; (f) a VH sequence of SEQ ID NO: 46 and a VL sequence of SEQ ID NO: 58; or (g) a VH sequence of SEQ ID NO: 47 and a VL sequence of SEQ ID NO: 57.

13. The antibody of any of the preceding items, wherein said antibody:
   (i) binds to human PDL1 with a dissociation constant (KD) of less than 5 nM, particularly less than 1 nM, particularly less than 500 pM, more particularly less than 100 pM, preferably less than 50 pM, more preferably less than 10 pM as measured by surface plasmon resonance (SPR), particularly wherein said antibody is an scFv (monovalent affinity);
   (ii) binds to human PDL1 with a $K_{off}$ rate of $10^{-3}$ $s^{-1}$ or less, or $10^{-4}$ $s^{-1}$ or less, or $10^{-5}$ $s^{-1}$ or less as measured by SPR, particularly wherein said antibody is an scFv;
   (iii) binds to human PDL1 with a $K_{on}$ rate of at least $10^3$ $M^{-1}$ $s^{-1}$ or greater, at least $10^4$ $M^{-1}$ $s^{-1}$ or greater, at least $10^5$ $M^{-1}$ $s^{-1}$ or greater, at least $10^6$ $M^{-1}$ $s^{-1}$ or greater as measured by SPR, particularly wherein said antibody is an scFv;
   (iv) is cross-reactive with Macaca fascicularis (Cynomolgus) PDL1, in particular binds to Cynomolgus PDL1 with a KD of less than 5 nM, particularly less than 1 nM, particularly less than 500 pM, more particularly less than 100 pM, preferably less than 10 pM as measured by SPR, particularly wherein said antibody is an scFv;
   (v) is non-cross-reactive to Mus musculus PDL1, in particular as measured by SPR; and/or
   (vi) does not bind to human PDL2, in particular as measured by SPR.

14. The antibody of any one of the preceding items, wherein said antibody has the following properties:
   (i) has the ability to neutralize PDL1/PD-1 interaction with a potency relative to that of avelumab (relative potency), determined in ELISA assay, greater than 1.5, e.g. greater than 2, greater than 2.5, preferably greater than 3, more preferably greater than 4, and wherein said relative potency is the ratio of the $IC_{50}$ value in ng/mL of avelumab as measured in the ELISA assay to the $IC_{50}$ value in ng/mL of said antibody as measured in the ELISA assay, in particular wherein said antibody is an scFv; and/or
   (ii) optionally, has the ability to neutralize PDL1/PD-1 interaction with a potency relative to that of avelumab (relative potency), determined in NFAT reporter gene assay, greater than 1.5, e.g. greater than 2, greater than 2.5, preferably greater than 3, more preferably greater than 4, and wherein said relative potency is the ratio of the $IC_{50}$ value in ng/mL of avelumab as measured in the NFAT reporter gene assay to the $IC_{50}$ value in ng/mL of said antibody as measured in the NFAT reporter gene assay, in particular wherein said antibody is an scFv; and/or
   (iii) has the ability to neutralize PDL1/B7-1 interaction with a potency relative to that of avelumab (relative potency), determined in ELISA assay, greater than 1.5, e.g. greater than 2, greater than 2.5, preferably greater than 3, more preferably greater than 4 and wherein said relative potency is the ratio of the $IC_{50}$ value in ng/mL of avelumab as measured in the ELISA assay to the $IC_{50}$ value in ng/mL of said antibody as measured in the ELISA assay, in particular wherein said antibody is an scFv.

15. The antibody of any of the preceding items, wherein said antibody:
    (i) when in scFv format, has a melting temperature (Tm), determined by differential scanning fluorimetry, of at least 60° C., preferably at least 65° C., more preferably at least 70° C., in particular wherein said antibody is formulated in 50 mM phosphate-citrate buffer at pH 6.4, 150 mM NaCl;
    (ii) when in scFv format, has a loss in monomer content, after five consecutive freeze-thaw cycles, of less than 5%, preferably less than 3%, more preferably less than 1%, when the antibody of the invention is at a starting concentration of 10 mg/ml, and in particular wherein the antibody is formulated 50 mM phosphate citrate buffer with 150 mM NaCl at pH 6.4; and/or
    (iii) when in scFv format, has a loss in monomer content, after storage for at least two weeks, particularly for at least four weeks, at 4° C., of less than 15%, e.g. less than 12%, less than 10%, less than 7%, less than 5%, less than 4%, less than 3%, less than 2%, preferably less than 1%, when the antibody of the invention is at a starting concentration of 10 mg/ml, and in particular wherein the antibody of the invention is formulated in 50 mM phosphate citrate buffer with 150 mM NaCl at pH 6.4.
16. The antibody of any of the previous items, wherein the antibody is selected from the group consisting of: a monoclonal antibody, a chimeric antibody, a Fab, an Fv, an scFv, dsFv, a scAb, and binding domains based on alternative scaffolds including but limited to ankyrin-based domains, fynomers, avimers, anticalins, fibronectins, and binding sites being built into constant regions of antibodies (e.g. F-star's Modular Antibody Technology™)
17. The antibody of any one of the preceding items, wherein said antibody is a single-chain variable fragment (scFv) or Fv.
18. The antibody of item 17, wherein said scFv has the amino acid sequence selected from the group consisting of SEQ ID NO: 29, SEQ ID NO: 30, SEQ ID NO: 31, SEQ ID NO: 60, SEQ ID NO: 61 and SEQ ID NO: 62, preferably SEQ ID NO: 29 and SEQ ID NO: 31, more preferably SEQ ID NO: 31.
19. The antibody of item 16, wherein the antibody is an IgG selected from the group consisting of an IgG1, an IgG2, an IgG3 and an IgG4, preferably wherein the antibody is an IgG1.
20. The antibody of any of the previous items, wherein the antibody is chimeric or humanized.
21. An antibody binding to essentially the same epitope as the antibody of any one of items 1 to 20.
22. The antibody of any of the preceding items which is a multispecific molecule, in particular a multispecific molecule having at least a second functional molecule.
23. The antibody of item 22, wherein said antibody is in a format selected from the group consisting of a single-chain diabody (scDb), a tandem scDb (Tandab), a linear dimeric scDb (LD-scDb), a circular dimeric scDb (CD-scDb), a bispecific T-cell engager (BiTE; tandem di-scFv), a tandem tri-scFv, a tribody (Fab-(scFv)2) or bibody (Fab-(scFv)1), Fab, Fab-Fv2, Morrison (IgG CH₃-scFv fusion (Morrison L) or IgG CL-scFv fusion (Morrison H)), triabody, scDb-scFv, bispecific Fab2, di-miniantibody, tetrabody, scFv-Fc-scFv fusion, scFv-HSA-scFv fusion, di-diabody, DVD-Ig, COVD, IgG-scFab, scFab-dsscFv, Fv2-Fc, IgG-scFv fusions, such as bsAb (scFv linked to C-terminus of light chain), BslAb (scFv linked to N-terminus of light chain), Bs2Ab (scFv linked to N-terminus of heavy chain), Bs3Ab (scFv linked to C-terminus of heavy chain), TslAb (scFv linked to N-terminus of both heavy chain and light chain), Ts2Ab (dsscFv linked to C-terminus of heavy chain), Bispecific antibodies based on heterodimeric Fc domains, such as Knob-into-Hole antibodies (KiHs); an Fv, scFv, scDb, tandem-di-scFv, tandem tri-scFv, Fab-(scFv)2, Fab-(scFv)1, Fab, Fab-Fv2, COVD fused to the N- and/or the C-terminus of either chain of a heterodimeric Fc domain or any other heterodimerization domain, a MATCH and DuoBodies.
24. A pharmaceutical composition comprising the antibody of any one of items 1 to 23, and a pharmaceutically acceptable carrier.
25. The antibody of any one of items 1 to 23, or the composition of item 24 for use as a medicament.
26. The antibody of any one of items 1 to 23, or the composition of item 24 for use in the treatment of a cancer in a subject in need thereof.
27. Use of the antibody of any one of items 1 to 23, or the composition of item 24 to treat a cancer in a subject in need thereof.
28. Use of the antibody of any one of items 1 to 23, or the composition of item 24 in the manufacture of a medicament for the treatment of a cancer in a subject in need thereof.
29. A method of treating a cancer in a subject in need thereof comprising administering to the subject a therapeutically effective amount of the antibody of any one of items 1 to 23, or the composition of item 24.
30. A nucleic acid encoding the antibody of any one of items 1-23.
31. A vector comprising the nucleic acid of item 31.
32. A host cell comprising the nucleic acid of item 31 or the vector of item 32.
33. A method of producing the antibody of any one of items 1-23, the method comprising the step of culturing a host cell comprising the nucleic acid of item 31 or the vector of item 31.
34. A kit comprising the antibody of any one of items 1 to 23, or the composition of item 24.

BRIEF DESCRIPTION OF THE DRAWINGS

Avelumab was used as reference.

DETAILED DESCRIPTION OF THE INVENTION

Figure 1:
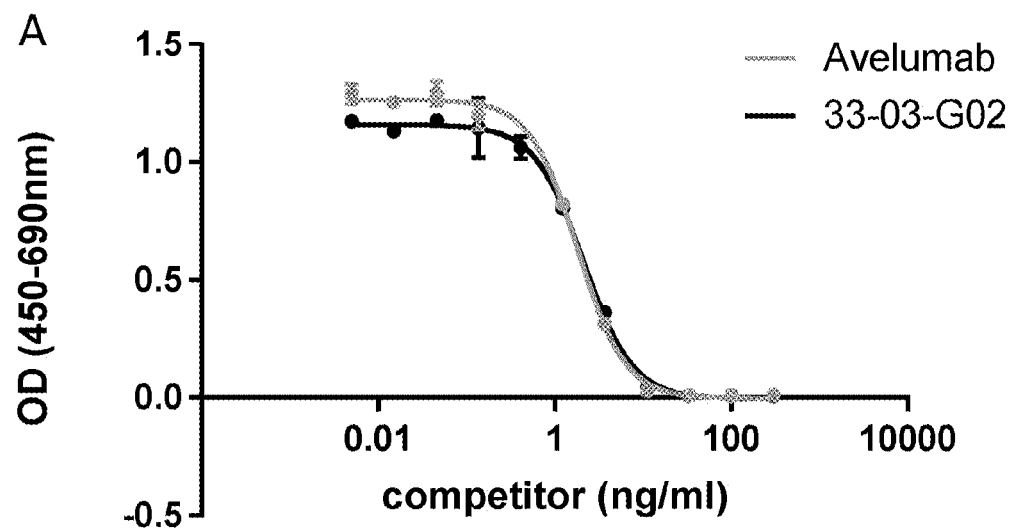
FIG. 1 Neutralization of PDL1/PD-1 interaction by the rabbit IgG clones having the best affinity to PDL1. Absorbances measured by ELISA are represented in function of the 33-03-G02 (A) or 37-20-B03 (B) molecules concentrations in ng/ml. Avelumab was used as a reference.
Figure 1:
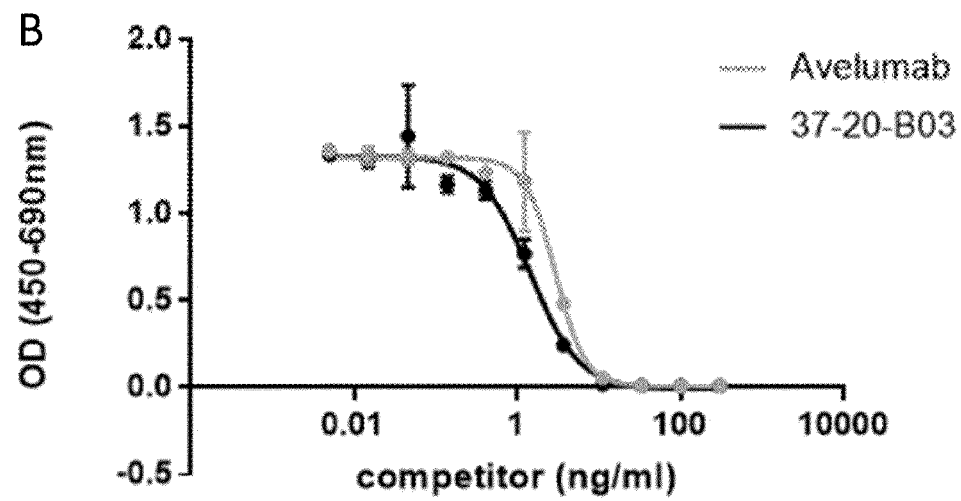

The present invention provides antibodies that specifically bind to human PDL1 protein, and pharmaceutical compositions, production methods, and methods of use of such antibodies and compositions.

Unless defined otherwise, all technical and scientific terms used herein have the same meaning as commonly understood by those of ordinary skill in the art to which this invention pertains.

The terms "comprising" and "including" are used herein in their open-ended and non-limiting sense unless otherwise noted. With respect to such latter embodiments, the term "comprising" thus includes the narrower term "consisting of".

The terms "a" and "an" and "the" and similar references in the context of describing the invention (especially in the context of the following claims) are to be construed to cover both the singular and the plural, unless otherwise indicated herein or clearly contradicted by context. For example, the term "a cell" includes a plurality of cells, including mixtures thereof. Where the plural form is used for compounds, salts, and the like, this is taken to mean also a single compound, salt, or the like.

In a first aspect, the present invention relates to antibodies that specifically bind to human PDL1.

The term "antibody" and the like, as used herein, includes: whole antibodies or single chains thereof; and any antigen-binding fragments (i.e., "antigen-binding portions") or single chains thereof; and molecules comprising antibody CDRs, VH regions or VL regions (including without limitation multispecific antibodies). A naturally occurring "whole antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FRs). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The terms "antigen-binding fragment", "antigen-binding fragment thereof", "antigen binding portion", and the like, as used herein, refer to one or more fragments of an intact whole antibody that retain the ability to specifically bind to a given antigen (e.g., PDL1). Examples of binding fragments encompassed within the term "antigen binding portion" of an antibody include a Fab fragment, a monovalent fragment consisting of the VL, VH, CL and CH1 domains; a F(ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; and binding domains based on alternative scaffolds including but limited to ankyrin-based domains, fynomers, avimers, scaffolds commercialized under the registered trade mark ANTICALIN®, fibronectins, and binding sites being built into constant regions of antibodies (e.g. F-star Therapeutics's technology commercialized under the trade mark Modular Antibody Technology™).

The term "Complementarity Determining Regions" ("CDRs") are amino acid sequences with boundaries determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme), ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme) and numbering scheme described in Honegger & Plückthun, J. Mol. Biol. 309 (2001) 657-670 ("AHo" numbering). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 24-34 (LCDR1), 50-56 (LCDR2), and 89-97 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (HCDR1), 51-57 (HCDR2) and 93-102 (HCDR3), and the CDR amino acid residues in the VL are numbered approximately 27-32 (LCDR1), 50-52 (LCDR2), and 89-97 (LCDR3) (numbering according to "Kabat"). Under IMGT, the CDRs of an antibody can be determined using the program IMGT/DomainGap Align. In the context of the present invention, the numbering system suggested by Honegger & Plückthun ("AHo") is used (Honegger & Plückthun, J. Mol. Biol. 309 (2001) 657-670), unless specifically mentioned otherwise. Furthermore, the following residues are defined as CDRs according to AHo numbering scheme: LCDR1 (also referred to as CDR-L1): L24-L42; LCDR2 (also referred to as CDR-L2): L58-L72; LCDR3 (also referred to as CDR-L3): L107-L138; HCDR1 (also referred to as CDR-H1): H27-H42; HCDR2 (also referred to as CDR-H2): H57-H76; HCDR3 (also referred to as CDR-H3): H108-H138. For the sake of clarity, the numbering system according to Honegger & Plückthun takes the length diversity into account that is found in naturally occurring antibodies, both in the different VH and VL subfamilies and, in particular, in the CDRs, and provides for gaps in the sequences. Thus, in a given antibody variable domain usually not all positions 1 to 149 will be occupied by an amino acid residue.

Antigen binding portions can also be incorporated into maxibodies, minibodies, intrabodies, diabodies, triabodies, tetrabodies, scDb-scFv, v-NAR and bis-scFv (see, e.g., Holliger and Hudson, 2005, Nature Biotechnology, 23, 1126-36). Antigen binding portions of antibodies can be grafted into scaffolds based on polypeptides such as Fibronectin type III (Fn3) (see U.S. Pat. No. 6,703,199, which describes fibronectin polypeptide monobodies). Antigen binding portions can be incorporated into single chain molecules comprising a pair of tandem Fv segments (VH-CH1-VH-CH1) which, together with complementary light chain polypeptides, form a pair of antigen binding regions (Zapata et al., 1995 Protein Eng. 8 (10): 1057-1062; and U.S. Pat. No. 5,641,870).

The term "binding specificity" as used herein refers to the ability of an individual antibody to react with one antigenic determinant and not with a different antigenic determinant. As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In its most general form (and when no defined reference is mentioned), "specific binding" is referring to the ability of the antibody to discriminate between the target of interest and an unrelated molecule, as determined, for example, in accordance with a specificity assay methods known in the art. Such methods comprise, but are not limited to Western blots, ELISA, RIA, ECL, IRMA, SPR (Surface plasmon resonance) tests and peptide scans. For example, a standard ELISA assay can be carried out. The scoring may be carried out by standard colour development (e.g. secondary antibody with horseradish peroxide and tetramethyl benzidine with hydrogen peroxide). The reaction in certain wells is scored by the optical density, for example, at 450 nm. Typical background (=negative reaction) may be about 0.1 OD; typical positive reaction may be about 1 OD. This means the ratio between a positive and a negative score can be 10-fold or higher. In a further example, an SPR assay can be carried out, wherein at least 10-fold, preferably at least 100-fold difference between a background and signal indicates on specific binding. Typically, determination of binding specificity is performed by using not a single reference molecule, but a set of about three to five unrelated molecules, such as milk powder, transferrin or the like. The antibody of the invention has a binding specificity for human PDL1. In a specific embodiment, the antibody of the invention has a binding specificity for human PDL1 and does not bind to human PDL2, in particular as determined by SPR.

Suitably, the antibody of the invention is an isolated antibody. The term "isolated antibody", as used herein, refers to an antibody that is substantially free of other antibodies having different antigenic specificities (e.g., an isolated antibody that specifically binds PDL1 is substantially free of antibodies that specifically bind antigens other than PDL1). An isolated antibody that specifically binds PDL1 may, however, have cross-reactivity to other antigens, such PDL1 molecules from other species. Thus, in one embodiment, the antibody of the invention has a binding specificity for human PDL1 and Macaca fascicularis (also known as Cynomolgus monkey or "Cynomolgus") PDL1. Moreover, an isolated antibody may be substantially free of other cellular material and/or chemicals.

Suitably, the antibody of the invention is a monoclonal antibody. The term "monoclonal antibody" or "monoclonal antibody composition" as used herein refers to antibodies that are substantially identical to amino acid sequence or are derived from the same genetic source. A monoclonal antibody composition displays a binding specificity and affinity for a particular epitope, or binding specificities and affinities for specific epitopes.

Antibodies of the invention include, but are not limited to, the chimeric and humanized.

The term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

A "humanized" antibody, as used herein, is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). Additional framework region modifications may be made within the human framework sequences as well as within the CDR sequences derived from the germline of another mammalian species. The humanized antibodies of the invention may include amino acid residues not encoded by human sequences (e.g., mutations introduced by random or site-specific mutagenesis in vitro or by somatic mutation in vivo, or a conservative substitution to promote stability or manufacturing). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239: 1534-1536, 1988; Padlan, Molec. Immun., 28:489-498, 1991; and Padlan, Molec. Immun., 31: 169-217, 1994. Other examples of human engineering technology include, but are not limited to Xoma technology disclosed in U.S. Pat. No. 5,766, 886.

The term "recombinant humanized antibody" as used herein, includes all human antibodies that are prepared, expressed, created or isolated by recombinant means, such as antibodies isolated from a host cell transformed to express the humanized antibody, e.g., from a transfectoma, and antibodies prepared, expressed, created or isolated by any other means that involve splicing of all or a portion of a human immunoglobulin gene, sequences to other DNA sequences.

The term "PDL1" refers in particular to human PDL1 with UniProt ID number Q9NZQ7, reproduced herein as SEQ ID NO: 63. Suitably, the antibodies of the present invention target PDL1, in particular human PDL1 as shown in UniProt ID number Q9NZQ7, reproduced herein as SEQ ID NO: 63. Suitably, the antibodies of the present invention target human and cynomolgus (Macaca fascicularis) PDL1, and preferably do not cross-react with Mus musculus PDL1, in particular as measured by surface plasmon resonance (SPR). Suitably, the antibodies of the present invention have a binding specificity for human PDL1. In particular, the antibodies of the invention do not bind to human PDL2, in particular as measured by SPR.

The antibody of the invention is a PDL1 inhibitor. The term "blocker" or "blocking antibody" or "inhibitor" or "inhibiting antibody" or "antagonist" or "antagonist antibody" refers to an antibody that inhibits or reduces a biological activity of the antigen it binds to. In some embodiments, blocking antibodies or antagonist antibodies substantially or completely inhibit the biological activity of the antigen. The antibody of the invention targets, decreases, inhibits the binding ability of PDL1 to its binding partners, thereby interfering with the PDL1 function. In particular, the antibody of the invention blocks the interaction of PDL1 with PD-1. In some embodiments, the antibody of the invention blocks the interaction of PDL1 with PD-1 and B7-1.

Antibodies of the invention include, but are not limited to, the humanized monoclonal antibodies isolated as described herein, including in the Examples. Examples of such anti-human PDL1 antibodies are antibodies whose sequences are listed in Table 1. Additional details regarding the generation and characterization of the antibodies described herein are provided in the Examples.

The isolated antibody of the invention having a binding specificity for human PDL1 comprises a heavy chain variable region (VH) and a light chain variable region (VL), wherein: (a) said VH comprises, in sequence, the three complementary determining regions HCDR1, HCDR2 and HCDR3, and (b) said VL comprises, in sequence, the three complementary determining regions LCDR1, LCDR2 and LCDR3.

The present invention provides antibodies that specifically bind to PDL1 protein, said antibodies comprising a VH CDR having an amino acid sequence of any one of the VH CDRs listed in Table 1. In particular, the invention provides antibodies that specifically bind to PDL1 protein, said antibodies comprising one, two, three, or more VH CDRs having an amino acid sequence of any of the VH CDRs listed in Table 1.

The present invention also provides antibodies that specifically bind to PDL1 protein, said antibodies comprising a VL CDR having an amino acid sequence of any one of the VL CDRs listed in Table 1. In particular, the invention provides antibodies that specifically bind to PDL1 protein, said antibodies comprising one, two, three or more VL CDRs having an amino acid sequence of any of the VL CDRs listed in Table 1.

Other antibodies of the invention include amino acids that have been mutated, yet specifically bind to PDL1 protein and have at least 60, 70, 80, 90, 91, 92, 93, 94, 95, 96, 97, 98 or 99 percent identity in the CDR regions with the CDR regions depicted in the sequences described in Table 1. In one aspect, other antibodies of the invention includes mutant amino acid sequences that specifically bind to PDL1 protein wherein no more than 1, 2, 3, 4 or 5 amino acids have been mutated in the CDR regions when compared with the CDR regions depicted in the sequences described in Table 1.

The terms "identical" or "identity", in the context of two or more nucleic acids or polypeptide sequences, refer to two or more sequences or subsequences that are the same. "Percent (%) sequence identity" and "homology" with respect to a nucleic acid, a peptide, a polypeptide or an antibody sequence are defined as the percentage of nucleotides or amino acid residues in a candidate sequence that are identical with the nucleotides or amino acid residues in the specific nucleic acid, peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2 or ALIGN software. Those skilled in the art can determine appropriate parameters for measuring alignment, including any algorithms needed to achieve maximal alignment over the full length of the sequences being compared.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Two examples of algorithms that are suitable for determining percent sequence identity and sequence similarity are the BLAST and BLAST 2.0 algorithms, which are described in Altschul et al., Nucl. Acids Res. 25:3389-3402, 1977; and Altschul et al., J. Mol. Biol. 215:403-410, 1990, respectively. Software for performing BLAST analyses is publicly available through the National Center for Biotechnology Information. The percent identity between two amino acid sequences can also be determined using the algorithm of E. Meyers and W. Miller (Comput. Appl. Biosci., 4: 11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The present invention provides an isolated antibody having a binding specificity for human PDL1, which comprises (a) a heavy chain variable region CDR1 (HCDR1) comprising, preferably consisting of, an amino acid sequence selected from any one of SEQ ID NOs: 1, 4, 5, 8, 11, 32, 35, 36, 39 and 42, preferably SEQ ID NO: 1 or 32, more preferably SEQ ID NO: 1; (b) a heavy chain variable region CDR2 (HCDR2) comprising, preferably consisting of, an amino acid sequence selected from any of SEQ ID NOs: 2, 6, 9, 12, 33, 37, 40 and 43, preferably SEQ ID NO: 2 or 33, more preferably SEQ ID NO: 2; (c) a heavy chain variable region CDR3 (HCDR3) comprising, preferably consisting of, an amino acid sequence selected from any of SEQ ID NOs: 3, 7, 10, 13, 34, 38, 41 and 44, preferably SEQ ID NO: 3 or 34, more preferably SEQ ID NO: 3; (d) a light chain variable region CDR1 (LCDR1) comprising, preferably consisting of, an amino acid sequence selected from any of SEQ ID NOs: 17, 20, 23, 48, 51 and 54, preferably SEQ ID NO: 17 or 48, more preferably SEQ ID NO: 17; (e) a light chain variable region CDR2 (LCDR2) comprising, preferably consisting of, an amino acid sequence selected from any of SEQ ID NOs: 18, 21, 24, 49, 52 and 55, preferably SEQ ID NO: 18 or 49, more preferably SEQ ID NO: 18; and (f) a light chain variable region CDR3 (LCDR3) comprising, preferably consisting of, an amino acid sequence selected from any of SEQ ID NOs: 19, 22, 25, 50, 53 and 56, preferably SEQ ID NO: 19 or 50, more preferably SEQ ID NO: 19.

Suitably, the isolated antibody of the invention having a binding specificity for human PDL1 comprises: (a) a heavy chain variable region CDR1 (HCDR1) comprising, preferably consisting of, an amino acid sequence having at least 60, 70, 80, 90, 91, 92, 93, 94, 95, 96, 97, 98 or 99 percent identity to any one of SEQ ID NOs: 1, 4, 5, 8, 11, 32, 35, 36, 39 and 42, preferably SEQ ID NO: 1 or 32, more preferably SEQ ID NO: 1; (b) a heavy chain variable region CDR2 (HCDR2) comprising, preferably consisting of, an amino acid sequence having at least 60, 70, 80, 90, 91, 92, 93, 94, 95, 96, 97, 98 or 99 percent identity to any of SEQ ID NOs: 2, 6, 9, 12, 33, 37, 40 and 43, preferably SEQ ID NO: 2 or 33, more preferably SEQ ID NO: 2; (c) a heavy chain variable region CDR3 (HCDR3) comprising, preferably consisting of, an amino acid sequence having at least 60, 70, 80, 90, 91, 92, 93, 94, 95, 96, 97, 98 or 99 percent identity to any of SEQ ID NOs: 3, 7, 10, 13, 34, 38, 41 and 44, preferably SEQ ID NO: 3 or 34, more preferably SEQ ID NO: 3; (d) a light chain variable region CDR1 (LCDR1) comprising, preferably consisting of, an amino acid sequence having at least 60, 70, 80, 90, 91, 92, 93, 94, 95, 96, 97, 98 or 99 percent identity to any of SEQ ID NOs: 17, 20, 23, 48, 51 and 54, preferably SEQ ID NO: 17 or 48, more preferably SEQ ID NO: 17; (e) a light chain variable region CDR2 (LCDR2) comprising, preferably consisting of, an amino acid sequence having at least 60, 70, 80, 90, 91, 92, 93, 94, 95, 96, 97, 98 or 99 percent identity to any of SEQ ID NOs: 18, 21, 24, 49, 52 and 55, preferably SEQ ID NO: 18 or 49, more preferably SEQ ID NO: 18; and (f) a light chain variable region CDR3 (LCDR3) comprising, preferably consisting of, an amino acid sequence having at least 60, 70, 80, 90, 91, 92, 93, 94, 95, 96, 97, 98 or 99 percent identity to any of SEQ ID NOs: 19, 22, 25, 50, 53 and 56, preferably SEQ ID NO: 19 or 50, more preferably SEQ ID NO: 19.

In one embodiment, the antibody of the invention having a binding specificity for human PDL1 comprises: (a)

HCDR1, HCDR2, and HCDR3 sequences of SEQ ID NOs: 1, 2 and 3, respectively, and LCDR1, LCDR2, and LCDR3 sequences of SEQ ID NOs: 17, 18 and 19, respectively; (b) HCDR1, HCDR2, and HCDR3 sequences of SEQ ID NOs: 4, 6, and 7, respectively, and LCDR1, LCDR2, and LCDR3 sequences of SEQ ID NOs: 20, 21, and 22, respectively; (c) HCDR1, HCDR2, and HCDR3 sequences of SEQ ID NOs: 5, 6, and 7, respectively, and LCDR1, LCDR2, and LCDR3 sequences of SEQ ID NOs: 20, 21, and 22, respectively; (d) HCDR1, HCDR2, and HCDR3 sequences of SEQ ID NOs: 8, 9, and 10, respectively, and LCDR1, LCDR2, and LCDR3 sequences of SEQ ID NOs: 17, 18, and 19, respectively; (e) HCDR1, HCDR2, and HCDR3 sequences of SEQ ID NOs: 11, 12, and 13, respectively, and LCDR1, LCDR2, and LCDR3 sequences of SEQ ID NOs: 23, 24, and 25, respectively; (f) HCDR1, HCDR2, and HCDR3 sequences of SEQ ID NOs: 32, 33 and 34, respectively, and LCDR1, LCDR2, and LCDR3 sequences of SEQ ID NOs: 48, 49 and 50, respectively; (g) HCDR1, HCDR2, and HCDR3 sequences of SEQ ID NOs: 35, 37, and 38, respectively, and LCDR1, LCDR2, and LCDR3 sequences of SEQ ID NOs: 51, 52, and 53, respectively; (h) HCDR1, HCDR2, and HCDR3 sequences of SEQ ID NOs: 36, 37, and 38, respectively, and LCDR1, LCDR2, and LCDR3 sequences of SEQ ID NOs: 51, 52, and 53, respectively; (i) HCDR1, HCDR2, and HCDR3 sequences of SEQ ID NOs: 39, 40, and 41, respectively, and LCDR1, LCDR2, and LCDR3 sequences of SEQ ID NOs: 48, 49, and 50, respectively; (j) HCDR1, HCDR2, and HCDR3 sequences of SEQ ID NOs: 42, 43, and 44, respectively, and LCDR1, LCDR2, and LCDR3 sequences of SEQ ID NOs: 54, 55, and 56, respectively. In one embodiment, the antibody of the invention having a binding specificity for human PDL1 comprises HCDR1, HCDR2, and HCDR3 sequences of SEQ ID NOs: 1, 2 and 3, respectively, and LCDR1, LCDR2, and LCDR3 sequences of SEQ ID NOs: 17, 18 and 19, respectively. In another embodiment, the antibody of the invention having a binding specificity for human PDL1 comprises HCDR1, HCDR2, and HCDR3 sequences of SEQ ID NOs: 32, 33 and 34, respectively, and LCDR1, LCDR2, and LCDR3 sequences of SEQ ID NOs: 48, 49 and 50, respectively.

Suitably, the antibody of the invention having a binding specificity for human PDL1 comprises: (a) HCDR1, HCDR2, and HCDR3 sequences having at least 60, 70, 80, 90, 91, 92, 93, 94, 95, 96, 97, 98 or 99 percent identity to SEQ ID NOs: 1, 2 and 3, respectively, and LCDR1, LCDR2, and LCDR3 sequences having at least 60, 70, 80, 90, 91, 92, 93, 94, 95, 96, 97, 98 or 99 percent identity to SEQ ID NOs: 17, 18 and 19, respectively; (b) HCDR1, HCDR2, and HCDR3 sequences having at least 60, 70, 80, 90, 91, 92, 93, 94, 95, 96, 97, 98 or 99 percent identity to SEQ ID NOs: 4, 6, and 7, respectively, and LCDR1, LCDR2, and LCDR3 sequences having at least 60, 70, 80, 90, 91, 92, 93, 94, 95, 96, 97, 98 or 99 percent identity to SEQ ID NOs: 20, 21, and 22, respectively; (c) HCDR1, HCDR2, and HCDR3 sequences having at least 60, 70, 80, 90, 91, 92, 93, 94, 95, 96, 97, 98 or 99 percent identity to SEQ ID NOs: 5, 6, and 7, respectively, and LCDR1, LCDR2, and LCDR3 sequences having at least 60, 70, 80, 90, 91, 92, 93, 94, 95, 96, 97, 98 or 99 percent identity to SEQ ID NOs: 20, 21, and 22, respectively; (d) HCDR1, HCDR2, and HCDR3 sequences having at least 60, 70, 80, 90, 91, 92, 93, 94, 95, 96, 97, 98 or 99 percent identity to SEQ ID NOs: 8, 9, and 10, respectively, and LCDR1, LCDR2, and LCDR3 sequences having at least 60, 70, 80, 90, 91, 92, 93, 94, 95, 96, 97, 98 or 99 percent identity to SEQ ID NOs: 17, 18, and 19, respectively; (e) HCDR1, HCDR2, and HCDR3 sequences having at least 60, 70, 80, 90, 91, 92, 93, 94, 95, 96, 97, 98 or 99 percent identity to SEQ ID NOs: 11, 12, and 13, respectively, and LCDR1, LCDR2, and LCDR3 sequences having at least 60, 70, 80, 90, 91, 92, 93, 94, 95, 96, 97, 98 or 99 percent identity to SEQ ID NOs: 23, 24, and 25, respectively; (f) HCDR1, HCDR2, and HCDR3 sequences having at least 60, 70, 80, 90, 91, 92, 93, 94, 95, 96, 97, 98 or 99 percent identity to SEQ ID NOs: 32, 33 and 34, respectively, and LCDR1, LCDR2, and LCDR3 sequences having at least 60, 70, 80, 90, 91, 92, 93, 94, 95, 96, 97, 98 or 99 percent identity to SEQ ID NOs: 48, 49 and 50, respectively; (g) HCDR1, HCDR2, and HCDR3 sequences having at least 60, 70, 80, 90, 91, 92, 93, 94, 95, 96, 97, 98 or 99 percent identity to SEQ ID NOs: 35, 37, and 38, respectively, and LCDR1, LCDR2, and LCDR3 sequences having at least 60, 70, 80, 90, 91, 92, 93, 94, 95, 96, 97, 98 or 99 percent identity to SEQ ID NOs: 51, 52, and 53, respectively; (h) HCDR1, HCDR2, and HCDR3 sequences having at least 60, 70, 80, 90, 91, 92, 93, 94, 95, 96, 97, 98 or 99 percent identity to SEQ ID NOs: 36, 37, and 38, respectively, and LCDR1, LCDR2, and LCDR3 sequences having at least 60, 70, 80, 90, 91, 92, 93, 94, 95, 96, 97, 98 or 99 percent identity to SEQ ID NOs: 51, 52, and 53, respectively; (i) HCDR1, HCDR2, and HCDR3 sequences having at least 60, 70, 80, 90, 91, 92, 93, 94, 95, 96, 97, 98 or 99 percent identity to SEQ ID NOs: 39, 40, and 41, respectively, and LCDR1, LCDR2, and LCDR3 sequences having at least 60, 70, 80, 90, 91, 92, 93, 94, 95, 96, 97, 98 or 99 percent identity to SEQ ID NOs: 48, 49, and 50, respectively; (j) HCDR1, HCDR2, and HCDR3 sequences having at least 60, 70, 80, 90, 91, 92, 93, 94, 95, 96, 97, 98 or 99 percent identity to SEQ ID NOs: 42, 43, and 44, respectively, and LCDR1, LCDR2, and LCDR3 sequences having at least 60, 70, 80, 90, 91, 92, 93, 94, 95, 96, 97, 98 or 99 percent identity to SEQ ID NOs: 54, 55, and 56, respectively. In one embodiment, the antibody of the invention having a binding specificity for human PDL1 comprises HCDR1, HCDR2, and HCDR3 sequences having at least 60, 70, 80, 90, 91, 92, 93, 94, 95, 96, 97, 98 or 99 percent identity to SEQ ID NOs: 1, 2 and 3, respectively, and LCDR1, LCDR2, and LCDR3 sequences having at least 60, 70, 80, 90, 91, 92, 93, 94, 95, 96, 97, 98 or 99 percent identity to SEQ ID NOs: 17, 18 and 19, respectively. In another embodiment, the antibody of the invention having a binding specificity for human PDL1 comprises HCDR1, HCDR2, and HCDR3 sequences having at least 60, 70, 80, 90, 91, 92, 93, 94, 95, 96, 97, 98 or 99 percent identity to SEQ ID NOs: 32, 33 and 34, respectively, and LCDR1, LCDR2, and LCDR3 sequences having at least 60, 70, 80, 90, 91, 92, 93, 94, 95, 96, 97, 98 or 99 percent identity to SEQ ID NOs: 48, 49 and 50, respectively.

Suitably, the antibody of the invention having a binding specificity for human PDL1 comprises: (a) a HCDR1 comprising, preferably consisting of, the amino acid sequence of SEQ ID NO: 1; (b) a HCDR2 comprising, preferably consisting of, the amino acid sequence of SEQ ID NO: 2; (c) a HCDR3 comprising, preferably consisting of, the amino acid sequence of SEQ ID NO: 3; (d) a LCDR1 comprising, preferably consisting of, the amino acid sequence of SEQ ID NOs: 17; (e) a LCDR2 comprising, preferably consisting of, the amino acid sequence of SEQ ID NOs: 18; and (f) a LCDR3 comprising, preferably consisting of, the amino acid sequence of SEQ ID NO: 19. Suitably, the antibody of the invention having a binding specificity for human PDL1 comprises: (a) a HCDR1 comprising, preferably consisting of, the amino acid sequence having at least 60, 70, 80, 90, 91, 92, 93, 94, 95, 96, 97, 98 or 99 percent identity to SEQ ID NO: 1; (b) a HCDR2 comprising, preferably consisting of, the amino acid sequence having at least 60, 70, 80, 90, 91, 92, 93, 94, 95, 96, 97, 98 or 99 percent identity to SEQ ID NO: 2; (c) a HCDR3 comprising, preferably consisting of, the amino acid sequence having at least 60, 70, 80, 90, 91, 92, 93, 94, 95, 96, 97, 98 or 99 percent identity to SEQ ID NO: 3; (d) a LCDR1 comprising, preferably consisting of, the amino acid sequence having at least 60, 70, 80, 90, 91, 92, 93, 94, 95, 96, 97, 98 or 99 percent identity to SEQ ID NOs: 17; (e) a LCDR2 comprising, preferably consisting of, the amino acid sequence having at least 60, 70, 80, 90, 91, 92, 93, 94, 95, 96, 97, 98 or 99 percent identity to SEQ ID NOs: 18; and (f) a LCDR3 comprising, preferably consisting of, the amino acid sequence having at least 60, 70, 80, 90, 91, 92, 93, 94, 95, 96, 97, 98 or 99 percent identity to SEQ ID NO: 19.

In a further embodiment, the antibody of the invention having a binding specificity for human PDL1 comprises: (a) a HCDR1 comprising, preferably consisting of, the amino acid sequence of SEQ ID NO: 4 or SEQ ID NO: 5; (b) a HCDR2 comprising, preferably consisting of, the amino acid sequence of SEQ ID NO: 6; (c) a HCDR3 comprising, preferably consisting of, the amino acid sequence of SEQ ID NO: 7; (d) a LCDR1 comprising, preferably consisting of, the amino acid sequence of SEQ ID NOs: 20; (e) a LCDR2 comprising, preferably consisting of, the amino acid sequence of SEQ ID NOs: 21; and (f) a LCDR3 comprising, preferably consisting of, the amino acid sequence of SEQ ID NO: 22. Suitably, the antibody of the invention having a binding specificity for human PDL1 comprises: (a) a HCDR1 comprising, preferably consisting of, the amino acid sequence having at least 60, 70, 80, 90, 91, 92, 93, 94, 95, 96, 97, 98 or 99 percent identity to SEQ ID NO: 4 or SEQ ID NO: 5; (b) a HCDR2 comprising, preferably consisting of, the amino acid sequence having at least 60, 70, 80, 90, 91, 92, 93, 94, 95, 96, 97, 98 or 99 percent identity to SEQ ID NO: 6; (c) a HCDR3 comprising, preferably consisting of, the amino acid sequence having at least 60, 70, 80, 90, 91, 92, 93, 94, 95, 96, 97, 98 or 99 percent identity to SEQ ID NO: 7; (d) a LCDR1 comprising, preferably consisting of, the amino acid sequence having at least 60, 70, 80, 90, 91, 92, 93, 94, 95, 96, 97, 98 or 99 percent identity to SEQ ID NOs: 20; (e) a LCDR2 comprising, preferably consisting of, the amino acid sequence having at least 60, 70, 80, 90, 91, 92, 93, 94, 95, 96, 97, 98 or 99 percent identity to SEQ ID NOs: 21; and (f) a LCDR3 comprising, preferably consisting of, the amino acid sequence having at least 60, 70, 80, 90, 91, 92, 93, 94, 95, 96, 97, 98 or 99 percent identity to SEQ ID NO: 22.

Suitably, the antibody of the invention having a binding specificity for human PDL1 comprises: (a) a HCDR1 comprising, preferably consisting of, the amino acid sequence of SEQ ID NO: 32; (b) a HCDR2 comprising, preferably consisting of, the amino acid sequence of SEQ ID NO: 33; (c) a HCDR3 comprising, preferably consisting of, the amino acid sequence of SEQ ID NO: 34; (d) a LCDR1 comprising, preferably consisting of, the amino acid sequence of SEQ ID NOs: 48; (e) a LCDR2 comprising, preferably consisting of, the amino acid sequence of SEQ ID NOs: 49; and (f) a LCDR3 comprising, preferably consisting of, the amino acid sequence of SEQ ID NO: 50. Suitably, the antibody of the invention having a binding specificity for human PDL1 comprises: (a) a HCDR1 comprising, preferably consisting of, the amino acid sequence having at least 60, 70, 80, 90, 91, 92, 93, 94, 95, 96, 97, 98 or 99 percent identity to SEQ ID NO: 32; (b) a HCDR2 comprising, preferably consisting of, the amino acid sequence having at least 60, 70, 80, 90, 91, 92, 93, 94, 95, 96, 97, 98 or 99 percent identity to SEQ ID NO: 33; (c) a HCDR3 comprising, preferably consisting of, the amino acid sequence having at least 60, 70, 80, 90, 91, 92, 93, 94, 95, 96, 97, 98 or 99 percent identity to SEQ ID NO: 34; (d) a LCDR1 comprising, preferably consisting of, the amino acid sequence having at least 60, 70, 80, 90, 91, 92, 93, 94, 95, 96, 97, 98 or 99 percent identity to SEQ ID NOs: 48; (e) a LCDR2 comprising, preferably consisting of, the amino acid sequence having at least 60, 70, 80, 90, 91, 92, 93, 94, 95, 96, 97, 98 or 99 percent identity to SEQ ID NOs: 49; and (f) a LCDR3 comprising, preferably consisting of, the amino acid sequence of SEQ ID NO: 50.

In a further embodiment, the antibody of the invention having a binding specificity for human PDL1 comprises: (a) a HCDR1 comprising, preferably consisting of, the amino acid sequence of SEQ ID NO: 35 or SEQ ID NO: 36; (b) a HCDR2 comprising, preferably consisting of, the amino acid sequence of SEQ ID NO: 37; (c) a HCDR3 comprising, preferably consisting of, the amino acid sequence of SEQ ID NO: 38; (d) a LCDR1 comprising, preferably consisting of, the amino acid sequence of SEQ ID NOs: 51; (e) a LCDR2 comprising, preferably consisting of, the amino acid sequence of SEQ ID NOs: 52; and (f) a LCDR3 comprising, preferably consisting of, the amino acid sequence of SEQ ID NO: 53. Suitably, the antibody of the invention having a binding specificity for human PDL1 comprises: (a) a HCDR1 comprising, preferably consisting of, the amino acid sequence having at least 60, 70, 80, 90, 91, 92, 93, 94, 95, 96, 97, 98 or 99 percent identity to SEQ ID NO: 35 or SEQ ID NO: 36; (b) a HCDR2 comprising, preferably consisting of, the amino acid sequence having at least 60, 70, 80, 90, 91, 92, 93, 94, 95, 96, 97, 98 or 99 percent identity to SEQ ID NO: 37; (c) a HCDR3 comprising, preferably consisting of, the amino acid sequence having at least 60, 70, 80, 90, 91, 92, 93, 94, 95, 96, 97, 98 or 99 percent identity to SEQ ID NO: 38; (d) a LCDR1 comprising, preferably consisting of, the amino acid sequence having at least 60, 70, 80, 90, 91, 92, 93, 94, 95, 96, 97, 98 or 99 percent identity to SEQ ID NOs: 51; (e) a LCDR2 comprising, preferably consisting of, the amino acid sequence having at least 60, 70, 80, 90, 91, 92, 93, 94, 95, 96, 97, 98 or 99 percent identity to SEQ ID NOs: 52; and (f) a LCDR3 comprising, preferably consisting of, the amino acid sequence of SEQ ID NO: 53.

In a further embodiment, the invention provides an isolated antibody that specifically binds PDL1 (e.g., human PDL1 protein), wherein said antibody comprises a VH domain and a VL domain. In the context of the present invention the terms "VH" (variable heavy chain), "VL" (variable light chain), "Vκ" and "Vλ" refer to families of antibody heavy and light chain sequences that are grouped according to sequence identity and homology. Methods for the determination of sequence homologies, for example by using a homology search matrix such as BLOSUM (Henikoff, S. & Henikoff, J. G., Proc. Natl. Acad. Sci. USA 89 (1992) 10915-10919), and methods for the grouping of sequences according to homologies are well known to one of ordinary skill in the art. For VH, Vκ and Vλ different subfamilies can be identified, as shown, for example, in Knappik et al., J. Mol. Biol. 296 (2000) 57-86, which groups VH in VH1A, VH1B and VH2 to VH6, Vκ in Vκ1 to Vκ4 and Vλ in Vλ1 to Vλ3. In vivo, antibody Vκ chains, Vλ chains, and VH chains are the result of the random rearrangement of germline κ chain V and J segments, germline λ chain V and J segments, and heavy chain V, D and J segments, respectively. To which subfamily a given antibody variable chain belongs is determined by the corresponding V segment, and in particular by the framework regions FR1 to FR3. Thus, any VH sequence that is characterized by a particular set of framework regions HFR1 to HFR3 only, may be combined with any HFR4 sequence, for example a HFR4 sequence taken from one of the heavy chain germline J segments, or a HFR4 sequence taken from a rearranged VH sequence.

Suitably, the present invention provides an isolated antibody that specifically binds PDL1 (e.g., human PDL1 protein), wherein said antibody comprises a VH1A, VH1B, VH3 or VH4.

A specific example of a VH belonging to VH1 family is represented under SEQ ID NO: 15. In particular, framework regions FR1 to FR4 taken from SEQ ID NO: 15 belong to VH1 family (Table 1, regions marked in non-bold). Suitably, a VH belonging to VH1 family, as used herein, is a VH comprising FR1 to FR4 having at least 85%, preferably at least 90%, more preferably at least 95% sequence identity to FR1 to FR4 of SEQ ID NO: 15.

A specific example of a VH belonging to VH3 family is represented under SEQ ID NO: 16. In particular, framework regions FR1 to FR4 taken from SEQ ID NO: 16 belong to VH3 family (Table 1, regions marked in non-bold). Suitably, a VH belonging to VH3 family, as used herein, is a VH comprising FR1 to FR4 having at least 85%, preferably at least 90%, more preferably at least 95% sequence identity to FR1 to FR4 of SEQ ID NO: 16.

A specific example of a VH belonging to VH4 family is represented under SEQ ID NO: 14. In particular, framework regions FR1 to FR4 taken from SEQ ID NO: 14 belong to VH4 family (Table 1, regions marked in non-bold). Suitably, a VH belonging to VH4 family, as used herein, is a VH comprising FR1 to FR4 having at least 85%, preferably at least 90%, more preferably at least 95% sequence identity to FR1 to FR4 of SEQ ID NO: 14.

Alternative examples of VH sequences may be found in Knappik et al., J. Mol. Biol. 296 (2000) 57-86.

In one embodiment, an isolated antibody of the present invention comprises VH4 or VH3 domain.

Suitably, the present invention provides an isolated antibody that specifically binds PDL1 (e.g., human PDL1 protein), wherein said antibody comprises Vκ frameworks FR1, FR2 and FR3, particularly Vκ1 or Vκ3 frameworks, preferably Vκ1 frameworks FR1 to 3, and a framework FR4, which is selected from a Vκ FR4, particularly Vκ1 FR4, Vκ3 FR4, and a Vλ FR4. Suitable Vκ1 frameworks FR1 to 3 are set forth in SEQ ID NO: 26 (Table 1, FR regions are marked in non-bold). Suitable Vκ1 frameworks FR1 to 3 comprise the amino acid sequences having at least 60, 70, 80, 90 percent identity to amino acid sequences corresponding to FR1 to 3 and taken from SEQ ID NO: 26 (Table 1, FR regions are marked in non-bold).

Alternative examples of Vκ1 sequences, and examples of Vκ2, Vκ3 or Vκ4 sequences, may be found in Knappik et al., J. Mol. Biol. 296 (2000) 57-86.

Suitable Vλ FR4 s are as set forth in SEQ ID NO: 64 to SEQ ID NO: 70. In a preferred embodiment, Vλ FR4 is as set forth in SEQ ID NO: 64 or 65, more preferably Vλ FR4 is as set forth in SEQ ID NO: 64. In one embodiment the present invention provides an isolated antibody that specifically binds PDL1 (e.g., human PDL1 protein), wherein said antibody comprises Vλ FR4 comprising the amino acid sequence having at least 60, 70, 80, 90 percent identity to an amino acid sequence selected from any of SEQ ID NO: 64 to SEQ ID NO: 70, preferably to SEQ ID NO: 64 or 65, more preferably to SEQ ID NO: 64.

Thus, in one embodiment, the invention thus provides an antibody comprising:
(i) the HCDR1, HCDR2, HCDR3, LCDR1, LCDR2, and LCDR3 sequences of:
  a. the HCDR1, HCDR2, and HCDR3 sequences of SEQ ID NOs: 4, 6, and 7, respectively, and the LCDR1, LCDR2, and LCDR3 sequences of SEQ ID NOs: 20, 21, and 22, respectively;
  b. the HCDR1, HCDR2, and HCDR3 sequences of SEQ ID NOs: 35, 37, and 38, respectively, and the LCDR1, LCDR2, and LCDR3 sequences of SEQ ID NOs: 51, 52, and 53, respectively; or
  c. the HCDR1, HCDR2, and HCDR3 sequences of SEQ ID NOs: 36, 37, and 38, respectively, and the LCDR1, LCDR2, and LCDR3 sequences of SEQ ID NOs: 51, 52, and 53, respectively;
(ii) VH3 or VH4 domain framework sequences; and
(iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vκ FR4, particularly Vκ1 FR4, Vκ3 FR4, and a Vλ FR4, particularly Vλ FR4 comprising the amino acid sequence having at least 60, 70, 80, 90 percent identity to an amino acid sequence selected from any of SEQ ID NO: 64 to SEQ ID NO: 70, preferably Vλ FR4 is as set forth in SEQ ID NO: 64 to SEQ ID NO: 70, more preferably Vλ FR4 is as set forth in SEQ ID NO: 64.

In another embodiment, the present invention thus provides an antibody having a binding specificity for human PDL1 comprising:
(i) the HCDR1, HCDR2, and HCDR3 sequences of: SEQ ID NOs: 5, 6, and 7, respectively, and the LCDR1, LCDR2, and LCDR3 sequences of SEQ ID NOs: 20, 21, and 22, respectively;
(ii) VH1A, VH1B, VH3 or VH4 domain framework sequences, preferably VH1A or VH1B domain framework sequences; and
(iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vκ FR4, particularly Vκ1 FR4, Vκ3 FR4, and a Vλ FR4, particularly Vλ FR4 comprising the amino acid sequence having at least 60, 70, 80, 90 percent identity to an amino acid sequence selected from any of SEQ ID NO: 64 to SEQ ID NO: 70, preferably Vλ FR4 comprising an amino acid sequence selected from any of SEQ ID NO: 64 to SEQ ID NO: 70, more preferably Vλ FR4 is as set forth in SEQ ID NO: 64.

In a specific embodiment, the invention thus provides an antibody comprising:
(i) the HCDR1, HCDR2, and HCDR3 sequences of SEQ ID NOs: 32, 33 and 34, respectively, and the LCDR1, LCDR2, and LCDR3 sequences of SEQ ID NOs: 48, 49 and 50, respectively;
(ii) VH3 or VH4 domain framework sequences, preferably VH4 domain framework sequences; and
(iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vκ FR4, particularly Vκ1 FR4, Vκ3 FR4, and a Vλ FR4, particularly Vλ FR4 comprising the amino acid sequence having at least 60, 70, 80, 90 percent identity to an amino acid sequence selected from any of SEQ ID NO: 64 to SEQ ID NO: 70, preferably Vλ FR4 is as set forth in SEQ ID NO: 64 to SEQ ID NO: 70, more preferably Vλ FR4 is as set forth in SEQ ID NO: 64.

In a preferred embodiment, the invention thus provides an antibody comprising:
(i) the HCDR1, HCDR2, and HCDR3 sequences of SEQ ID NOs: 1, 2 and 3, respectively, and the LCDR1, LCDR2, and LCDR3 sequences of SEQ ID NOs: 17, 18 and 19, respectively;
(ii) VH3 or VH4 domain framework sequences, preferably VH3 domain framework sequences; and
(iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vκ FR4, particularly Vκ1 FR4, Vκ3 FR4, and a Vλ FR4, particularly Vλ FR4 comprising the amino acid sequence having at least 60, 70, 80, 90 percent identity to an amino acid sequence selected from any of SEQ ID NO: 64 to SEQ ID NO: 70, preferably Vλ FR4 is as set forth in SEQ ID NO: 64 to SEQ ID NO: 70, more preferably Vλ FR4 is as set forth in SEQ ID NO: 64.

In one embodiment, the invention thus provides an antibody having a binding specificity for human PDL1 and comprising a VL comprising:
(i) CDR domains CDR1, CDR2 and CDR3;
(ii) human Vκ framework regions FR1 to FR3, particularly human Vκ1 framework regions FR1 to FR3;
(iii) FR4, which is selected from (a) a human Vλ germ line sequence for FR4, particularly a Vλ germ line sequence selected from the list of: SEQ ID NO: 64 to 70, preferably SEQ ID NO: 64; and (b) a Vλ-based sequence, which has one or two mutations, particularly one mutation, compared to the closest human Vλ germ line sequence for FR4 comprising an amino acid sequence selected from any of SEQ ID NO: 64 to SEQ ID NO: 70, preferably SEQ ID NO: 64.

The present invention provides an isolated antibody that specifically binds PDL1 (e.g., human PDL1 protein), wherein said antibody comprises a VH domain listed in Table 1.

The invention also provides an isolated antibody that specifically binds to PDL1, wherein said antibody comprises a VH amino acid sequence listed in Table 1, wherein no more than about 10 amino acids in a framework sequence (for example, a sequence which is not a CDR) have been mutated (wherein a mutation is, as various non-limiting examples, an addition, substitution or deletion).

The invention also provides an isolated antibody that specifically binds to PDL1, wherein said antibody comprises a VH amino acid sequence listed in Table 1, wherein no more than about 20 amino acids in a framework sequence (for example, a sequence which is not a CDR) have been mutated (wherein a mutation is, as various non-limiting examples, an addition, substitution or deletion).

Other antibodies of the invention include amino acids that have been mutated, yet specifically bind to PDL1 and have at least 60, 70, 80, 90, 91, 92, 93, 94, 95, 96, 97, 98 or 99 percent identity in the VH regions with the VH regions depicted in the sequences described in Table 1.

The present invention provides an isolated antibody that specifically binds to PDL1 protein, said antibody comprises a VL domain listed in Table 1.

The invention also provides an isolated antibody that specifically binds to PDL1, wherein said antibody comprises a VL amino acid sequence listed in Table 1, wherein no more than about 10 amino acids in a framework sequence (for example, a sequence which is not a CDR) have been mutated (wherein a mutation is, as various non-limiting examples, an addition, substitution or deletion).

The invention also provides an isolated antibody that specifically binds to PDL1, wherein said antibody comprises a VL amino acid sequence listed in Table 1, wherein no more than about 20 amino acids in a framework sequence (for example, a sequence which is not a CDR) have been mutated (wherein a mutation is, as various non-limiting examples, an addition, substitution or deletion).

Other antibodies of the invention include amino acids that have been mutated, yet specifically bind to PDL1 and have at least 60, 70, 80, 90, 91, 92, 93, 94, 95, 96, 97, 98 or 99 percent identity in the VL regions with the VL regions depicted in the sequences described in Table 1.

The invention also provides an isolated antibody that specifically binds to PDL1, wherein said antibody comprises a heavy chain variable region comprising an amino acid sequence that is at least 60, 70, 80, 90, 91, 92, 93, 94, 95, 96, 97, 98 or 99 percent, preferably at least 90 percent, identical to the amino acid sequence selected from the group consisting of SEQ ID NOs: 14, 15, 16, 45, 46 and 47, preferably SEQ ID NO: 14 or 16, more preferably SEQ ID NO: 16; and a light chain variable region comprising an amino acid sequence that is at least 60, 70, 80, 90, 91, 92, 93, 94, 95, 96, 97, 98 or 99 percent, preferably at least 90 percent, identical to the amino acid sequence selected from the group consisting of SEQ ID NOs: 26, 27, 57 and 58, preferably SEQ ID NO: 26 or 27, more preferably SEQ ID NO: 27.

In one embodiment, the antibody of the invention having a binding specificity for human PDL1 comprises: a heavy chain variable region comprising an amino acid sequence selected from any of SEQ ID NOs: 14, 15, 16, 45, 46 and 47, preferably SEQ ID NO: 14 or 16, more preferably SEQ ID NO: 16; and a light chain variable region comprising an amino acid sequence selected from any of SEQ ID NOs: 26, 27, 57 and 58, preferably SEQ ID NO: 26 or 27, more preferably SEQ ID NO: 27.

In one embodiment, the antibody of the invention having a binding specificity for human PDL1 comprises:
(a) HCDR1, HCDR2, and HCDR3 sequences of SEQ ID NOs: 4, 6, and 7, respectively, and the LCDR1, LCDR2, and LCDR3 sequences of SEQ ID NOs: 20, 21, and 22, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 14 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 26;
(b) the HCDR1, HCDR2, and HCDR3 sequences of: SEQ ID NOs: 5, 6, and 7, respectively, and the LCDR1, LCDR2, and LCDR3 sequences of SEQ ID NOs: 20, 21, and 22, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 15 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 26;
(c) HCDR1, HCDR2, and HCDR3 sequences of SEQ ID NOs: 4, 6, and 7, respectively, and the LCDR1, LCDR2, and LCDR3 sequences of SEQ ID NOs: 20, 21, and 22, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 16 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 27, preferably wherein said VH comprises G56A and Y105F mutations (AHo numbering) and said VL comprises S9A and A51P mutations (AHo numbering);

(d) HCDR1, HCDR2, and HCDR3 sequences of SEQ ID NOs: 35, 37, and 38, respectively, and the LCDR1, LCDR2, and LCDR3 sequences of SEQ ID NOs: 51, 52, and 53, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 45 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 57;

(e) HCDR1, HCDR2, and HCDR3 sequences of SEQ ID NOs: 36, 37, and 38, respectively, and the LCDR1, LCDR2, and LCDR3 sequences of SEQ ID NOs: 51, 52, and 53, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 46 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 58, preferably wherein said VH comprises V2S, V25A, I44V, G56A, V82K, F89V and Y105F mutations (AHo numbering) and said VL comprises I2F, M4L and A51P mutations (AHo numbering); or (f) HCDR1, HCDR2, and HCDR3 sequences of SEQ ID NOs: 35, 37, and 38, respectively, and the LCDR1, LCDR2, and LCDR3 sequences of SEQ ID NOs: 51, 52, and 53, respectively, a VH sequence at least 60, 70, 80, 90, 91, 92, 93, 94, 95, 96, 97, 98 or 99 percent identical to SEQ ID NO: 47, and a VL sequence at least 60, 70, 80, 90, 91, 92, 93, 94, 95, 96, 97, 98 or 99 percent identical to SEQ ID NO: 57, preferably wherein said VH comprises V25A, I44V, G56A, V82K and F89V mutation (AHo numbering).

In one embodiment, the antibody of the invention having a binding specificity for human PDL1 comprises:

(a) HCDR1, HCDR2, and HCDR3 sequences of SEQ ID NOs: 1, 2 and 3, respectively, and the LCDR1, LCDR2, and LCDR3 sequences of SEQ ID NOs: 17, 18 and 19, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 14 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 26;

(b) the HCDR1, HCDR2, and HCDR3 sequences of: SEQ ID NOs: 1, 2 and 3, respectively, and the LCDR1, LCDR2, and LCDR3 sequences of SEQ ID NOs: 17, 18 and 19, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 15 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 26;

(c) HCDR1, HCDR2, and HCDR3 sequences of SEQ ID NOs: 1, 2 and 3, respectively, and the LCDR1, LCDR2, and LCDR3 sequences of SEQ ID NOs: 17, 18 and 19, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 16 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 27, preferably wherein said VH comprises G56A and Y105F mutations (AHo numbering) and said VL comprises S9A and A51P mutations (AHo numbering);

(d) HCDR1, HCDR2, and HCDR3 sequences of SEQ ID NOs: 32, 33 and 34, respectively, and the LCDR1, LCDR2, and LCDR3 sequences of SEQ ID NOs: 48, 49 and 50, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 45 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 57;

(e) HCDR1, HCDR2, and HCDR3 sequences of SEQ ID NOs: 32, 33 and 34, respectively, and the LCDR1, LCDR2, and LCDR3 sequences of SEQ ID NOs: 48, 49 and 50, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 46 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 58, preferably wherein said VH comprises V2S, V25A, I44V, G56A, V82K, F89V and Y105F mutations (AHo numbering) and said VL comprises I2F, M4L and A51P mutations (AHo numbering); or (f) HCDR1, HCDR2, and HCDR3 sequences of SEQ ID NOs: 32, 33 and 34, respectively, and the LCDR1, LCDR2, and LCDR3 sequences of SEQ ID NOs: 48, 49 and 50, respectively, a VH sequence at least 60, 70, 80, 90, 91, 92, 93, 94, 95, 96, 97, 98 or 99 percent identical to SEQ ID NO: 47, and a VL sequence at least 60, 70, 80, 90, 91, 92, 93, 94, 95, 96, 97, 98 or 99 percent identical to SEQ ID NO: 57, preferably wherein said VH comprises V25A, I44V, G56A, V82K and F89V mutation (AHo numbering).

In a preferred embodiment, the antibody of the invention having a binding specificity for human PDL1 comprises the HCDR1, HCDR2, and HCDR3 sequences of SEQ ID NOs: 1, 2 and 3, respectively, and the LCDR1, LCDR2, and LCDR3 sequences of SEQ ID NOs: 17, 18 and 19, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 16 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 27, preferably wherein said VH comprises G56A and Y105F mutations (AHo numbering) and said VL comprises S9A and A51P mutations (AHo numbering).

In a further embodiment, the isolated antibody of the invention having a binding specificity for human PDL1 comprises: (a) a VH sequence of SEQ ID NO: 14 and a VL sequence of SEQ ID NO: 26; (b) a VH sequence of SEQ ID NO: 15 and a VL sequence of SEQ ID NO: 26; (c) a VH sequence of SEQ ID NO: 16 and a VL sequence of SEQ ID NO: 27; (d) a VH sequence of SEQ ID NO: 45 and a VL sequence of SEQ ID NO: 57; (e) a VH sequence of SEQ ID NO: 46 and a VL sequence of SEQ ID NO: 58; or (f) a VH sequence of SEQ ID NO: 47 and a VL sequence of SEQ ID NO: 57. In a preferred embodiment, the isolated antibody of the invention having a binding specificity for human PDL1 comprises a VH sequence of SEQ ID NO: 14 and a VL sequence of SEQ ID NO: 26. In a more preferred embodiment, the isolated antibody of the invention having a binding specificity for human PDL1 comprises a VH sequence of SEQ ID NO: 16 and a VL sequence of SEQ ID NO: 27.

In one embodiment, an antibody that specifically binds to PDL1 is an antibody that is described in Table 1. In one embodiment, an antibody that specifically binds to PDL1 comprises an amino acid sequence that is at least 60, 70, 80, 90, 91, 92, 93, 94, 95, 96, 97, 98 or 99 percent, preferably at least 90 percent, identical to the amino acid sequence selected from the group consisting of SEQ ID NOs: 29, SEQ ID NO: 30, SEQ ID NO: 31, SEQ ID NO: 60, SEQ ID NO: 61 and SEQ ID NO: 62. In one embodiment, an antibody that specifically binds to PDL1 is as set forth in SEQ ID NO: 29 or SEQ ID NO: 30 or SEQ ID NO: 31, preferably SEQ ID NO: 29, more preferably SEQ ID NO: 31. In one embodiment, an antibody that specifically binds to PDL1 is as set forth in SEQ ID NO: 60 or SEQ ID NO: 61 or SEQ ID NO: 62, preferably SEQ ID NO: 60, more preferably SEQ ID NO: 62.

Other antibodies of the invention having a binding specificity for human PDL1 include those wherein the amino acids or nucleic acids encoding the amino acids have been mutated, yet have at least 60, 70, 80, 90 or 95 percent identity to the sequences described in Table 1. In one embodiment, it includes mutant amino acid sequences wherein no more than 1, 2, 3, 4 or 5 amino acids have been mutated in the variable regions when compared with the variable regions depicted in the sequence described in Table 1, while retaining substantially the same activity. The term "substantially the same activity" as used herein refers to the activity as indicated by substantially the same activity being at least 50%, at least 60%, at least 70%, at least 80%, at least 90%, at least 95%, at least 98% or even at least 100% or at least 110%, or at least 120%, or at least 130%, or at least 140%, or at least 150%, or at least 160%, or at least 170%, or at least 180%, or at least 190%, e.g. up to 200% of the activity as determined for the parent antibody, e.g., the antibody of the invention, in particular the antibody of the invention described in Table 1.

Given that each of these antibodies can bind to PDL1 and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and match, although each antibody must contain a VH CDR1, 2 and 3 and a VL CDR1, 2 and 3 to create other PDL1-binding binding molecules of the invention. Such "mixed and matched" PDL1-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by mutating one or more VH and/or VL CDR region sequences with structurally similar sequences from the CDR sequences shown herein for monoclonal antibodies of the present invention.

In yet another embodiment, the present invention provides an antibody comprising amino acid sequences that are homologous to the sequences described in Table 1, and said antibody binds to PDL1, and retains the desired functional properties of those antibodies described in Table 1.

For example, the invention provides an isolated monoclonal antibody comprising a heavy chain variable region and a light chain variable region, wherein the heavy chain variable region comprises an amino acid sequence that is at least 80 percent, at least 90 percent, or at least 95 percent identical to an amino acid sequence selected from the group consisting of SEQ ID NOs: 14, 15, 16, 45, 46 and 47, preferably SEQ ID NO: 14 or 16, more preferably SEQ ID NO: 16; the light chain variable region comprises an amino acid sequence that is at least 80 percent, at least 90 percent, or at least 95 percent identical to an amino acid sequence selected from the group consisting of SEQ ID NOs: 26, 27, 57 and 58, preferably SEQ ID NO: 26 or 27, more preferably SEQ ID NO: 27; wherein the antibody specifically binds to human PDL1 protein.

In one embodiment, the VH and/or VL amino acid sequences may be 50 percent, 60 percent, 70 percent, 80 percent, 90 percent, 95 percent, 96 percent, 97 percent, 98 percent or 99 percent identical to the sequences set forth in Table 1. In one embodiment, the VH and/or VL amino acid sequences may be identical except an amino acid substitution in no more than 1, 2, 3, 4 or 5 amino acid positions.

In one embodiment, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the PDL1-binding antibodies of the invention.

The term "conservatively modified variant" or "conservative variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations", which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" or "conservative variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In one embodiment, the term "conservative sequence modifications" are used to refer to amino acid modifications that do not significantly affect or alter the binding characteristics of the antibody containing the amino acid sequence.

Accordingly, the invention provides an isolated monoclonal antibody comprising or consisting of a heavy chain variable region comprising CDR1, CDR2, and CDR3 sequences and a light chain variable region comprising CDR1, CDR2, and CDR3 sequences, wherein:

the heavy chain variable region CDR1 comprises, preferably consists of, an amino acid sequence selected from any of SEQ ID NOs: 1, 4, 5, 8, 11, 32, 35, 36, 39 and 42, preferably SEQ ID NO: 1 or 32, more preferably SEQ ID NO: 1, or conservative variants thereof; the heavy chain variable region CDR2 comprises, preferably consists of, an amino acid sequence selected from any of SEQ ID NOs: 2, 6, 9, 12, 33, 37, 40 and 43, preferably SEQ ID NO: 2 or 33, more preferably SEQ ID NO: 2, or conservative variants thereof; the heavy chain variable region CDR3 comprises, preferably consists of, an amino acid sequence selected from any of SEQ ID NOs: 3, 7, 10, 13, 34, 38, 41 and 44, preferably SEQ ID NO: 3 or 34, more preferably SEQ ID NO: 3, or conservative variants thereof;

the light chain variable region CDR1 comprises, preferably consists of, an amino acid sequence selected from any of SEQ ID NOs: 17, 20, 23, 48, 51 and 54, preferably SEQ ID NO: 17 or 48, more preferably SEQ ID NO: 17, or conservative variants thereof; the light chain variable region CDR2 comprises, preferably consists of, an amino acid sequence selected from any of SEQ ID NOs: 18, 21, 24, 49, 52 and 55, preferably SEQ ID NO: 18 or 49, more preferably SEQ ID NO: 18, or conservative variants thereof; and the light chain variable region CDR3 comprises, preferably consists of, an amino acid sequence selected from any of SEQ ID NOs: 19, 22, 25, 50, 53 and 56, preferably SEQ ID NO: 19 or 50, more preferably SEQ ID NO: 19, or conservative variants thereof;

wherein the antibody specifically binds to PDL1 and is capable of blocking PD-1/PDL1 interaction.

In one embodiment, an antibody of the invention is optimized for expression in a mammalian cell has a heavy chain variable region and a light chain variable region, wherein one or more of these sequences have specified amino acid sequences based on the antibodies described herein or conservative modifications thereof, and wherein the antibodies retain the desired functional properties of the PDL1-binding antibodies of the invention. Accordingly, the invention provides an isolated monoclonal antibody optimized for expression in a mammalian cell comprising a heavy chain variable region and a light chain variable region wherein: the heavy chain variable region comprises an amino acid sequence selected from any of SEQ ID NOs: 14, 15, 16, 45, 46 and 47, preferably SEQ ID NO: 14 or 16, more preferably SEQ ID NO: 16, and conservative modifications thereof; and the light chain variable region comprises an amino acid sequence selected from any of SEQ ID NOs: 26, 27, 57 and 58, preferably SEQ ID NO: 26 or 27, more preferably SEQ ID NO: 27, and conservative modifications thereof; wherein the antibody specifically binds to PDL1 and is capable of blocking PD-1/PDL1 interaction.

In one embodiment, an antibody of the invention is optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the PDL1-binding antibodies of the invention.

As used herein, the term, "optimized" means that a nucleotide sequence has been altered to encode an amino acid sequence using codons that are preferred in the production cell or organism, generally a eukaryotic cell, for example, a cell of Pichia, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

An "affinity-matured" antibody is one with one or more alterations in one or more variable domains thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al, Bio/Technology 10:779-783 (1992) describes affinity maturation by VH- and VL-domain shuffling. Random mutagenesis of hypervariable region ("HVR") and/or framework residues is described by, for example: Barbas et al. Proc Nat. Acad. Sci. USA 91:3809-3813 (1994); Schier et al. Gene 169:147-155 (1995); Jackson et al, J. Immunol. 154(7): 3310-9 (1995); and Hawkins et al, J. Mol. Biol. 226:889-896 (1992).

In one embodiment, the invention provides an isolated monoclonal antibody comprising a VH3 comprising G56A and Y105F mutations, in particular comprising an amino acid sequence according to SEQ ID NO: 16; and preferably a VL comprising S9A; A51P mutations, in particular comprising an amino acid sequence according to SEQ ID NO: 27.

In one embodiment, an "affinity-matured" antibody of the invention comprises: a VH4 comprising V25A; I44V; G56A; V82K; F89V mutations, in particular comprising an amino acid sequence according to SEQ ID NO: 47; and preferably a VL comprising an amino acid sequence according to SEQ ID NO: 57. In a further embodiment, an "affinity-matured" antibody of the invention comprises: a VH4 comprising V2S; V25A; I44V; G56A; V82K; F89V; Y105F mutations, in particular comprising an amino acid sequence according to SEQ ID NO: 46; and a VL comprising I2F; M4L; A51P mutations, in particular comprising an amino acid sequence according to SEQ ID NO: 58.

An antibody of the invention further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86: 10029-10033; U.S. Pat. No. 5,225,539 to Winter, and U.S. Pat. Nos. 5,530,101; 5,585,089; 5,693,762 and 6,180,370 to Queen et al.).

Such framework sequences can be obtained from public DNA databases or published references that include germline antibody gene sequences or rearranged antibody sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J Immunol. 24:827-836; the contents of each of which are expressly incorporated herein by reference. For example, germline DNA sequences for human heavy and light chain variable region genes and rearranged antibody sequences can be found in "IMGT" database (available on the Internet at www.imgt.org; see Lefranc, M. P. et al., 1999 Nucleic Acids Res. 27:209-212; the contents of each of which are expressly incorporated herein by reference).

An example of framework sequences for use in the antibodies of the invention are those that are structurally similar to the framework sequences used by selected antibodies of the invention, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180, 370 to Queen et al).

A wide variety of antibody/immunoglobulin frameworks or scaffolds can be employed so long as the resulting polypeptide includes at least one binding region which specifically binds to PDL1. Such frameworks or scaffolds include the five main idiotypes of human immunoglobulins, antigen-binding fragments thereof, and include immunoglobulins of other animal species, preferably having humanized aspects.

In one aspect, the invention pertains to a method of generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target PDL1 protein. Known non-immunoglobulin frameworks or scaffolds include, but are not limited to, fibronectin (Compound Therapeutics, Inc., Waltham, Mass.), ankyrin (Molecular Partners AG, Zurich, Switzerland), lipocalin (Pieris Proteolab AG, Freising, Germany), small modular immunopharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

Suitably, the antibodies of the invention specifically bind to PDL1 and is characterized by one or more of the following parameters:

(i) binds to human PDL1 with a dissociation constant (KD) of less than 10 nM, particularly less than 5 nM, particularly less than 1 nM, particularly less than 500 pM, more particularly less than 100 pM, preferably less than 50 pM, more preferably less than 10 pM, more preferably 5 pM, in particular as measured by surface plasmon resonance (SPR), particularly wherein said antibody is an scFv;

(ii) binds to human PDL1 with a $K_{off}$ rate of $10^{-3}$ $s^{-1}$ or less, or $10^{-4}$ $s^{-1}$ or less, or $10^{-5}$ $s^{-1}$ or less as measured by SPR, particularly wherein said antibody is an scFv;

(iii) binds to human PDL1 with a $K_{on}$ rate of at least $10^3$ $M^{-1}$ $s^{-1}$ or greater, at least $10^4$ $M^{-1}$ $s^{-1}$ or greater, at least $10^5$ $M^{-1}$ $s^{-1}$ or greater, at least $10^6$ $M^{-1}$ $s^{-1}$ or greater as measured by SPR, particularly wherein said antibody is an scFv;

(iv) is cross-reactive with Macaca fascicularis (Cynomolgus) PDL1, in partilular binds to Cynomolgus PDL1 with a KD of less than 5 nM, particularly less than 1 nM, particularly less than 500 pM, more particularly less than 100 pM, preferably less than 10 pM as measured by surface plasmon resonance, particularly wherein said antibody is an scFv; is non-cross reactive to Mus musculus PDL1, in particular as measured by SPR; and/or (v) does not bind to human PDL2, in particular as measured by SPR.

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

"Binding affinity" generally refers to the strength of the sum total of non-covalent interactions between a single binding site of a molecule (e.g., of an antibody) and its binding partner (e.g., an antigen). Unless indicated otherwise, as used herein, "binding affinity", "bind to", "binds to" or "binding to" refers to intrinsic binding affinity that reflects a 1:1 interaction between members of a binding pair (e.g., an antibody fragment and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity, i.e. binding strength are described in the following.

The term "$K_{assoc}$", "Ka" or "$K_{on}$", as used herein, is intended to refer to the association rate of a particular antibody-antigen interaction, whereas the term "$K_{dis}$", "Kd" or "$K_{off}$", as used herein, is intended to refer to the dissociation rate of a particular antibody-antigen interaction. In one embodiment, the term "KD", as used herein, is intended to refer to the dissociation constant, which is obtained from the ratio of Kd to Ka (i.e. Kd/Ka) and is expressed as a molar concentration (M). The "KD" or "KD value" or "$K_D$" or "$K_D$ value" according to this invention is in one embodiment measured by using surface-plasmon resonance assays using a MASS-1 SPR instrument (Sierra Sensors). To measure affinity, an antibody specific for the Fc region of rabbit IgGs (Bethyl Laboratories, Cat. No. A120-111A) is immobilized on a sensor chip (SPR-2 Affinity Sensor, High Capacity Amine, Sierra Sensors) using a standard amine-coupling procedure. Rabbit monoclonal antibodies in B-cell supernatants are captured by the immobilized anti-rabbit IgG antibody. A minimal IgG concentration in the B-cell supernatants is required to allow sufficient capture. After capturing of the monoclonal antibodies, human PDL1 (Peprotech) is injected into the flow cells for 3 min at a concentration of 90 nM, and dissociation of the protein from the IgG captured on the sensor chip is allowed to proceed for 5 min. After each injection cycle, surfaces are regenerated with two injections of 10 mM Glycine-HCl. The apparent dissociation (kd) and association (ka) rate constants and the apparent dissociation equilibrium constant (KD) are calculated with the MASS-1 analysis software (Analyzer, Sierra Sensors) using one-to-one Langmuir binding model and quality of the fits is monitored based on relative $Chi^2$ ($Chi^2$ normalized to the extrapolated maximal binding level of the analyte), which is a measure for the quality of the curve fitting. The smaller the value for the $Chi^2$ the more accurate is the fitting to the one-to-one Langmuir binding model. Results are deemed valid if the response units (RU) for ligand binding are at least 2% of the RUs for antibody capturing. Samples with RUs for ligand binding with less than 2% of the RUs for antibody capturing are considered to show no specific binding of PDL1 to the captured antibody. The equilibrium dissociation constant ($K_D$) is calculated as the ratio $k_{off}/k_{on}$. See, e.g., Chen et al, J. Mol. Biol. 293:865-881 (1999).

Suitably, the affinity of the antibody of the invention to PDL1 may be higher than the affinity of PDL1 to PD-1. It will be appreciated that a higher affinity of the PDL1 antibody as compared to the affinity of PDL1 to PD-1 may be particularly useful for dissociating or neutralizing the pre-formed PD-1/PDL1 complexes. In one embodiment, the PDL1 antibody of the present invention neutralizes PD-1/PDL1 interaction. In another embodiment, the PDL1 antibody of the present invention neutralizes B7-1/PDL1 interaction. Suitably, the affinity of the PDL1 antibody of the present invention to PDL1 may be comparable to or higher than the affinity of avelumab to PD-1. In one embodiment, the PDL1 antibody of the present invention neutralizes PD-1/PDL1 interaction with potency equal to or higher than avelumab. In a further embodiment, the PDL1 antibody of the present invention neutralizes B7-1/PDL1 interaction with potency equal to or higher than avelumab. The binding affinity of an antibody may be determined, for example, by the dissociation constant (KD). A stronger affinity is represented by a lower KD, while a weaker affinity is represented by a higher KD.

Thus, in a suitable embodiment, the antibody of the invention may have a KD of between 1 to 50,000 pM, 1 to 40,000 pM, 1 to 30,000 pM, 1 to 20,000 pM, 1 to 10,000 pM, 1 to 5,000 pM, 1 to 2,500 pM, 1 to 1,000 pM, 1 to 750 pM, 1 to 500 pM, 1 to 250 pM, 1 to 100 pM, 1 to 50 pM, 1 to 10 pM. In a suitable embodiment, the antibody of the invention may have a KD of less than approximately 50 nM, less than approximately 45 nM, less than approximately 40 nM, less than approximately 35 nM, less than approximately 30 nM, less than approximately 25 nM, less than 20 nM, less than approximately 15 nM, less than approximately 10 nM, less than approximately 9 nM, less than approximately 8 nM, less than approximately 7 nM, less than approximately 6 nM, less than approximately 5 nM, less than approximately 4 nM, less than approximately 3 nM, less than 2 nM, less than 1 nM, less than 0.5 nM, less than 0.25 nM, less than 100 pM, less than 10 pM, or less than 5 pM, in particular as measured by SPR, particularly wherein said antibody is an scFv. Suitably, the antibody of the invention has a KD of less than 5 nM, in particular as measured by SPR. Suitably, the antibody of the invention has a KD of less than 1 nM, in particular as measured by SPR. Suitably, the antibody of the invention has a KD of less than 100 pM, in particular as measured by SPR. Suitably, the antibody of the invention has a KD of less than 50 pM, in particular as measured by SPR. Preferably, the PDL1-BD of the invention binds to human PDL1 with a KD of less than 10 pM, in particular as measured by SPR. More preferably, the PDL1-BD of the invention binds to human PDL1 with a KD of less than 5 pM, in particular as measured by SPR.

Suitably, the antibody of the invention binds to human PDL1 with a $K_{on}$ rate of at least $10^3$ $M^{-1}$ $s^{-1}$ or greater, at least $10^4$ $M^{-1}$ $s^{-1}$ or greater, at least $5 \times 10^4$ $M^{-1}$ $s^{-1}$ or greater, at least $10^5$ $M^{-1}$ $s^{-1}$ or greater, at least $5 \times 10^5$ $M^{-1}$ $s^{-1}$ or greater, at least $10^6$ $M^{-1}$ $s^{-1}$ or greater, at least $5 \times 10^6$ $M^{-1}$ $s^{-1}$ or greater, at least $10^7$ $M^{-1}$ $s^{-1}$ or greater, at least $5 \times 10^7$ $M^{-1}$ $s^{-1}$ or greater as measured by surface plasmon resonance (SPR). Preferably, the antibody of the invention has a $K_{on}$ rate of at least $10^5$ $M^{-1}$ $s^{-1}$ or greater, in particular at least $10^6$ $M^{-1}$ $s^{-1}$ or greater, as measured by SPR.

Suitably, the antibody of the invention binds to human PDL1 with a $K_{off}$ rate of $10^{-3}$ s$^{-1}$ or less, $3 \times 10^{-3}$ s$^{-1}$ or less, $5 \times 10^{-3}$ s$^{-1}$ or less, $10^{-4}$ s$^{-1}$ or less, $5 \times 10^{-4}$ s$^{-1}$ or less, $10^{-5}$ s$^{-1}$ or less, $5 \times 10^{-5}$ s$^{-1}$ or less, $10^{-6}$ s$^{-1}$ or less, or $10^{-7}$ s$^{-1}$ or less as measured by surface plasmon resonance (SPR). Preferably, the antibody of the invention has a $K_{off}$ rate of $10^{-3}$ s$^{-1}$ or less, $10^{-4}$ s$^{-1}$ or less, in particular $10^{-5}$ s$^{-1}$ or less as measured by SPR.

Suitably, the antibody of the invention specifically binds to PDL1 and is characterized by one or more of the following parameters:
(i) has the ability to neutralize PDL1/PD-1 interaction with a potency relative to that of avelumab (relative potency), determined in ELISA assay, greater than 1.5, e.g. greater than 2, greater than 2.5, preferably greater than 3, more preferably greater than 4, and wherein said relative potency is the ratio of the IC$_{50}$ value in ng/mL of avelumab as measured in the ELISA assay to the IC$_{50}$ value in ng/mL of said antibody as measured in the ELISA assay, in particular wherein said antibody is an scFv; and
(ii) optionally, has the ability to neutralize PDL1/PD-1 interaction with a potency relative to that of avelumab (relative potency), determined in NFAT reporter gene assay, greater than 1.5, e.g. greater than 2, greater than 2.5, preferably greater than 3, more preferably greater than 4, and wherein said relative potency is the ratio of the IC$_{50}$ value in ng/mL of avelumab as measured in the NFAT reporter gene assay to the IC$_{50}$ value in ng/mL of said antibody as measured in the NFAT reporter gene assay, in particular wherein said antibody is an scFv; and
(iii) has the ability to neutralize PDL1/B7.1 interaction with a potency relative to that of avelumab (relative potency), determined in ELISA assay, greater than 1.5, e.g. greater than 2, greater than 2.5, preferably greater than 3, more preferably greater than 4 and wherein said relative potency is the ratio of the IC$_{50}$ value in ng/mL of avelumab as measured in the ELISA assay to the IC$_{50}$ value in ng/mL of said antibody as measured in the ELISA assay, in particular wherein said antibody is an scFv.

Suitably, the antibody of the invention has beneficial biophysical properties.

Suitably, the antibodies of the invention, when in scFv format, has a melting temperature (Tm), determined by differential scanning fluorimetry, of at least 55° C., e.g. at least 60° C., preferably at least 65° C., more preferably at least 70° C., in particular wherein said antibody is formulated in 50 mM phosphate-citrate buffer at pH 6.4, 150 mM NaCl. DSF is described earlier (Egan, et al., MAbs, 9(1) (2017), 68-84; Niesen, et al., Nature Protocols, 2(9) (2007) 2212-2221). The midpoint of transition for the thermal unfolding of the scFv constructs is determined by Differential Scanning Fluorimetry using the fluorescence dye SYPRO® Orange (see Wong & Raleigh, Protein Science 25 (2016) 1834-1840). Samples in phosphate-citrate buffer at pH 6.4 are prepared at a final protein concentration of 50 µg/mL and containing a final concentration of 5×SYPRO® Orange in a total volume of 100 µl. Twenty-five microliters of prepared samples are added in triplicate to white-walled AB gene PCR plates. The assay is performed in a qPCR machine used as a thermal cycler, and the fluorescence emission is detected using the software's custom dye calibration routine. The PCR plate containing the test samples is subjected to a temperature ramp from 25° C. to 96° C. in increments of 1° C. with 30 s pauses after each temperature increment. The total assay time is about two hours. The Tm is calculated by the software GraphPad Prism using a mathematical second derivative method to calculate the inflection point of the curve. The reported Tm is an average of three measurements.

Suitably, the antibodies of the invention, when in scFv format, has a loss in monomer content, after five consecutive freeze-thaw cycles, of less than 5%, preferably less than 3%, more preferably less than 1%, when the antibody of the invention is at a starting concentration of 10 mg/ml, and in particular wherein said antibody is formulated 50 mM phosphate citrate buffer with 150 mM NaCl at pH 6.4.

Suitably, the antibodies of the invention, when in scFv format, has a loss in monomer content, after storage for at least two weeks, particularly for at least four weeks, at 4° C., of less than 15%, e.g. less than 12%, less than 10%, less than 7%, less than 5%, less than 4%, less than 3%, less than 2%, preferably less than 1%, when the antibody of the invention is at a starting concentration of 10 mg/ml, and in particular wherein the antibody of the invention is formulated in 50 mM phosphate citrate buffer with 150 mM NaCl at pH6.4.

The loss in monomer content is as determined by area under the curve calculation of SE-HPLC chromatograms. SE-HPLC is a separation technique based on a solid stationary phase and a liquid mobile phase as outlined by the USP chapter 621. This method separates molecules based on their size and shape utilizing a hydrophobic stationary phase and aqueous mobile phase. The separation of molecules is occurring between the void volume (VO) and the total permeation volume (VT) of a specific column. Measurements by SE-HPLC are performed on a Chromaster HPLC system (Hitachi High-Technologies Corporation) equipped with automated sample injection and a UV detector set to the detection wavelength of 280 nm. The equipment is controlled by the software EZChrom Elite (Agilent Technologies, Version 3.3.2 SP2) which also supports analysis of resulting chromatograms. Protein samples are cleared by centrifugation and kept at a temperature of 4-6° C. in the autosampler prior to injection. For the analysis of scFv samples the column Shodex KW403-4F (Showa Denko Inc., #F6989202) is employed with a standardized buffered saline mobile phase (50 mM sodium-phosphate pH 6.5, 300 mM sodium chloride) at the recommended flow rate of 0.35 mL/min. The target sample load per injection was 5 µg. Samples are detected by an UV detector at a wavelength of 280 nm and the data recorded by a suitable software suite. The resulting chromatograms are analyzed in the range of VO to VT thereby excluding matrix associated peaks with >10 min elution time.

The term "recognize" as used herein refers to an antibody that finds and interacts (e.g., binds) with its conformational epitope.

The terms "compete" or "cross-compete" and related terms are used interchangeably herein to mean the ability of an antibody to interfere with the binding of other antibodies or binding agents to PDL1 in a standard competitive binding assay.

The ability or extent to which an antibody is able to interfere with the binding of another antibody or binding molecule to PDL1, and therefore whether it can be said to cross-compete according to the invention, can be determined using standard competition binding assays. One particularly suitable quantitative cross-competition assay uses a FACS- or an AlphaScreen-based approach to measure competition between the labelled (e.g. His tagged, biotinylated or radioactive labelled) an antibody or fragment thereof and the other an antibody or fragment thereof in terms of their binding to the target. In general, a cross-competing antibody or fragment thereof is for example one which will bind to the target in the cross-competition assay such that, during the assay and in the presence of a second antibody or fragment thereof, the recorded displacement of the immunoglobulin single variable domain or polypeptide according to the invention is up to 100% (e.g. in FACS based competition assay) of the maximum theoretical displacement (e.g. displacement by cold (e.g. unlabeled) antibody or fragment thereof that needs to be cross-blocked) by the to be tested potentially cross-blocking antibody or fragment thereof that is present in a given amount. Preferably, cross-competing antibodies or fragments thereof have a recorded displacement that is between 10% and 100%, more preferred between 50% and 100%.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. "Conformational" and "linear" epitopes are distinguished in that the binding to the former but not the latter is lost in the presence of denaturing solvents. The term "conformational epitope" as used herein refers to amino acid residues of an antigen that come together on the surface when the polypeptide chain folds to form the native protein, and show a significantly reduced rate of HD exchange due to Fab binding. The conformation epitope contains, but is not limited to, the functional epitope. The term "linear epitope" refers to an epitope with all of the points of interaction between the protein and the interacting molecule (such as an antibody) occurring linearly along the primary amino acid sequence of the protein (continuous).

The present invention also provides antibodies that bind to the same epitope as do the PDL1-binding antibodies listed in Table 1. Additional antibodies can therefore be identified based on their ability to cross-compete (e.g., to competitively inhibit the binding of, in a statistically significant manner) with other antibodies of the invention in PDL1 binding assays.

Suitably, the isolated antibody of the present invention is selected from the group consisting of: a monoclonal antibody, a chimeric antibody, an IgG antibody, a Fab, an Fv, an scFv, dsFv, a scAb, STAB, and binding domains based on alternative scaffolds including but limited to ankyrin-based domains, fynomers, avimers, scaffolds commercialized under the registered trade mark ANTICALIN®, fibronectins, and binding sites being built into constant regions of antibodies (e.g. F-star Therapeutics's technology commercialized under the trade mark Modular Antibody Technology™).

Suitably, the isolated antibody of the invention is an Fv. Suitably, the isolated antibody of the invention is scFv antibody fragment. "Single-chain Fv" or "scFv" or "sFv" antibody fragments comprise the VH and VL domains of an antibody, wherein these domains are present in a single polypeptide chain. Generally, the Fv polypeptide further comprises a polypeptide linker between the VH and VL domains which enables the sFv to form the desired structure for target binding. "Single-chain Fv" or "scFv" antibody fragments comprise the VH and VL domains of antibody, wherein these domains are present in a single polypeptide chain. Generally, the scFv polypeptides further comprises a polypeptide linker between the VH and VL domains which enables the scFv to form the desired structure for antigen binding (see, for example, Plückthun, The pharmacology of Monoclonal Antibodies, vol. 113, Rosenburg and Moore eds., (Springer-Verlag, New York, 1994), pp. 269-315). In particular embodiments, said functional fragment is an scFv format comprising the linker according to SEQ ID NO: 28. In a further embodiment, the isolated antibody of the invention is a single-chain variable fragment (scFv) as shown in SEQ ID NO: 29, SEQ ID NO: 30, SEQ ID NO: 31, SEQ ID NO: 60, SEQ ID NO: 61 or SEQ ID NO: 62. In a preferred embodiment, the isolated antibody of the invention is a single-chain variable fragment (scFv) as shown in SEQ ID NO: 31.

Suitably, the isolated antibody of the invention is an IgG antibody fragment. The term "isotype" refers to the antibody class (e.g., IgM, IgE, IgG such as IgG1 or IgG4) that is provided by the heavy chain constant region genes. Isotype also includes modified versions of one of these classes, where modifications have been made to after the Fc function, for example, to enhance or reduce effector functions or binding to Fc receptors. In one embodiment, the isolated antibody of the invention is an IgG selected from the group consisting of an IgG1, an IgG2, an IgG3 and an IgG4, preferably an IgG1.

Suitably, the isolated antibody of the invention is IgG1 comprising HCDR1, HCDR2, and HCDR3 sequences of SEQ ID NOs: 4, 6, and 7, respectively, and the LCDR1, LCDR2, and LCDR3 sequences of SEQ ID NOs: 20, 21, and 22, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 14 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 26. In a more specific embodiment, the antibody of the invention is IgG1 comprising HCDR1, HCDR2, and HCDR3 sequences of SEQ ID NOs: 4, 6, and 7, respectively, and the LCDR1, LCDR2, and LCDR3 sequences of SEQ ID NOs: 20, 21, and 22, respectively, a heavy chain sequence comprising an amino acid sequence that is at least 60, 70, 80, 90, 91, 92, 93, 94, 95, 96, 97, 98 or 99 percent, preferably at least 90 percent, identical to SEQ ID NO: 93 and a light chain sequence comprising an amino acid sequence that is at least 60, 70, 80, 90, 91, 92, 93, 94, 95, 96, 97, 98 or 99 percent, preferably at least 90 percent, identical to SEQ ID NO: 92. Suitably, the isolated antibody of the invention is IgG1 comprising HCDR1, HCDR2, and HCDR3 sequences of SEQ ID NOs: 1, 2 and 3, respectively, and the LCDR1, LCDR2, and LCDR3 sequences of SEQ ID NOs: 17, 18 and 19, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 14 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 26. In a more specific embodiment, the antibody of the invention is IgG1 comprising HCDR1, HCDR2, and HCDR3 sequences of SEQ ID NOs: 1, 2 and 3, respectively, and the LCDR1, LCDR2, and LCDR3 sequences of SEQ ID NOs: 17, 18 and 19, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 16 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 27.

Suitably, the isolated antibody of the invention is IgG1 comprising HCDR1, HCDR2, and HCDR3 sequences of SEQ ID NOs: 35, 37, and 38, respectively, and the LCDR1, LCDR2, and LCDR3 sequences of SEQ ID NOs: 51, 52, and 53, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 45 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 57. In a more specific embodiment, the antibody of the invention is IgG1 comprising HCDR1, HCDR2, and HCDR3 sequences of SEQ ID NOs: 35, 37, and 38, respectively, and the LCDR1, LCDR2, and LCDR3 sequences of SEQ ID NOs: 51, 52, and 53, respectively, a heavy chain sequence comprising an amino acid sequence that is at least 60, 70, 80, 90, 91, 92, 93, 94, 95, 96, 97, 98 or 99 percent, preferably at least 90 percent, identical to SEQ ID NO: 91 and a light chain sequence comprising an amino acid sequence that is at least 60, 70, 80, 90, 91, 92, 93, 94, 95, 96, 97, 98 or 99 percent, preferably at least 90 percent, identical to SEQ ID NO: 90.

Suitably, the isolated antibody of the invention is IgG1 comprising HCDR1, HCDR2, and HCDR3 sequences of SEQ ID NOs: 32, 33 and 34, respectively, and the LCDR1, LCDR2, and LCDR3 sequences of SEQ ID NOs: 48, 49 and 50, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 45 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 57. In a more specific embodiment, the antibody of the invention is IgG1 comprising HCDR1, HCDR2, and HCDR3 sequences of SEQ ID NOs: 32, 33 and 34, respectively, and the LCDR1, LCDR2, and LCDR3 sequences of SEQ ID NOs: 48, 49 and 50, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 47 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 57.

In another particular embodiment of the present invention, the isolated antibody of the present invention is a multispecific molecule, in particular a multispecific molecule having at least a second functional molecule, e.g., bispecific molecule, trispecific molecule, tetraspecific, pentaspecific, hexaspecific molecule.

The term "multispecific molecule" or "multispecific antibody" as used herein, refers to an antibody that binds to two or more different epitopes on at least two or more different targets (e.g., PDL1 and another target different from PDL1), or binds to two or more different epitopes of the same target. The term "multispecific molecule" includes bispecific, trispecific, tetraspecific, pentaspecific and hexaspecific antibodies. The term "bispecific antibody" as used herein, refers to an antibody that binds to two different epitopes on two different targets or on the same target. The term "trispecific antibody" as used herein, refers to an antibody that binds to three different epitopes on three different targets or on the same target.

An antibody of the invention can be derivatized or linked to another functional molecule, e.g., another peptide or protein (e.g., another antibody or ligand for a receptor) to generate a multispecific molecule that binds to at least two binding sites and/or different target molecules. The antibody of the invention may in fact be derivatized or linked to more than one other functional molecule to generate multispecific molecules that bind to more than two different binding sites and/or target molecules. To create a multispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a multispecific molecule results.

Accordingly, the present invention includes multispecific molecules comprising at least one first binding specificity for PDL1 and a second binding specificity for a second target epitope. For example, the second target epitope is present on another target molecule different from PDL1. Accordingly, the present invention includes multispecific molecules comprising at least one first binding specificity for PDL1 and a second binding specificity for a second target epitope. For example, the second target epitope is another epitope of PDL1 different from the first target epitope. The multispecific molecule can further include a third binding specificity, in addition to the first and second target epitope.

In a further embodiment, the present invention includes multispecific molecules monovalent, bivalent or multivalent for PDL1 specificity, preferably monovalent.

In another particular embodiment of the present invention, the isolated antibody of the present invention is a monovalent or multivalent for PDL1 specificity molecule, e.g., bivalent, trivalent, tetravalent, pentavalent, hexavalent.

The term "monovalent molecule" or "monovalent antibody", as used herein, refers to an antibody that binds to a single epitope on a target molecule, such as PDL1.

The term "multivalent antibody" refers to a single binding molecule with more than one valency, where "valency" is described as the number of antigen-binding moieties that binds to epitopes on identical target molecules. As such, the single binding molecule can bind to more than one target molecule, or more than one binding site on a target molecule that contains multiple copies of the epitope. Examples of multivalent antibodies include, but are not limited to bivalent antibodies, trivalent antibodies, tetravalent antibodies, pentavalent antibodies, and the like. The term "bivalent antibody" as used herein, refers to an antibody that has two antigen binding moieties, each of which binds to an identical epitope.

Suitable, the isolated antibody of the present invention is a multispecific molecule, e.g., bispecific molecule, and/or a multivalent molecule, e.g., monovalent for PDL1 specificity molecule, bivalent for PDL1 specificity molecule, which is an antibody format selected from any suitable multispecific, e.g. bispecific, format known in the art, including, by way of non-limiting example, formats based on a single-chain diabody (scDb), a tandem scDb (Tandab), a linear dimeric scDb (LD-scDb), a circular dimeric scDb (CD-scDb), a bispecific T-cell engager (BiTE; tandem di-scFv), a tandem tri-scFv, a tribody (Fab-(scFv)2) or bibody (Fab-(scFv)1), Fab, Fab-Fv2, Morrison (IgG $CH_3$-scFv fusion (Morrison L) or IgG CL-scFv fusion (Morrison H)), triabody, scDb-scFv, bispecific Fab2, di-miniantibody, tetrabody, scFv-Fc-scFv fusion, scFv-HSA-scFv fusion, di-diabody, DVD-Ig, COVD, IgG-scFab, scFab-dsscFv, Fv2-Fc, IgG-scFv fusions, such as bsAb (scFv linked to C-terminus of light chain), Bs1Ab (scFv linked to N-terminus of light chain), Bs2Ab (scFv linked to N-terminus of heavy chain), Bs3Ab (scFv linked to C-terminus of heavy chain), Ts1Ab (scFv linked to N-terminus of both heavy chain and light chain), Ts2Ab (dsscFv linked to C-terminus of heavy chain), Bispecific antibodies based on heterodimeric Fc domains, such as Knob-into-Hole antibodies (KiHs) (bispecific IgGs prepared by the KiH technology); an Fv, scFv, scDb, tandem-di-scFv, tandem tri-scFv, Fab-(scFv)2, Fab-(scFv)1, Fab, Fab-Fv2, COVD fused to the N- and/or the C-terminus of either chain of a heterodimeric Fc domain or any other heterodimerization domain, a MATCH (described in WO2016/0202457; Egan T., et al., mAbs 9 (2017) 68-84) and DuoBodies (bispecific IgGs prepared by the Duobody technology) (MAbs. 2017 February/March; 9(2):182-212. doi: 10.1080/19420862.2016.1268307). Particularly suitable for use herein is a single-chain diabody (scDb) or scDb-scFv.

The term "diabodies" refers to antibody fragments with two antigen-binding sites, which fragments comprise a VH connected to VL in the same polypeptide chain (VH-VL). By using a linker that is too short to allow pairing between the two domains on the same chain, the domains are forced to pair with the complementary domains of another chain to create two antigen-binding sites. In particular embodiments, said polypeptide linker comprises one or two units of four (4) glycine amino acid residues and one (1) serine amino acid residue (GGGGS)$_n$ (SEQ ID NO: 94), wherein n=1 or 2, preferably 1. Diabodies may be bivalent or bispecific. Diabodies are described more fully in, for example, EP 404097, WO 93/01161, Hudson et al., Nat. Med. 9:129-134 (2003), and Holliger et al., Proc. Natl. Acad. Sci. USA 90: 6444-6448 (1993). Triabodies and tetrabodies are also described in Hudson et al., Nat. Med. 9:129-134 (2003).

The bispecific scDb, in particular the bispecific monomeric scDb, particularly comprises two variable heavy chain domains (VH) or fragments thereof and two variable light chain domains (VL) or fragments thereof connected by linkers L1, L2 and L3 in the order VHA-L1-VLB-L2-VHB-L3-VLA, VHA-L1-VHB-L2-VLB-L3-VLA, VLA-L1-VLB-L2-VHB-L3-VHA, VLA-L1-VHB-L2-VLB-L3-VHA, VHB-L1-VLA-L2-VHA-L3-VLB, VHB-L1-VHA-L2-VLA-L3-VLB, VLB-L1-VLA-L2-VHA-L3-VHB or VLB-L1-VHA-L2-VLA-L3-VHB, wherein the VLA and VHA domains jointly form the antigen binding site for the first antigen, and VLB and VHB jointly form the antigen binding site for the second antigen.

The linker L1 particularly is a peptide of 2-10 amino acids, more particularly 3-7 amino acids, and most particularly 5 amino acids, and linker L3 particularly is a peptide of 1-10 amino acids, more particularly 2-7 amino acids, and most particularly 5 amino acids. In particular embodiments, the linker L1 and/or L3 comprises one or two units of four (4) glycine amino acid residues and one (1) serine amino acid residue (GGGGS)$_n$ (SEQ ID NO: 94), wherein n=1 or 2, preferably n=1.

The middle linker L2 particularly is a peptide of 10-40 amino acids, more particularly 15-30 amino acids, and most particularly 20-25 amino acids. In particular embodiments, said linker L2 comprises one or more units of four (4) glycine amino acid residues and one (1) serine amino acid residue (GGGGS)$_n$ (SEQ ID NO: 95), wherein n=1, 2, 3, 4, 5, 6, 7 or 8, preferably n=4.

In one embodiment of the present invention, the isolated antibody is a multispecific and/or multivalent antibody in a scDb-scFv format. The term "scDb-scFv" refers to an antibody format, wherein a single-chain Fv (scFv) fragment is fused by a flexible Gly-Ser linker to a single-chain diabody (scDb). In one embodiment, said flexible Gly-Ser linker is a peptide of 2-40 amino acids, e.g., 2-35, 2-30, 2-25, 2-20, 2-15, 2-10 amino acids, particularly 10 amino acids. In particular embodiments, said linker comprises four (4) Gly- cine amino acid residues and one (1) Serine amino acid residue (GGGGS)$_n$ (SEQ ID NO: 95), wherein n=1, 2, 3, 4, 5, 6, 7 or 8, preferably n=2.

In one embodiment of the present invention, the isolated antibody is a multispecific and/or multivalent antibody in a MATCH format described in WO 2016/0202457; Egan T., et al., mAbs 9 (2017) 68-84.

Multispecific and/or multivalent molecules of the present invention can be produced using any convenient antibody manufacturing method known in the art (see, e.g., Fischer, N. & Leger, O., Pathobiology 74 (2007) 3-14 with regard to the production of bispecific constructs; Hornig, N. & Fairber-Schwarz, A., Methods Mol. Biol. 907 (2012) 713-727, and WO 99/57150 with regard to bispecific diabodies and tandem scFvs). Specific examples of suitable methods for the preparation of the bispecific construct of the present invention further include, inter alia, the Genmab (see Labrijn et al., Proc. Natl. Acad. Sci. USA 110 (2013) 5145-5150) and Merus (see de Kruif et al., Biotechnol. Bioeng. 106 (2010) 741-750) technologies. Methods for production of bispecific antibodies comprising a functional antibody Fc part are also known in the art (see, e.g., Zhu et al., Cancer Lett. 86 (1994) 127-134); and Suresh et al., Methods Enzymol. 121 (1986) 210-228).

Other antibodies which can be employed in the multispecific and in the multivalent molecules of the invention are murine, chimeric and humanized monoclonal antibodies.

The multispecific molecules of the present invention can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis (2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al., 1984 J. Exp. Med. 160: 1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, two or more binding specificities can be encoded in the same vector and expressed and assembled in the same host cell. This method is particularly useful where the bispecific molecule is a mAb X mAb, mAb X Fab, Fab X F (ab')2 or ligand X Fab fusion protein. A multispecific molecule of the invention can be a single chain molecule comprising one single chain antibody and a binding determinant, or a single chain multispecific molecule comprising two binding determinants. Multispecific molecules may comprise at least two single chain molecules. Methods for preparing multispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In a further aspect, the invention provides a nucleic acid encoding the antibody of the invention. The present invention also provides nucleic acid sequences that encode CDRs, VH, VL, the full length heavy chain, and the full length light chain of the antibodies that specifically bind to PDL1 protein. Such nucleic acid sequences can be optimized for expression in mammalian cells.

The term "nucleic acid" is used herein interchangeably with the term "polynucleotide(s)" and refers to one or more deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphorates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260: 2605-2608, 1985; and Rossolini et al., Mol. Cell. Probes 8:91-98, 1994).

The invention provides substantially purified nucleic acid molecules which encode polypeptides comprising segments or domains of the PDL1-binding antibody chains described above. When expressed from appropriate expression vectors, polypeptides encoded by these nucleic acid molecules are capable of exhibiting PDL1 antigen binding capacity.

Also provided in the invention are polynucleotides which encode at least one CDR region and usually all three CDR regions from the heavy or light chain of the PDL1-binding antibody set forth in Table 1. Some other polynucleotides encode all or substantially all of the variable region sequence of the heavy chain and/or the light chain of the PDL1-binding antibody set forth in Table 1. Because of the degeneracy of the code, a variety of nucleic acid sequences will encode each of the immunoglobulin amino acid sequences.

The polynucleotide sequences can be produced by de novo solid-phase DNA synthesis or by PCR mutagenesis of an existing sequence (e.g., sequences as described in the Examples below) encoding a PDL1-binding antibody. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22: 1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the PDL1-binding antibodies described above.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

Various expression vectors can be employed to express the polynucleotides encoding the PDL1-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet. 15:345, 1997). For example, nonviral vectors useful for expression of the PDL1-binding polynucleotides and polypeptides in mammalian (e.g., human) cells include pThioHis A, B and C, pcDNA3.1/His, pEBVHis A, B and C, (Invitrogen, San Diego, Calif.), MPS V vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68: 143, 1992.

The choice of expression vector depends on the intended host cells in which the vector is to be expressed. Typically, the expression vectors contain a promoter and other regulatory sequences (e.g., enhancers) that are operably linked to the polynucleotides encoding a PDL1-binding antibody. In one embodiment, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a PDL1-binding antibody. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20: 125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted PDL1-binding antibody sequences. More often, the inserted PDL1-binding antibody sequences are linked to signal sequences before inclusion in the vector. Vectors to be used to receive sequences encoding PDL1-binding antibody light and heavy chain variable domains sometimes also encode constant regions or parts thereof. Such vectors allow expression of the variable regions as fusion proteins with the constant regions thereby leading to production of intact antibodies and antigen-binding fragments thereof. Typically, such constant regions are human.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The host cells for harboring and expressing the PDL1-binding antibody chains can be either prokaryotic or eukaryotic. E. coli is one prokaryotic host useful for cloning and expressing the polynucleotides of the present invention. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express PDL1-binding polypeptides of the invention. Insect cells in combination with baculovirus vectors can also be used.

In one embodiment, mammalian host cells are used to express and produce the PDL1-binding polypeptides of the present invention. For example, they can be either a hybridoma cell line expressing endogenous immunoglobulin genes or a mammalian cell line harboring an exogenous expression vector. These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP pollII promoter, the constitutive MPS V promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express PDL1-binding antibody chains or binding fragments can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type. The present invention thus provides a method of producing the antibody of the invention, wherein said method comprises the step of culturing a host cell comprising, in particular expressing, a nucleic acid or a vector encoding the antibody of the invention, whereby said antibody of the invention or a fragment thereof is expressed.

In a further aspect, the present invention relates to a pharmaceutical composition comprising the antibody of the present invention, and a pharmaceutically acceptable carrier. Pharmaceutically acceptable carriers enhance or stabilize the composition, or facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. Administration can be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound, i.e., antibody, and multispecific molecule, may be coated in a material to protect the compound from the action of acids and other natural conditions that may inactivate the compound.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the PDL1-binding antibody is employed in the pharmaceutical compositions of the invention. The PDL1-binding antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

Antibody is usually administered on multiple occasions. Intervals between single dosages can be weekly, monthly or yearly. Intervals can also be irregular as indicated by measuring blood levels of PDL1-binding antibody in the patient. Alternatively, antibody can be administered as a sustained release formulation, in which case less frequent administration is required. Dosage and frequency vary depending on the half-life of the antibody in the patient. In general, humanized antibodies show longer half-life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

The antibodies of the present invention have in vitro and in vivo diagnostic and therapeutic utilities. For example, these molecules can be administered to cells in culture, e.g. in vitro or in vivo, or in a subject, e.g., in vivo, to treat, prevent or diagnose a variety of disorders.

In one aspect, the present invention relates to the antibody of the present invention, or the composition of the present invention for use as a medicament.

In one aspect, the present invention relates to the antibody of the present invention, or the composition of the present invention for use in the treatment of a proliferative disease, in particular a cancer in a subject in need thereof.

In another aspect, the present invention relates to use of the antibody of the present invention, or the composition of the present invention to treat a proliferative disease, in particular a cancer in a subject in need thereof.

In a further aspect, the present invention relates to use of the antibody of the present invention, or the composition of the present invention in the manufacture of a medicament for the treatment of a proliferative disease, in particular a cancer, in a subject in need thereof.

In one aspect, the present invention provides a method of treating a proliferative disease, in particular a cancer in a subject in need thereof comprising administering to the subject a therapeutically effective amount of the antibody of the invention, or the composition of the invention.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The terms "treatment", "treating", "treat", "treated", and the like, as used herein, refer to obtaining a desired pharmacologic and/or physiologic effect. The effect may be therapeutic in terms of a partial or complete cure for a disease and/or adverse effect attributable to the disease or delaying the disease progression. "Treatment", as used herein, covers any treatment of a disease in a mammal, e.g., in a human, and includes: (a) inhibiting the disease, i.e., arresting its development; and (b) relieving the disease, i.e., causing regression of the disease.

The term "therapeutically effective amount" or "efficacious amount" refers to the amount of an agent that, when administered to a mammal or other subject for treating a disease, is sufficient to effect such treatment for the disease. The "therapeutically effective amount" will vary depending on the agent, the disease and its severity and the age, weight, etc., of the subject to be treated.

In one embodiment, the proliferative disease is a cancer. The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors. The term "cancer" is used herein to mean a broad spectrum of tumors, including all solid and haematological malignancies. Examples of such tumors include, but are not limited to: a benign or especially malignant tumor, solid tumors, brain cancer, kidney cancer, liver cancer, adrenal gland cancer, bladder cancer, breast cancer, stomach cancer (e.g., gastric tumors), oesophageal cancer, ovarian cancer, cervical cancer, colon cancer, rectum cancer, prostate cancer, pancreatic cancer, lung cancer (e.g. non-small cell lung cancer and small cell lung cancer), vaginal cancer, thyroid cancer, melanoma (e.g., unresectable or metastatic melanoma), renal cell carcinoma, sarcoma, glioblastoma, multiple myeloma or gastrointestinal cancer, especially colon carcinoma or colorectal adenoma, a tumor of the neck and head, endometrial cancer, Cowden syndrome, Lhermitte-Duclos disease, Bannayan-Zonana syndrome, prostate hyperplasia, a neoplasia, especially of epithelial character, preferably mammary carcinoma or squamous cell carcinoma, chronic lymphocytic leukemia, chronic myelogenous leukemia (e.g., Philadelphia chromosome-positive chronic myelogenous leukemia), acute lymphoblastic leukemia (e.g., Philadelphia chromosome-positive acute lymphoblastic leukemia), non-Hodgkin's lymphoma, plasma cell myeloma, Hodgkin's lymphoma, a leukemia, and any combination thereof. In a preferred embodiment, the cancer is a lung cancer, preferably non-small cell lung cancer (NSCLC). In another embodiment, said cancer is a colorectal cancer.

The antibody of the present invention, or the composition of the present invention, inhibits the growth of solid tumors, but also liquid tumors. In a further embodiment, the proliferative disease is a solid tumor. The term "solid tumor" especially means a breast cancer, ovarian cancer, colon cancer, rectum cancer, prostate cancer, stomach cancer (especially gastric cancer), cervical cancer, lung cancer (e.g., non-small cell lung cancer and small cell lung cancer), and a tumor of the head and neck. Further, depending on the tumor type and the particular combination used, a decrease of the tumor volume can be obtained. The antibody of the present invention, or the composition of the present invention, is also suited to prevent the metastatic spread of tumors and the growth or development of micrometastases in a subject having a cancer.

The term "prevent" or "prevention" refers to a complete inhibition of development of a disease, or any secondary effects of disease. The term "prevent" or "prevention" as used herein covers prevention of a disease or condition from occurring in an individual who may be predisposed to the disease but has not yet been diagnosed as having it.

In one aspect, the present invention relates to a kit comprising the antibody of the invention or the pharmaceutical composition of the invention. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody molecule for administration; pharmaceutically acceptable carriers; and devices or other materials for administration to a subject. In a specific embodiment, the kit comprises the antibody of the invention in a pharmaceutically effective amount. In a further embodiment, the kit comprises a pharmaceutically effective amount of the antibody of the invention in lyophilized form and a diluent and, optionally, instructions for use. Said kit may further comprise a filter needle for reconstitution and a needle for injecting.

TABLE 1

Examples of PDL1 antibodies of the present invention
(CDR residues shown in bold and italic letters).

| SEQ ID NUMBER | Ab region | Sequence |
|---|---|---|
| 37-20-B03 | | |
| SEQ ID NO: 1 | HCDR1 (H27-H42; AHo numbering) | GFSFNSDYWIY |
| SEQ ID NO: 2 | HCDR2 (H57-H76; AHo numbering) | SIYGGSSGNTQYASWAQG |
| SEQ ID NO: 3 | HCDR3 (H108-H138; AHo numbering) | RGYVDYGGATDL |
| SEQ ID NO: 4 | HCDR1 (AHo definition) (37-20-B03sc01) | VSGFSFNSDYW |
| SEQ ID NO: 5 | HCDR1 (AHo definition) (37-20-B03sc02) (37-20-B03 sc09.1) | ASGFSFNSDYW |

TABLE 1-continued

Examples of PDL1 antibodies of the present invention
(CDR residues shown in bold and italic letters).

| SEQ ID NUMBER | Ab region | Sequence |
|---|---|---|
| SEQ ID NO: 6 | HCDR2 (AHo definition) | IYGGSSGNTQYASWAQGR |
| SEQ ID NO: 7 | HCDR3 (AHo definition) | GYVDYGGATD |
| SEQ ID NO: 8 | HCDR1 (Kabat definition) | SDYWIY |
| SEQ ID NO: 9 | HCDR2 (Kabat definition) | SIYGGSSGNTQYASWAQG |
| SEQ ID NO: 10 | HCDR3 (Kabat definition) | GYVDYGGATDL |
| SEQ ID NO: 11 | HCDR1 (Chothia definition) | GFSFNSDY |
| SEQ ID NO: 12 | HCDR2 (Chothia definition) | GGSSG |
| SEQ ID NO: 13 | HCDR3 (Chothia definition) | YVDYGGATD |
| SEQ ID NO: 14 | VH (VH4) (37-20-B03sc01) | QVQLQESGPGLVKPSETLSLTCKVS*GFSFNSDYWIY*WIRQPPGKGLEWIG*SIYGGSSGNTQYASWAQG*RVTISVDSSKNQFSLKLSSVTAADTAVYYCA*RGYVDYGGATDL*WGQGTLVTVSS |
| SEQ ID NO: 15 | VH (VH1) (37-20-B03sc02) | QVQLVQSGAEVKKPGASVKVSCKAS*GFSFNSDYWIY*WVRQAPGQGLEWMG*SIYGGSSGNTQYASWAQG*RVTMTRDTSISTAYMELSSLRSEDTAVYYCA*RGYVDYGGATDL*WGQGTLVTVSS |
| SEQ ID NO: 16 | VH (VH3) (37-20-B03 sc09.1) Mutations: G56A; Y105F | EVQLVESGGGLVQPGGSLRLSCAAS*GFSFNSDYWIY*WVRQAPGKGLEWIA*SIYGGSSGNTQYASWAQG*RFTISRDNSKNTVYLQMNSLRAEDTAVYFCA*RGYVDYGGATDL*WGQGTLVTVSS |
| SEQ ID NO: 17 | LCDR1 (L24-L42; AHo numbering) Kabat definition) | QASQSIGTYLA |
| SEQ ID NO: 18 | LCDR2 (L58-L72; AHo numbering) (Kabat definition) | RAFILAS |
| SEQ ID NO: 19 | LCDR3 (L107-L138; AHo numbering) (Kabat definition) | QSNFYSDSTTIGPNA |
| SEQ ID NO: 20 | LCDR1 (AHo definition) | ASQSIGTY |
| SEQ ID NO: 21 | LCDR2 (AHo definition) | RAFILASGVPSR |
| SEQ ID NO: 22 | LCDR3 (AHo definition) | NFYSDSTTIGPN |
| SEQ ID NO: 23 (Chothia) | LCDR1 (Chothia definition) | SQSIGTY |
| SEQ ID NO: 24 (Chothia) | LCDR2 (Chothia definition) | RAF |
| SEQ ID NO: 25 (Chothia) | LCDR3 (Chothia definition) | NFYSDSTTIGPN |
| SEQ ID NO: 26 | VL (Vk1-sk17) (37-20-B03sc01) (37-20-B03sc02) | DIQMTQSPSSLSASVGDRVTITC*QASQSIGTYLA*WYQQKPGKAPKLLIY*RAFILAS*GVPSRFSGSGSGTDFTLTISSLQPEDFATYYC*QSNFYSDSTTIGPNA*FGTGTKVTVLG |

TABLE 1-continued

Examples of PDL1 antibodies of the present invention
(CDR residues shown in bold and italic letters).

| SEQ ID NUMBER | Ab region | Sequence |
|---|---|---|
| SEQ ID NO: 27 | VL (Vk1-sk17) (37-20-B03 sc09.1) Mutations: S9A; A51P | DIQMTQSPASLSASVGDRVTITC*QASQSIGTYLA*WYQQKPGKPPKLLIY*RAFILAS*GVPSRFSGSGSGTDFTLTISSLQPEDFATYYC*QSNFYSDSTTIGPNA*FGTGTKVTVLG |
| SEQ ID NO: 28 | Linker | GGGGSGGGGSGGGGSGGGGS |
| SEQ ID NO: 29 | scFv (VL-linker-VH) (37-20-B03sc01) | DIQMTQSPSSLSASVGDRVTITC*QASQSIGTYLA*WYQQKPGKAPKLLIY*RAFILAS*GVPSRFSGSGSGTDFTLTISSLQPEDFATYYC*QSNFYSDSTTIGPNA*FGTGTKVTVLGGGGGSGGGGSGGGGSGGGGSQVQLQESGPGLVKPSETLSLTCKVS*GFSFNSDYWIY*WIRQPPGKGLEWIG*SIYGGSSGNTQYASWAQG*RVTISVDSSKNQFSLKLSSVTAADTAVYYCA*RGYVDYGGATDL*WGQGTLVTVSS |
| SEQ ID NO: 30 | scFv (VL-linker-VH) (37-20-B03sc02) | DIQMTQSPSSLSASVGDRVTITC*QASQSIGTYLA*WYQQKPGKAPKLLIY*RAFILAS*GVPSRFSGSGSGTDFTLTISSLQPEDFATYYC*QSNFYSDSTTIGPNA*FGTGTKVTVLGGGGGSGGGGSGGGGSGGGGSQVQLVQSGAEVKKPGASVKVSCKAS*GFSFNSDYWIY*WVRQAPGQGLEWMG*SIYGGSSGNTQYASWAQG*RVTMTRDTSISTAYMELSSLRSEDTAVYYCA*RGYVDYGGATDL*WGQGTLVTVSS |
| SEQ ID NO: 31 | scFv (VL-linker-VH) (37-20-B03 sc09.1) | DIQMTQSPASLSASVGDRVTITC*QASQSIGTYLA*WYQQKPGKPPKLLIY*RAFILAS*GVPSRFSGSGSGTDFTLTISSLQPEDFATYYC*QSNFYSDSTTIGPNA*FGTGTKVTVLGGGGGSGGGGSGGGGSGGGGSEVQLVESGGGLVQPGGSLRLSCAAS*GFSFNSDYWIY*WVRQAPGKGLEWIAS*IYGGSSGNTQYASWAQG*RFTISRDNSKNTVYLQMNSLRAEDTAVYFCA*RGYVDYGGATDL*WGQGTLVTVSS |

33-03-G02

| SEQ ID NO: 32 | HCDR1 (H27-H42; AHo numbering) | GFSFSSGYDMC |
| SEQ ID NO: 33 | HCDR2 (H57-H76; AHo numbering) | CVVAGSVDITYYASWAKG |
| SEQ ID NO: 34 | HCDR3 (H108-H138; AHo numbering) | RKDAYSDAFNL |
| SEQ ID NO: 35 | HCDR1 (AHo definition) (33-03-G02 sc01) | VSGFSFSSGYD |
| SEQ ID NO: 36 | HCDR1 (AHo definition) (33-03-G02 sc03 Full) (33-03-G02 sc18) | ASGFSFSSGYD |
| SEQ ID NO: 37 | HCDR2 (AHo definition) | VVAGSVDITYYASWAKGR |
| SEQ ID NO: 38 | HCDR3 (AHo definition) | KDAYSDAFN |
| SEQ ID NO: 39 | HCDR1 (Kabat definition) | SGYDMC |
| SEQ ID NO: 40 | HCDR2 (Kabat definition) | CVVAGSVDITYYASWAKG |
| SEQ ID NO: 41 | HCDR3 (Kabat definition) | KDAYSDAFNL |
| SEQ ID NO: 42 | HCDR1 (Chothia definition) | GFSFSSGY |
| SEQ ID NO: 43 | HCDR2 (Chothia definition) | AGSVD |
| SEQ ID NO: 44 | HCDR3 (Chothia definition) | DAYSDAFN |
| SEQ ID NO: 45 | VH (VH4) (33-03-G02 sc01) | QVQLQESGPGLVKPSETLSLTCKVS*GFSFSSGYDMC*WIRQPPGKGLEWIG*CVVAGSVDITYYASWAKG*RVTISVDSSKNQFSLKLSSVTAADTAVYYCA*RKDAYSDAFNL*WGQGTLVTVSS |

TABLE 1-continued

Examples of PDL1 antibodies of the present invention
(CDR residues shown in bold and italic letters).

| SEQ ID NUMBER | Ab region | Sequence |
|---|---|---|
| SEQ ID NO: 46 | VH (VH4) (33-03-G02 sc03 Full) (Mutations: V2S; V25A; I44V; G56A; V82K; F89V; Y105F) | QSQLQESGPGLVKPSETLSLTCKAS*GFSFSSGYDMC*WVRQPPGKGLEWIA*C VVAGSVDITYYASWAKG*RVTISKDSSKNQVSLKLSSVTAADTAVYFCA*RKD AYSDAFNL*WGQGTLVTVSS |
| SEQ ID NO: 47 | VH (VH4) (33-03-G02 sc18) Mutations VH: V25A; I44; G56A; V82K; F89V (AHo numbering) | QVQLQESGPGLVKPSETLSLTCKAS*GFSFSSGYDMC*WVRQPPGKGLEWIA*C VVAGSVDITYYASWAKG*RVTISKDSSKNQVSLKLSSVTAADTAVYYCA*RKD AYSDAFNL*WGQGTLVTVSS |
| SEQ ID NO: 48 | LCDR1 (L24-L42; AHo numbering) (Kabat definition) | QASQSINDYLA |
| SEQ ID NO: 49 | LCDR2 (L58-L72; AHo numbering) (Kabat definition) | KASTLAS |
| SEQ ID NO: 50 | LCDR3 (L107-L138; AHo numbering) (Kabat definition) | QQGYIITDIDNV |
| SEQ ID NO: 51 | LCDR1 (AHo definition) | ASQSINDY |
| SEQ ID NO: 52 | LCDR2 (AHo definition) | KASTLASGVPSR |
| SEQ ID NO: 53 | LCDR3 (AHo definition) | GYIITDIDN |
| SEQ ID NO: 54 | LCDR1 (Chothia definition) | SQSINDY |
| SEQ ID NO: 55 | LCDR2 (Chothia definition) | KAS |
| SEQ ID NO: 56 | LCDR3 (Chothia definition) | GYIITDIDN |
| SEQ ID NO: 57 | VL (Vk1-sk17) (33_03_G02 sc01) (33-03-G02 sc18) | DIQMTQSPSSLSASVGDRVTITC*QASQSINDYLA*WYQQKPGKAPKLLIY*KAS TLAS*GVPSRFSGSGSGTDFTLTISSLQPEDFATYYC*QQGYIITDIDNV*FGTGTK VTVLG |
| SEQ ID NO: 58 | VL (Vk1-sk17) (33_03_G02 sc03 Full) (Mutations VL: I2F; M4L; A51P) | DFQLTQSPSSLSASVGDRVTITC*QASQSINDYLA*WYQQKPGKSPKLLIY*KAST LAS*GVPSRFSGSGSGTDFTLTISSLQPEDFATYYC*QQGYIITDIDNV*FGTGTKV TVLG |
| SEQ ID NO: 59 | Linker | GGGGSGGGGSGGGGSGGGGS |
| SEQ ID NO: 60 | scFv (VL-linker-VH) (33_03_G02 sc01) | DIQMTQSPSSLSASVGDRVTITC*QASQSINDYLA*WYQQKPGKAPKLLIY*KAS TLAS*GVPSRFSGSGSGTDFTLTISSLQPEDFATYYC*QQGYIITDIDNV*FGTGTK VTVLGGGGGSGGGGSGGGGSGGGGSQVQLQESGPGLVKPSETLSLTCKVS *GFSFSSGYDMC*WIRQPPGKGLEWIG*CVVAGSVDITYYASWAKG*RVTISVDSS KNQFSLKLSSVTAADTAVYYCA*RKDAYSDAFNL*WGQGTLVTVSS |
| SEQ ID NO: 61 | scFv (VL-linker-VH) (33_03_G02 sc03 Full) | DFQLTQSPSSLSASVGDRVTITC*QASQSINDYLA*WYQQKPGKSPKLLIY*KAST LAS*GVPSRFSGSGSGTDFTLTISSLQPEDFATYYC*QQGYIITDIDNV*FGTGTKV TVLGGGGSGGGGSGGGGSGGGGSQSQLQESGPGLVKPSETLSLTCKAS*GF SFSSGYDMC*WVRQPPGKGLEWIA*CVVAGSVDITYYASWAKG*RVTISKDSSK NQVSLKLSSVTAADTAVYFCA*RKDAYSDAFNL*WGQGTLVTVSS |

TABLE 1-continued

Examples of PDL1 antibodies of the present invention
(CDR residues shown in bold and italic letters).

| SEQ ID NUMBER | Ab region | Sequence |
| --- | --- | --- |
| SEQ ID NO: 62 | scFv (VL-linker-VH) (33-03-G02 sc18) | DIQMTQSPSSLSASVGDRVTITCQASQSINDYLAWYQQKPGKAPKLLIYKAS TLASGVPSRFSGSGSGTDFTLTISSLQPEDFATYYCQQGYIITDIDNVFGTGTK VTVLGGGGGSGGGGSGGGGSGGGGSQVQLQESGPGLVKPSETLSLTCKAS GFSFSSGYDMCWVRQPPGKGLEWIACVVAGSVDITYYASWAKGRVTISKDS SKNQVSLKLSSVTAADTAVYYCARKDAYSDAFNLWGQGTLVTVSS |

TABLE 2

Other sequences related to the present invention.

| SEQ ID NUMBER | Ab region | Sequence |
| --- | --- | --- |
| SEQ ID NO: 63 | Human PDL1 | MRIFAVFIFMTYWHLLNAFTVTVPKDLYVV EYGSNMTIECKFPVEKQLDLAALIVYWEME DKNIIQFVHGEEDLKVQHSSYRQRARLLKD QLSLGNAALQITDVKLQDAGVYRCMISYGG ADYKRITVKVNAPYNKINQRILVVDPVTSE HELTCQAEGYPKAEVIWTSSDHQVLSGKTT TTNSKREEKLFNVTSTLRINTTTNEIFYCT FRRLDPEENHTAELVIPELPLAHPPNERTH LVILGAILLCLGVALTFIFRLRKGRMMDVK KCGIQDTNSKKQSDTHLEET |
| SEQ ID NO: 64 | Vλ germline-based FR4 Sk17 | FGTGTKVTVLG |
| SEQ ID NO: 65 | Vλ germline-based FR4 Sk12 | FGGGTKLTVLG |
| SEQ ID NO: 66 | Vλ germline-based FR4 | FGGGTQLIILG |
| SEQ ID NO: 67 | Vλ germline-based FR4 | FGEGTELTVLG |
| SEQ ID NO: 68 | Vλ germline-based FR4 | FGSGTKVTVLG |
| SEQ ID NO: 69 | Vλ germline-based FR4 | FGGGTQLTVLG |
| SEQ ID NO: 70 | Vλ germline-based FR4 | FGGGTQLTALG |

TABLE 3

Examples of multispecific molecules comprising the antibody of the invention.

| SEQ ID NUMBER | Ab Format | Sequence |
| --- | --- | --- |
| PRO885 (38-02-A04 sc01 scDb-i/33-03-G02 sc01 scDb-o) | | |
| SEQ ID NO: 71 | scDb | DIQMTQSPSSLSASVGDRVTITCQASQSINDYLAWYQQKPGKAPKLLIYKAS TLASGVPSRFSGSGSGTDFTLTISSLQPEDFATYYCQQGYIITDIDNVFGTGTK VTVLGGGGGSQVQLQESGPGLVKPSETLSLTCKVSGFSFSNSYWICWIRQPP GKGLEWIGCTFVGSSDSTYYANWAKGRVTISVDSSKNQFSLKLSSVTAADT AVYYCARHPSDAVYGYANNLWGQGTLVTVSSGGGSGGGGSGGGGSG GGGSIQMTQSPSSLSASVGDRVTITCQASQSINNVLAWYQQKPGKAPKLLIY RASTLASGVPSRFSGSGSGTDFTLTISSLQPEDFATYYCQSSYGNYGDFGTGT KVTVLGGGGGSQVQLQESGPGLVKPSETLSLTCKVSGFSFSSGYDMCWIRQ PPGKGLEWIGCVVAGSVDITYYASWAKGRVTISVDSSKNQFSLKLSSVTAA DTAVYYCARKDAYSDAFNLWGQGTLVTVSS |
| PRO951 (38-27-C05 sc02 scDb-i/33-03-G02 sc01 scDb-o) | | |
| SEQ ID NO: 72 | scDb | DIQMTQSPSSLSASVGDRVTITCQASQSINDYLAWYQQKPGKAPKLLIYKAS TLASGVPSRFSGSGSGTDFTLTISSLQPEDFATYYCQQGYIITDIDNVFGTGTK VTVLGGGGGSEVQLVESGGGLVQPGGSLRLSCAASGFSFNNDYDMCWVR QAPGKGLEWIGCIDTGDGSTYYASWAKGRFTISRDNSKNTVYLQMNSLRAE DTAVYYCAREAASSSGYGMGYFDLWGQGTLVTVSSGGGGSGGGGSGGG GSGGGGSIQMTQSPSSLSASVGDRVTITCQSSQSVYDNNWLAWYQQKPGK APKLLIYRASNLASGVPSRFSGSGSGTDFTLTISSLQPEDFATYYCQGTYLSS |

TABLE 3-continued

Examples of multispecific molecules comprising the antibody of the invention.

| SEQ ID NUMBER | Ab Format | Sequence |
|---|---|---|
| | | NWYWAFGTGTKVTVLGGGGGSQVQLQESGPGLVKPSETLSLTCKVSGFSF SSGYDMCWIRQPPGKGLEWIGCVVAGSVDITYYASWAKGRVTISVDSSKNQ FSLKLSSVTAADTAVYYCARKDAYSDAFNLWGQGTLVTVSS |

PRO1123 (38-02-A04 sc05 IF scDb-i/33_03_G02 sc01 scDb-o)

| SEQ ID NO: 73 | scDb | DIQMTQSPSSLSASVGDRVTITCQASQSINDYLAWYQQKPGKAPKLLIYKAS TLASGVPSRFSGSGSGTDFTLTISSLQPEDFATYYCQQGYIITDIDNVFGTGTK VTVLGGGGGSQVQLQESGPGLVKPSETLSLTCKVSGFSFSNSYWICWVRQP PGKGLEWIGCTFVGSSDSTYYANWAKGRVTISVDSSKNQVSLKLSSVTAAD TAVYFCARHPSDAVYGYANNLWGQGTLVTVSSGGGGSGGGGSGGGGSG GGGSIQMTQSPSSLSASVGDRVTITCQASQSINNVLAWYQQKPGKPPKLLIY RASTLASGVPSRFSGSGSGTDFTLTISSLQPEDFATYYCQSSYGNYGDFGTGT KVTVLGGGGGSQVQLQESGPGLVKPSETLSLTCKVSGFSFSSGYDMCWIRQ PPGKGLEWIGCVVAGSVDITYYASWAKGRVTISVDSSKNQFSLKLSSVTAA DTAVYYCARKDAYSDAFNLWGQGTLVTVSS |

PRO1124 (38-02-A04 sc06 Full scDb-i/33_03_G02 sc01 scDb-o)

| SEQ ID NO: 74 | scDb | DIQMTQSPSSLSASVGDRVTITCQASQSINDYLAWYQQKPGKAPKLLIYKAS TLASGVPSRFSGSGSGTDFTLTISSLQPEDFATYYCQQGYIITDIDNVFGTGTK VTVLGGGGGSQVQLQESGPGLVKPSETLSLTCKASGFSFSNSYWICWVRQP PGKGLEWIGCTFVGSSDSTYYANWAKGRVTISKDSSKNQVSLKLSSVTAAD TAVYFCARHPSDAVYGYANNLWGQGTLVTVSSGGGGSGGGGSGGGGSG GGGSLQMTQSPSSLSASVGDRVTITCQASQSINNVLAWYQQKPGKPPKLLI YRASTLASGVPSRFSGSGSGTDFTLTISSLQPEDFATYYCQSSYGNYGDFGT GTKVTVLGGGGGSQVQLQESGPGLVKPSETLSLTCKVSGFSFSSGYDMCWI RQPPGKGLEWIGCVVAGSVDITYYASWAKGRVTISVDSSKNQFSLKLSSVT AADTAVYYCARKDAYSDAFNLWGQGTLVTVSS |

PRO1125 (38-02-A04 sc01 scDb-i/33_03_G02 sc02 IF scDb-o)

| SEQ ID NO: 75 | scDb | DIQMTQSPSSLSASVGDRVTITCQASQSINDYLAWYQQKPGKSPKLLIYKAS TLASGVPSRFSGSGSGTDFTLTISSLQPEDFATYYCQQGYIITDIDNVFGTGTK VTVLGGGGGSQVQLQESGPGLVKPSETLSLTCKVSGFSFSNSYWICWIRQPP GKGLEWIGCTFVGSSDSTYYANWAKGRVTISVDSSKNQFSLKLSSVTAADT AVYYCARHPSDAVYGYANNLWGQGTLVTVSSGGGGSGGGGSGGGGSG GGGSIQMTQSPSSLSASVGDRVTITCQASQSINNVLAWYQQKPGKAPKLLIY RASTLASGVPSRFSGSGSGTDFTLTISSLQPEDFATYYCQSSYGNYGDFGTGT KVTVLGGGGGSQVQLQESGPGLVKPSETLSLTCKVSGFSFSSGYDMCWVR QPPGKGLEWIACVVAGSVDITYYASWAKGRVTISVDSSKNQFSLKLSSVTA ADTAVYFCARKDAYSDAFNLWGQGTLVTVSS |

PRO1126 (38-02-A04 sc01 scDb-i/33_03_G02 sc03 Full scDb-o)

| SEQ ID NO: 76 | scDb | DFQLTQSPSSLSASVGDRVTITCQASQSINDYLAWYQQKPGKSPKLLIYKAS TLASGVPSRFSGSGSGTDFTLTISSLQPEDFATYYCQQGYIITDIDNVFGTGTK VTVLGGGGGSQVQLQESGPGLVKPSETLSLTCKVSGFSFSNSYWICWIRQPP GKGLEWIGCTFVGSSDSTYYANWAKGRVTISVDSSKNQFSLKLSSVTAADT AVYYCARHPSDAVYGYANNLWGQGTLVTVSSGGGGSGGGGSGGGGSG GGGSIQMTQSPSSLSASVGDRVTITCQASQSINNVLAWYQQKPGKAPKLLIY RASTLASGVPSRFSGSGSGTDFTLTISSLQPEDFATYYCQSSYGNYGDFGTGT KVTVLGGGGGSQSQLQESGPGLVKPSETLSLTCKASGFSFSSGYDMCWVR QPPGKGLEWIACVVAGSVDITYYASWAKGRVTISKDSSKNQVSLKLSSVTA ADTAVYFCARKDAYSDAFNLWGQGTLVTVSS |

PRO1134 (38-02-A04 sc01 scDb-i/33_03_G02 sc07 GL VH3 scDb-o)

| SEQ ID NO: 77 | scDb | DIQMTQSPSSLSASVGDAVTITCQASQSINDYLAWYQQKPGKSPKLLIYKAS TLASGVPSRFSGSGSGTDFTLTISSLQPEDFATYYCQQGYIITDIDNVFGTGTK VTVLGGGGGSQVQLQESGPGLVKPSETLSLTCKVSGFSFSNSYWICWIRQPP GKGLEWIGCTFVGSSDSTYYANWAKGRVTISVDSSKNQFSLKLSSVTAADT AVYYCARHPSDAVYGYANNLWGQGTLVTVSSGGGGSGGGGSGGGGSG GGGSIQMTQSPSSLSASVGDRVTITCQASQSINNVLAWYQQKPGKAPKLLIY RASTLASGVPSRFSGSGSGTDFTLTISSLQPEDFATYYCQSSYGNYGDFGTGT KVTVLGGGGGSEVQLVESGGGLVQPGGSLRLSCAASGFSFSSGYDMCWVR QAPGKGLEWVGCVVAGSVDITYYASWAKGRFTISRDNSKNTVYLQMNSLR AEDTATYYCARKDAYSDAFNLWGPGTLVTVSS |

PRO963 (= PRO1051)(38_02_A04 sc01 scDb-i/33-03-G02 sc01 scDb-o/19-01-H04-sc03 scFv)

| SEQ ID NO: 78 | scDb-scFv | DIQMTQSPSSLSASVGDRVTITCQASQSINDYLAWYQQKPGKAPKLLIYKAS TLASGVPSRFSGSGSGTDFTLTISSLQPEDFATYYCQQGYIITDIDNVFGTGTK VTVLGGGGGSQVQLQESGPGLVKPSETLSLTCKVSGFSFSNSYWICWIRQPP GKGLEWIGCTFVGSSDSTYYANWAKGRVTISVDSSKNQFSLKLSSVTAADT |

TABLE 3-continued

Examples of multispecific molecules comprising the antibody of the invention.

| SEQ ID NUMBER | Ab Format | Sequence |
|---|---|---|
| | | AVYYCARHPSDAVGYANNLWGQGTLVTVSSGGGGSGGGGSGGGGSG GGGSIQMTQSPSSLSASVGDRVTITCQASQSINNVLAWYQQKPGKAPKLLIY RASTLASGVPSRFSGSGSGTDFTLTISSLQPEDFATYYCQSSYGNYGDFGTGT KVTVLGGGGGSQVQLQESGPGLVKPSETLSLTCKVSGFSFSSGYDMCWIRQ PPGKGLEWIGCVVAGSVDITYYASWAKGRVTISVDSSKNQFSLKLSSVTAA DTAVYYCARKDAYSDAFNLWGQGTLVTVSSGGGGSGGGGSIQMTQSPSS LSASVGDRVTITCQSSESVYSNNQLSWYQQKPGQPPKLLIYDASDLASGVPS RFSGSGSGTDFTLTISSLQPEDFATYYCAGGFSSSSDTAFGGGTKLTVLGGG GGSGGGGSGGGGSGGGGSEVQLVESGGGLVQPGGSLRLSCAASGFSLSSN AMGWVRQAPGKGLEYIGIISVGGFTYYASWAKGRFTISRDNSKNTVYLQM NSLRAEDTATYFCARDRHGGDSSGAFYLWGQGTLVTVSS |

PRO966 (= PRO1052)(38_27_C05 sc01 scDb-i/33-03-G02 sc01 scDb-o/19-01-H04-sc03 scFv)

| SEQ ID NO: 79 | scDb-scFv | DIQMTQSPSSLSASVGDRVTITCQASQSINDYLAWYQQKPGKAPKLLIYKAS TLASGVPSRFSGSGSGTDFTLTISSLQPEDFATYYCQQGYIITDIDNVFGTGTK VTVLGGGGGSQVQLQESGPGLVKPSETLSLTCKVSGFSFNNDYDMCWIRQ PPGKGLEWIGCIDTGDGSTYYASWAKGRVTISVDSSKNQFSLKLSSVTAADT AVYYCAREAASSSGYGMGYFDLWGQGTLVTVSSGGGGSGGGGSGGGGS GGGGSIQMTQSPSSLSASVGDRVTITCQSSQSVYDNNWLAWYQQKPGKAP KLLIYRASNLASGVPSRFSGSGSGTDFTLTISSLQPEDFATYYCQGTYLSSNW YWAFGTGTKVTVLGGGGGSQVQLQESGPGLVKPSETLSLTCKVSGFSFSSG YDMCWIRQPPGKGLEWIGCVVAGSVDITYYASWAKGRVTISVDSSKNQFSL KLSSVTAADTAVYYCARKDAYSDAFNLWGQGTLVTVSSGGGGSGGGGSI QMTQSPSSLSASVGDRVTITCQSSESVYSNNQLSWYQQKPGQPPKLLIYDAS DLASGVPSRFSGSGSGTDFTLTISSLQPEDFATYYCAGGFSSSSDTAFGGGTK LTVLGGGGGSGGGGSGGGGSGGGGSEVQLVESGGGLVQPGGSLRLSCAA SGFSLSSNAMGWVRQAPGKGLEYIGIISVGGFTYYASWAKGRFTISRDNSKN TVYLQMNSLRAEDTATYFCARDRHGGDSSGAFYLWGQGTLVTVSS |

PRO1057 (38_02_A04 sc01 scDb-i/33-03-G02 sc01 scDb-o/mxr HSA (23-13-A01-sc03, sk17sh4))

| SEQ ID NO: 80 | scDb-scFv | DIQMTQSPSSLSASVGDRVTITCQASQSINDYLAWYQQKPGKAPKLLIYKAS TLASGVPSRFSGSGSGTDFTLTISSLQPEDFATYYCQQGYIITDIDNVFGTGTK VTVLGGGGGSQVQLQESGPGLVKPSETLSLTCKVSGFSFSNSYWICWIRQPP GKGLEWIGCTFVGSSDSTYYANWAKGRVTISVDSSKNQFSLKLSSVTAADT AVYYCARHPSDAVGYANNLWGQGTLVTVSSGGGGSGGGGSGGGGSG GGGSIQMTQSPSSLSASVGDRVTITCQASQSINNVLAWYQQKPGKAPKLLIY RASTLASGVPSRFSGSGSGTDFTLTISSLQPEDFATYYCQSSYGNYGDFGTGT KVTVLGGGGGSQVQLQESGPGLVKPSETLSLTCKVSGFSFSSGYDMCWIRQ PPGKGLEWIGCVVAGSVDITYYASWAKGRVTISVDSSKNQFSLKLSSVTAA DTAVYYCARKDAYSDAFNLWGQGTLVTVSSGGGGSGGGGSVVMTQSPSS LSASVGDRVTITCQASQIISSRSAWYQQKPGQPPKLLIYQASKLASGVPSRFS GSGSGTDFTLTISSLQPEDFATYYCQCTYIDSNFGAFGGGTKLTVLGGGGGS GGGGSGGGGSGGGGSEVQLVESGGGLVQPGGSLRLSCAASGFSFSSSYWI CWRQAPGKGLEWVGCVFTGDGTTYYASWAKGRFTISRDNSKNTVYLQM NSLRAEDTATYFCARPVSVYYYGMDLWGQGTLVTVSS |

PRO1058 (38_27_C05 sc01 scDb-i/33-03-G02 sc01 scDb-o/mxr HSA (23-13-A01-sc03, sk17sh4))

| SEQ ID NO: 81 | scDb-scFv | DIQMTQSPSSLSASVGDRVTITCQASQSINDYLAWYQQKPGKAPKLLIYKAS TLASGVPSRFSGSGSGTDFTLTISSLQPEDFATYYCQQGYIITDIDNVFGTGTK VTVLGGGGGSQVQLQESGPGLVKPSETLSLTCKVSGFSFNNDYDMCWIRQ PPGKGLEWIGCIDTGDGSTYYASWAKGRVTISVDSSKNQFSLKLSSVTAADT AVYYCAREAASSSGYGMGYFDLWGQGTLVTVSSGGGGSGGGGSGGGGS GGGGSIQMTQSPSSLSASVGDRVTITCQSSQSVYDNNWLAWYQQKPGKAP KLLIYRASNLASGVPSRFSGSGSGTDFTLTISSLQPEDFATYYCQGTYLSSNW YWAFGTGTKVTVLGGGGGSQVQLQESGPGLVKPSETLSLTCKVSGFSFSSG YDMCWIRQPPGKGLEWIGCVVAGSVDITYYASWAKGRVTISVDSSKNQFSL KLSSVTAADTAVYYCARKDAYSDAFNLWGQGTLVTVSSGGGGSGGGGSV VMTQSPSSLSASVGDRVTITCQASQIISSRSAWYQQKPGQPPKLLIYQASKLA SGVPSRFSGSGSGTDFTLTISSLQPEDFATYYCQCTYIDSNFGAFGGGTKLTV LGGGGGSGGGGSGGGGSGGGGSEVQLVESGGGLVQPGGSLRLSCAASGF SFSSSYWICWRQAPGKGLEWVGCVFTGDGTTYYASWAKGRFTISRDNSK NTVYLQMNSLRAEDTATYFCARPVSVYYYGMDLWGQGTLVTVSS |

PRO1059 (33-03-G02 IgG1 LC with 38_02_A04 sc01 scFv, PDL1/CD137 (scFv) silent Morrison)

| SEQ ID NO: 82 | Morrison-L Light chain | DIQMTQSPSSLSASVGDRVTITCQASQSINDYLAWYQQKPGKAPKLLIYKAS TLASGVPSRFSGSGSGTDFTLTISSLQPEDFATYYCQQGYIITDIDNVFGTGTK VTVLGTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGECGGGGSGGGGSIQMTQSPSSLSASVGDRVTITCQASQSINNVL AWYQQKPGKAPKLLIYRASTLASGVPSRFSGSGSGTDFTLTISSLQPEDFATY YCQSSYGNYGDFGTGTKVTVLGGGGGSGGGGSGGGGSGGGGSQVQLQE |

TABLE 3-continued

Examples of multispecific molecules comprising the antibody of the invention.

| SEQ ID NUMBER | Ab Format | Sequence |
|---|---|---|
| | | SGPGLVKPSETLSLTCKVSGFSFSNSYWICWIRQPPGKGLEWIGCTFVGSSDS<br>TYYANWAKGRVTISVDSSKNQFSLKLSSVTAADTAVYYCARHPSDAVYGY<br>ANNLWGQGTLVTVSS |
| SEQ ID NO: 83 | Morrison-L Heavy chain | QVQLQESGPGLVKPSETLSLTCKVSGFSFSSGYDMCWIRQPPGKGLEWIGCV<br>VAGSVDITYYASWAKGRVTISVDSSKNQFSLKLSSVTAADTAVYYCARKD<br>AYSDAFNLWGQGTLVTVSSASTKGPSVFPLAPSSKSTSGGTAALGCLVKDY<br>FPEPVTVSWNSGALTSGVHTFPAVLQSSGLYSLSSVVTVPSSSLGTQTYICNV<br>NHKPSNTKVDKRVEPKSCDKTHTCPPCPAPEAAGGPSVFLFPPKPKDTLMIS<br>RTPEVTCVVVDVSHEDPEVKFNWYVDGVEVHNAKTKPREEQYNSTYRVVS<br>VLTVLHQDWLNGKEYKCKVSNKALGAPIEKTISKAKGQPREPQVYTLPPSR<br>EEMTKNQVSLTCLVKGFYPSDIAVEWESNGQPENNYKTTPPVLDSDGSFFL<br>YSKLTVDKSRWQQGNVFSCSVMHEALHNHYTQKSLSLSPGK |

PRO1060 (33-03-G02 IgG1 HC with 38_02_A04 sc01 scFv, PDL1/CD137 (scFv) silent Morrison)

| SEQ ID NUMBER | Ab Format | Sequence |
|---|---|---|
| SEQ ID NO: 84 | Morrison-H Light chain | DIQMTQSPSSLSASVGDRVTITCQASQSINDYLAWYQQKPGKAPKLLIYKAS<br>TLASGVPSRFSGSGSGTDFTLTISSLQPEDFATYYCQQGYIITDIDNVFGTGTK<br>VTVLGTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPV<br>TKSFNRGEC |
| SEQ ID NO: 85 | Morrison-H Heavy chain | QVQLQESGPGLVKPSETLSLTCKVSGFSFSSGYDMCWIRQPPGKGLEWIGCV<br>VAGSVDITYYASWAKGRVTISVDSSKNQFSLKLSSVTAADTAVYYCARKD<br>AYSDAFNLWGQGTLVTVSSASTKGPSVFPLAPSSKSTSGGTAALGCLVKDY<br>FPEPVTVSWNSGALTSGVHTFPAVLQSSGLYSLSSVVTVPSSSLGTQTYICNV<br>NHKPSNTKVDKRVEPKSCDKTHTCPPCPAPEAAGGPSVFLFPPKPKDTLMIS<br>RTPEVTCVVVDVSHEDPEVKFNWYVDGVEVHNAKTKPREEQYNSTYRVVS<br>VLTVLHQDWLNGKEYKCKVSNKALGAPIEKTISKAKGQPREPQVYTLPPSR<br>EEMTKNQVSLTCLVKGFYPSDIAVEWESNGQPENNYKTTPPVLDSDGSFFL<br>YSKLTVDKSRWQQGNVFSCSVMHEALHNHYTQKSLSLSPGKGGGGSGGG<br>GSIQMTQSPSSLSASVGDRVTITCQASQSINNVLAWYQQKPGKAPKLLIYRA<br>STLASGVPSRFSGSGSGTDFTLTISSLQPEDFATYYCQSSYGNYGDFGTGTKV<br>TVLGGGGGSGGGGSGGGGSGGGGSQVQLQESGPGLVKPSETLSLTCKVS<br>GFSFSNSYWICWIRQPPGKGLEWIGCTFVGSSDSTYYANWAKGRVTISVDSS<br>KNQFSLKLSSVTAADTAVYYCARHPSDAVYGYANNLWGQGTLVTVSS |

PRO1061 (33-03-G02 sc01 IgG1 LC with 38_27_C05 sc01 scFv, PDL1/CD137 (scFv) silent Morrison)

| SEQ ID NUMBER | Ab Format | Sequence |
|---|---|---|
| SEQ ID NO: 86 | Morrison-L Light chain | DIQMTQSPSSLSASVGDRVTITCQASQSINDYLAWYQQKPGKAPKLLIYKAS<br>TLASGVPSRFSGSGSGTDFTLTISSLQPEDFATYYCQQGYIITDIDNVFGTGTK<br>VTVLGTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPV<br>TKSFNRGECGGGGSGGGGSIQMTQSPSSLSASVGDRVTITCQASQSINNVL<br>AWYQQKPGKAPKLLIYRASTLASGVPSRFSGSGSGTDFTLTISSLQPEDFATY<br>YCQSSYGNYGDFGTGTKVTVLGGGGGSGGGGSGGGGSGGGGSQVQLQE<br>SGPGLVKPSETLSLTCKVSGFSFSNSYWICWIRQPPGKGLEWIGCTFVGSSDS<br>TYYANWAKGRVTISVDSSKNQFSLKLSSVTAADTAVYYCARHPSDAVYGY<br>ANNLWGQGTLVTVSS |
| SEQ ID NO: 87 | Morrison-L Heavy chain | QVQLQESGPGLVKPSETLSLTCKVSGFSFSSGYDMCWIRQPPGKGLEWIGCV<br>VAGSVDITYYASWAKGRVTISVDSSKNQFSLKLSSVTAADTAVYYCARKD<br>AYSDAFNLWGQGTLVTVSSASTKGPSVFPLAPSSKSTSGGTAALGCLVKDY<br>FPEPVTVSWNSGALTSGVHTFPAVLQSSGLYSLSSVVTVPSSSLGTQTYICNV<br>NHKPSNTKVDKRVEPKSCDKTHTCPPCPAPEAAGGPSVFLFPPKPKDTLMIS<br>RTPEVTCVVVDVSHEDPEVKFNWYVDGVEVHNAKTKPREEQYNSTYRVVS<br>VLTVLHQDWLNGKEYKCKVSNKALGAPIEKTISKAKGQPREPQVYTLPPSR<br>EEMTKNQVSLTCLVKGFYPSDIAVEWESNGQPENNYKTTPPVLDSDGSFFL<br>YSKLTVDKSRWQQGNVFSCSVMHEALHNHYTQKSLSLSPGK |

PRO1062 (33-03-G02 sc01 IgG1 HC with 38_27_C05 sc01 scFv, PDL1/CD137 (scFv) silent Morrison)

| SEQ ID NUMBER | Ab Format | Sequence |
|---|---|---|
| SEQ ID NO: 88 | Morrison-H Light chain | DIQMTQSPSSLSASVGDRVTITCQASQSINDYLAWYQQKPGKAPKLLIYKAS<br>TLASGVPSRFSGSGSGTDFTLTISSLQPEDFATYYCQQGYIITDIDNVFGTGTK<br>VTVLGTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPV<br>TKSFNRGEC |
| SEQ ID NO: 89 | Morrison-H Heavy chain | QVQLQESGPGLVKPSETLSLTCKVSGFSFSSGYDMCWIRQPPGKGLEWIGCV<br>VAGSVDITYYASWAKGRVTISVDSSKNQFSLKLSSVTAADTAVYYCARKD<br>AYSDAFNLWGQGTLVTVSSASTKGPSVFPLAPSSKSTSGGTAALGCLVKDY<br>FPEPVTVSWNSGALTSGVHTFPAVLQSSGLYSLSSVVTVPSSSLGTQTYICNV<br>NHKPSNTKVDKRVEPKSCDKTHTCPPCPAPEAAGGPSVFLFPPKPKDTLMIS<br>RTPEVTCVVVDVSHEDPEVKFNWYVDGVEVHNAKTKPREEQYNSTYRVVS<br>VLTVLHQDWLNGKEYKCKVSNKALGAPIEKTISKAKGQPREPQVYTLPPSR |

TABLE 3-continued

Examples of multispecific molecules comprising the antibody of the invention.

| SEQ ID NUMBER | Ab Format | Sequence |
|---|---|---|
| | | EEMTKNQVSLTCLVKGFYPSDIAVEWESNGQPENNYKTTPPVLDSDGSFFL YSKLTVDKSRWQQGNVFSCSVMHEALHNHYTQKSLSLSPGKGGGGSGGG GSIQMTQSPSSLSASVGDRVTITCQASQSINNVLAWYQQKPGKAPKLLIYRA STLASGVPSRFSGSGSGTDFTLTISSLQPEDFATYYCQSSYGNYGDFGTGTKV TVLGGGGSGGGGSGGGGSGGGGSQVQLQESGPGLVKPSETLSLTCKVS GFSFSNSYWICWIRQPPGKGLEWIGCTFVGSSDSTYYANWAKGRVTISVDSS KNQFSLKLSSVTAADTAVYYCARHPSDAVYGYANNLWGQGTLVTVSS |
| PRO1137 (33-03-G02-sc01 IgG1) | | |
| SEQ ID NO: 90 | Light chain IgG | DIQMTQSPSSLSASVGDRVTITCQASQSINDYLAWYQQKPGKAPKLLIYKAS TLASGVPSRFSGSGSGTDFTLTISSLQPEDFATYYCQQGYIITDIDNVFGTGTK VTVLGTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGEC |
| SEQ ID NO: 91 | Heavy chain IgG | QVQLQESGPGLVKPSETLSLTCKVSGFSFSSGYDMCWIRQPPGKGLEWIGCV VAGSVDITYYASWAKGRVTISVDSSKNQFSLKLSSVTAADTAVYYCARKD AYSDAFNLWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFLY SKLTVDKSRWQQGNVFSCSVMHEALHNHYTQKSLSLSPGK |
| PRO1196 (37-20-B03 sc01 IgG1) | | |
| SEQ ID NO: 92 | Light chain IgG | DIQMTQSPSSLSASVGDRVTITCQASQSIGTYLAWYQQKPGKAPKLLIYRAFI LASGVPSRFSGSGSGTDFTLTISSLQPEDFATYYCQSNFYSDSTTIGPNAFGTG TKVTVLGTVAAPSVFIFPPSDEQLKSGTASVVCLLNNFYPREAKVQWKVDN ALQSGNSQESVTEQDSKDSTYSLSSTLTLSKADYEKHKVYACEVTHQGLSS PVTKSFNRGEC |
| SEQ ID NO: 93 | Heavy chain IgG | QVQLQESGPGLVKPSETLSLTCKVSGFSFNSDYWIYWIRQPPGKGLEWIGSI YGGSSGNTQYASWAQGRVTISVDSSKNQFSLKLSSVTAADTAVYYCARGY VDYGGATDLWGQGTLVTVSSASTKGPSVFPLAPSSKSTSGGTAALGCLVKD YFPEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFLY SKLTVDKSRWQQGNVFSCSVMHEALHNHYTQKSLSLSPGK |

Throughout the text of this application, should there be a discrepancy between the text of the specification (e.g., Tables 1 to 3) and the sequence listing, the text of the specification shall prevail.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

To the extent possible under the respective patent law, all patents, applications, publications, test methods, literature, and other materials cited herein are hereby incorporated by reference.

The following Examples illustrates the invention described above, but is not, however, intended to limit the scope of the invention in any way. Other test models known as such to the person skilled in the pertinent art can also determine the beneficial effects of the claimed invention.

EXAMPLES

Novel Antibodies Directed Against Human PDL1

Example 1: Generation of Rabbit Antibodies Directed Against Human PDL1

Rabbits have been immunized with recombinantly produced and purified human PDL1 extracellular domain. During the course of the immunization, the strength of the humoral immune response against the antigen was qualitatively assessed by determining the maximal dilution (titer) for the serum of each rabbit that still produced detectable binding of the polyclonal serum antibodies to the antigen.

Serum antibody titers against the immobilized antigen (recombinant human PDL1 extracellular domain) were assessed using an enzyme-linked immunosorbent assay (ELISA). All rabbits immunized showed very high titers of at least 1:2.64×10⁶ dilution of the serum. Serum from the same rabbits before the first antigen injection was used as background control.

Example 2: Hit Identification and Selection

Within the Hit identification procedure, a flow-cytometry-based sorting procedure was developed that specifically detects and allows for the isolation of high-affinity hPDL1 binding B-cells. To identify hPDL1 binding B-cells, hPDL1 ECD was labeled with the fluorescent dye R-Phycoerythrin (R-PE). Since the PD-1 binding site as well as the binding site of an anti-PDL1 neutralizing antibody on the labeled PDL1 could potentially be blocked by the bulky R-PE label, accessibility of the epitopes was confirmed by flow-cytometry. PD-1 extracellular domains fused to the Fc part of a human IgG1 or avelumab were captured on protein G beads, and binding of R-PE labeled PDL1 was confirmed by flow-cytometry. The fluorescence intensity was proportional to the amount of labeled PDL1 bound to the receptors immobilized on the beads. Binding of PDL1 to PD-1 and the neutralizing antibody has been confirmed while no binding of an unrelated cytokine to the anti-PDL1 antibody was detected.

Screening:

The results obtained during the screening phase are based on assays performed with non-purified antibodies from culture supernatants of antibody secreting cells (ASC), as the scale of the high-throughput culture does not allow for purification of the individual rabbit antibodies. Such supernatants allow to rank large numbers of antibodies relative to each other, however do not provide absolute values except for binding affinity. During the course of at least four weeks, supernatants from every individually cultured clone were collected. At the end of the cultivation period, the rabbit monoclonal antibodies in each cell culture supernatant were characterized in a high-throughput ELISA for binding to recombinant human PDL1 extracellular domain. PDL1-binding supernatants were further characterized for binding kinetics to human and cynomolgus PDL1. In addition, neutralization potential of the PDL1/PD-1 interaction was determined by competition ELISA as well as by a cell based reporter gene assay. Neutralization of the PDL1/B7-1 interaction was also assessed by competition ELISA. With the exception of binding kinetics, the reporting values of the high-throughput screenings should be interpreted as "yes" or "no" answers, which are based on single-point measurements (no dose-response). Mouse PDL1 binding potential of the supernatants was analyzed by direct ELISA and binding kinetics were determined only for the positive supernatants.

Direct ELISA for hPDL1 Binding

ELISA plates were coated by adding 50 µl of PBS containing 500 ng/ml PDL1 overnight at 4° C. Next day, plates were washed three times in overflow mode with 450 µl wash buffer (PBS, 0.005% Tween 20) per wells and 300 µl of blocking buffer (PBS, 1% BSA, 0.2% Tween 20) were added to each well for 1 h at RT on a nutating mixer. Then, plates were washed three times in overflow mode with 450 µl wash buffer and 50 µl of each supernatant was added, plates were incubated 1.5 h at RT under gentle agitation. After 3 washes in overflow mode with 450 µl wash buffer, 50 µl of a HRP coupled goat and rabbit IgG antibody was added to each well. After 1 h incubation at RT on a nutating mixer, plates were washed with 450 µl of washing buffer per well prior to the addition of 50 µl TMB (3,3',5,5'-tetramethylbenzidine, KPL, Cat. No. 53-00-00). After 5 to 10 minutes development the enzymatic reaction was stopped by addition of 50 µl of 1 M HCl per well and plate was read at 450 nm using 690 nm as a reference wavelength.

Affinity to hPDL1 by SPR

Binding affinities of antibodies towards human PDL1 were measured by surface plasmon resonance (SPR) using a MASS-1 SPR instrument (Sierra Sensors). For affinity screening, an antibody specific for the Fc region of rabbit IgGs (Bethyl Laboratories, Cat. No. A120-111A) was immobilized on a sensor chip (SPR-2 Affinity Sensor, High Capacity Amine, Sierra Sensors) using a standard amine-coupling procedure. Rabbit monoclonal antibodies in B-cell supernatants were captured by the immobilized anti-rabbit IgG antibody. A minimal IgG concentration in the B-cell supernatants is required to allow sufficient capture. After capturing of the monoclonal antibodies, human PDL1 (Peprotech) was injected into the flow cells for 3 min at a concentration of 90 nM, and dissociation of the protein from the IgG captured on the sensor chip was allowed to proceed for 5 min. After each injection cycle, surfaces were regenerated with two injections of 10 mM Glycine-HCl. The apparent dissociation ($k_d$) and association ($k_a$) rate constants and the apparent dissociation equilibrium constant ($K_D$) were calculated with the MASS-1 analysis software (Analyzer, Sierra Sensors) using one-to-one Langmuir binding model and quality of the fits was monitored based on relative Chi² (Chi² normalized to the extrapolated maximal binding level of the analyte), which is a measure for the quality of the curve fitting. The smaller the value for the Chi² the more accurate is the fitting to the one-to-one Langmuir binding model. For most of the Hits the relative Chi² value was below 10%. Results were deemed valid if the response units (RU) for ligand binding were at least 2% of the RUs for antibody capturing. Samples with RUs for ligand binding with less than 2% of the RUs for antibody capturing were considered to show no specific binding of PDL1 to the captured antibody PDL1/PD-1 Blocking ELISA ELISA plates were coated by adding 50 µl of PBS containing 2 µg/ml PD-1 overnight at 4° C. Next day, plates were washed three times in overflow mode with 450 µl wash buffer per wells and 300 µl of blocking buffer were added to each well for 1 h at RT on a nutating mixer. Then, PDL1 was diluted in blocking buffer at 20-fold higher concentration than the desired final concentration of 250 ng/ml. Assay sensitivity was further adapted and several clones were analyzed in presence of 40 ng/ml PDL1. Next, in non-binding plates 114 µl of each supernatant were diluted with 6 µl PDL1 containing blocking buffer plates were incubated 1 h at RT on a nutating mixer. ELISA plates were washed 3 times in overflow mode with 450 µl wash buffer per well and 50 µl of each dilution was added on the ELISA plates. Plates were incubated 1.5 h at RT under gentle agitation. After three washes with 450 µl of washing buffer per well, 50 µl of 10 ng/ml streptavidin-polyHRP40 was added to each well of the ELISA plates. After 1 h incubation at RT, plates were washed three times with 450 µl wash buffer and developed for 5 to 10 minutes after addition of 50 µl TMB. Finally, the enzymatic reaction was stopped by addition of 50 µl of 1 M HCl and plate was read at 450 nm using 690 nm as a reference wavelength.

PDL1/B7-1 Blocking ELISA

ELISA plates were coated by adding 50 µl of PBS containing 4 µg/ml B7-1 overnight at 4° C. Next day, plates were washed three times in overflow mode with 450 µl wash buffer per wells and 300 µl of blocking buffer were added to each well for 1 h at RT on a nutating mixer. Then, PDL1 was diluted in blocking buffer at 20-fold higher concentration than the desire final concentration of 500 ng/ml. Next, in non-binding plates 114 µl of each supernatant were diluted with 6 µl PDL1 containing blocking buffer plates were incubated 1 h at RT on a nutating mixer. ELISA plates were washed 3 times in overflow mode with 450 µl wash buffer per well and 50 µl of each dilution was added on the ELISA plates. Plates were incubated 1.5 h at RT under gentle agitation. After three washes with 450 µl of washing buffer per well, 50 µl of 10 ng/ml streptavidin-polyHRP40 was added to each wells of the ELISA plates. After 1 h incubation at RT, plates were washed three times with 450 µl wash buffer and developed for 5 to 10 minutes after addition of 50 µl TMB. Finally, the enzymatic reaction was stopped by addition of 50 µl of 1 M HCl and plate was read at 450 nm using 690 nm as a reference wavelength.

PDL1/PD-1 Blocking on Cell Based Assay (Reporter Gene)

In order to further characterize the hits, their ability to neutralize the PDL1/PD-1 interaction when both interacting molecules are expressed on the cell surface was tested using CHO/PDL1/TCR activator and Jurkat/PD-1 cells. 35,000 CHO/PDL1/TCR activator cells in 100 µl of cell culture medium (DMEM/F12, 10% FCS) were added to the inner wells of a white cell culture plate and incubated for 16-20 h at 37° C. and 5% $CO_2$. Next day, 95 µl of cell culture medium was removed from each well and 50 µl of screened B-cell supernatant or positive controls, avelumab at concentrations determined to give 0%, 50% and 100% of the maximal signal, was added and plates were incubated at 37° C. for 30 min. Then, 50 µl of effector Jurkat cells diluted at 400,000 cell/ml in assay buffer (RPMI1640 with 10% FCS) were added to each wells and plates were incubated 6 h at 37° C. and 5% $CO_2$. Finally, 50 µL luciferase substrate (BPS Bioscience) prepared according to manufacturer's protocol, was added per well and plates were incubated 30 min in the dark, luminescence was measured using Topcount.

Species Specificity by SPR: Cyno and Mouse

Binding kinetics to cynomolgus and mouse PDL1 were also determined using the same SPR setup as described for the binding to the human PDL1, but replacing human PDL1 by cynomolgus or mouse PDL1, respectively.

Selection of Screening Hits

Pharmacologic properties of monoclonal antibodies of final clones in B-cell supernatant are presented in Table 4.

Example 3: Hit Confirmation

Cloning and Production

Following the identification of the clones chosen for Hit Confirmation these rabbit antibodies were cloned expressed and purified for further characterization. The cloning of the corresponding light and heavy chain variable domains entailed the in-vitro ligation of the DNA fragments into a suitable mammalian expression vector. These expression vectors contained consensus sequences for the constant domains of the rabbit IgG light and heavy chains to allow for the assembly and secretion of fully functional rabbit monoclonal IgGs upon co-expression. Subsequent to the vector construction the sequence of the resulting constructs was confirmed again and the plasmid DNA was amplified and purified for mammalian cell transfections.

The expression vectors for the rabbit antibody heavy and light chains were transfected into a mammalian suspension cell line for transient heterologous expression by a lipid-based transfection reagent. The conditions like the ratio of heavy to light chain vector were optimized for robust expression levels of secreted monoclonal IgG. The expression culture was cultivated for 7 days in a shaking incubator. At the end of the heterologous expression period the cell culture supernatant was harvested by centrifugation. Subsequently the secreted rabbit IgGs were affinity purified by Protein A beads. The IgG loaded beads were washed and the purified antibodies were eluted by a pH shift. The elution fractions were analyzed by sodium dodecyl sulfate polyacrylamide gel electrophoresis (SDS-PAGE), UV absorbance at 280 nm and size-exclusion high performance liquid chromatography (SE-HPLC) to verify identity, content and purity. Table 5 summarizes manufacture and characterization of rIgGs.

TABLE 4

Pharmacodynamic properties of monoclonal antibodies in B-cell supernatants: 33-03-G02 and 37-20-B03.

| Clone ID | Affinity to hPD-L1 (SPR) | | | Affinity to cynomolgus PD-L1 (SPR) | | | Affinity to mouse PD-L1 (SPR) |
|---|---|---|---|---|---|---|---|
| | $k_a$ [$M^{-1}s^{-1}$] | $k_d$ [$s^{-1}$] | $K_D$ [M] | $k_a$ [$M^{-1}s^{-1}$] | $k_d$ [$s^{-1}$] | $K_D$ [M] | $k_a$ [$M^{-1}s^{-1}$] |
| 33-03-G02 | 1.02E+05 | 3.41E−05 | 3.34E−10 | 1.31E+05 | 7.33E−06 | 5.60E−11 | N/A |
| 37-20-B03 | 5.98E+05 | 7.39E−04 | 1.24E−09 | 8.11E+05 | 3.23E−04 | 3.99E−10 | 8.45E+04 |

| Clone ID | Affinity to mouse PD-L1 (SPR) | | Neutralization of PD-L1 in reporter gene assay | Neutralization in PD-L1/PD-1 inhibition ELISA | | Neutralization in PD-L1/B7-1 inhibition ELISA |
|---|---|---|---|---|---|---|
| | $k_d$ [$s^{-1}$] | $K_D$ [M] | Inhibition (%) | 250 ng/mL hPD-L1 inhibition (%) | 40 ng/mL hPD-L1 inhibition (%) | 500 ng/mL hPD-L1 inhibition (%) |
| 33-03-G02 | N/A | N/A | 100 | 101 | | 100 |
| 37-20-B03 | 9.40E−03 | 1.11E−07 | 51 | | 100 | 58 |

TABLE 5

Summary of the rabbit monoclonal antibody manufacturing analysis data.

| Clone ID | Averaged conc. [µg/µl] | Aliquot vol. [mL] | Amount [µg] | Final Yield [mg/L] | Expression vol. [mL] | monomeric content [%] |
|---|---|---|---|---|---|---|
| 33-03-G02 | 0.816 | 0.75 | 612 | 15.3 | 40 | 98.4 |

| Construct ID | Expression volume [mL] | Final yield [mg] | Yield per L expression [mg/L] | Purity SE-HPLC [% monomer] | Buffer |
|---|---|---|---|---|---|
| 33-03-G02 | 40 | 0.61 | 15.3 | 98.4 | PBS 1X, pH 7.4 |
| 37-20-B03 | 40 | 0.29 | 6.7 | 99.0 | PBS 1X, pH 7.4 |

Affinity to hPDL1 by SPR

Binding kinetics of the purified monoclonal rabbit antibodies to human PDL1 were determined by surface plasmon resonance (SPR) using a MASS-1 SPR instrument (Sierra Sensors). Since most of the antibodies showed very slow off rates, experiments were conducted at 37° C. in a buffer containing high salt concentrations to allow discrimination of binding affinities of the different antibodies. An antibody specific for the Fc region of rabbit IgGs (Bethyl Laboratories, Cat. No. A120-111A) was immobilized on a sensor chip (SPR-2 Affinity Sensor, High Capacity Amine, Sierra Sensors) using a standard amine-coupling procedure. Rabbit monoclonal antibodies were captured by the immobilized anti-rabbit IgG antibody. After capturing of the monoclonal antibodies, two-fold serial dilutions in HEPES buffer containing 150 mM NaCl and 150 mM $MgCl_2$ of PDL1 ranging from 90 to 0.35 nM were tested for binding to the IgG captured on the biosensor chip and dissociation of the protein from the IgG captured on the sensor chip was allowed to proceed for 5 min. After each injection cycle, surfaces were regenerated with two injections of 10 mM Glycine-HCl. The apparent dissociation ($k_d$) and association ($k_a$) rate constants and the apparent dissociation equilibrium constant ($K_D$) were calculated with the MASS-1 analysis software (Analyzer, Sierra Sensors) using one-to-one Langmuir binding model and quality of the fits was monitored based on relative $Chi^2$ ($Chi^2$ normalized to the extrapolated maximal binding level of the analyte), which is a measure for the quality of the curve fitting. The smaller the value for the $Chi^2$ the more accurate is the fitting to the one-to-one Langmuir binding model. For most of the Hits the relative $Chi^2$ value was below 10%. Table 6 shows the rabbit IgG antibodies selected for further development.

TABLE 6

Summary of affinity measurement to hPDL1 for rabbit IgGs 33-03-G02 and 37-20-B03.

| clone ID | $k_a$ [$M^{-1} s^{-1}$] | $k_d$ [$s^{-1}$] | $K_D$ [M] | Binding level normalized to theoretical Rmax (%) |
|---|---|---|---|---|
| 33-03-G02 | 3.76E+05 | 1.99E−05 | 5.28E−11 | 70.00% |
| 37-20-B03 | 5.26E+05 | 4.08E−05 | 7.76E−11 | 94.00% |

Potency in PDL1/PD-1 Blocking ELISA

Potency to neutralize PDL1 binding to PD-1 was assessed in the competition ELISA. ELISA plates were coated by adding 50 µl of PBS containing 4 µg/ml PD-1 overnight at 4° C. Next day, plates were washed three times in overflow mode with 450 µl wash buffer (PBS, 0.005% Tween 20) per wells and 300 µl of blocking buffer (PBS, 1% BSA, 0.2% Tween 20) were added to each well for 1 h at RT on a nutating mixer. Then, PDL1 was diluted in blocking buffer to a final concentration of 1 ng/ml. Next, in non-binding plates 120 µl of serial dilutions in the PDL1 containing buffer ranging from 300 to 0.005 ng/ml of the tested rIgGs were prepared per well and plates were incubated 30 min at RT. ELISA pates were washed 3 times in overflow mode with 450 µl wash buffer and two times 50 µl of each dilution was added in adjacent wells of the ELISA plates in order to generate duplicates. Plates were incubated 90 minutes at RT under gentle agitation. After three washes with 450 µl of washing buffer, 50 µl of 10 ng/ml streptavidin-polyHRP40 were added to each wells of the ELISA plates. After 1 h incubation at RT, plates were washed three times with 450 µl wash buffer and developed for 5 to 10 minutes after addition of 50 µl TMB. Finally, the enzymatic reaction was stopped by addition of 50 µl of 1 M HCl and plate was read at 450 nm using 690 nm as a reference wavelength.

The rabbit IgGs derived from clones 33-03-G02 and 37-20-B03 showed high potency to neutralize PDL1/PD-1 interaction. The clone 37-20-B03 had almost two times better potency than avelumab (Table 7). Dose response curves obtained for the selected clones is displayed in FIG. 1.

TABLE 7

Summary of neutralization potency in the PDL1/PD-1 competition ELISA of rabbit IgGs 33-03-G02 and 37-20-B03.

| | potency in PDL1/PD-1 competition ELISA | | |
|---|---|---|---|
| clone ID | $IC_{50}$ [ng/ml] | rel. $IC_{50}$ [$IC_{50, avelumab}$/$IC_{50, IgG}$] | Maximum Inhibition (%) |
| 33-03-G02 | 2.13 | 0.85 | 100.0 |
| 37-20-B03 | 1.44 | 2.03 | 99.9 |

Potency in PDL1/B7-1 Blocking ELISA

Figure 2:
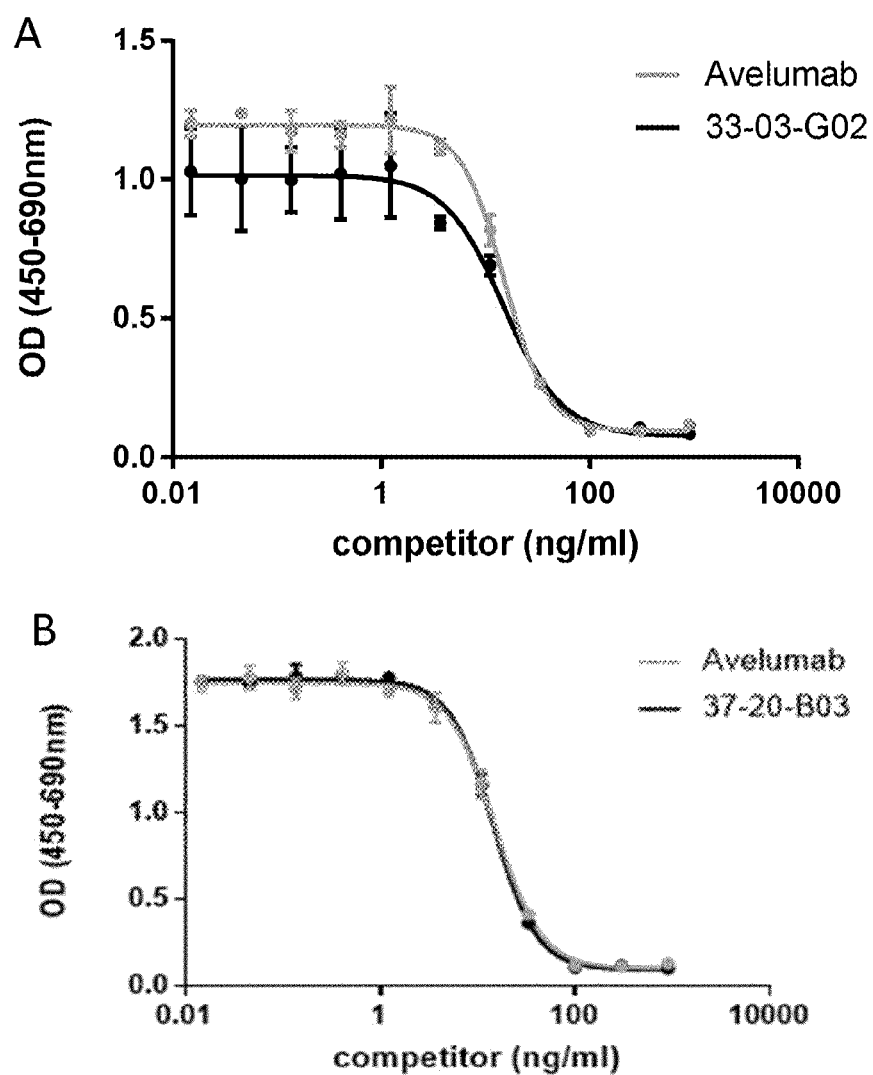
FIG. 2 Neutralization of PDL1/B7-1 interaction by the selected rabbit IgG clones 33-03-G02 (A) and 37-20-B03 (B) having the best affinity to PDL1. Absorbances measured by ELISA are represented in function of the molecules concentrations in ng/ml. Avelumab was used as reference.

Potency to neutralize the PDL1/B7-1 interaction was assessed in the competition ELISA. ELISA plates were coated by adding 50 µl of PBS containing 4 µg/ml B7-1 overnight at 4° C. Next day, plates were washed three times in overflow mode with 450 µl wash buffer (PBS, 0.005% Tween 20) per wells and 300 µl of blocking buffer (PBS, 1% BSA, 0.2% Tween 20) were added to each well for 1 h at RT on a nutating mixer. Then, PDL1 was diluted in blocking buffer to 40 ng/ml. Next, in non-binding plates 120 µl of serial dilutions in the PDL1 containing buffer ranging from 900 to 0.015 ng/ml of the tested rIgGs were prepared per well and plates were incubated 30 min at RT. ELISA pates were washed 3 times in overflow mode with 450 µl wash buffer and two times 50 µl of each dilution was added in adjacent wells of the ELISA plates in order to generate duplicates. Plates were incubated 90 minutes at RT under gentle agitation. After three washes with 450 µl of washing buffer, 50 µl of streptavidin-polyHRP40 was added to each wells of the ELISA plate. After 1 h incubation at RT, plates were washed three times with 450 µl wash buffer and developed for 5 to 10 minutes after addition of 50 µl TMB. Finally, the enzymatic reaction was stopped by addition of 50 µl of 1 M HCl and plate was read at 450 nm using 690 nm as a reference wavelength. The selected rabbit IgGs were able to block PDL1/B7-1 interaction to a similar potency as avelumab as shown in Table 8. Dose response curve obtained for the selected clone is displayed in FIG. 2.

TABLE 8

Neutralization potency in the PDL1/B7-1 competition ELISA of selected rIgG.

| | potency in PDL1/B7-1 competition ELISA | | |
|---|---|---|---|
| clone ID | $IC_{50}$ [ng/ml] | rel. $IC_{50}$ [$IC_{50, avelumab}$/$IC_{50, IgG}$] | Maximum Inhibition (%) |
| 33-03-G02 | 14.85 | 1.01 | 94.7 |
| 37-20-B03 | 14.82 | 1.02 | 95.0 |

Potency in Cell Based PDL1/PD-1 Blocking Assay (Reporter Gene)

Figure 3:
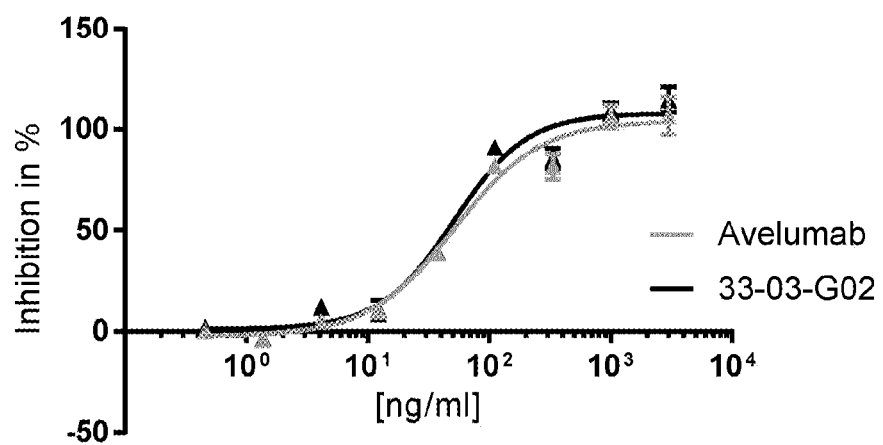
FIG. 3 Neutralization of PDL1/PD-1 interaction by a selected rabbit IgG clone having the best affinity to PDL1 in the cell-based reporter gene assay. % inhibition proportional to the luminescence signal obtained in the assay is represented in function of the molecules concentrations in ng/ml. Avelumab was used as reference.

Potency to neutralize PDL1 binding to PD-1 was assessed in the cell based reporter gene assay. 35,000 CHO/PDL1/TCR activator cells in 100 µl of cell culture medium (DMEM/F12, 10% FCS) were added to the inner wells of a white cell culture plate and incubated for 16-20 h at 37° C. and 5% $CO_2$. Next day, 95 µl of cell culture medium was removed from each well and 50 µl of 2-fold concentrated serial dilutions of the respective molecules to be tested (from 3,000 to 0.46 ng/ml), including the reference avelumab, were added. Then, 50 µl of effector Jurkat cells diluted at 400,000 cell/ml in assay buffer (RPMI1640 with 10% FCS) were added to each well and plates were incubated 6 h at 37° C. and 5% $CO_2$. Finally, 50 µL luciferase substrate (BPS Bioscience) prepared according to manufacturer's protocol, was added per well and plates were incubated 30 min in the dark, luminescence was measured using Topcount. The selected clones were able to block PDL1/PD-1 interaction in the cell-based reporter gene assay Table 9. Dose response curves obtained for the selected clone are displayed in FIG. 3.

TABLE 9

Summary of neutralization potency of PDL1/PD-1 interaction of selected rIgG in reporter gene assay.

| | NFAT reporter gene assay | | |
|---|---|---|---|
| clone ID | $EC_{50}$ [ng/ml] | rel. $EC_{50}$ [$EC_{50, Avelumab}$/$EC_{50, IgG}$] | Maximum inhibition (relative to Avelumab, in %) |
| 33-03-G02 | 50.99 | 1.01 | 114.5 |

Binding to PDL1 Expressing Cells by FACS

Binding potency to PDL1 expressing cells was also determined for the selected IgGs. 50,000 CHO-PDL1 expressing cells were distributed to round bottom non-tissue culture treated 96 well plates. Cells were washed twice with 100 µl PBS by centrifugation at 400×g for 5 min. Cells were resuspended in 100 µl of serial dilutions prepared in staining buffer (PBS, 2% BCS heat inactivated, 2 mM EDTA) of the tested rIgGs as well as of the control IgG avelumab and ranging from 2,000 to 0.128 ng/ml. After 1 h incubation at 4° C. on a nutating mixer, cells were wash 3 times with 100 µl staining buffer and centrifugation steps of 5 min at 400×g. Then, cells treated with rabbit IgGs were resuspended in 100 µl of staining buffer containing 2 µg/ml of goat anti-rabbit IgG APC labelled and cells treated with avelumab (human IgG1) were resuspended in 100 µl of staining buffer containing 2 µg/ml of goat anti-human IgG APC labelled. Plates were incubated 1 h at 4° C. on a nutating mixer. Plates were washed 3 times with 100 µl of staining buffer and resuspended in a final volume of 50 µl of staining buffer. Finally, APC signal of 20,000 events per well was analyzed by flow cytometry using a Novocyte flow cytometer system (ACEA Bioscience). PDL1 expressing cell binding could be confirmed for all assessed rabbit IgGs. Binding potency to cellular PDL1 of the selected rabbit IgG is shown in Table 10.

TABLE 10

Binding potency to cellular PDL1 of the selected rabbit IgGs.

| | Binding to cellullar PD-L1 | | |
|---|---|---|---|
| clone ID | $EC_{50}$ [ng/ml] | rel. $EC_{50}$ [$EC_{50, avelumab}$/$EC_{50, IgG}$] | Maximum binding (relative to Avelumab, in %) |
| 33-03-G02 | 113.7 | 1.091 | 85% |

Species Specificity by SPR: Cyno

Binding kinetics to cynomolgus PDL1 were also determined using the same setup as described for the binding to the human PDL1, but in this case human PDL1 was replaced by cynomolgus PDL1. Binding to cynomolgus PDL1 was confirmed for all selected IgGs (Table 11).

TABLE 11

Summary of affinity measurement to cynomolgus PDL1 for the selected rabbit IgG.

| clone ID | $k_a$ [$M^{-1}s^{-1}$] | $k_d$ [$s^{-1}$] | $K_D$ [M] | Binding level normalized to theoretical Rmax (%) |
|---|---|---|---|---|
| 33-03-G02 | 1.68E+05 | 3.91E−06 | 2.34E−11 | 39.59% |

Species Specificity by SPR: Mouse

Binding kinetics to cynomolgus PDL1 were also determined using the same setup as described for the binding to the human PDL1, but in this case human PDL1 was replaced by mouse PDL1. No binding to mouse PDL1 was detected for the selected rabbit IgGs derived from the clones 33-03-G02 and 37-20-B03.

Example 4: Selection of Clones for Humanization

Based on data obtained during hit confirmation, all clones were humanized by grafting the CDRs on VH3, VH4 or VH1A or VH1B based framework. In order to achieve the best affinity and potency, further optimization with different structural grafts was done for the two clone which displayed the best affinity to human PDL1 as rIgG, 33-03-G02 and 37-20-B03. The following grafting variants were applied for the clones 33-03-G02 and 37-20-B03: CDR graft—grafting of rabbit CDRs on human framework; IF graft—CDR graft plus grafting of all rabbit VL/VH interface residues; full graft—CDR graft plus framework residues following AHo humanization protocol (antigen interface (AIF) residues (rabbit residues potentially in contact with antigen (according to AHo)) were limited to residues with >20% change in solvent accessibility upon interface formation in order to reduce total number of mutations (rabbit framework residues)).

Heterologous expression of the proteins was performed in E. coli as insoluble inclusion bodies by induced overnight expression in small scale (except for PRO997, which were produced in mammalian CHO-S cells similar to rIgG expression described above). Inclusion bodies were isolated from the homogenized cell pellet by a centrifugation protocol that included several washing steps to remove cell debris and other host cell impurities. The purified inclusion bodies were solubilized in a denaturing buffer and the scFvs were refolded by a scalable refolding protocol that generated milligram amounts of natively folded, monomeric scFv. At this point a standardized protocol was employed to purify the scFvs. The product after refolding was captured by an affinity chromatography to yield the purified scFvs. Only the main fraction with desired purity was used as the available amounts did not allow SEC polishing of the samples. In addition, melting temperatures of scFvs were determined by differential scanning fluorimetry (DSF) measurement (which is described in more detail later). Table 12 summarizes manufacture of VH4 CDR graft scFv molecules. As two of the clones contained unpaired Cysteine residues in their CDR-loops, a C57S mutation was introduced in clone 37-20-B03 as indicated in Table 12.

Additional grafting variants were designed for some selected clones and are described in the Table 13 (AHo numbering) and Table 14 summarizing their initial production and characterization.

Example 5: Pharmacodynamics Characterization of Humanized scFvs

In the following the humanized scFvs were characterized for the primary pharmacodynamics properties, using the same assay systems as described for the Hit confirmation phase, with certain adaptations though to accommodate for the different format of the scFv molecules.

5.1 Affinity to Human PDL1

Affinity of the humanized scFvs to human PDL1 was determined by SPR analysis on a T200 device (Biacore, GE Healthcare). In this experiment, Fc tagged human PDL1 was captured using the Human Antibody Capture kit from GE healthcare. After each analyte injection cycle, the CM5 sensor chip was regenerated and new antigen was captured. The scFvs were injected as analyte using a dose response multicycle kinetic assay with concentrations of the analyte ranging from 0.12 to 30 nM diluted in running buffer for 5 min and dissociation of the protein was allowed to proceed for 12 min. Obtained sensorgrams were fitted using the 1:1 binding model. As shown in Table 15, binding to human PDL1 was confirmed for the humanized scFvs tested.

5.2. Neutralization of PDL1/PD-1 Interaction by Competition ELISA

Potency to neutralize PDL1 binding to PD-1 was assessed by competition ELISA with the same procedure as described earlier. Individual $IC_{50}$ values on each plate were calibrated against the $IC_{50}$ of the reference molecule avelumab that was taken along on each plate (relative $IC_{50}$: $IC_{50,\ avelumab}/IC_{50,\ test\ scFv}$). Potencies are summarized in Table 16 which shows that $IC_{50}$ up to 5-fold that of avelumab can be resolved in this assay. All of the scFvs tested had a similar or better potency than avelumab.

5.3. Neutralization of PDL1/B7-1 Interaction by Competition ELISA

Potency to neutralize PDL1 binding to B7-1 was assessed by competition ELISA with the same procedure as described earlier. Individual $IC_{50}$ values on each plate were calibrated against the $IC_{50}$ of the reference molecule avelumab that was taken along on each plate (relative $IC_{50}$: $IC_{50,\ avelumab}/IC_{50,\ test\ scFv}$). Potencies are summarized in Table 17 which shows that $IC_{50}$ up to 10-fold that of avelumab can be resolved in this assay. The scFvs tested had a better or similar potency than avelumab.

5.4. Neutralization of PDL1/PD-1 Interaction in NFAT Reporter Gene Assay

Potency to neutralize PDL1 binding to PD-1 was assessed in the cell based reporter gene assay as described above. Serial dilutions of the respective molecules to be tested as well as the reference avelumab, were added to the plates. Individual $IC_{50}$ values on each plate were calibrated against the $IC_{50}$ of the reference molecule avelumab that was taken along on each plate (relative $IC_{50}$: $IC_{50,\ avelumab}/IC_{50,\ test\ scFv}$). Potencies are summarized in Table 18 which shows that $IC_{50}$ up to 5-fold that of avelumab can be resolved in this assay. The scFvs tested had a better or similar potency.

TABLE 12

Summary of the scFv manufacturing and initial stability data.

| Clone ID | PRO ID | Framework | Grafting Strategy | Expression volume [mL] | Yield post Capto L [mg] | Final yield [mg] | Yield per L expression [mg/L] | Purity SE-HPLC [% monomer] | Tm [° C.] |
|---|---|---|---|---|---|---|---|---|---|
| 33-03-G02-sc01 | PRO830 | VH4 | CDR | 300.00 | 2.00 | 2.00 | 6.67 | 100.0 | 80.00 |
| 37-20-B03-sc01 | PRO997 (PRO908) | VH4 | CDR | 1,000.00 | 0.72 | 0.72 | 0.72 | 71.9 | — |

TABLE 13

Listing of humanized scFv variants.

| Clone ID | Protein ID | VL Mutations (lambda-caped Vk1) | VH Mutations | VH Framework | Grafting Strategy |
|---|---|---|---|---|---|
| 33-03-G02-sc02 | PRO1066 | | | VH3 | CDR |
| 33-03-G02-sc03 | PRO1183 | | | VH4 | FULL |
| 33-03-G02-sc18 | PRO1392 | | V25A; I44V; G56A; V82K; F89V | VH4 | PRO1183 optimized |
| 37-20-B03-sc09** | PRO1347 | S9A; A51P | G56A; Y105F | VH3 | IF |

**unpaired Cys at position 57 in CDRH2 (AHo numbering)

TABLE 14

Production summary table.

| Clone ID | Protein ID | VH Framework | Grafting Strategy | Expression volume [mL] | Yield post Capto L [mg] | Final yield [mg] | Yield per L expression [mg/L] | Purity SE-HPLC [% monomer] | Tm [° C.] |
|---|---|---|---|---|---|---|---|---|---|
| 33-03-G02-sc02 | PRO1066 | VH3 | CDR | 300.00 | 2.80 | 1.36 | 9.07 | 99.0 | |
| 33-03-G02-sc03 | PRO1183 | VH4 | FULL | 1200.00 | 16.90 | 4.00 | 3.33 | 99.0 | |
| 33-03-G02-sc18 | PRO1392 | VH4 | PRO1183 optimized | 200.00 | 46.70 | 7.44 | 37.18 | 97.0 | 66.19 |
| 37-20-B03-sc09 | PRO1347 | VH3 | IF | 200.00 | 38.90 | 2.30 | 11.50 | 98.1 | 74.85 |
| 37-20-B03-sc10 | PRO1355 | VH3 | GL | 200.00 | 59.63 | 4.59 | 22.95 | 98.2 | 74.64 |

TABLE 15

Affinities of scFv to human PDL1.

| Clone ID | Protein ID | Framework | Grafting Strategy | $k_a$ [$M^{-1}s^{-1}$] | $k_d$ [$s^{-1}$] | $K_D$ [M] | Binding level normalized to theoretical Rmax (%) |
|---|---|---|---|---|---|---|---|
| 33-03-G02-sc01 | PRO830 | VH4 | CDR | 2.10E+06 | 1.59E−04 | 7.60E−11 | 68.7 |
| 33-03-G02-sc02 | PRO1066 | VH3 | CDR | 3.27E+06 | 6.95E−05 | 2.13E−11 | 127.8 |
| 33-03-G02-sc03 | PRO1183 | VH4 | FULL | 4.77E+06 | <1.00E−05 | <2.10E−12 | 84.1 |
| 33-03-G02-sc18 | PRO1392 | VH4 | reduced mut | 6.19E+06 | 6.16E−05 | 9.94E−12 | 91.0 |
| 37-20-B03-sc01 | PRO997/PRO908 | VH4 | CDR | 6.76E+06 | 4.02E−05 | 5.94E−12 | 85.8 |
| 37-20-B03-sc09 | PRO1347 | VH3 | IF | 7.38E+06 | 6.64E−05 | 9.00E−12 | 90.7 |

TABLE 16

Potencies of scFvs to inhibit the interaction between PDL1 and PD-1.

| Clone ID | Protein ID | VH Framework | Grafting Strategy | $IC_{50}$ [ng/ml] | rel. $IC_{50}$ [$IC_{50, avelumab}$/$IC_{50, scFv}$] | Maximum Inhibition (%) |
|---|---|---|---|---|---|---|
| 33-03-G02-sc01 | PRO830 | VH4 | CDR | 3.446 | 0.47 | 99.84 |
| 33-03-G02-sc02 | PRO1066 | VH3 | CDR | 2.073 | 0.93 | 99.90 |
| 33-03-G02-sc03 | PRO1183 | VH4 | FULL | 0.36 | 3.57 | 99.80 |
| 33-03-G02-sc18 | PRO1392 | VH4 | reduced mut | 0.4699 | 2.77 | 99.91 |
| 37-20-B03-sc01 | PRO997/PRO908 | VH4 | CDR | 0.33 | 3.81 | 100.00 |
| 37-20-B03-sc09 | PRO1347 | VH3 | IF | 0.29 | 5.16 | 100.10 |

TABLE 17

Potencies of scFvs to inhibit the interaction between PDL1 and B7-1.

| Clone ID | Protein ID | VH Framework | Grafting Strategy | $IC_{50}$ [ng/ml] | rel. $IC_{50}$ [$IC_{50, avelumab}$/$IC_{50, scFv}$] | Maximum Inhibition (%) |
|---|---|---|---|---|---|---|
| 33-03-G02-sc01 | PRO830 | VH4 | CDR | 6.11 | 1.76 | 94.5 |
| 33-03-G02-sc02 | PRO1066 | VH3 | CDR | | Not measured | |
| 33-03-G02-sc03 | PRO1183 | VH4 | FULL | 0.977 | 4.67 | 95.4 |
| 33-03-G02-sc18 | PRO1392 | VH4 | reduced mut | 1.19 | 3.51 | 93.24 |
| 37-20-B03-sc01 | PRO997/PRO908 | VH4 | CDR | 1.212 | 3.77 | 93.08 |
| 37-20-B03-sc09 | PRO1347 | VH3 | IF | 0.541 | 8.04 | 91.8 |

TABLE 18

Potencies of scFvs to neutralize PDL1/PD-1 interaction in reporter gene assay.

| Clone ID | Protein ID | VH Framework | Grafting Strategy | $IC_{50}$ [ng/ml] | rel. $IC_{50}$ [$IC_{50, avelumab}$/$IC_{50, scFv}$] | Maximum Inhibition (%) |
|---|---|---|---|---|---|---|
| 33-03-G02-sc01 | PRO830 | VH4 | CDR | 37.52 | 1.62 | 105% |
| 33-03-G02-sc02 | PRO1066 | VH3 | CDR | | Not measured | |
| 33-03-G02-sc03 | PRO1183 | VH4 | FULL | 9.98 | 3.84 | 102.40 |
| 33-03-G02-sc18 | PRO1392 | VH4 | reduced mut | 11.98 | 4.13 | 96.68 |
| 37-20-B03-sc01 | PRO997/PRO908 | VH4 | CDR | 8.02 | 4.78 | 95.28 |
| 37-20-B03-sc09 | PRO1347 | VH3 | IF | 7.53 | 4.68 | 88.88 |

5.5. Binding to hPDL1 Expressing Cells by Flow Cytometry

Binding potency to PDL1 expressing cells was determined for some molecules. The same cell lines were used as during hit confirmation (CHO-PDL1 and CHO-K1) but scFv were detected by APC labelled protein-L. Serial dilutions of the respective molecules to be tested as well as the reference avelumab, were added to the plates. Individual $IC_{50}$ values on each plate were calibrated against the $IC_{50}$ of the reference molecule avelumab that was taken along on each plate (relative $IC_{50}$: $IC_{50, avelumab}$/$IC_{50, test\ scFv}$). Potencies are summarized in Table 19.

TABLE 19

Summary of binding potency to cellular PDL1 of the tested scFvs.

| Clone ID | Protein ID | VH Framework | Grafting Strategy | $EC_{50}$ [ng/ml] | rel. $EC_{50}$ ($EC_{50, avelumab}$/$EC_{50}$, scFv) | Maximum binding (Δ MFI; ($MFI_{Test}$ − $MFI_{control}$; (RFU))) | Relative maximum binding ($Max_{scFv}$/$Max_{Avelumab}$) |
|---|---|---|---|---|---|---|---|
| 33-03-G02-sc01 | PRO830 | VH4 | CDR | 20.2 | 4.8 | 21455 | 0.48 |

5.6. Species Cross-Reactivity (Binding to Cynomolgus Monkey and Mouse PDL1 by SPR)

Cross-reactivity to cynomolgus PDL1 was measured in a similar assay as used to measure binding to human PDL1, with the recombinant PDL1 produced by Sino Biological. Table 20 summarizes the affinities obtained for all tested scFvs. All tested scFvs that showed binding to human PDL1 also showed binding to cynomolgus PDL1.

TABLE 20

Affinities of scFv to cynomolgus PDL1

| Clone ID | Protein ID | VH Framework | Grafting Strategy | $k_a$ [M$^{-1}$s$^{-1}$] | $k_d$ [s$^{-1}$] | $K_D$ [M] | $K_{D, cyno}/K_{D, human}$ | Binding level normalized to theoretical Rmax (%) |
|---|---|---|---|---|---|---|---|---|
| 33-03-G02-sc01 | PRO830 | VH4 | CDR | 2.46E+06 | 1.82E−04 | 7.40E−11 | 0.97 | 77.52 |
| 33-03-G02-sc02 | PRO1066 | VH3 | CDR | | | Not measured | | |
| 33-03-G02-sc03 | PRO1183 | VH4 | FULL | 1.55E+06 | 1.82E−05 | 1.17E−11 | <5.58 | 65.4% |
| 33-03-G02-sc18 | PRO1392 | VH4 | reduced mut | 4.45E+06 | 8.87E−05 | 1.99E−11 | 2.00 | 70.3% |
| 33-03-G02-sc19 | PRO1393 | VH4 | reduced mut | | | Not measured | | |
| 37-20-B03-sc01 | PRO997/PRO908 | VH4 | CDR | 5.96E+06 | <1E−05 | <1.68E−12 | <0.28 | 79.4 |
| 37-20-B03-sc09 | PRO1347 | VH3 | IF | 6.88E+06 | 8.77E−05 | 1.27E−11 | 1.41 | 71.2% |

5.7. Selectivity for PDL1 Versus PDL2 by SPR

Humanized scFvs were tested for binding to PDL2 by SPR analysis on a T200 device (Biacore, GE Healthcare). In this experiment, Fc tagged human PDL2 was captured using the Human Antibody Capture kit from GE healthcare. After each analyte injection cycle the CM5 sensor chip was regenerated and new antigen was captured. The scFvs were injected as analyte at a concentration of 180 nM diluted in running buffer for 5 min and dissociation of the protein was allowed to proceed for 12 min. No binding to PDL2 was observed for all humanized scFvs tested which are listed in Table 21.

TABLE 21

ScFvs tested for binding to mouse PDL1 and PDL2 by SPR.

| Clone ID | Protein ID | VH Framework | Grafting Strategy |
|---|---|---|---|
| 33-03-G02-sc03 | PR01183 | VH4 | FULL |
| 33-03-G02-sc18 | PR01392 | VH4 | reduced mut |
| 37-20-B03-sc09 | PR01347 | VH3 | IF |

Example 6: Biophysical Characterization of the Humanized scFvs

Selected domains with affinities better than avelumab were produced at larger scale (0.2 L-1.2 L expression volume). Additionally, protein samples were concentrated to >10 mg/mL using centrifugal concentration tubes with a molecular weight cut-off of 5 kD after purification. Manufacture of material for stability assessment is compiled in Table 22.

6.1. Storage Stability Study

Humanized scFvs were subjected to stability studies such as a four-week stability study, in which the scFvs were formulated in an aqueous buffer (final buffer, 50 mM NaCiP, 150 mM NaCl, pH 6.4) at 10 mg/ml and stored at <−80° C., 4° C. and 40° C. for four weeks. At the minimum, the fraction of monomers and oligomers in the formulation were evaluated by integration of SE-HPLC peak areas after one week, two weeks and at the end of each study. Additional time points were recorded for some of the molecules. Table 23 compares d7 and endpoint measurements obtained at d28 of the study.

TABLE 22

Manufacture of domains for stability study.

| Clone ID | Protein ID | Framework | Expression volume [mL] | Yield post Capto L [mg] | Yield post capture [mg/L] | SEC purification? | Final yield [mg] | Final yield per L expression [mg/L] | Purity SE-HPLC [% monomer] | Tm [° C.] | Monomer content at 10 mg/mL [% monomer] | Monomer content loss upon concentration [%] |
|---|---|---|---|---|---|---|---|---|---|---|---|---|
| 33-03-G02-sc01 | PRO830* | VH4 | 300 | 2.0 | 6.7 | NO | 2.0 | 6.7 | 99.0 | 80.0 | 98.3 | −0.7 |
| 33-03-G02-sc02 | PRO1066 | VH3 | 300 | 0.8 | 2.8 | NO | 1.4 | 9.1 | 99.0 | NA | 92.7 | −6.4 |
| 33-03-G02-sc03 | PRO1183* | VH4 | 1200 | 16.9 | 14.1 | YES | 4.0 | 3.3 | 100.0 | NA | 99.7 | −0.3 |
| 33-03-G02-sc18 | PRO1392 | VH4 | 200 | 9.3 | 46.7 | NO | 7.4 | 37.2 | 97.0 | 72.4 | 97.4 | 0.4 |
| 37-20-B03-sc01 | PRO908* | VH4 | 1200 | 18.6 | 15.5 | YES | 5.3 | 4.4 | 89.0 | NA | 75.4 | −15.3 |
| 37-20-B03-sc09 | PRO1347 | VH3 | 200 | 8.0 | 38.9 | YES | 2.3 | 11.5 | 98.1 | 74.8 | 98.5 | 0.4 |

*bacterial expression

TABLE 23

4 w stability study of the selected domains.

| | | | Monomeric content [%] | | | Monomeric content loss [%] | | Protein concentration [mg/mL] | | | Protein content loss [%] | |
|---|---|---|---|---|---|---|---|---|---|---|---|---|
| Clone ID | Protein ID | Temp. [° C.] | d 0 | d 7 | d 28 | d 7 | d 28 | d 0 | d 7 | d 28 | d 7 | d 28 |
| 33-03-G02-sc01 | PRO830 | −80 | 98.3 | 98.5 | 98.4 | −0.2 | −0.1 | 10.5 | 12.0 | 11.4 | −14.2 | −9.2 |
| | | 4 | 98.3 | 97.9 | 96.8 | 0.4 | 1.6 | 10.5 | 12.4 | 12.0 | −18.6 | −14.5 |
| | | 40 | 98.3 | 93.3 | 84.9 | 5.0 | 13.6 | 10.5 | 10.4 | 11.6 | 0.6 | −10.6 |
| | | −80 | NA | NA | NA | NA | NA | NA | NA | NA | NA | NA |

TABLE 23-continued 4 w stability study of the selected domains.

| Clone ID | Protein ID | Temp. [° C.] | Monomeric content [%] | | | Monomeric content loss [%] | | Protein concentration [mg/mL] | | | Protein content loss [%] | |
|---|---|---|---|---|---|---|---|---|---|---|---|---|
| | | | d 0 | d 7 | d 28 | d 7 | d 28 | d 0 | d 7 | d 28 | d 7 | d 28 |
| 33-03-G02-sc02 | PRO1066 | 4 | 92.7 | 81.7 | 77.7 | 11.9 | 16.2 | 10.7 | 10.9 | 11.7 | −1.7 | −9.2 |
| | | 40 | 92.7 | 84.5 | NA | 8.8 | 100.0 | 10.7 | 10.4 | NA | 2.7 | 100.0 |
| | | −80 | 99.7 | NA | 99.4 | NA | 0.3 | 20.6 | 20.8 | 21.1 | NA | −2.6 |
| 33-03-G02-sc03 | PRO1183 | 4 | 99.7 | NA | 87.9 | NA | 11.8 | 20.6 | 20.8 | 21.0 | NA | −1.9 |
| | | 40 | 99.7 | NA | 71.0 | NA | 28.8 | 20.6 | 21.0 | 22.0 | NA | −7.1 |
| | | −80 | 97.4 | 97.4 | 97.2 | 0.0 | 0.2 | 10.6 | 9.4 | 11.0 | 11.7 | −3.9 |
| 33-03-G02-sc18 | PRO1392 | 4 | 97.4 | 97.1 | 96.9 | 0.2 | 0.5 | 10.6 | 10.7 | 10.7 | −0.9 | −1.3 |
| | | 40 | 97.4 | 94.2 | 84.7 | 3.2 | 13.0 | 10.6 | 10.7 | 11.2 | −0.8 | −5.9 |
| | | −80 | 75.4 | 74.4 | 73.5 | 1.4 | 2.5 | 10.4 | 10.3 | 9.9 | 1.1 | 4.8 |
| 37-20-B03-sc01 | PRO908 | 4 | 75.4 | 74.1 | 73.8 | 1.7 | 2.1 | 10.4 | 9.9 | 9.9 | 4.9 | 4.7 |
| | | 40 | 75.4 | 75.4 | 73.2 | 0.0 | 3.0 | 10.4 | 11.5 | 11.4 | −11.0 | −9.6 |
| | | −80 | 90.5 | 88.2 | 85.5 | 2.6 | 5.5 | 10.1 | 12.2 | 10.3 | −21.0 | −1.5 |
| 37-20-B03-sc02 | PRO1013 | 4 | 90.5 | 78.8 | 76.9 | 12.9 | 15.0 | 10.1 | 13.3 | 10.7 | −31.3 | −5.8 |
| | | 40 | 90.5 | 79.7 | 79.4 | 12.0 | 12.3 | 10.1 | 14.7 | 12.8 | −45.1 | −26.1 |
| | | −80 | NA | NA | NA | NA | NA | NA | NA | NA | NA | NA |
| 37-20-B03-sc09 | PRO1347 | 4 | 98.5 | 97.1 | 94.6 | 1.4 | 4.0 | 10.6 | 11.4 | 11.5 | −7.6 | −8.0 |
| | | 40 | 98.5 | 83.1 | 75.6 | 15.6 | 23.3 | 10.6 | 11.9 | 11.7 | −12.1 | −10.0 |

NA: not assessed, no data point could be recorded due to limiting sample amount

6.2. Freeze-Thaw Stability Study

In addition to the storage stability study described above, the compatibility of the top performing scFv molecules was assessed with respect to freeze-thawing (F/T) cycles (colloidal stability). For the F/T stability assessment the same analytical methods and parameters (% monomer content and % monomer loss) as for the storage stability study (SE-HPLC, SDS-PAGE) were applied to monitor the quality of the molecules over five F/T cycles. Table 24 illustrates the course of % monomer content loss over five repeated F/T cycles. As no dedicated freeze-thaw study was performed, freeze-thaw data obtained with the −80° C. samples from storage stability study which was acquired over 28 days is shown in the graph below. None of the molecules lost >4% monomeric content after repeated F/T cycles.

TABLE 24

F/T stability - % monomeric loss upon repetitive freeze thawing.

| Clone ID | Grafting Strategy | Framework | PRO ID | F/T-1* | F/T-2* | F/T-3* | F/T-4* | F/T-5* |
|---|---|---|---|---|---|---|---|---|
| 37-20-B03-sc01 | CDR | VH4 | PRO908 | −0.8 | −1.0 | −1.1 | −0.4 | −1.9 |
| 33-03-G02-sc03 | FULL | VH4 | PRO1183 | −0.1 | −0.4 | −0.3 | −0.4 | −0.3 |
| 33-03-G02-sc18 | PRO1183 opt. | VH4 | PRO1392 | −0.1 | 0.0 | 0.0 | −0.2 | −0.2 |
| 33-03-G02-sc01 | CDR | VH4 | PRO830 | 0.2 | 0.1 | 0.1 | NA | NA |

*monomeric loss % upon F/T cycle X
NA: not assessed

6.3. Thermal Unfolding

Thermal unfolding data obtained from DSF measurements of the selected scFv constructs is shown in Table 25. Resulting Tm values have been determined by fitting of data to a Boltzmann equation. Table 25 summarizes calculated melting temperatures measured by DSF.

TABLE 25

DSF of success criteria compliant domains.

| Clone ID | Protein ID | Tm [° C.] | Tonset [° C.] |
|---|---|---|---|
| 33-03-G02-sc02 | PRO1066 | NA | NA |
| 33-03-G02-sc18 | PRO1392 | 72.40 | 67.00 |

TABLE 25-continued

DSF of success criteria compliant domains.

| Clone ID | Protein ID | Tm [° C.] | Tonset [° C.] |
|---|---|---|---|
| 37-20-B03-sc01 | PRO997 | 64.39 | 59.00 |
| 37-20-B03-sc09 | PRO1347 | 74.85 | 67.33 |

NA: not assessed, ND: not determinable

The Multispecific Molecules Comprising the Antibody of the Invention

The exemplary multispecific molecules comprising the antibody of the invention are included in Table 3.

Example 7: Affinities to PDL1, CD137, HSA and MSA

Methods:

Affinity to PDL1 of the different species was determined by SPR measurements using a Biacore T200 device (GE Healthcare). An antibody specific for the Fc region of human IgGs was immobilized on a sensor chip (CM5 sensor chip, GE Healthcare) by amine-coupling. For all formats, with the exception of the Fc containing Morrison formats, PDL1-Fc chimeric protein from different species were captured by the immobilized antibody. Three-fold serial dilutions of the molecules specific for PDL1 (0.12-90 nM) were injected into the flow cells for three minutes and dissociation was monitored for 10 minutes. After each injection cycle, surfaces were regenerated with one injection of a 3 M $MgCl_2$ solution. The apparent dissociation ($k_d$) and association ($k_a$) rate constants and the apparent dissociation equilibrium constant (KD) were calculated using one-to-one Langmuir binding model. Affinity to CD137 of the different species was determined using the identical setup as for PDL1 with the exception that CD137-Fc chimeric proteins from different species were captured by the immobilized antibody.

The Fc containing formats were directly captured by the antibody specific for the Fc region of human IgGs. Two-fold serial dilutions of PDL1 extracellular domain or CD137 extracellular domain ranging from 90 to 0.35 nM were tested for binding to the IgG captured on the biosensor chip. After each injection cycle, surfaces were regenerated with one injection of a 3 M MgCl2 solution.

Affinity of molecules to serum albumin (SA) of the different species was determined by SPR measurements using a Biacore T200 device (GE Healthcare). SA was directly coupled to a CM5 sensor chip (GE Healthcare) using amine coupling chemistry. After performing a regeneration scouting and surface performance test to find best assay conditions, a dose response was measured and obtained binding curves were double-referenced (empty reference channel and zero analyte injection) and fitted using the 1:1 Langmuir model to retrieve kinetic parameters. The assay was run in a 1×PBS-Tween buffer at pH 5.5.

Results:

The measurements of the binding kinetics for the humanized constructs show a difference in binding affinity for PDL1 when comparing the CDR and structural grafts (STR) of clone 33-03-G02 the STR graft shows a 20-fold improvement in affinity compared to the CDR graft of the same clone (PRO885 versus PRO1126 in Table 26). The CDR graft derived from clone 37-20-B03 (PRO997) shows approximately two-fold higher affinity when compared to the STR graft of clone 33-03-G02. The binding affinities for the CDR graft of 33-03-G02 are similar to the binding affinity of the parental scFv when they are combined into different multi-specific formats (compare PRO830 to PRO885, PRO951, PRO1123, PRO1124, PRO963, PRO966, PRO1057, PRO1058, PRO1059 and PRO1060 in Table 26). The scFv derived from both clones show nearly identical affinity to human and cynomolgus monkey PDL1 (see PRO977 and PRO830 in Table 26).

TABLE 26

Affinities of different formats to PDL1, CD137 and serum albumin from different species.

| PRO ID | Clone ID PD-L1 | Clone ID CD137 | Clone ID SA | Format | Affinity to human PD-L1 $k_a$ ($M^{-1}s^{-1}$) | $k_d$ ($s^{-1}$) |
|---|---|---|---|---|---|---|
| PRO885 | 33-03-G02 CDR | 38-02-A04 CDR | NA | scDb | 2.1E+06 | 1.4E−04 |
| PRO951 | 33-03-G02 CDR | 38-27-C05 CDR | NA | scDb | 2.2E+06 | 1.5E−04 |
| PRO1123 | 33-03-G02 CDR | 38-02-A04 IF | NA | scDb | 2.3E+06 | 1.7E−04 |
| PRO1124 | 33-03-G02 CDR | 38-02-A04 STR | NA | scDb | 3.1E+06 | 2.0E−04 |
| PRO1125 | 33-03-G02 IF | 38-02-A04 CDR | NA | scDb | 1.7E+06 | 1.1E−04 |
| PRO1126 | 33-03-G02 STR | 38-02-A04CDR | NA | scDb | 2.8E+06 | <1.0E−05 |
| PRO1134 | 33-03-G02 STR2, VH3 | 38-02-A04 CDR | NA | scDb | 2.8E+06 | 7.6E−05 |
| PRO963 | 33-03-G02 CDR | 38-02-A04 CDR | 19-01-H04 STR | scDb-scFv | 2.0E+06 | 1.3E−04 |
| PRO966 | 33-03-G02 CDR | 38-27-C05 CDR | 19-01-H04 STR | scDb-scFv | 1.6E+06 | 1.4E−04 |
| PRO1057 | 33-03-G02 CDR | 38-02-A04 CDR | 23-13-A01 STR | scDb-scFv | 1.6E+06 | 1.7E−04 |
| PRO1058 | 33-03-G02 CDR | 38-27-C05 CDR | 23-13-A01 STR | scDb-scFv | 1.2E+06 | 1.9E−04 |
| PRO1059 | 33-03-G02 CDR | 38-02-A04 CDR | NA | Morrison-L | 1.2E+06 | 6.5E−05 |
| PRO1060 | 33-03-G02 CDR | 38-02-A04 CDR | NA | Morrison-H | 1.3E+06 | 4.6E−05 |
| PRO1061 | 33-03-G02 CDR | 38-27-C05 CDR | NA | Morrison-L | ND | ND |
| PRO1062 | 33-03-G02 CDR | 38-27-C05 CDR | NA | Morrison-H | 1.3E+06 | 5.0E−05 |
| PRO997 | 37-20-B03 CDR | NA | NA | scFv | 5.9E+06 | <1.0E−05 |
| PRO1013 | 37-20-B03 CDR, VH1 | NA | NA | scFv | 6.0E+06 | 2.7E−04 |
| PRO830 | 33-03-G02 CDR | NA | NA | scFv | 2.1E+06 | 1.6E−04 |
| PRO1186 | 37-20-B03 sc01 | 38-02-A04 sc01 | 23-13-A01 sc03 | scDb-scFv | 6.2E+06 | 2.3E−05 |
| PRO1430 | 37-20-B03 sc01 | 38-02-A04 sc013 | 19-01-H04 sc03 | scDb-scFv | 5.3E+06 | 2.4E−05 |
| PRO1479 | 37-20-B03 sc09.1 | 38-02-A04 sc013 | 19-01-H04 sc03 | scDb-scFv | 4.2E+06 | 3.9E−05 |
| PRO1482 | 37-20-B03 sc09.1 | 38-02-A04 sc013 | 19-01-H04 sc03 | scDb-scFv | 3.4E+06 | 3.3E−05 |
| PRO1431 | 33-03-G02 sc18 | 38-02-A04 sc013 | 19-01-H04 sc03 | scDb-scFv | 3.3E+06 | 4.5E−05 |
| PRO1473 | 33-03-G02 sc03 | 38-02-A04 sc013 | 19-01-H04 sc03 | scDb-scFv | 3.6E+06 | 2.9E−05 |
| PRO1476 | 33-03-G02 sc03 | 38-02-A04 sc013 | 19-01-H04 sc03 | scDb-scFv | 3.4E+06 | 3.1E−05 |
| PRO1432 | 33-03-G02 sc18 | 38-02-A04 sc013 | 19-01-H04 sc03 | scDb-scFv | 4.2E+06 | 4.4E−05 |

| PRO ID | Affinity to human PD-L1 KD (M) | Affinity to cynomolgus PD-L1 ($M^{-1}s^{-1}$) | $k_d$ ($s^{-1}$) | KD (M) | Affinity to human CD137 $k_a$ ($M^{-1}s^{-1}$) | $k_d$ ($s^{-1}$) | KD (M) |
|---|---|---|---|---|---|---|---|
| PRO885 | 6.5E−11 | ND | ND | ND | 2.4E+05 | 7.6E−04 | 3.2E−09 |
| PRO951 | 7.0E−11 | ND | ND | ND | 1.5E+06 | 6.3E−03 | 4.2E−09 |
| PRO1123 | 7.5E−11 | ND | ND | ND | 3.1E+05 | 2.7E−04 | 8.8E−10 |
| PRO1124 | 6.7E−11 | ND | ND | ND | 6.8E+05 | <1.0E−05 | 1.5E−11 |
| PRO1125 | 6.7E−11 | ND | ND | ND | 2.0E+05 | 7.5E−04 | 3.7E−09 |
| PRO1126 | 3.5E−12 | ND | ND | ND | 2.1E+05 | 7.5E−04 | 3.5E−09 |
| PRO1134 | 2.8E−11 | ND | ND | ND | 2.5E+05 | 8.4E−04 | 3.4E−09 |
| PRO963 | 6.6E−11 | ND | ND | ND | 2.0E+05 | 6.2E−04 | 3.0E−09 |
| PRO966 | 8.3E−11 | ND | ND | ND | 1.0E+06 | 2.2E−03 | 2.2E−09 |
| PRO1057 | 1.1E−10 | ND | ND | ND | 1.4E+05 | 7.0E−04 | 5.1E−09 |
| PRO1058 | 1.6E−10 | ND | ND | ND | 1.7E+06 | 2.1E−03 | 1.2E−09 |
| PRO1059 | 5.6E−11 | ND | ND | ND | 1.8E+05 | 4.2E−04 | 2.3E−09 |
| PRO1060 | 3.6E−11 | ND | ND | ND | 3.0E+05 | 3.9E−04 | 1.3E−09 |

TABLE 26-continued

Affinities of different formats to PDL1, CD137 and serum albumin from different species.

| | | | | | | | |
|---|---|---|---|---|---|---|---|
| PRO1061 | ND | ND | ND | ND | ND | ND | ND |
| PRO1062 | 3.8E−11 | ND | ND | ND | 2.8E+05 | 3.7E−04 | 1.3E−09 |
| PRO997 | 1.7E−12 | 6.0E+06 | <1.0E−05 | <1.67E−12 | NA | NA | NA |
| PRO1013 | 4.5E−11 | 5.9E+06 | 3.2E−04 | 5.3E−11 | NA | NA | NA |
| PRO830 | 7.6E−11 | 2.2E+06 | 2.0E−04 | 9.4E−11 | NA | NA | NA |
| PRO1186 | 3.7E−12 | TBD | TBD | TBD | 1.9E+05 | 5.0E−04 | 2.6E−09 |
| PRO1430 | 4.5E−12 | TBD | TBD | TBD | 4.6E+05 | 7.1E−04 | 1.5E−09 |
| PRO1479 | 9.2E−12 | TBD | TBD | TBD | 3.3E+05 | 5.4E−04 | 1.7E−09 |
| PRO1482 | 9.8E−12 | TBD | TBD | TBD | 3.2E+05 | 3.6E−04 | 1.1E−09 |
| PRO1431 | 1.4E−11 | ND | ND | ND | 4.5E+05 | 7.5E−04 | 1.7E−09 |
| PRO1473 | 8.2E−12 | ND | ND | ND | 3.1E+05 | 6.0E−04 | 2.0E−09 |
| PRO1476 | 9.0E−12 | ND | ND | ND | 3.5E+05 | 3.7E−04 | 1.1E−09 |
| PRO1432 | 1.1E−11 | ND | ND | ND | 6.0E+05 | 4.5E−04 | 7.5E−10 |

| | Affinity to cynomolgus CD137 | | | Affinity to mouse CD137 | | |
|---|---|---|---|---|---|---|
| PRO ID | $k_a$ (m$^{-1}$ s$^{-1}$) | $k_d$ (s$^{-1}$) | KD (M) | $k_a$ (M$^{-1}$ s$^{-1}$) | $k_d$ (s$^{-1}$) | KD (M) |
| PRO885 | 3.4E+05 | 7.0E−04 | 2.1E−09 | 2.9E+05 | 1.8E−01 | 6.0E−07 |
| PRO951 | 1.5E+06 | 1.0E−02 | 6.9E−09 | NB | NB | NB |
| PRO1123 | 2.6E+05 | 3.3E−04 | 1.3E−09 | 6.5E+04 | 2.7E−02 | 4.1E−07 |
| PRO1124 | 5.6E+05 | 3.3E−04 | 5.9E−10 | 2.0E+05 | 2.2E−03 | 1.1E−08 |
| PRO1125 | ND | ND | ND | 5.4E+05 | 2.7E−01 | 5.1E−07 |
| PRO1126 | ND | ND | ND | NB | NB | NB |
| PRO1134 | ND | ND | ND | 4.5E+05 | 1.9E−01 | 4.2E−07 |
| PRO963 | ND | ND | ND | NB | NB | NB |
| PRO966 | ND | ND | ND | 5.1E+03 | 1.0E−03 | 2.0E−07 |
| PRO1057 | 1.6E+05 | 7.9E−04 | 4.8E−09 | 6.9E+04 | 8.5E−02 | 1.2E−06 |
| PRO1058 | ND | ND | ND | 1.1E+06 | 7.5E−04 | 7.0E−10 |
| PRO1059 | ND | ND | ND | ND | ND | ND |
| PRO1060 | ND | ND | ND | ND | ND | ND |
| PRO1061 | ND | ND | ND | ND | ND | ND |
| PRO1062 | ND | ND | ND | ND | ND | ND |
| PRO997 | NA | NA | NA | NA | NA | NA |
| PRO1013 | NA | NA | NA | NA | NA | NA |
| PRO830 | NA | NA | NA | NA | NA | NA |
| PRO1186 | TBD | TBD | TBD | ND | ND | ND |
| PRO1430 | TBD | TBD | TBD | ND | ND | ND |
| PRO1479 | TBD | TBD | TBD | ND | ND | ND |
| PRO1482 | TBD | TBD | TBD | ND | ND | ND |
| PRO1431 | TBD | TBD | TBD | ND | ND | ND |
| PRO1473 | TBD | TBD | TBD | ND | ND | ND |
| PRO1476 | TBD | TBD | TBD | ND | ND | ND |
| PRO1432 | TBD | TBD | TBD | ND | ND | ND |

| | Affinity to human SA | | | Affinity to mouse SA | | |
|---|---|---|---|---|---|---|
| PRO ID | $k_a$ (M$^{-1}$ s$^{-1}$) | $k_d$ (s$^{-1}$) | KD (M) | $k_a$ (M$^{-1}$ s$^{-1}$) | $k_d$ (s$^{-1}$) | KD (M) |
| PRO885 | NA | NA | NA | NA | NA | NA |
| PRO951 | NA | NA | NA | NA | NA | NA |
| PRO1123 | NA | NA | NA | NA | NA | NA |
| PRO1124 | NA | NA | NA | NA | NA | NA |
| PRO1125 | NA | NA | NA | NA | NA | NA |
| PRO1126 | NA | NA | NA | NA | NA | NA |
| PRO1134 | NA | NA | NA | NA | NA | NA |
| PRO963 | 1.1E+05 | 3.0E−04 | 2.8E−09 | NB | NB | NB |
| PRO966 | ND | ND | ND | NA | NA | NA |
| PRO1057 | 2.4E+05 | 6.7E−04 | 2.8E−09 | 1.3E+05 | 8.5E−03 | 6.6E−08 |
| PRO1058 | ND | ND | ND | ND | ND | ND |
| | NA | NA | NA | NA | NA | NA |
| PRO1059 | NA | NA | NA | NA | NA | NA |
| PRO1060 | NA | NA | NA | NA | NA | NA |
| PRO1061 | NA | NA | NA | NA | NA | NA |
| PRO1062 | NA | NA | NA | NA | NA | NA |
| PRO997 | NA | NA | NA | NA | NA | NA |
| PRO1013 | NA | NA | NA | NA | NA | NA |
| PRO830 | NA | NA | NA | NA | NA | NA |
| PRO1186 | 2.5E+05 | 7.2E−04 | 2.9E−09 | 2.2E+05 | 9.5E−03 | 4.3E−08 |
| PRO1430 | TBD | TBD | TBD | NA | NA | NA |
| PRO1479 | TBD | TBD | TBD | NA | NA | NA |
| PRO1482 | TBD | TBD | TBD | NA | NA | NA |
| PRO1431 | ND | ND | ND | NA | NA | NA |
| PRO1473 | ND | ND | ND | NA | NA | NA |

TABLE 26-continued

Affinities of different formats to PDL1, CD137 and serum albumin from different species.

| | | | | | | |
|---|---|---|---|---|---|---|
| PRO1476 | ND | ND | ND | NA | NA | NA |
| PRO1432 | ND | ND | ND | NA | NA | NA |

NA: not applicable
TBD: to be determined
NB: no significant binding
ND: not determined

Example 8: Blockade of the PDL1/PD-1 Interaction in a Cell-Based Reporter Gene Assay Using CHO Cells Expressing PDL1 and a TCR Activator Molecule, and Jurkat Cells Expressing PD-1 and Containing a Luciferase Gene Under the NFAT Response Element Methods In the bioluminescent reporter gene assay, engineered Jurkat T cells stably expressing NFAT (nuclear factor of activated T-cells)-luciferase reporter and human PD-1 act as effector T cells. Cells stably expressing human PDL1 and a T cell receptor (TCR) activator act as antigen presenting cells. Co-cultivating the two cell lines induces activation of the Jurkat NFAT pathway via crosslinking of TCR activator/TCR complex. Upon engagement of PDL1 expressing cells, PD-1 signaling in PD-1 effector T cells inhibits T-cell function, and results in NFAT pathway inhibition. Blockade of PD-1 and PDL1 receptor interaction leads to re-activation of the NFAT pathway.

35,000 CHO/PDL1/TCR activator (BPS Bioscience) cells in 100 µl of cell culture medium (DMEM/F12, 10% FCS) were added to the inner wells of a white cell culture plate and incubated for 16-20 h at 37° C. and 5% $CO_2$. Next day, 95 µl of cell culture medium was removed from each well and 50 µl of 2-fold concentrated serial dilutions of the respective molecules to be tested (from 3,000 to 0.46 ng/ml), including the reference avelumab, were added. Then, 50 µl of effector Jurkat cells expressing PD-1 (BPS Bioscience) diluted at 400,000 cell/ml in assay buffer (RPMI1640 with 10% FCS) were added to each well and plates were incubated 6 h at 37° C. and 5% $CO_2$. Finally, 50 µL luciferase substrate (BPS Bioscience) prepared according to manufacturer's protocol, was added per well and plates were incubated 30 min in the dark, luminescence was measured using Topcount.

Results

Figure 4:
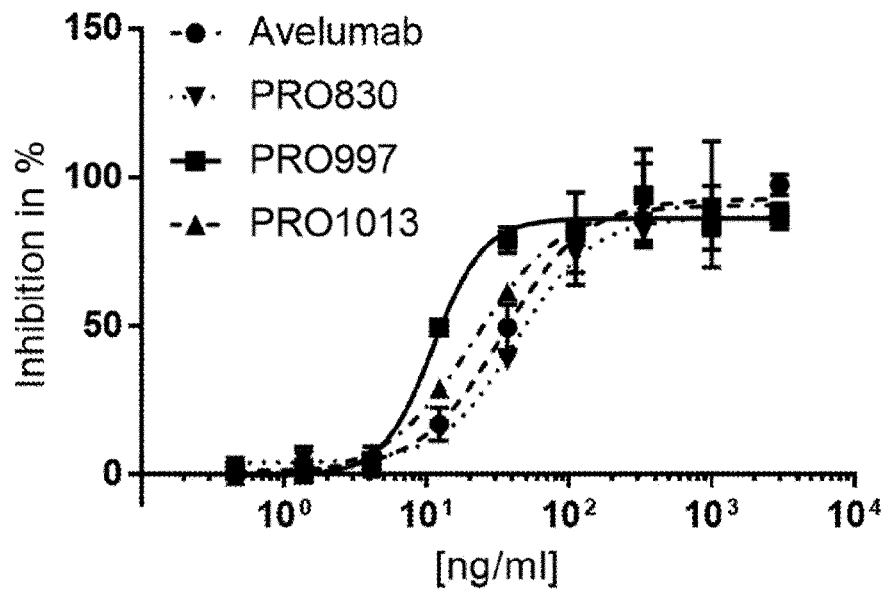
FIG. 4A shows an effect of CDR set and framework selection on neutralization of the PDL1/PD-1 interaction in the NFAT-Luciferase reporter gene assay. % inhibition proportional to the luminescence signal obtained in the assay is represented in function of the scFvs concentrations in ng/ml.
FIG. 4B shows an effect of domain optimization on neutralization potency of the PDL1/PD-1 interaction in the NFAT-Luciferase reporter gene assay. % inhibition proportional to the luminescence signal obtained in the assay is represented in function of the scDbs concentrations in ng/ml. Avelumab was used as reference.
Figure 4:
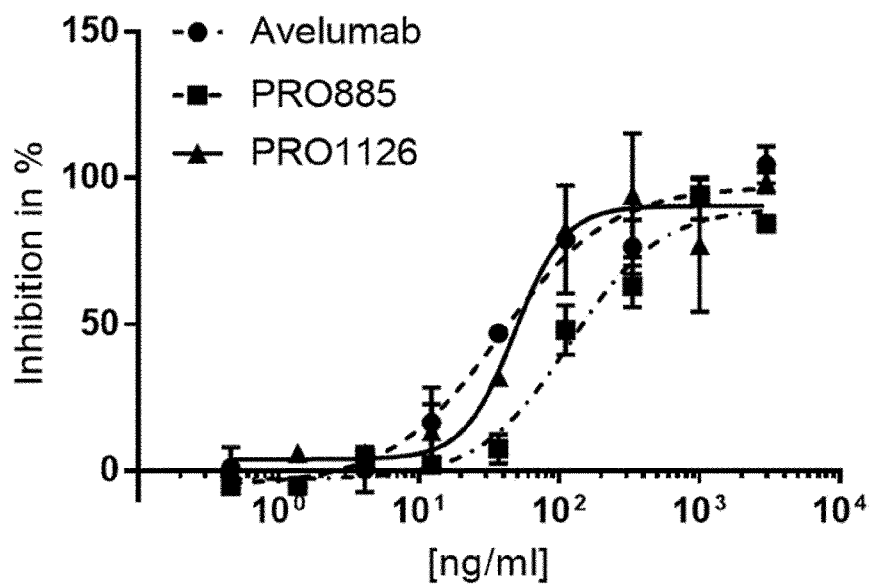

In order to assess the influence of the CDR set and framework selection on potency to neutralize the PDL1 binding to PD-1, three anti-PDL1 scFvs were tested in the NFAT reporter gene cell-based assay. PRO830 comprises the CDR set of clone 33-03-G02 grafted on a VH4 framework and PRO997 and PRO1013 comprise the CDR set of clone 37-20-B03 grafted on either a VH4 or a VH1 framework, respectively. PRO830 has the lowest potency of the three scFvs tested, $IC_{50}$ value of 42.88 ng/ml, and has similar potency as avelumab with an $IC_{50}$ value of 34.09 ng/ml. PRO997 is the most potent molecule. Potency of the same CDR set was about 2-fold higher when grafted on a VH4 framework than on VH1 framework. $IC_{50}$ values were 11.12 ng/ml versus 21.29 ng/ml, respectively. (FIG. 4A and Table 27)

Neutralization potency of the PDL1 binding to PD-1 was determined for bi-specific molecules possessing the 33-03-G02 PDL1 domain before (CDR graft) and after (structural graft) domain optimization. The CDR graft (PRO885) was compared to a structural graft (PRO1126). The domain optimization improved the neutralization potency by a factor of three with $IC_{50}$ values being 137.2 ng/ml for PRO885 and 48.15 ng/ml for PRO1126. (FIG. 4B and Table 27).

Figure 5:
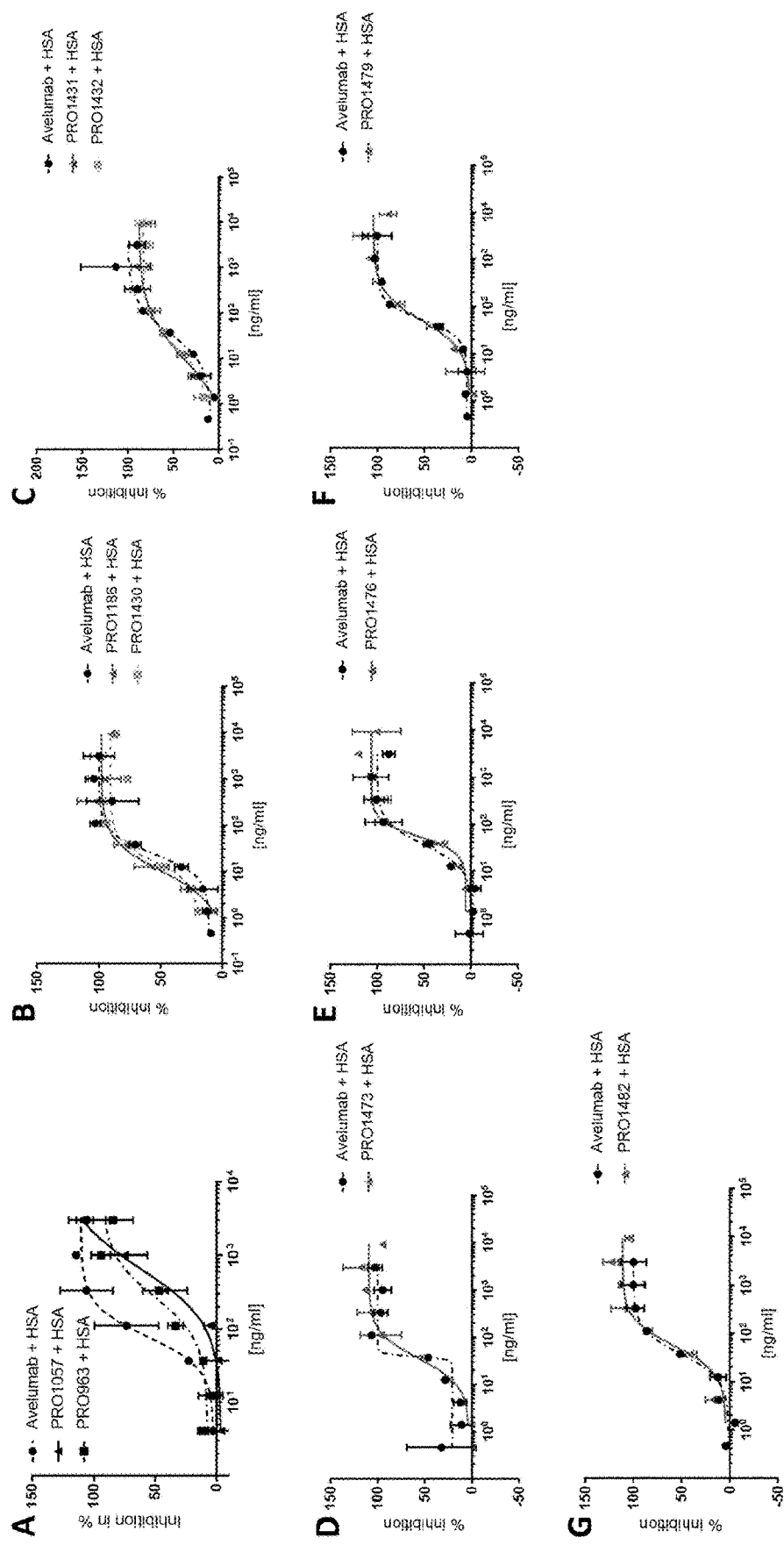
FIG. 5 Neutralization potency of the PDL1/PD-1 interaction in the reporter gene assay by scDb-scFvs PRO963 and PRO1057 (A), PRO1186 and PRO1430 (B), PRO1431 and PRO1432 (C), PRO1473 (D), PRO1476 (E), PRO1479 (F) and PRO1482 (G) in presence of recombinant human serum albumin. % inhibition proportional to the luminescence signal obtained in the assay is represented in function of the molecules concentrations in ng/ml. Avelumab was used as reference.

Potency to neutralize the PDL1/PD-1 interaction was also assessed for two tri-specific molecules possessing the anti-PDL1 domain of the CDR graft of clone 33-03-G02 and two different human serum albumin binding domain, for half-life extension. The HSA domain of PRO1057 is also binding mouse serum albumin. Experiments were performed in the presence of 25 mg/ml HSA. Neutralization potency ($IC_{50}$=665.1 ng/ml) was lower than for avelumab. (FIG. 5 and Table 27).

TABLE 27

Neutralization of PDL1 PD-1 interaction in the NFAT reporter gene assay.

| PRO ID | Clone ID PD-L1 | Clone ID CD137 | Clone ID SA | Format | Neutralization of PD-L1 in NF-AT Potency assay | | HSA |
|---|---|---|---|---|---|---|---|
| | | | | | $IC_{50}$ (ng/ml) | rel. $IC_{50}$* | |
| PRO885 | 33-03-G02 CDR | 38-02-A04 CDR | NA | scDb | 137.20 | 0.28 | no |
| PRO951 | 33-03-G02 CDR | 38-27-C05 CDR | NA | scDb | 88.50 | 0.47 | no |
| PRO963 | 33-03-G02 CDR | 38-02-A04 CDR | 19-01-H04 STR | scDb-scFv | 274.80 | 0.25 | yes |
| PRO1057 | 33-03-G02 CDR | 38-02-A04 CDR | 23-13-A01 STR | scDb-scFv | 665.10 | 0.10 | yes |
| PRO1059 | 33-03-G02 CDR | 38-02-A04 CDR | NA | Morrison-L | 93.76 | 0.52 | no |
| PRO1060 | 33-03-G02 CDR | 38-02-A04 CDR | NA | Morrison-H | 132.70 | 0.44 | no |
| PRO1062 | 33-03-G02 CDR | 38-27-C05 CDR | NA | Morrison-H | 96.55 | 0.68 | no |
| PRO997 | 37-20-B03 CDR | NA | NA | scFv | 11.12 | 3.07 | no |
| PRO1013 | 37-20-B03 CDR, VH1 | NA | NA | scFv | 21.29 | 1.60 | no |
| PRO830 | 33-03-G02 CDR | NA | NA | scFv | 42.88 | 0.73 | no |
| PRO1186 | 37-20-B03 sc01 | 38-02-A04 sc01 | 23-13-A01 sc03 | scDb-scFv | 10.17 | 2.31 | yes |
| PRO1430 | 37-20-B03 sc01 | 38-02-A04 sc013 | 19-01-H04 sc03 | scDb-scFv | 16.19 | 1.45 | yes |
| PRO1479 | 37-20-B03 sc09.1 | 38-02-A04 sc013 | 19-01-H04 sc03 | scDb-scFv | 50.36 | 1.04 | yes |
| PRO1482 | 37-20-B03 sc09.1 | 38-02-A04 sc013 | 19-01-H04 sc03 | scDb-scFv | 54.79 | 0.68 | yes |

TABLE 27-continued

Neutralization of PDL1 PD-1 interaction in the NFAT reporter gene assay.

| PRO ID | Clone ID PD-L1 | Clone ID CD137 | Clone ID SA | Format | Neutralization of PD-L1 in NF-AT Potency assay $IC_{50}$ (ng/ml) | rel. $IC_{50}$* | HSA |
|---|---|---|---|---|---|---|---|
| PRO1431 | 33-03-G02 sc18 | 38-02-A04 sc013 | 19-01-H04 sc03 | scDb-scFv | 9.83 | 3.73 | yes |
| PRO1473 | 33-03-G02 sc03 | 38-02-A04 sc013 | 19-01-H04 sc03 | scDb-scFv | 35.17 | 1.11 | yes |
| PRO1476 | 33-03-G02 sc03 | 38-02-A04 sc013 | 19-01-H04 sc03 | scDb-scFv | 53.53 | 0.66 | yes |
| PRO1432 | 33-03-G02 sc18 | 38-02-A04 sc013 | 19-01-H04 sc03 | scDb-scFv | 18.51 | 1.98 | yes |

NA: not applicable

*$IC_{50, Avelumab}$ (ng/ml)/$IC_{50, test molecule}$ (ng/ml)

Figure 6:
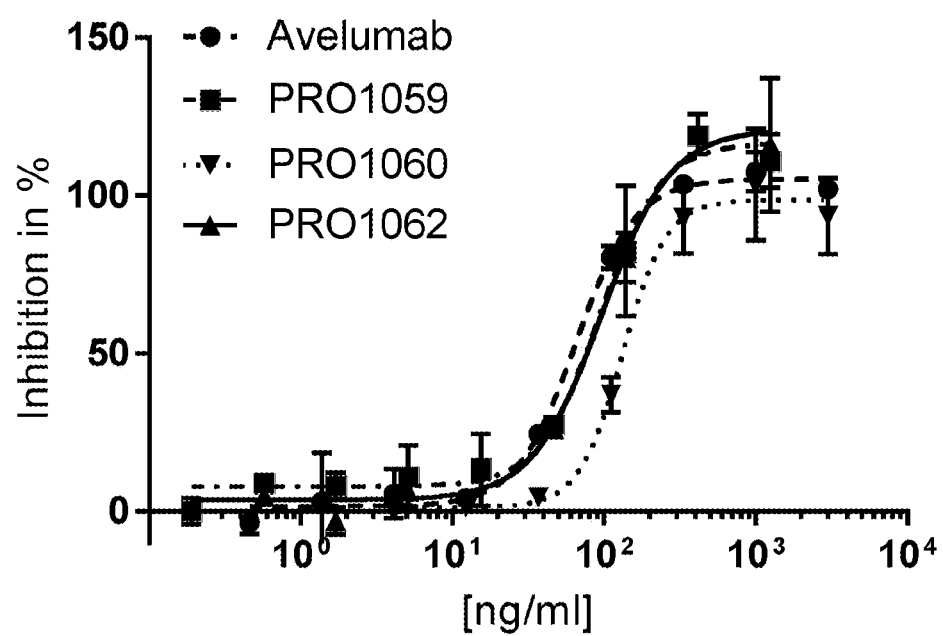
FIG. 6 Potency of bivalent molecule and influence of LC or HC scFv fusion in Morrison formats on neutralization potency of the PDL1/PD-1 interaction in the NFAT-Luciferase reporter gene assay. % inhibition proportional to the luminescence signal obtained in the assay is represented in function of the molecules concentrations in ng/ml. Avelumab was used as reference.

In serum, the so-called Morrison format was tested in the cell based potency reporter gene assay. In this format, one specificity is carried by the IgG moiety (bi-valency) and two scFvs with specificities to the second target are linked by flexible peptide linkers either to the heavy chain (HC) or light chain (LC) of the IgG. All Morrison molecules tested carried the anti-PDL1 domain of the CDR graft of clone 33-03-G02 on both IgG arms. The two constructs PRO1059 and PRO1060 differ by the fusion of two anti-CD137 scFvs either on the heavy chain (HC) or to the (LC). PRO1062 has the same architecture as PRO1060 with a different CD137 domain. Neutralization potencies of all molecules were similar (FIG. 6 and Table 27).

Example 9: Blockade of the Interaction of PDL1 with PD-1 and B7-1 Using Competition ELISA These assays were performed to assess the ability of PDL1 inhibitors to block the interaction between PDL1 and PD-1 or PDL1 and B.71. Different formats including scFvs, scDbs, scDb-scFv and Morrison were analyzed in the competition ELISA and compared to the reference IgG avelumab.

PDL1/PD-1 Competition ELISA

ELISA microplates coated overnight at 4° C. with 4 μg/ml human PD-1 were washed three times with 450 μl wash buffer per well. Plates were blocked for 1 hour at room temperature by adding 300 μl of PBS with 1% BSA and 0.2% tween (dilution buffer) to each well. Inhibitors were serially diluted in 3-fold steps to final concentrations ranging from 300 to 0.005 ng/ml in dilution buffer containing 1 ng/ml biotinylated human PDL1. The mixtures were pre-incubated for 1 hour at room temperature under gentle agitation on a rotating mixer (21 rpm) and added to the microplates after 3 wash cycles with 450 μl wash buffer per well. Plates were incubated for 1.5 hours at room temperature under gentle agitation, then 10 ng/ml streptavidin-polyHRP40 was added to each microplate well after three washes with 450 μl of wash buffer per well. After 1 h incubation at RT, plates were washed three times with 450 μl wash buffer and TMB substrate solution was added. The enzymatic reaction was stopped after 6 minutes by addition of 1 M HCl and absorbance was measured at 450 nm using 690 nm as a reference wavelength. For calculation of $IC_{50}$ values, a four-parameter logistic (4PL) curve fit was performed in Graph Pad Prism using reference subtracted values.

Figure 7:
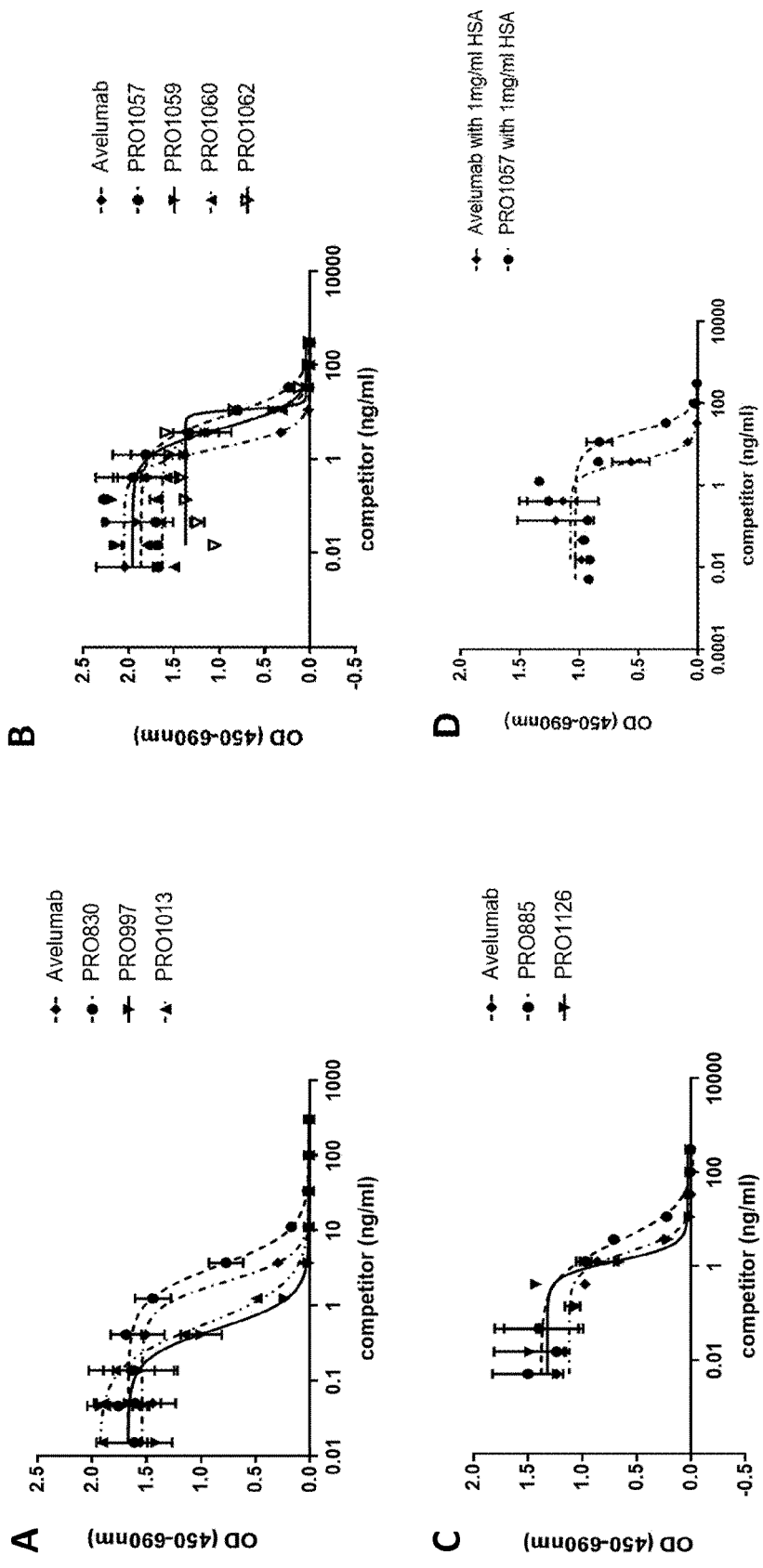
FIG. 7 PD-1/PDL1 competition ELISA. All molecules potently blocked the interaction between PD-1 and PDL1, with similar or smaller $IC_{50}$ values than the reference IgG Avelumab.

As illustrated in FIG. 7 and Table 28, all PDL1 inhibitors blocked the interaction of PD-1 with PDL1 when tested in the competition ELISA. The scFv PRO830 blocked the interaction with similar potency while PRO997 and PRO1013 exhibited significantly lower $IC_{50}$ values than avelumab and are thus more potent inhibitors. When combined into multispecific formats, i.e. scDbs or Morrisons, all molecules conserved their inhibiting properties. PRO885 was less potent than avelumab whereas a lower $IC_{50}$ value was determined for PRO1126 comprising an improved anti-PDL1 domain. The Morrison formats were slightly less potent when compared to avelumab. The neutralizing effect of PRO1057 was also shown in presence of human serum albumin, where $IC_{50}$ values were approximately two-fold higher.

PDL1/B7-1 Competition ELISA

ELISA microplates coated overnight at 4° C. with 4 μg/ml human B7-1 were washed three times with 450 μl wash buffer per well. Plates were blocked for 1 hour at room temperature by adding 300 μl of PBS with 1% BSA and 0.2% tween (dilution buffer) to each well. Inhibitors were serially diluted in 3-fold steps to final concentrations ranging from 900 to 0.015 ng/ml in dilution buffer containing 40 ng/ml biotinylated PDL1. The mixtures were pre-incubated for 1 hour at room temperature under gentle agitation on a rotating mixer (21 rpm) and added to the microplates after 3 wash cycles with 450 μl wash buffer per well. Plates were incubated for 1.5 hours at room temperature under gentle agitation, then 10 ng/ml streptavidin-polyHRP40 was added to each microplate well after three washes with 450 μl of wash buffer per well. After 1 h incubation at RT, plates were washed three times with 450 μl wash buffer and TMB substrate solution was added. The enzymatic reaction was stopped after 6 minutes by addition of 1 M HCl and absorbance was measured at 450 nm using 690 nm as a reference wavelength. For calculation of $IC_{50}$ values, a four-parameter logistic (4PL) curve fit was performed in Graph Pad Prism using reference subtracted values.

Figure 8:
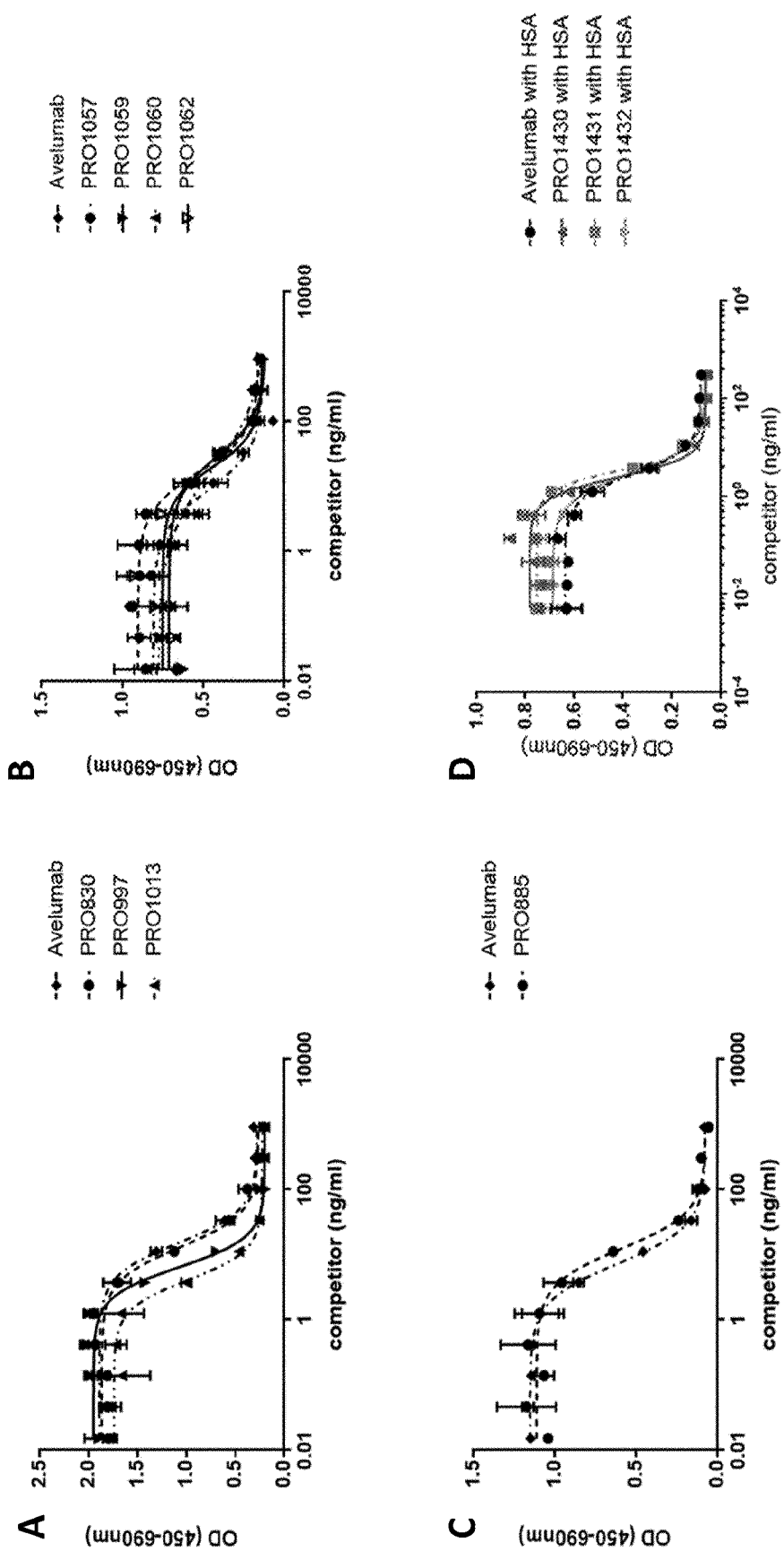
FIG. 8 B7-1/PDL1 competition ELISA. Similar to avelumab, all molecules potently blocked the interaction between B7-1 and PDL1.

Except for PRO1126, all PDL1 inhibitors were also tested for their ability to block the interaction of PD-1 with B7-1. PRO830 showed similar potency to avelumab, whereas lower $IC_{50}$ values were determined for PRO997 and PRO1013. All scDbs and Morrisons also inhibited the interaction between PDL1 and B.7-1. The scDb PRO885 exhibited similar potency to avelumab, whereas the $IC_{50}$ values for the Morrisons were about 2-3.4 fold lower. Data shown in FIG. 8 and Table 28.

TABLE 28

Blockade of the interaction of PDL1 with PD-1 and B7-1 using competition ELISA.

| PRO ID | Clone ID PD-L1 | Clone ID CD137 | Clone ID SA | Format | Blocking of PD-L1/PD-1 interaction | | Blocking of PD-L1/B7.1 interaction | |
|---|---|---|---|---|---|---|---|---|
| | | | | | $IC_{50}$ (ng/ml) | rel. $IC_{50}$ | $IC_{50}$ (ng/ml) | rel. $IC_{50}$* |
| PRO885 | 33-03-G02 CDR | 38-02-A04 CDR | NA | scDb | 8.35 | 0.17 | 12.2 | 0.59 |
| PRO951 | 33-03-G02 CDR | 38-27-C05 CDR | NA | scDb | 9.50 | 0.15 | 9.30 | 0.78 |
| PRO1126 | 33-03-G02 STR | 38-02-A04 CDR | NA | scDb | 1.28 | 1.59 | TBD | TBD |
| PRO1057 | 33-03-G02 CDR | 38-02-A04 CDR | 23-13-A01 STR | scDb-scFv | 8.61 | 0.20 | 16.29 | 0.53 |
| PRO1059 | 33-03-G02 CDR | 38-02-A04 CDR | NA | Morrison-L | 4.54 | 0.37 | 28.98 | 0.30 |
| PRO1060 | 33-03-G02 CDR | 38-02-A04 CDR | NA | Morrison-H | 5.67 | 0.30 | 17.42 | 0.49 |
| PRO1062 | 33-03-G02 CDR | 38-27-C05 CDR | NA | Morrison-H | 11.33 | 0.32 | 19.53 | 0.51 |
| PRO997 | 37-20-B03 CDR | NA | NA | scFv | 0.50 | 4.16 | 6.359 | 2.34 |
| PRO1013 | 37-20-B03 CDR, VH1 | NA | NA | scFv | 0.57 | 3.67 | 4.05 | 3.68 |
| PRO830 | 33-03-G02 CDR | NA | NA | scFv | 3.40 | 0.61 | 12.87 | 1.16 |
| PRO1186 | 37-20-B03 sc01 | 38-02-A04 sc01 | 23-13-A01 sc03 | scDb-scFv | 1.74 | 1.26 | 7.81 | 1.58 |
| PRO1430 | 37-20-B03 sc01 | 38-02-A04 sc013 | 19-01-H04 sc03 | scDb-scFv | 1.92 | 0.73 | 2.42 | 1.15 |
| PRO1479 | 37-20-B03 sc09.1 | 38-02-A04 sc013 | 19-01-H04 sc03 | scDb-scFv | 2.65 | 0.86 | 10.71 | 1.38 |
| PRO1482 | 37-20-B03 sc09.1 | 38-02-A04 sc013 | 19-01-H04 sc03 | scDb-scFv | 1.78 | 1.24 | 8.18 | 1.51 |
| PRO1431 | 33-03-G02 sc18 | 38-02-A04 sc013 | 19-01-H04 sc03 | scDb-scFv | 2.75 | 0.51 | 3.31 | 0.84 |
| PRO1473 | 33-03-G02 sc03 | 38-02-A04 sc013 | 19-01-H04 sc03 | scDb-scFv | 4.14 | 0.56 | 8.89 | 1.49 |
| PRO1476 | 33-03-G02 sc03 | 38-02-A04 sc013 | 19-01-H04 sc03 | scDb-scFv | 2.84 | 0.80 | 9.49 | 1.10 |
| PRO1432 | 33-03-G02 sc18 | 38-02-A04 sc013 | 19-01-H04 sc03 | scDb-scFv | 3.26 | 0.43 | 2.83 | 0.99 |

NA: not applicable

*: $IC_{50, Avelumab}$ (ng/ml)/$IC_{50, test\ molecule}$ (ng/ml)

Example 10: Assessment of the Stimulatory Effect of Concomitant PDL1 Blockade and CD137 Stimulation in a Cell-Based Assay Using Human PBMC Stimulated with Superantigen SEA In this experiment, the synergistic effect of PD-1/PDL1 inhibition and CD137 agonism was assessed. The assay used peripheral blood mononuclear cells (PBMC) that were stimulated with the superantigen Staphylococcal Enterotoxin A (SEA) in order to induce expression of PDL1 on antigen-presenting cells (APC) and T cells respectively and CD137 on T-cells. By applying anti-PDL1×CD137 molecules two T-cell regulatory signaling pathways were targeted concomitantly: inhibition of the inhibitory PD-1/PDL1 pathway as well as activation of the CD137 pathway via formation of an immunological synapse mediated by the bispecific anti-PDL1×CD137 molecule (PRO885). The activation of T-cells was assessed by the secretion of Interleukin-2 (IL-2) and compared to the effect mediated by PDL1 inhibition mediated by the benchmarking reference antibody avelumab. In addition, the anti-PDL1 scFv, PRO997, was tested and compared to avelumab in the same experimental setup.

Peripheral blood mononuclear cells (PBMC) were isolated from fresh human whole blood by means of density gradient centrifugation. Then, PBMC were depleted for NK cells using anti-CD56 antibody and the MACS cell separation kit (Miltenyi Biotec). Next, 100,000 PBMCs per well were added to the 96-well plate, followed by the addition of serial dilutions of PRO885, PR0997 and avelumab in assay buffer containing SEA at a concentration of 10 ng/ml. After 96 hours of incubation at 37° C. and 5% $CO_2$, cell supernatants were harvested and human Interleukin-2 (IL-2) levels in the culture supernatants were quantified using the IL-2 human ELISA MAX assay from BioLegend according to kit instructions. IL-2 concentrations were interpolated from a IL-2 standard curve, back-calculated and plotted against avelumab and PRO885 concentrations for calculation of $EC_{50}$ values.

Figure 9:
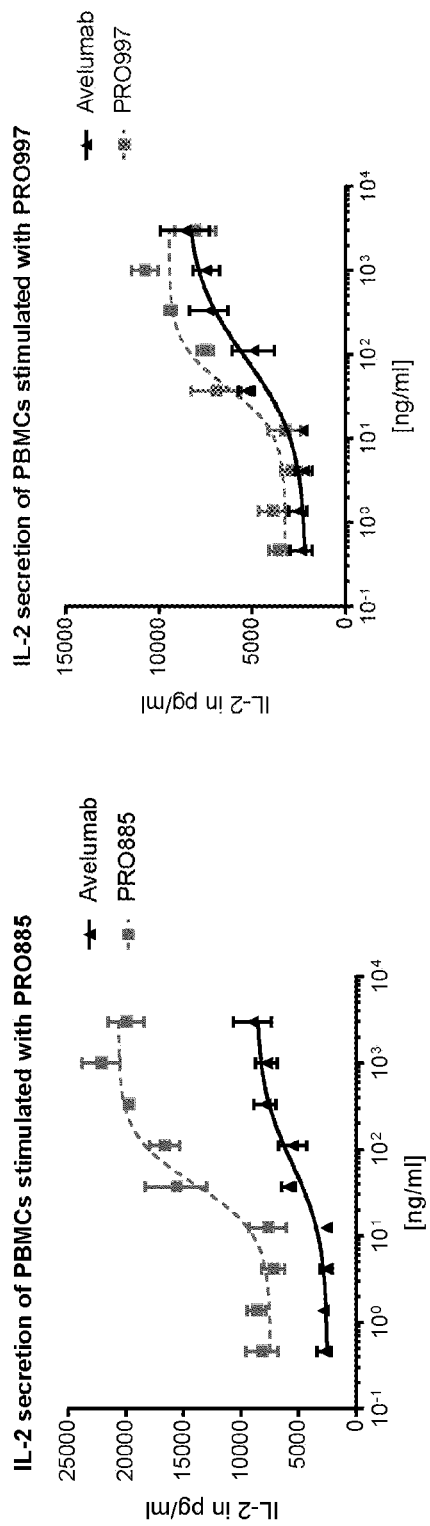
FIG. 9 Ex vivo T cell activation assay. PBMC were stimulated with 10 ng/ml SEA and treated with serial dilutions of the scFv PRO997 or the scDb PRO885 for 96 h. Activation of T-cells was assessed by quantification of IL-2 in harvested supernatants by ELISA. Treatment with PRO885 and PRO997 resulted in pronounced IL-2 secretion. PRO997 showed higher potency than Avelumab. PRO885 showed much increased effect size when compared to Avelumab. Data were fitted using sigmoidal 4PL fit (GraphPad Prism).

As shown in FIG. 9, IL-2 was secreted by T-cells following concomitant blockade of PD-1/PDL1 interaction and stimulation of CD137 by the addition of the bispecific molecule PRO885. When compared to avelumab, PRO885 showed higher T cell activation and better potency (PRO885, $EC_{50}$=39.92 ng/ml; avelumab, $EC_{50}$=69.89 ng/ml, Table 29). This finding demonstrates that the bispecific anti-PDL1×CD137 scDb PRO885 is able to induce stronger T cell stimulation than mere PDL1 blockade by avelumab. Moreover, the high-affinity anti-PDL1 scFv PRO997 was found to be more potent in stimulation of T-cells than avelumab (PRO997, $EC_{50}$=40.86 ng/ml; avelumab, $EC_{50}$=90.18 ng/ml, Table 29).

TABLE 29

$EC_{50}$ values for PRO885 and PRO997 in PBMC assay using SEA stimulation.

| | Avelumab | PRO885 | | Avelumab | PRO997 |
|---|---|---|---|---|---|
| Bottom | 2479 | 7463 | Bottom | 2117 | 3226 |
| Top | 8687 | 20663 | Top | 8588 | 9480 |
| EC50 in ng/ml | 69.89 | 39.92 | EC50 in ng/ml | 90.18 | 40.86 |
| R square | 0.8589 | 0.9052 | R square | 0.8783 | 0.867 |

Example 11: Assessment of the Anti-Tumor Efficacy of the Anti-PDL1 Antibody in the Human Cell Line-Derived Lung Cancer Xenograft Model HCC827

Anti-tumor activity of the anti-PDL1 IgG1 antibody PRO1137 (SEQ ID Nos: 90 and 91) was assessed in human HCC827 NSCLC xenografts using the immunodeficient NOG mice strain from Taconic and allogeneic human peripheral blood mononuclear cells. Engrafted human T lymphocytes show xeno-reactivity against foreign major histocompatibility (MHC) class I and II and other antigens from mice cells. As a result, T lymphocytes cause an inflammatory infiltrate in different organs that leads to death of the animals after several weeks, a process known as xenograft-versus-host disease (xGVHD). Treatment with immunomodulatory antibodies such as anti-PDL1 and anti-CD137 was shown to exacerbate xGVHD (Sanmamed M F et al. Nivolumab and urelumab enhance antitumor activity of human T lymphocytes engrafted in Rag2−/−IL2Rgnull immunodeficient mice. Cancer Res 2015; 75(17):3466-3478).

Study Set-Up and Treatment Schedule:

Female NOG mice received unilateral injections of $5\times10^6$ HCC827 cells. Cells were injected in a mixture of 50% cell suspension in PBS and 50% matrigel in a total injection volume of 100 µl. After injection of tumor cells into NOG mice and successful tumor engraftment (median group tumor volume of 80-100 mm$^3$), mice were substituted with $5\times10^6$ human PBMCs by intravenous injection. On the day of randomization, four mice of each group were reconstituted with PBMCs of donor A and another four mice with PBMCs of donor B. Treatment started 1-2 hours after the injection of PBMCs and was applied as follows.

| group ID | compound | total daily dose [mg] | Relative units (r.U) | dosing days | route | no. of mice |
|---|---|---|---|---|---|---|
| 1 | Vehicle | na | na | 0, 3, 7, 10 | ip | 8 |
| 2 | PRO1137 | 0.2 | 1 r.U | 0, 3, 7, 10 | ip | 8 |

The 0.2 mg dose for PRO1137 was set to achieve the same relative activity modeled for a 0.1 mg dose of avelumab (per mouse) based on in vitro activity of the antibodies to block the PD-1/PDL1 interaction in the NF-AT reporter gene assay. Thus, a dose of 0.2 mg of PRO1137 could be represented as one relative unit (1 r.U) in relation to the 0.1 mg dose of avelumab. Body weight measurements and tumor volume by caliper measurements were performed twice weekly. Animals were terminated at defined time-points depending on the study results. All animals were terminated at the 'same' time-point (on day 17 and day 18). Sample collection and processing of the first half of each group were performed on the first day, and sample collection and processing of the second half of each group were performed on the following day for capacity reasons. Animals reconstituted with PBMCs from the two different donors were equally represented in the two sampling cohorts.

Figure 10:
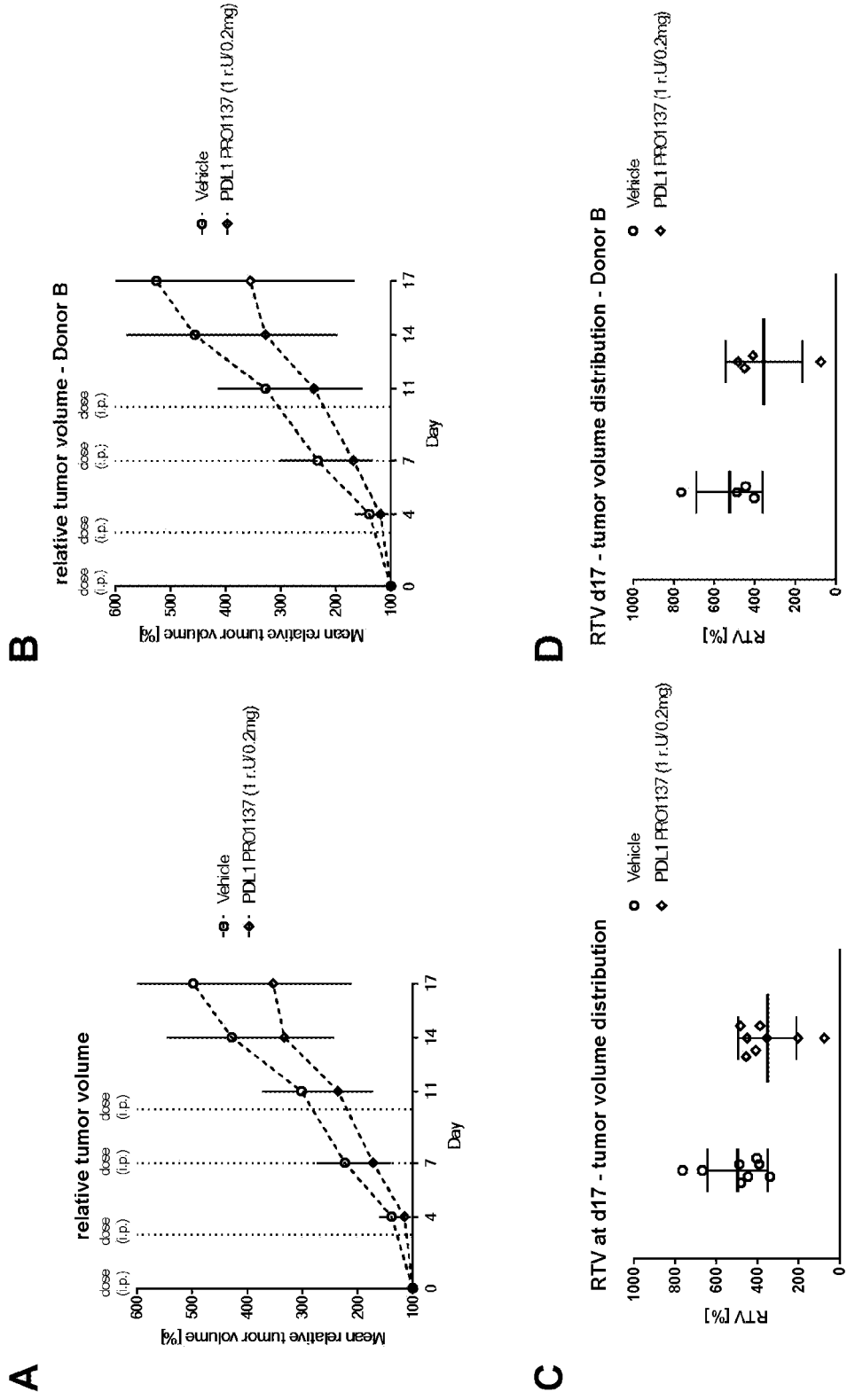
FIG. 10 Anti-tumor activity of the anti-PDL1 IgG1 (PRO1137) therapy in human HCC827 NSCLC xenografts using the immunodeficient NOG mice strain and allogeneic human peripheral blood mononuclear cells (hPBMC). Mice were treated with the anti-PDL1 IgG1 (PRO1137) or vehicle i.p. on days 0, 3, 7 and 10. Tumor volumes were measured twice per week until mice were sacrificed on day 17 and 18. Tumor volumes were normalized to the tumor volume at the start of the treatment (relative tumor volume). (A) Mean relative tumor volumes (n=8 mice per group) of mice reconstituted with PBMCs from two donors. The dotted line indicates the time of treatment. (B) Mean relative tumor volumes from mice reconstituted with PBMCs from donor B (n=4 mice per group). (C) Individual relative tumor volumes of mice reconstituted with PBMCs from two donors. Each symbol represents an individual animal within the same treatment group. (D) Individual relative tumor volumes of mice reconstituted with PBMCs from donor B. Each symbol represents an individual animal within the same treatment group.
Figure 11:
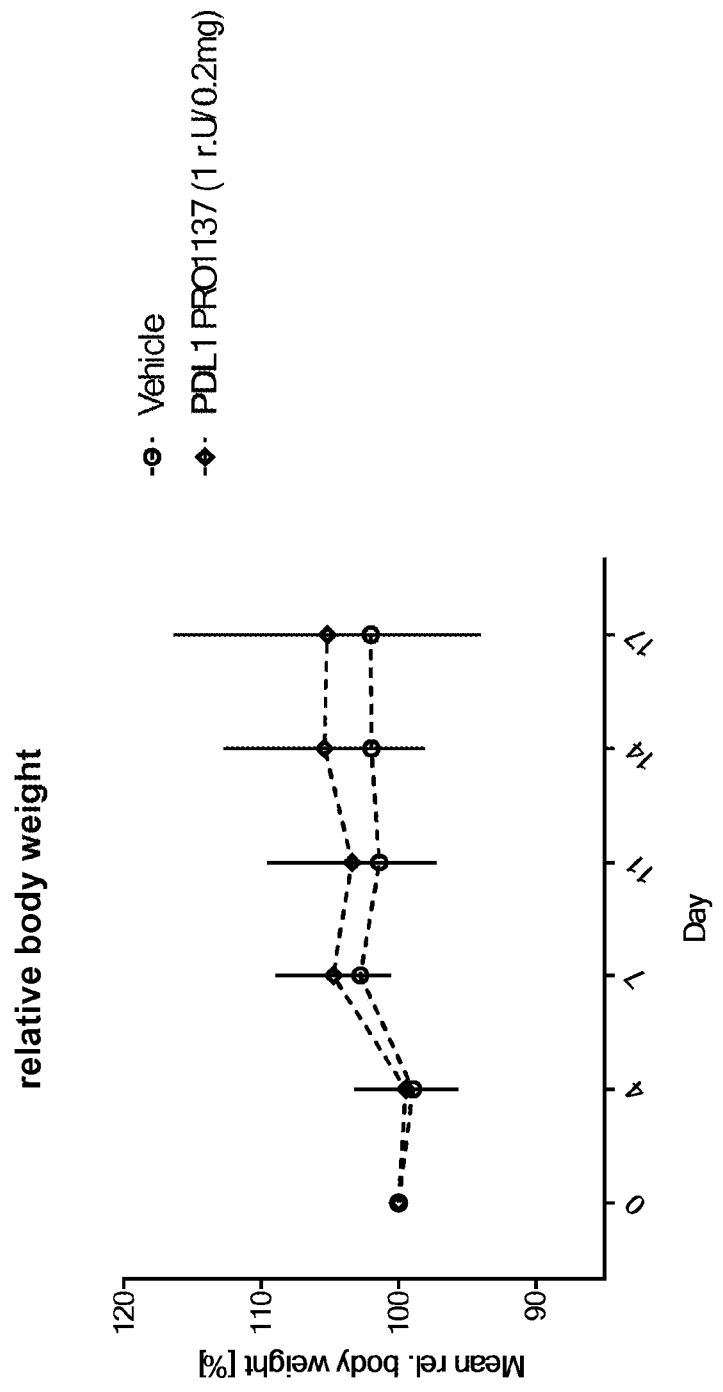
FIG. 11 HCC827 xenograft in hPBMC substituted NOG mice. Body weight of HCC827 challenged NOG mice upon treatment with the anti-PDL1 IgG1 (PRO1137) therapy. Body weight was measured twice per week until mice were sacrificed on day 17 and 18. Body weight was normalized to the body weight at the start of the treatment (relative body weight).

Results:

Anti-tumor activity of the anti-PDL1 PRO1137 in human HCC827 NSCLC xenografts using the immunodeficient NOG mice strain and allogeneic human peripheral blood mononuclear cells (hPBMC) was assessed by measuring tumor volumes (FIG. 10). Tumor volumes were measured twice per week until mice were sacrificed on day 17 or day 18. Tumor volumes were normalized to the tumor volume at the start of the treatment (relative tumor volume). As shown in FIG. 10, treatment with PRO1137 monoclonal antibodies showed reduced tumor growth in comparison to the vehicle control group. Notably, treatment with PRO1137 did not lead to loss in median body weight implicating that the molecule is well tolerated at the dose levels tested (FIG. 11).

Example 12: Assessment of the Anti-Tumor Efficacy of PRO1137 in NOG Mice Engrafted with Human Umbilical Cord Blood-Derived CD34+ Hematopoietic Stem Cells (UCB HSCs)

Anti-tumor activity of PRO1196 (anti-PDL1 IgG1; SEQ ID NOs: 92 and 93) was compared to a vehicle therapy or to avelumab in human HCC827 NSCLC xenografts using NOG mice strain engrafted with human umbilical cord blood-derived CD34+ hematopoietic stem cells (UCB HSCs).

Study Set-Up and Treatment Schedule:

Female NOG mice engrafted with human umbilical cord blood-derived CD34+ hematopoietic stem cells (UCB HSCs) were subcutaneously injected with HCC827 NSCLC cells. The mice received unilateral injections of $5\times10^6$ HCC827 cells. Cells were injected in a mixture of 50% cell suspension in PBS and 50% matrigel in a total injection volume of 100 µl. After injection of tumor cells into NOG mice and successful tumor engraftment (median group tumor volume of 80-100 mm$^3$), the mice (n=10) were randomized into treatment groups:

| group ID | compound | total daily dose [mg] | dosing days | route | no. of mice |
|---|---|---|---|---|---|
| 1 | Vehicle (palivizumab) | 0.1 mg | 0, 5, 10, 15, 20 | ip | 10 |
| 2 | anti-PDL1 IgG (PRO1196) | 0.1 mg | 0, 5, 10, 15, 20 | ip | 10 |
| 3 | avelumab | 0.1 mg | 0, 5, 10, 15, 20 | ip | 10 |

Body weight measurements and tumor volume measurements by caliper were performed twice weekly. Tumors were harvested on day 25, 29 and 30 post-treatment.

Figure 12:
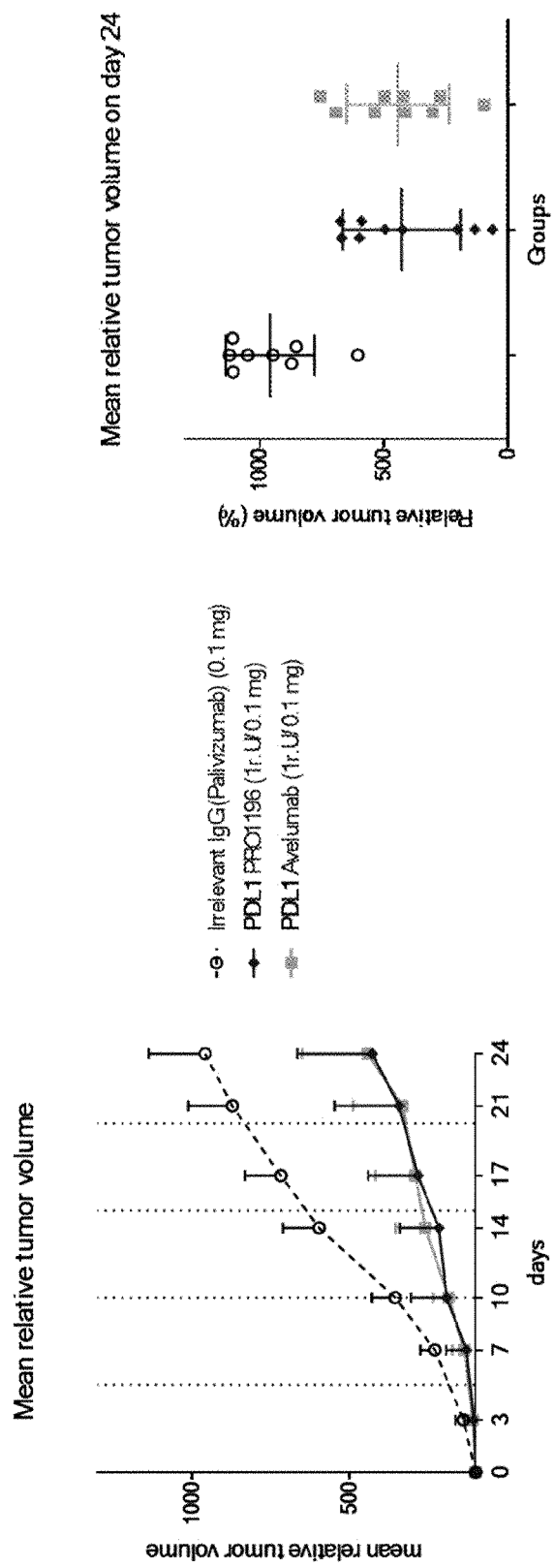
FIG. 12 Assessment of the anti-tumor efficacy of anti-PDL1 IgG1 (PRO1196) in human HCC827 NSCLC xenografts in NOG mice engrafted with human umbilical cord blood-derived CD34+ hematopoietic stem cells (UCB HSCs). Anti-tumor activity of PRO1196 (0.1 mg) was compared to avelumab (0.1 mg) or a vehicle treatment (palivizumab, 0.1 mg). Mice were treated on day 0, 5, 10, 15 and 20 (dotted line). Tumor growth and body weight were recorded twice weekly. Tumor volumes were normalized to the tumor volume at the start of the treatment (relative tumor volume).

Results:

Anti-tumor activity of PRO1196 (anti-PDL1 IgG1; SEQ ID NOs: 92 and 93) in human HCC827 NSCLC xenografts using the immunodeficient NOG mice strain engrafted with human umbilical cord blood-derived CD34+ hematopoietic stem cells (UCB HSCs) was assessed by measuring tumor volumes (FIG. 12). Tumor volumes were measured twice per week until mice were sacrificed on day 25, 29 or 30. Tumor volumes were normalized to the tumor volume at the start of the treatment (relative tumor volume). As shown in FIG. 12, treatment with PRO1196 as well as with avelumab resulted in a stabilization of the tumor growth in comparison to the control group.

Example 13: Assessment of the Anti-Tumor Efficacy of PDL1 Blockade and Concomitant Localized Stimulation of CD137 in a Syngeneic MC38 Colon Cancer Model In addition, anti-tumor activity of the multispecific antibody comprings the PDL1 domain of the present invention will be tested in a MC38 colon carcinoma model in syngeneic C57BL/6 mice with an intact immune system. This model has been used by others to show enhanced antitumor activity by combination treatment with CD137 agonists and PD-1/PDL1 antagonists (Chen S et al. Combination of 4-1BB agonist and PD-1 antagonist promotes antitumor effector/memory CD8 T cells in a poorly immunogenic tumor model. Cancer Immunol Res 2014; 3(2): 149-160 and Rodriguez-Ruiz M E et al. Abscopal effects of radiotherapy are enhanced by combined immunostimulatory mAbs and are dependent on CD8 T cells and crosspriming. Cancer Res 2016; 76(20):5994-6005).

Since both, the anti-CD137 domain and the anti-PDL1 domain of the multispecific antibody to be tested are not cross-reactive to mouse PDL1 and mouse CD137 an engineered human CD137 knock-in model established by CrownBio will be used. In this model, the extracellular and transmembrane domain of mouse CD137 was replaced by the respective sequence of human CD137 in the C57BL/6 mice background using the CRISPR/Cas9 system. In addition, a modified MC38 tumor cell line expressing human PDL1 under control of a CMV promoter instead of mouse PDL1 will be used. Effects of said multispecific antibody on tumor volume will be compared to combination treatment with the humanized IgG1 containing the same PDL1 specific variable domain as said multispecific antibody and with the humanized IgG4 with the same CD137 specific variable domain. To provide further evidence of localized antitumor immune response, frequency of tumor infiltrating lymphocytes such as CD8+, CD4+ and regulatory T cells will be analyzed by flow cytometry. To explore modulation of the immune system systemically following anti-CD137/anti-PDL1 treatment, the frequency of CD4+ and CD8+ T cells in liver and spleen will be analyzed by flow cytometry and possibly immunohistochemistry. Moreover, systemic IFNγ levels could be analyzed using a quantitative ELISA method. To further characterize the safety profile of the anti-CD137/anti-PDL1 combination therapy, clinical chemistry pathology parameters associated primarily with liver toxicity (observed for anti-CD137 therapy in the clinic), such as increased levels of alanine aminotransferase, glutamate dehydrogenase and aspartate aminotransferase could be assessed.

The invention claimed is:

1. An isolated antibody having a binding specificity for human PDL1 comprising an HCDR1, HCDR2, HCDR3 sequence of SEQ ID NO: 1, SEQ ID NO: 2 and SEQ ID NO: 3, respectively, and an LCDR1, LCDR2 and LCDR3 sequence of SEQ ID NO: 17, SEQ ID NO: 18 and SEQ ID NO: 19, respectively.

2. The antibody of claim 1, wherein the antibody comprises a heavy chain variable region (VH), wherein said VH is VH3 or VH4.

3. The antibody of claim 1, wherein the antibody comprises a light chain variable region (VL), wherein said VL comprises Vκ frameworks FR1, FR2 and FR3 and a framework FR4, which is selected from a Vκ FR4 and Vλ FR4.

4. The antibody of claim 2, wherein the antibody comprises a heavy chain variable region VH3.

5. The antibody of claim 3, wherein said VL comprises Vκ1 or Vκ3 FR1, FR2 and FR3.

6. The antibody of claim 5, wherein said VL comprises Vκ1 FR1, FR2 and FR3.

7. The antibody of claim 3, wherein said VL comprises a Vκ FR4 selected from Vκ1 FR4 or Vκ3 FR4.

8. The antibody of claim 3, wherein said VL comprises a Vλ FR4 that is at least 90 percent identical to an amino acid sequence selected from any of SEQ ID NO: 64 to SEQ ID NO: 70.

9. The antibody of claim 8, wherein said VL comprises a Vλ FR4 that is selected from any of SEQ ID NO: 64 to SEQ ID NO: 70.

10. The antibody of claim 9, wherein said Vλ FR4 is a Vλ FR4 having the amino acid sequence according to SEQ ID NO: 64 or 65.

11. The antibody of claim 10, wherein said Vλ FR4 is a Vλ FR4 having the amino acid sequence according to SEQ ID NO: 64.

12. The antibody of claim 1, wherein the antibody comprises a heavy chain variable region comprising an amino acid sequence that is at least 90 percent identical to the amino acid sequence selected from the group consisting of SEQ ID NO: 14, SEQ ID NO: 15, SEQ ID NO: 16; and a light chain variable region comprising an amino acid sequence that is at least 90 percent identical to the amino acid sequence selected from the group consisting of SEQ ID NO: 26 and SEQ ID NO: 27.

13. The antibody of claim 12, wherein the antibody comprises a heavy chain variable region comprising an amino acid sequence that is at least 90 percent identical to the amino acid sequence according to SEQ ID NO: 14 or 16; and a light chain variable region comprising an amino acid sequence that is at least 90 percent identical to the amino acid sequence selected from the group consisting of SEQ ID NO: 26 and SEQ ID NO: 27.

14. The antibody of claim 13, wherein the antibody comprises a heavy chain variable region comprising an amino acid sequence that is at least 90 percent identical to the amino acid sequence of SEQ ID NO: 16.

15. The antibody of claim 12, wherein the antibody comprises a light chain variable region comprising an amino acid sequence that is at least 90 percent identical to the amino acid sequence of SEQ ID NO: 27.

16. The antibody of claim 12, wherein the antibody is selected from the group consisting of: a monoclonal antibody, a chimeric antibody, a Fab, an Fv, an scFv, dsFv, and a scAb.

17. The antibody of claim 16, wherein the antibody is an scFv.

18. The antibody of claim 16, which is an scFv, wherein said scFv has an amino acid sequence selected from the group consisting of SEQ ID NO: 29, SEQ ID NO: 30, and SEQ ID NO: 31.

19. The antibody of claim 18, wherein said scFv has the amino acid sequence of SEQ ID NO: 31.

20. The antibody of claim 1, comprising: (a) a VH sequence of SEQ ID NO: 14 and a VL sequence of SEQ ID NO: 26; or (b) a VH sequence of SEQ ID NO: 15 and a VL sequence of SEQ ID NO: 26; or (c) a VH sequence of SEQ ID NO: 16 and a VL sequence of SEQ ID NO: 27.

21. The antibody of claim 20, wherein said antibody:
(i) binds to human PDL1 with a dissociation constant (KD) of less than 5 nM as measured by surface plasmon resonance (SPR);
(ii) binds to human PDL1 with a $K_{off}$ rate of $10^{-3}$ $s^{-1}$ or less as measured by SPR;
(iii) binds to human PDL1 with a $K_{on}$ rate of at least $10^3$ $M^{-1}s^{-1}$ or greater as measured by SPR;
(iv) is cross-reactive with Macaca fascicularis (Cynomolgus) PDL1 and binds to Cynomolgus PDL1 with a KD of less than 5 nM as measured by surface plasmon resonance;
(v) is non-cross-reactive to Mus musculus PDL1 as measured by SPR;
(vi) does not bind to human PDL2 as measured by SPR; and
(vii) has the ability to neutralize PDL1/PD-1 interaction with greater than 4 times potency relative to that of avelumab (relative potency), and wherein said relative potency is the ratio of the $IC_{50}$ value in ng/ml of avelumab as measured in the NFAT reporter gene assay to the $IC_{50}$ value in ng/ml of said antibody, wherein said antibody is an scFv, as measured in the NFAT reporter gene assay.

22. The antibody of claim 20, wherein said antibody:
(i) when in scFv format, has a melting temperature (Tm), determined by differential scanning fluorimetry, of at least 60° C., wherein said antibody is formulated in 50 mM phosphate-citrate buffer at pH 6.4, 150 mM NaCl; and
(ii) when in scFv format, has a loss in monomer content, after storage for at least two weeks, at 4° C., of less than 15%, when said antibody is at a starting concentration of 10 mg/ml, wherein said antibody is formulated in 50 mM phosphate citrate buffer with 150 mM NaCl at pH 6.4.

23. The antibody of claim 1, wherein said antibody is comprised in a multispecific molecule.

24. The antibody of claim 23, wherein said multispecific molecule additionally comprises at least a second antibody or a ligand for a receptor.

25. A pharmaceutical composition comprising the isolated antibody of claim 1, and a pharmaceutically acceptable carrier.

26. A nucleic acid encoding an isolated antibody having a binding specificity for human PDL1 comprising an HCDR1, HCDR2, HCDR3 sequence of SEQ ID NO: 1, SEQ ID NO: 2 and SEQ ID NO: 3, respectively, and an LCDR1, LCDR2 and LCDR3 sequence of SEQ ID NO: 17, SEQ ID NO: 18 and SEQ ID NO: 19, respectively.

27. A method of producing the antibody of claim 1, the method comprising the steps of culturing a host cell comprising a nucleic acid encoding the antibody of claim 1 and expressing said antibody.

28. A method of treating a proliferative disease, comprising the step of administering an effective amount of the antibody of claim 1 to a subject in need thereof, wherein said proliferative disease is cancer.

* * * * *

SEQUENCE LISTING

```
<160> NUMBER OF SEQ ID NOS: 95

<210> SEQ ID NO 1
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 1

Gly Phe Ser Phe Asn Ser Asp Tyr Trp Ile Tyr
1               5                   10

<210> SEQ ID NO 2
<211> LENGTH: 18
<212> TYPE: PRT
<213> ORGANISM: Artificial Sequence
<220> FEATURE:
<223> OTHER INFORMATION: sequence of recombinant antibody or functional
      part thereof

<400> SEQUENCE: 2

Ser Ile Tyr Gly Gly Ser Ser Gly Asn Thr Gln Tyr Ala Ser Trp Ala
1               5                   10                  15

Gln Gly

<210> SEQ ID NO 3
<211> LENGTH: 12
<212> TYPE: PRT
<213> ORGANISM: Artificial Sequence
<220> FEATURE:
<223> OTHER INFORMATION: sequence of recombinant antibody or functional
      part thereof

<400> SEQUENCE: 3

Arg Gly Tyr Val Asp Tyr Gly Gly Ala Thr Asp Leu
1               5                   10

<210> SEQ ID NO 4
<211> LENGTH: 11
<212> TYPE: PRT
<213> ORGANISM: Artificial Sequence
<220> FEATURE:
```

<223> OTHER INFORMATION: sequence of recombinant antibody or functional
      part thereof

<400> SEQUENCE: 4

Val Ser Gly Phe Ser Phe Asn Ser Asp Tyr Trp
1               5                   10

<210> SEQ ID NO 5
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 5

Ala Ser Gly Phe Ser Phe Asn Ser Asp Tyr Trp
1               5                   10

<210> SEQ ID NO 6
<211> LENGTH: 18
<212> TYPE: PRT
<213> ORGANISM: Artificial Sequence
<220> FEATURE:
<223> OTHER INFORMATION: sequence of recombinant antibody or functional
      part thereof

<400> SEQUENCE: 6

Ile Tyr Gly Gly Ser Ser Gly Asn Thr Gln Tyr Ala Ser Trp Ala Gln
1               5                   10                  15

Gly Arg

<210> SEQ ID NO 7
<211> LENGTH: 10
<212> TYPE: PRT
<213> ORGANISM: Artificial Sequence
<220> FEATURE:
<223> OTHER INFORMATION: sequence of recombinant antibody or functional
      part thereof

<400> SEQUENCE: 7

Gly Tyr Val Asp Tyr Gly Gly Ala Thr Asp
1               5                   10

<210> SEQ ID NO 8
<211> LENGTH: 6
<212> TYPE: PRT
<213> ORGANISM: Artificial Sequence
<220> FEATURE:
<223> OTHER INFORMATION: sequence of recombinant antibody or functional
      part thereof

<400> SEQUENCE: 8

Ser Asp Tyr Trp Ile Tyr
1               5

<210> SEQ ID NO 9
<211> LENGTH: 18
<212> TYPE: PRT
<213> ORGANISM: Artificial Sequence
<220> FEATURE:
<223> OTHER INFORMATION: sequence of recombinant antibody or functional
      part thereof

<400> SEQUENCE: 9

Ser Ile Tyr Gly Gly Ser Ser Gly Asn Thr Gln Tyr Ala Ser Trp Ala
1               5                   10                  15

Gln Gly

<210> SEQ ID NO 10
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 10

Gly Tyr Val Asp Tyr Gly Gly Ala Thr Asp Leu
1               5                   10

<210> SEQ ID NO 11
<211> LENGTH: 8
<212> TYPE: PRT
<213> ORGANISM: Artificial Sequence
<220> FEATURE:
<223> OTHER INFORMATION: sequence of recombinant antibody or functional
      part thereof

<400> SEQUENCE: 11

Gly Phe Ser Phe Asn Ser Asp Tyr
1               5

<210> SEQ ID NO 12
<211> LENGTH: 5
<212> TYPE: PRT
<213> ORGANISM: Artificial Sequence
<220> FEATURE:
<223> OTHER INFORMATION: sequence of recombinant antibody or functional
      part thereof

<400> SEQUENCE: 12

Gly Gly Ser Ser Gly
1               5

<210> SEQ ID NO 13
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 13

Tyr Val Asp Tyr Gly Gly Ala Thr Asp
1               5

<210> SEQ ID NO 14
<211> LENGTH: 122
<212> TYPE: PRT
<213> ORGANISM: Artificial Sequence
<220> FEATURE:
<223> OTHER INFORMATION: sequence of recombinant antibody or functional
      part thereof

<400> SEQUENCE: 14

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Asn Ser Asp
                20                  25                  30

Tyr Trp Ile Tyr Trp Ile Arg Gln Pro Pro Gly Lys Gly Leu Glu Trp
            35                  40                  45

```
Ile Gly Ser Ile Tyr Gly Gly Ser Ser Gly Asn Thr Gln Tyr Ala Ser
    50                  55                  60

Trp Ala Gln Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Gly Tyr Val Asp Tyr Gly Ala Thr Asp Leu Trp
                100                 105                 110

Gly Gln Gly Thr Leu Val Thr Val Ser Ser
            115                 120
```

<210> SEQ ID NO 15
<211> LENGTH: 122
<212> TYPE: PRT
<213> ORGANISM: Artificial Sequence
<220> FEATURE:
<223> OTHER INFORMATION: sequence of recombinant antibody or functional
      part thereof

<400> SEQUENCE: 15

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Ser Phe Asn Ser Asp
                20                  25                  30

Tyr Trp Ile Tyr Trp Val Arg Gln Ala Pro Gly Gln Gly Leu Glu Trp
            35                  40                  45

Met Gly Ser Ile Tyr Gly Gly Ser Ser Gly Asn Thr Gln Tyr Ala Ser
    50                  55                  60

Trp Ala Gln Gly Arg Val Thr Met Thr Arg Asp Thr Ser Ile Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Gly Tyr Val Asp Tyr Gly Ala Thr Asp Leu Trp
                100                 105                 110

Gly Gln Gly Thr Leu Val Thr Val Ser Ser
            115                 120
```

<210> SEQ ID NO 16
<211> LENGTH: 122
<212> TYPE: PRT
<213> ORGANISM: Artificial Sequence
<220> FEATURE:
<223> OTHER INFORMATION: sequence of recombinant antibody or functional
      part thereof

<400> SEQUENCE: 16

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Asn Ser Asp
                20                  25                  30

Tyr Trp Ile Tyr Trp Val Arg Gln Ala Pro Gly Lys Gly Leu Glu Trp
            35                  40                  45

Ile Ala Ser Ile Tyr Gly Gly Ser Ser Gly Asn Thr Gln Tyr Ala Ser
    50                  55                  60

Trp Ala Gln Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95
```

Phe Cys Ala Arg Gly Tyr Val Asp Tyr Gly Gly Ala Thr Asp Leu Trp
            100                 105                 110

Gly Gln Gly Thr Leu Val Thr Val Ser Ser
        115                 120

<210> SEQ ID NO 17
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 17

Gln Ala Ser Gln Ser Ile Gly Thr Tyr Leu Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: sequence of recombinant antibody or functional
      part thereof

<400> SEQUENCE: 18

Arg Ala Phe Ile Leu Ala Ser
1               5

<210> SEQ ID NO 19
<211> LENGTH: 15
<212> TYPE: PRT
<213> ORGANISM: Artificial Sequence
<220> FEATURE:
<223> OTHER INFORMATION: sequence of recombinant antibody or functional
      part thereof

<400> SEQUENCE: 19

Gln Ser Asn Phe Tyr Ser Asp Ser Thr Thr Ile Gly Pro Asn Ala
1               5                   10                  15

<210> SEQ ID NO 20
<211> LENGTH: 8
<212> TYPE: PRT
<213> ORGANISM: Artificial Sequence
<220> FEATURE:
<223> OTHER INFORMATION: sequence of recombinant antibody or functional
      part thereof

<400> SEQUENCE: 20

Ala Ser Gln Ser Ile Gly Thr Tyr
1               5

<210> SEQ ID NO 21
<211> LENGTH: 12
<212> TYPE: PRT
<213> ORGANISM: Artificial Sequence
<220> FEATURE:
<223> OTHER INFORMATION: sequence of recombinant antibody or functional
      part thereof

<400> SEQUENCE: 21

Arg Ala Phe Ile Leu Ala Ser Gly Val Pro Ser Arg
1               5                   10

<210> SEQ ID NO 22
<211> LENGTH: 12

```
<212> TYPE: PRT
<213> ORGANISM: Artificial Sequence
<220> FEATURE:
<223> OTHER INFORMATION: sequence of recombinant antibody or functional
      part thereof

<400> SEQUENCE: 22

Asn Phe Tyr Ser Asp Ser Thr Thr Ile Gly Pro Asn
1               5                   10

<210> SEQ ID NO 23
<211> LENGTH: 7
<212> TYPE: PRT
<213> ORGANISM: Artificial Sequence
<220> FEATURE:
<223> OTHER INFORMATION: sequence of recombinant antibody or functional
      part thereof

<400> SEQUENCE: 23

Ser Gln Ser Ile Gly Thr Tyr
1               5

<210> SEQ ID NO 24
<211> LENGTH: 3
<212> TYPE: PRT
<213> ORGANISM: Artificial Sequence
<220> FEATURE:
<223> OTHER INFORMATION: sequence of recombinant antibody or functional
      part thereof

<400> SEQUENCE: 24

Arg Ala Phe
1

<210> SEQ ID NO 25
<211> LENGTH: 12
<212> TYPE: PRT
<213> ORGANISM: Artificial Sequence
<220> FEATURE:
<223> OTHER INFORMATION: sequence of recombinant antibody or functional
      part thereof

<400> SEQUENCE: 25

Asn Phe Tyr Ser Asp Ser Thr Thr Ile Gly Pro Asn
1               5                   10

<210> SEQ ID NO 26
<211> LENGTH: 114
<212> TYPE: PRT
<213> ORGANISM: Artificial Sequence
<220> FEATURE:
<223> OTHER INFORMATION: sequence of recombinant antibody or functional
      part thereof

<400> SEQUENCE: 26

Asp Ile Gln Met Thr Gln Ser Pro Ser Leu Ser Ala Ser Val Gly
1               5                   10                  15

Asp Arg Val Thr Ile Thr Cys Gln Ala Ser Gln Ser Ile Gly Thr Tyr
                20                  25                  30

Leu Ala Trp Tyr Gln Gln Lys Pro Gly Lys Ala Pro Lys Leu Leu Ile
            35                  40                  45

Tyr Arg Ala Phe Ile Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly

<210> SEQ ID NO 27
<211> LENGTH: 114
<212> TYPE: PRT
<213> ORGANISM: Artificial Sequence
<220> FEATURE:
<223> OTHER INFORMATION: sequence of recombinant antibody or functional
      part thereof

<400> SEQUENCE: 27

Asp Ile Gln Met Thr Gln Ser Pro Ala Ser Leu Ser Ala Ser Val Gly
1               5                   10                  15

Asp Arg Val Thr Ile Thr Cys Gln Ala Ser Gln Ser Ile Gly Thr Tyr
                20                  25                  30

Leu Ala Trp Tyr Gln Gln Lys Pro Gly Lys Pro Pro Lys Leu Leu Ile
            35                  40                  45

Tyr Arg Ala Phe Ile Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly

<210> SEQ ID NO 28
<211> LENGTH: 20
<212> TYPE: PRT
<213> ORGANISM: Artificial Sequence
<220> FEATURE:
<223> OTHER INFORMATION: sequence of recombinant antibody or functional
      part thereof

<400> SEQUENCE: 28

Gly Gly Gly Gly Ser Gly Gly Gly Ser Gly Gly Gly Ser Gly
1               5                   10                  15

Gly Gly Gly Ser
            20

<210> SEQ ID NO 29
<211> LENGTH: 256
<212> TYPE: PRT
<213> ORGANISM: Artificial Sequence
<220> FEATURE:
<223> OTHER INFORMATION: sequence of recombinant antibody or functional
      part thereof

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Gly Thr Tyr
                20                  25                  30

Leu Ala Trp Tyr Gln Gln Lys Pro Gly Lys Ala Pro Lys Leu Leu Ile
            35                  40                  45
```

```
Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Ser Asn Phe Tyr Ser Asp Ser
                 85                  90                  95

Thr Thr Ile Gly Pro Asn Ala Phe Gly Thr Gly Thr Lys Val Thr Val
                100                 105                 110

Leu Gly Gly Gly Gly Ser Gly Gly Gly Ser Gly Gly Gly
                115                 120                 125

Ser Gly Gly Gly Ser Gln Val Gln Leu Gln Glu Ser Gly Pro Gly
    130                 135                 140

Leu Val Lys Pro Ser Glu Thr Leu Ser Leu Thr Cys Lys Val Ser Gly
145                 150                 155                 160

Phe Ser Phe Asn Ser Asp Tyr Trp Ile Tyr Trp Ile Arg Gln Pro Pro
                165                 170                 175

Gly Lys Gly Leu Glu Trp Ile Gly Ser Ile Tyr Gly Ser Ser Gly
                180                 185                 190

Asn Thr Gln Tyr Ala Ser Trp Ala Gln Gly Arg Val Thr Ile Ser Val
                195                 200                 205

Asp Ser Ser Lys Asn Gln Phe Ser Leu Lys Leu Ser Ser Val Thr Ala
    210                 215                 220

Ala Asp Thr Ala Val Tyr Tyr Cys Ala Arg Gly Tyr Val Asp Tyr Gly
225                 230                 235                 240

Gly Ala Thr Asp Leu Trp Gly Gln Gly Thr Leu Val Thr Val Ser Ser
                245                 250                 255

<210> SEQ ID NO 30
<211> LENGTH: 256
<212> TYPE: PRT
<213> ORGANISM: Artificial Sequence
<220> FEATURE:
<223> OTHER INFORMATION: sequence of recombinant antibody or functional
      part thereof

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Gly Thr Tyr
                20                  25                  30

Leu Ala Trp Tyr Gln Gln Lys Pro Gly Lys Ala Pro Lys Leu Leu Ile
            35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Ser Asn Phe Tyr Ser Asp Ser
                 85                  90                  95

Thr Thr Ile Gly Pro Asn Ala Phe Gly Thr Gly Thr Lys Val Thr Val
                100                 105                 110

Leu Gly Gly Gly Gly Ser Gly Gly Gly Ser Gly Gly Gly
                115                 120                 125

Ser Gly Gly Gly Ser Gln Val Gln Leu Val Gln Ser Gly Ala Glu
    130                 135                 140

Val Lys Lys Pro Gly Ala Ser Val Lys Val Ser Cys Lys Ala Ser Gly
145                 150                 155                 160
```

```
Phe Ser Phe Asn Ser Asp Tyr Trp Ile Tyr Trp Val Arg Gln Ala Pro
                165                 170                 175

Gly Gln Gly Leu Glu Trp Met Gly Ser Ile Tyr Gly Gly Ser Ser Gly
            180                 185                 190

Asn Thr Gln Tyr Ala Ser Trp Ala Gln Gly Arg Val Thr Met Thr Arg
        195                 200                 205

Asp Thr Ser Ile Ser Thr Ala Tyr Met Glu Leu Ser Ser Leu Arg Ser
    210                 215                 220

Glu Asp Thr Ala Val Tyr Tyr Cys Ala Arg Gly Tyr Val Asp Tyr Gly
225                 230                 235                 240

Gly Ala Thr Asp Leu Trp Gly Gln Gly Thr Leu Val Thr Val Ser Ser
                245                 250                 255

<210> SEQ ID NO 31
<211> LENGTH: 256
<212> TYPE: PRT
<213> ORGANISM: Artificial Sequence
<220> FEATURE:
<223> OTHER INFORMATION: sequence of recombinant antibody or functional
      part thereof

<400> SEQUENCE: 31

Asp Ile Gln Met Thr Gln Ser Pro Ala Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Pro Pro Lys Leu Leu Ile
        35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly Gly Gly Gly Ser Gly Gly Gly Ser Gly Gly Gly Gly
        115                 120                 125

Ser Gly Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Phe Ser Phe Asn Ser Asp Tyr Trp Ile Tyr Trp Val Arg Gln Ala Pro
                165                 170                 175

Gly Lys Gly Leu Glu Trp Ile Ala Ser Ile Tyr Gly Gly Ser Ser Gly
            180                 185                 190

Asn Thr Gln Tyr Ala Ser Trp Ala Gln Gly Arg Phe Thr Ile Ser Arg
        195                 200                 205

Asp Asn Ser Lys Asn Thr Val Tyr Leu Gln Met Asn Ser Leu Arg Ala
    210                 215                 220

Glu Asp Thr Ala Val Tyr Phe Cys Ala Arg Gly Tyr Val Asp Tyr Gly
225                 230                 235                 240

Gly Ala Thr Asp Leu Trp Gly Gln Gly Thr Leu Val Thr Val Ser Ser
                245                 250                 255
```

```
-continued

<210> SEQ ID NO 32
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 32

Gly Phe Ser Phe Ser Ser Gly Tyr Asp Met Cys
1               5                   10

<210> SEQ ID NO 33
<211> LENGTH: 18
<212> TYPE: PRT
<213> ORGANISM: Artificial Sequence
<220> FEATURE:
<223> OTHER INFORMATION: sequence of recombinant antibody or functional
      part thereof

<400> SEQUENCE: 33

Cys Val Val Ala Gly Ser Val Asp Ile Thr Tyr Tyr Ala Ser Trp Ala
1               5                   10                  15

Lys Gly

<210> SEQ ID NO 34
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 34

Arg Lys Asp Ala Tyr Ser Asp Ala Phe Asn Leu
1               5                   10

<210> SEQ ID NO 35
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 35

Val Ser Gly Phe Ser Phe Ser Ser Gly Tyr Asp
1               5                   10

<210> SEQ ID NO 36
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 36

Ala Ser Gly Phe Ser Phe Ser Ser Gly Tyr Asp
1               5                   10

<210> SEQ ID NO 37
<211> LENGTH: 18
<212> TYPE: PRT
<213> ORGANISM: Artificial Sequence
<220> FEATURE:
<223> OTHER INFORMATION: sequence of recombinant antibody or functional
      part thereof
```

```
<400> SEQUENCE: 37

Val Val Ala Gly Ser Val Asp Ile Thr Tyr Tyr Ala Ser Trp Ala Lys
1               5                   10                  15

Gly Arg

<210> SEQ ID NO 38
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 38

Lys Asp Ala Tyr Ser Asp Ala Phe Asn
1               5

<210> SEQ ID NO 39
<211> LENGTH: 6
<212> TYPE: PRT
<213> ORGANISM: Artificial Sequence
<220> FEATURE:
<223> OTHER INFORMATION: sequence of recombinant antibody or functional
      part thereof

<400> SEQUENCE: 39

Ser Gly Tyr Asp Met Cys
1               5

<210> SEQ ID NO 40
<211> LENGTH: 18
<212> TYPE: PRT
<213> ORGANISM: Artificial Sequence
<220> FEATURE:
<223> OTHER INFORMATION: sequence of recombinant antibody or functional
      part thereof

<400> SEQUENCE: 40

Cys Val Val Ala Gly Ser Val Asp Ile Thr Tyr Tyr Ala Ser Trp Ala
1               5                   10                  15

Lys Gly

<210> SEQ ID NO 41
<211> LENGTH: 10
<212> TYPE: PRT
<213> ORGANISM: Artificial Sequence
<220> FEATURE:
<223> OTHER INFORMATION: sequence of recombinant antibody or functional
      part thereof

<400> SEQUENCE: 41

Lys Asp Ala Tyr Ser Asp Ala Phe Asn Leu
1               5                   10

<210> SEQ ID NO 42
<211> LENGTH: 8
<212> TYPE: PRT
<213> ORGANISM: Artificial Sequence
<220> FEATURE:
<223> OTHER INFORMATION: sequence of recombinant antibody or functional
      part thereof

<400> SEQUENCE: 42

Gly Phe Ser Phe Ser Ser Gly Tyr
1               5
```

<210> SEQ ID NO 43
<211> LENGTH: 5
<212> TYPE: PRT
<213> ORGANISM: Artificial Sequence
<220> FEATURE:
<223> OTHER INFORMATION: sequence of recombinant antibody or functional
      part thereof

<400> SEQUENCE: 43

Ala Gly Ser Val Asp
1               5

<210> SEQ ID NO 44
<211> LENGTH: 8
<212> TYPE: PRT
<213> ORGANISM: Artificial Sequence
<220> FEATURE:
<223> OTHER INFORMATION: sequence of recombinant antibody or functional
      part thereof

<400> SEQUENCE: 44

Asp Ala Tyr Ser Asp Ala Phe Asn
1               5

<210> SEQ ID NO 45
<211> LENGTH: 121
<212> TYPE: PRT
<213> ORGANISM: Artificial Sequence
<220> FEATURE:
<223> OTHER INFORMATION: sequence of recombinant antibody or functional
      part thereof

<400> SEQUENCE: 45

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
            20                  25                  30

Tyr Asp Met Cys Trp Ile Arg Gln Pro Pro Gly Lys Gly Leu Glu Trp
        35                  40                  45

Ile Gly Cys Val Val Ala Gly Ser Val Asp Ile Thr Tyr Tyr Ala Ser
    50                  55                  60

Trp Ala Lys Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Lys Asp Ala Tyr Ser Asp Ala Phe Asn Leu Trp Gly
            100                 105                 110

Gln Gly Thr Leu Val Thr Val Ser Ser
        115                 120

<210> SEQ ID NO 46
<211> LENGTH: 121
<212> TYPE: PRT
<213> ORGANISM: Artificial Sequence
<220> FEATURE:
<223> OTHER INFORMATION: sequence of recombinant antibody or functional
      part thereof

<400> SEQUENCE: 46

Gln Ser Gln Leu Gln Glu Ser Gly Pro Gly Leu Val Lys Pro Ser Glu
1               5                   10                  15

Thr Leu Ser Leu Thr Cys Lys Ala Ser Gly Phe Ser Phe Ser Ser Gly

```
                 20                  25                  30

Tyr Asp Met Cys Trp Val Arg Gln Pro Pro Gly Lys Gly Leu Glu Trp
         35                  40                  45

Ile Ala Cys Val Val Ala Gly Ser Val Asp Ile Thr Tyr Tyr Ala Ser
     50                  55                  60

Trp Ala Lys Gly Arg Val Thr Ile Ser Lys Asp Ser Lys Asn Gln
65                  70                  75                  80

Val Ser Leu Lys Leu Ser Ser Val Thr Ala Ala Asp Thr Ala Val Tyr
                 85                  90                  95

Phe Cys Ala Arg Lys Asp Ala Tyr Ser Asp Ala Phe Asn Leu Trp Gly
             100                 105                 110

Gln Gly Thr Leu Val Thr Val Ser Ser
         115                 120

<210> SEQ ID NO 47
<211> LENGTH: 121
<212> TYPE: PRT
<213> ORGANISM: Artificial Sequence
<220> FEATURE:
<223> OTHER INFORMATION: sequence of recombinant antibody or functional
      part thereof

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Lys Ala Ser Gly Phe Ser Phe Ser Ser Gly
             20                  25                  30

Tyr Asp Met Cys Trp Val Arg Gln Pro Pro Gly Lys Gly Leu Glu Trp
         35                  40                  45

Ile Ala Cys Val Val Ala Gly Ser Val Asp Ile Thr Tyr Tyr Ala Ser
     50                  55                  60

Trp Ala Lys Gly Arg Val Thr Ile Ser Lys Asp Ser Lys Asn Gln
65                  70                  75                  80

Val Ser Leu Lys Leu Ser Ser Val Thr Ala Ala Asp Thr Ala Val Tyr
                 85                  90                  95

Tyr Cys Ala Arg Lys Asp Ala Tyr Ser Asp Ala Phe Asn Leu Trp Gly
             100                 105                 110

Gln Gly Thr Leu Val Thr Val Ser Ser
         115                 120

<210> SEQ ID NO 48
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 48

Gln Ala Ser Gln Ser Ile Asn Asp Tyr Leu Ala
1               5                   10

<210> SEQ ID NO 49
<211> LENGTH: 7
<212> TYPE: PRT
<213> ORGANISM: Artificial Sequence
<220> FEATURE:
<223> OTHER INFORMATION: sequence of recombinant antibody or functional
      part thereof

<400> SEQUENCE: 49
```

```
Lys Ala Ser Thr Leu Ala Ser
1               5
```

<210> SEQ ID NO 50
<211> LENGTH: 12
<212> TYPE: PRT
<213> ORGANISM: Artificial Sequence
<220> FEATURE:
<223> OTHER INFORMATION: sequence of recombinant antibody or functional
      part thereof

<400> SEQUENCE: 50

```
Gln Gln Gly Tyr Ile Ile Thr Asp Ile Asp Asn Val
1               5                   10
```

<210> SEQ ID NO 51
<211> LENGTH: 8
<212> TYPE: PRT
<213> ORGANISM: Artificial Sequence
<220> FEATURE:
<223> OTHER INFORMATION: sequence of recombinant antibody or functional
      part thereof

<400> SEQUENCE: 51

```
Ala Ser Gln Ser Ile Asn Asp Tyr
1               5
```

<210> SEQ ID NO 52
<211> LENGTH: 12
<212> TYPE: PRT
<213> ORGANISM: Artificial Sequence
<220> FEATURE:
<223> OTHER INFORMATION: sequence of recombinant antibody or functional
      part thereof

<400> SEQUENCE: 52

```
Lys Ala Ser Thr Leu Ala Ser Gly Val Pro Ser Arg
1               5                   10
```

<210> SEQ ID NO 53
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 53

```
Gly Tyr Ile Ile Thr Asp Ile Asp Asn
1               5
```

<210> SEQ ID NO 54
<211> LENGTH: 7
<212> TYPE: PRT
<213> ORGANISM: Artificial Sequence
<220> FEATURE:
<223> OTHER INFORMATION: sequence of recombinant antibody or functional
      part thereof

<400> SEQUENCE: 54

```
Ser Gln Ser Ile Asn Asp Tyr
1               5
```

<210> SEQ ID NO 55
<211> LENGTH: 3
<212> TYPE: PRT
<213> ORGANISM: Artificial Sequence

```
<220> FEATURE:
<223> OTHER INFORMATION: sequence of recombinant antibody or functional
      part thereof

<400> SEQUENCE: 55

Lys Ala Ser
1

<210> SEQ ID NO 56
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 56

Gly Tyr Ile Ile Thr Asp Ile Asp Asn
1               5

<210> SEQ ID NO 57
<211> LENGTH: 111
<212> TYPE: PRT
<213> ORGANISM: Artificial Sequence
<220> FEATURE:
<223> OTHER INFORMATION: sequence of recombinant antibody or functional
      part thereof

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly
            100                 105                 110

<210> SEQ ID NO 58
<211> LENGTH: 111
<212> TYPE: PRT
<213> ORGANISM: Artificial Sequence
<220> FEATURE:
<223> OTHER INFORMATION: sequence of recombinant antibody or functional
      part thereof

<400> SEQUENCE: 58

Asp Phe Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ser Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Gly Tyr Ile Ile Thr Asp
                    85                  90                  95

Ile Asp Asn Val Phe Gly Thr Gly Thr Lys Val Thr Val Leu Gly
                100                 105                 110
```

<210> SEQ ID NO 59
<211> LENGTH: 20
<212> TYPE: PRT
<213> ORGANISM: Artificial Sequence
<220> FEATURE:
<223> OTHER INFORMATION: sequence of recombinant antibody or functional
      part thereof

<400> SEQUENCE: 59

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 60
<211> LENGTH: 252
<212> TYPE: PRT
<213> ORGANISM: Artificial Sequence
<220> FEATURE:
<223> OTHER INFORMATION: sequence of recombinant antibody or functional
      part thereof

<400> SEQUENCE: 60

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
                20                  25                  30

Leu Ala Trp Tyr Gln Gln Lys Pro Gly Lys Ala Pro Lys Leu Leu Ile
            35                  40                  45

Tyr Lys Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
                100                 105                 110

Gly Gly Gly Ser Gly Gly Gly Gly Ser Gly Gly Gly Gly Ser Gly Gly
            115                 120                 125

Gly Gly Ser Gln Val Gln Leu Gln Glu Ser Gly Pro Gly Leu Val Lys
        130                 135                 140

Pro Ser Glu Thr Leu Ser Leu Thr Cys Lys Val Ser Gly Phe Ser Phe
145                 150                 155                 160

Ser Ser Gly Tyr Asp Met Cys Trp Ile Arg Gln Pro Pro Gly Lys Gly
                165                 170                 175

Leu Glu Trp Ile Gly Cys Val Val Ala Gly Ser Val Asp Ile Thr Tyr
                180                 185                 190

Tyr Ala Ser Trp Ala Lys Gly Arg Val Thr Ile Ser Val Asp Ser Ser
            195                 200                 205

Lys Asn Gln Phe Ser Leu Lys Leu Ser Ser Val Thr Ala Ala Asp Thr
        210                 215                 220

Ala Val Tyr Tyr Cys Ala Arg Lys Asp Ala Tyr Ser Asp Ala Phe Asn
```

```
                  225                 230                 235                 240
Leu Trp Gly Gln Gly Thr Leu Val Thr Val Ser Ser
                245                 250

<210> SEQ ID NO 61
<211> LENGTH: 252
<212> TYPE: PRT
<213> ORGANISM: Artificial Sequence
<220> FEATURE:
<223> OTHER INFORMATION: sequence of recombinant antibody or functional
      part thereof

<400> SEQUENCE: 61

Asp Phe Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ser Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gly Gly Gly Ser Gly Gly Gly Ser Gly Gly
        115                 120                 125

Gly Gly Ser Gln Ser Gln Leu Gln Glu Ser Gly Pro Gly Leu Val Lys
    130                 135                 140

Pro Ser Glu Thr Leu Ser Leu Thr Cys Lys Ala Ser Gly Phe Ser Phe
145                 150                 155                 160

Ser Ser Gly Tyr Asp Met Cys Trp Val Arg Gln Pro Pro Gly Lys Gly
                165                 170                 175

Leu Glu Trp Ile Ala Cys Val Val Ala Gly Ser Val Asp Ile Thr Tyr
            180                 185                 190

Tyr Ala Ser Trp Ala Lys Gly Arg Val Thr Ile Ser Lys Asp Ser Ser
        195                 200                 205

Lys Asn Gln Val Ser Leu Lys Leu Ser Ser Val Thr Ala Ala Asp Thr
    210                 215                 220

Ala Val Tyr Phe Cys Ala Arg Lys Asp Ala Tyr Ser Asp Ala Phe Asn
225                 230                 235                 240

Leu Trp Gly Gln Gly Thr Leu Val Thr Val Ser Ser
                245                 250

<210> SEQ ID NO 62
<211> LENGTH: 252
<212> TYPE: PRT
<213> ORGANISM: Artificial Sequence
<220> FEATURE:
<223> OTHER INFORMATION: sequence of recombinant antibody or functional
      part thereof

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
```

```
            20                  25                  30
Leu Ala Trp Tyr Gln Gln Lys Pro Gly Lys Ala Pro Lys Leu Leu Ile
            35                  40                  45
Tyr Lys Ala Ser Thr Leu Ala Ser Gly Val Pro Ser Arg Phe Ser Gly
     50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Tyr Ile Ile Thr Asp
                85                  90                  95
Ile Asp Asn Val Phe Gly Thr Gly Thr Lys Val Thr Val Leu Gly Gly
                100                 105                 110
Gly Gly Gly Ser Gly Gly Gly Ser Gly Gly Gly Ser Gly Gly
                115                 120                 125
Gly Gly Ser Gln Val Gln Leu Gln Glu Ser Gly Pro Gly Leu Val Lys
            130                 135                 140
Pro Ser Glu Thr Leu Ser Leu Thr Cys Lys Ala Ser Gly Phe Ser Phe
145                 150                 155                 160
Ser Ser Gly Tyr Asp Met Cys Trp Val Arg Gln Pro Pro Gly Lys Gly
                165                 170                 175
Leu Glu Trp Ile Ala Cys Val Val Ala Gly Ser Val Asp Ile Thr Tyr
                180                 185                 190
Tyr Ala Ser Trp Ala Lys Gly Arg Val Thr Ile Ser Lys Asp Ser Ser
            195                 200                 205
Lys Asn Gln Val Ser Leu Lys Leu Ser Ser Val Thr Ala Ala Asp Thr
            210                 215                 220
Ala Val Tyr Tyr Cys Ala Arg Lys Asp Ala Tyr Ser Asp Ala Phe Asn
225                 230                 235                 240
Leu Trp Gly Gln Gly Thr Leu Val Thr Val Ser Ser
                245                 250

<210> SEQ ID NO 63
<211> LENGTH: 290
<212> TYPE: PRT
<213> ORGANISM: Artificial Sequence
<220> FEATURE:
<223> OTHER INFORMATION: sequence of recombinant antibody or functional
      part thereof

<400> SEQUENCE: 63

Met Arg Ile Phe Ala Val Phe Ile Phe Met Thr Tyr Trp His Leu Leu
1               5                   10                  15
Asn Ala Phe Thr Val Thr Val Pro Lys Asp Leu Tyr Val Val Glu Tyr
                20                  25                  30
Gly Ser Asn Met Thr Ile Glu Cys Lys Phe Pro Val Glu Lys Gln Leu
            35                  40                  45
Asp Leu Ala Ala Leu Ile Val Tyr Trp Glu Met Glu Asp Lys Asn Ile
     50                  55                  60
Ile Gln Phe Val His Gly Glu Glu Asp Leu Lys Val Gln His Ser Ser
65                  70                  75                  80
Tyr Arg Gln Arg Ala Arg Leu Leu Lys Asp Gln Leu Ser Leu Gly Asn
                85                  90                  95
Ala Ala Leu Gln Ile Thr Asp Val Lys Leu Gln Asp Ala Gly Val Tyr
                100                 105                 110
Arg Cys Met Ile Ser Tyr Gly Gly Ala Asp Tyr Lys Arg Ile Thr Val
            115                 120                 125
```

```
Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
                180                 185                 190

Val Thr Ser Thr Leu Arg Ile Asn Thr Thr Thr Asn Glu Ile Phe Tyr
                195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285

Glu Thr
    290

<210> SEQ ID NO 64
<211> LENGTH: 11
<212> TYPE: PRT
<213> ORGANISM: Homo sapiens

<400> SEQUENCE: 64

Phe Gly Thr Gly Thr Lys Val Thr Val Leu Gly
1               5                   10

<210> SEQ ID NO 65
<211> LENGTH: 11
<212> TYPE: PRT
<213> ORGANISM: Homo sapiens

<400> SEQUENCE: 65

Phe Gly Gly Gly Thr Lys Leu Thr Val Leu Gly
1               5                   10

<210> SEQ ID NO 66
<211> LENGTH: 11
<212> TYPE: PRT
<213> ORGANISM: Homo sapiens

<400> SEQUENCE: 66

Phe Gly Gly Gly Thr Gln Leu Ile Ile Leu Gly
1               5                   10

<210> SEQ ID NO 67
<211> LENGTH: 11
<212> TYPE: PRT
<213> ORGANISM: Homo sapiens

<400> SEQUENCE: 67

Phe Gly Glu Gly Thr Glu Leu Thr Val Leu Gly
1               5                   10

<210> SEQ ID NO 68
```

```
<211> LENGTH: 11
<212> TYPE: PRT
<213> ORGANISM: Homo sapiens

<400> SEQUENCE: 68

Phe Gly Ser Gly Thr Lys Val Thr Val Leu Gly
1               5                   10

<210> SEQ ID NO 69
<211> LENGTH: 11
<212> TYPE: PRT
<213> ORGANISM: Homo sapiens

<400> SEQUENCE: 69

Phe Gly Gly Gly Thr Gln Leu Thr Val Leu Gly
1               5                   10

<210> SEQ ID NO 70
<211> LENGTH: 11
<212> TYPE: PRT
<213> ORGANISM: Homo sapiens

<400> SEQUENCE: 70

Phe Gly Gly Gly Thr Gln Leu Thr Ala Leu Gly
1               5                   10

<210> SEQ ID NO 71
<211> LENGTH: 493
<212> TYPE: PRT
<213> ORGANISM: Artificial Sequence
<220> FEATURE:
<223> OTHER INFORMATION: sequence of recombinant antibody or functional
      part thereof

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
                20                  25                  30

Leu Ala Trp Tyr Gln Gln Lys Pro Gly Lys Ala Pro Lys Leu Leu Ile
            35                  40                  45

Tyr Lys Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Ser Gln Val Gln Leu Gln Glu Ser Gly Pro Gly Leu Val
        115                 120                 125

Lys Pro Ser Glu Thr Leu Ser Leu Thr Cys Lys Val Ser Gly Phe Ser
        130                 135                 140

Phe Ser Asn Ser Tyr Trp Ile Cys Trp Ile Arg Gln Pro Pro Gly Lys
145                 150                 155                 160

Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Val Asp Ser
            180                 185                 190

Ser Lys Asn Gln Phe Ser Leu Lys Leu Ser Ser Val Thr Ala Ala Asp
```

```
                195                 200                 205
Thr Ala Val Tyr Tyr Cys Ala Arg His Pro Ser Asp Ala Val Tyr Gly
        210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Ser Gly Gly Gly Ser Gly
                245                 250                 255

Gly Gly Gly Ser Ile Gln Met Thr Gln Ser Pro Ser Ser Leu Ser Ala
        260                 265                 270

Ser Val Gly Asp Arg Val Thr Ile Thr Cys Gln Ala Ser Gln Ser Ile
        275                 280                 285

Asn Asn Val Leu Ala Trp Tyr Gln Gln Lys Pro Gly Lys Ala Pro Lys
        290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
        340                 345                 350

Asn Tyr Gly Asp Phe Gly Thr Gly Thr Lys Val Thr Val Leu Gly Gly
        355                 360                 365

Gly Gly Gly Ser Gln Val Gln Leu Gln Glu Ser Gly Pro Gly Leu Val
        370                 375                 380

Lys Pro Ser Glu Thr Leu Ser Leu Thr Cys Lys Val Ser Gly Phe Ser
385                 390                 395                 400

Phe Ser Ser Gly Tyr Asp Met Cys Trp Ile Arg Gln Pro Pro Gly Lys
                405                 410                 415

Gly Leu Glu Trp Ile Gly Cys Val Val Ala Gly Ser Val Asp Ile Thr
        420                 425                 430

Tyr Tyr Ala Ser Trp Ala Lys Gly Arg Val Thr Ile Ser Val Asp Ser
        435                 440                 445

Ser Lys Asn Gln Phe Ser Leu Lys Leu Ser Ser Val Thr Ala Ala Asp
        450                 455                 460

Thr Ala Val Tyr Tyr Cys Ala Arg Lys Asp Ala Tyr Ser Asp Ala Phe
465                 470                 475                 480

Asn Leu Trp Gly Gln Gly Thr Leu Val Thr Val Ser Ser
                485                 490

<210> SEQ ID NO 72
<211> LENGTH: 499
<212> TYPE: PRT
<213> ORGANISM: Artificial Sequence
<220> FEATURE:
<223> OTHER INFORMATION: sequence of recombinant antibody or functional
      part thereof

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
                20                  25                  30

Leu Ala Trp Tyr Gln Gln Lys Pro Gly Lys Ala Pro Lys Leu Leu Ile
            35                  40                  45

Tyr Lys Ala Ser Thr Leu Ala Ser Gly Val Pro Ser Arg Phe Ser Gly
        50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Ile Ile Thr Asp
                 85                  90                  95

Ile Asp Asn Val Phe Gly Thr Gly Thr Lys Val Thr Val Leu Gly Gly
            100                 105                 110

Gly Gly Gly Ser Glu Val Gln Leu Val Glu Ser Gly Gly Gly Leu Val
        115                 120                 125

Gln Pro Gly Gly Ser Leu Arg Leu Ser Cys Ala Ala Ser Gly Phe Ser
    130                 135                 140

Phe Asn Asn Asp Tyr Asp Met Cys Trp Val Arg Gln Ala Pro Gly Lys
145                 150                 155                 160

Gly Leu Glu Trp Ile Gly Cys Ile Asp Thr Gly Asp Gly Ser Thr Tyr
                165                 170                 175

Tyr Ala Ser Trp Ala Lys Gly Arg Phe Thr Ile Ser Arg Asp Asn Ser
            180                 185                 190

Lys Asn Thr Val Tyr Leu Gln Met Asn Ser Leu Arg Ala Glu Asp Thr
        195                 200                 205

Ala Val Tyr Tyr Cys Ala Arg Glu Ala Ala Ser Ser Ser Gly Tyr Gly
    210                 215                 220

Met Gly Tyr Phe Asp Leu Trp Gly Gln Gly Thr Leu Val Thr Val Ser
225                 230                 235                 240

Ser Gly Gly Gly Gly Ser Gly Gly Gly Gly Ser Gly Gly Gly Gly Ser
                245                 250                 255

Gly Gly Gly Gly Ser Ile Gln Met Thr Gln Ser Pro Ser Ser Leu Ser
            260                 265                 270

Ala Ser Val Gly Asp Arg Val Thr Ile Thr Cys Gln Ser Ser Gln Ser
        275                 280                 285

Val Tyr Asp Asn Asn Trp Leu Ala Trp Tyr Gln Gln Lys Pro Gly Lys
    290                 295                 300

Ala Pro Lys Leu Leu Ile Tyr Arg Ala Ser Asn Leu Ala Ser Gly Val
305                 310                 315                 320

Pro Ser Arg Phe Ser Gly Ser Gly Ser Gly Thr Asp Phe Thr Leu Thr
                325                 330                 335

Ile Ser Ser Leu Gln Pro Glu Asp Phe Ala Thr Tyr Tyr Cys Gln Gly
            340                 345                 350

Thr Tyr Leu Ser Ser Asn Trp Tyr Trp Ala Phe Gly Thr Gly Thr Lys
        355                 360                 365

Val Thr Val Leu Gly Gly Gly Gly Ser Gln Val Gln Leu Gln Glu
    370                 375                 380

Ser Gly Pro Gly Leu Val Lys Pro Ser Glu Thr Leu Ser Leu Thr Cys
385                 390                 395                 400

Lys Val Ser Gly Phe Ser Phe Ser Ser Gly Tyr Asp Met Cys Trp Ile
                405                 410                 415

Arg Gln Pro Pro Gly Lys Gly Leu Glu Trp Ile Gly Cys Val Val Ala
            420                 425                 430

Gly Ser Val Asp Ile Thr Tyr Tyr Ala Ser Trp Ala Lys Gly Arg Val
        435                 440                 445

Thr Ile Ser Val Asp Ser Ser Lys Asn Gln Phe Ser Leu Lys Leu Ser
    450                 455                 460

Ser Val Thr Ala Ala Asp Thr Ala Val Tyr Tyr Cys Ala Arg Lys Asp
465                 470                 475                 480

Ala Tyr Ser Asp Ala Phe Asn Leu Trp Gly Gln Gly Thr Leu Val Thr
```

```
                       485                 490                 495
Val Ser Ser

<210> SEQ ID NO 73
<211> LENGTH: 493
<212> TYPE: PRT
<213> ORGANISM: Artificial Sequence
<220> FEATURE:
<223> OTHER INFORMATION: sequence of recombinant antibody or functional
      part thereof

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
        115                 120                 125

Lys Pro Ser Glu Thr Leu Ser Leu Thr Cys Lys Val Ser Gly Phe Ser
130                 135                 140

Phe Ser Asn Ser Tyr Trp Ile Cys Trp Val Arg Gln Pro Pro Gly Lys
145                 150                 155                 160

Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Val Asp Ser
            180                 185                 190

Ser Lys Asn Gln Val Ser Leu Lys Leu Ser Ser Val Thr Ala Ala Asp
        195                 200                 205

Thr Ala Val Tyr Phe Cys Ala Arg His Pro Ser Asp Ala Val Tyr Gly
210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Ser Gly Gly Gly Ser
                245                 250                 255

Gly Gly Gly Ser Ile Gln Met Thr Gln Ser Pro Ser Ser Leu Ser Ala
            260                 265                 270

Ser Val Gly Asp Arg Val Thr Ile Thr Cys Gln Ala Ser Gln Ser Ile
        275                 280                 285

Asn Asn Val Leu Ala Trp Tyr Gln Gln Lys Pro Gly Lys Pro Pro Lys
290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
```

```
                340                 345                 350
Asn Tyr Gly Asp Phe Gly Thr Gly Thr Lys Val Thr Val Leu Gly Gly
            355                 360                 365

Gly Gly Gly Ser Gln Val Gln Leu Gln Glu Ser Gly Pro Gly Leu Val
        370                 375                 380

Lys Pro Ser Glu Thr Leu Ser Leu Thr Cys Lys Val Ser Gly Phe Ser
385                 390                 395                 400

Phe Ser Ser Gly Tyr Asp Met Cys Trp Ile Arg Gln Pro Pro Gly Lys
                405                 410                 415

Gly Leu Glu Trp Ile Gly Cys Val Val Ala Gly Ser Val Asp Ile Thr
            420                 425                 430

Tyr Tyr Ala Ser Trp Ala Lys Gly Arg Val Thr Ile Ser Val Asp Ser
        435                 440                 445

Ser Lys Asn Gln Phe Ser Leu Lys Leu Ser Ser Val Thr Ala Ala Asp
    450                 455                 460

Thr Ala Val Tyr Tyr Cys Ala Arg Lys Asp Ala Tyr Ser Asp Ala Phe
465                 470                 475                 480

Asn Leu Trp Gly Gln Gly Thr Leu Val Thr Val Ser Ser
                485                 490

<210> SEQ ID NO 74
<211> LENGTH: 493
<212> TYPE: PRT
<213> ORGANISM: Artificial Sequence
<220> FEATURE:
<223> OTHER INFORMATION: sequence of recombinant antibody or functional
      part thereof

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
        115                 120                 125

Lys Pro Ser Glu Thr Leu Ser Leu Thr Cys Lys Ala Ser Gly Phe Ser
    130                 135                 140

Phe Ser Asn Ser Tyr Trp Ile Cys Trp Val Arg Gln Pro Pro Gly Lys
145                 150                 155                 160

Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Lys Asp Ser
            180                 185                 190

Ser Lys Asn Gln Val Ser Leu Lys Leu Ser Ser Val Thr Ala Ala Asp
        195                 200                 205
```

```
Thr Ala Val Tyr Phe Cys Ala Arg His Pro Ser Asp Ala Val Tyr Gly
            210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Ser Gly Gly Gly Gly Ser Gly
                245                 250                 255

Gly Gly Gly Ser Leu Gln Met Thr Gln Ser Pro Ser Ser Leu Ser Ala
            260                 265                 270

Ser Val Gly Asp Arg Val Thr Ile Thr Cys Gln Ala Ser Gln Ser Ile
            275                 280                 285

Asn Asn Val Leu Ala Trp Tyr Gln Gln Lys Pro Gly Lys Pro Pro Lys
            290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
            340                 345                 350

Asn Tyr Gly Asp Phe Gly Thr Gly Thr Lys Val Thr Val Leu Gly Gly
            355                 360                 365

Gly Gly Gly Ser Gln Val Gln Leu Gln Glu Ser Gly Pro Gly Leu Val
            370                 375                 380

Lys Pro Ser Glu Thr Leu Ser Leu Thr Cys Lys Val Ser Gly Phe Ser
385                 390                 395                 400

Phe Ser Ser Gly Tyr Asp Met Cys Trp Ile Arg Gln Pro Pro Gly Lys
                405                 410                 415

Gly Leu Glu Trp Ile Gly Cys Val Val Ala Gly Ser Val Asp Ile Thr
            420                 425                 430

Tyr Tyr Ala Ser Trp Ala Lys Gly Arg Val Thr Ile Ser Val Asp Ser
            435                 440                 445

Ser Lys Asn Gln Phe Ser Leu Lys Leu Ser Ser Val Thr Ala Ala Asp
            450                 455                 460

Thr Ala Val Tyr Cys Ala Arg Lys Asp Ala Tyr Ser Asp Ala Phe
465                 470                 475                 480

Asn Leu Trp Gly Gln Gly Thr Leu Val Thr Val Ser Ser
            485                 490

<210> SEQ ID NO 75
<211> LENGTH: 493
<212> TYPE: PRT
<213> ORGANISM: Artificial Sequence
<220> FEATURE:
<223> OTHER INFORMATION: sequence of recombinant antibody or functional
      part thereof

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
                20                  25                  30

Leu Ala Trp Tyr Gln Gln Lys Pro Gly Lys Ser Pro Lys Leu Leu Ile
            35                  40                  45

Tyr Lys Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
                100                 105                 110

Gly Gly Gly Ser Gln Val Gln Leu Gln Glu Ser Gly Pro Gly Leu Val
                115                 120                 125

Lys Pro Ser Glu Thr Leu Ser Leu Thr Cys Lys Val Ser Gly Phe Ser
130                 135                 140

Phe Ser Asn Ser Tyr Trp Ile Cys Trp Ile Arg Gln Pro Pro Gly Lys
145                 150                 155                 160

Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Val Asp Ser
                180                 185                 190

Ser Lys Asn Gln Phe Ser Leu Lys Leu Ser Ser Val Thr Ala Ala Asp
                195                 200                 205

Thr Ala Val Tyr Tyr Cys Ala Arg His Pro Ser Asp Ala Val Tyr Gly
210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Ser Gly Gly Gly Gly Ser Gly
                245                 250                 255

Gly Gly Gly Ser Ile Gln Met Thr Gln Ser Pro Ser Ser Leu Ser Ala
                260                 265                 270

Ser Val Gly Asp Arg Val Thr Ile Thr Cys Gln Ala Ser Gln Ser Ile
                275                 280                 285

Asn Asn Val Leu Ala Trp Tyr Gln Gln Lys Pro Gly Lys Ala Pro Lys
290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
                340                 345                 350

Asn Tyr Gly Asp Phe Gly Thr Gly Thr Lys Val Thr Val Leu Gly Gly
                355                 360                 365

Gly Gly Gly Ser Gln Val Gln Leu Gln Glu Ser Gly Pro Gly Leu Val
                370                 375                 380

Lys Pro Ser Glu Thr Leu Ser Leu Thr Cys Lys Val Ser Gly Phe Ser
385                 390                 395                 400

Phe Ser Ser Gly Tyr Asp Met Cys Trp Val Arg Gln Pro Pro Gly Lys
                405                 410                 415

Gly Leu Glu Trp Ile Ala Cys Val Val Ala Gly Ser Val Asp Ile Thr
                420                 425                 430

Tyr Tyr Ala Ser Trp Ala Lys Gly Arg Val Thr Ile Ser Val Asp Ser
                435                 440                 445

Ser Lys Asn Gln Phe Ser Leu Lys Leu Ser Ser Val Thr Ala Ala Asp
450                 455                 460

Thr Ala Val Tyr Phe Cys Ala Arg Lys Asp Ala Tyr Ser Asp Ala Phe
465                 470                 475                 480

Asn Leu Trp Gly Gln Gly Thr Leu Val Thr Val Ser Ser
                485                 490
```

<210> SEQ ID NO 76
<211> LENGTH: 493
<212> TYPE: PRT
<213> ORGANISM: Artificial Sequence
<220> FEATURE:
<223> OTHER INFORMATION: sequence of recombinant antibody or functional part thereof

<400> SEQUENCE: 76

```
Asp Phe Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ser Pro Lys Leu Leu Ile
        35                  40                  45

Tyr Lys Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
        115                 120                 125

Lys Pro Ser Glu Thr Leu Ser Leu Thr Cys Lys Val Ser Gly Phe Ser
130                 135                 140

Phe Ser Asn Ser Tyr Trp Ile Cys Trp Ile Arg Gln Pro Pro Gly Lys
145                 150                 155                 160

Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Val Asp Ser
            180                 185                 190

Ser Lys Asn Gln Phe Ser Leu Lys Leu Ser Ser Val Thr Ala Ala Asp
        195                 200                 205

Thr Ala Val Tyr Tyr Cys Ala Arg His Pro Ser Asp Ala Val Tyr Gly
210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Ser Gly Gly Gly Gly Ser Gly
                245                 250                 255

Gly Gly Gly Ser Ile Gln Met Thr Gln Ser Pro Ser Ser Leu Ser Ala
            260                 265                 270

Ser Val Gly Asp Arg Val Thr Ile Thr Cys Gln Ala Ser Gln Ser Ile
        275                 280                 285

Asn Asn Val Leu Ala Trp Tyr Gln Gln Lys Pro Gly Lys Ala Pro Lys
290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
            340                 345                 350

Asn Tyr Gly Asp Phe Gly Thr Gly Thr Lys Val Thr Val Leu Gly Gly
        355                 360                 365
```

Gly Gly Gly Ser Gln Ser Gln Leu Gln Glu Ser Gly Pro Gly Leu Val
            370                 375                 380

Lys Pro Ser Glu Thr Leu Ser Leu Thr Cys Lys Ala Ser Gly Phe Ser
385                 390                 395                 400

Phe Ser Ser Gly Tyr Asp Met Cys Trp Val Arg Gln Pro Pro Gly Lys
                405                 410                 415

Gly Leu Glu Trp Ile Ala Cys Val Val Ala Gly Ser Val Asp Ile Thr
            420                 425                 430

Tyr Tyr Ala Ser Trp Ala Lys Gly Arg Val Thr Ile Ser Lys Asp Ser
        435                 440                 445

Ser Lys Asn Gln Val Ser Leu Lys Leu Ser Ser Val Thr Ala Ala Asp
    450                 455                 460

Thr Ala Val Tyr Phe Cys Ala Arg Lys Asp Ala Tyr Ser Asp Ala Phe
465                 470                 475                 480

Asn Leu Trp Gly Gln Gly Thr Leu Val Thr Val Ser Ser
                485                 490

<210> SEQ ID NO 77
<211> LENGTH: 493
<212> TYPE: PRT
<213> ORGANISM: Artificial Sequence
<220> FEATURE:
<223> OTHER INFORMATION: sequence of recombinant antibody or functional
      part thereof

<400> SEQUENCE: 77

Asp Ile Gln Met Thr Gln Ser Pro Ser Ser Leu Ser Ala Ser Val Gly
1               5                   10                  15

Asp Ala Val Thr Ile Thr Cys Gln Ala Ser Gln Ser Ile Asn Asp Tyr
            20                  25                  30

Leu Ala Trp Tyr Gln Gln Lys Pro Gly Lys Ser Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
        115                 120                 125

Lys Pro Ser Glu Thr Leu Ser Leu Thr Cys Lys Val Ser Gly Phe Ser
    130                 135                 140

Phe Ser Asn Ser Tyr Trp Ile Cys Trp Ile Arg Gln Pro Pro Gly Lys
145                 150                 155                 160

Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Val Asp Ser
            180                 185                 190

Ser Lys Asn Gln Phe Ser Leu Lys Leu Ser Ser Val Thr Ala Ala Asp
        195                 200                 205

Thr Ala Val Tyr Tyr Cys Ala Arg His Pro Ser Asp Ala Val Tyr Gly
    210                 215                 220

Tyr Ala Asn Asn Leu Trp Gly Gln Gly Thr Leu Val Thr Val Ser Ser

```
                    225                 230                 235                 240
Gly Gly Gly Gly Ser Gly Gly Gly Ser Gly Gly Gly Ser Gly
                245                 250                 255
Gly Gly Gly Ser Ile Gln Met Thr Gln Ser Pro Ser Ser Leu Ser Ala
                260                 265                 270
Ser Val Gly Asp Arg Val Thr Ile Thr Cys Gln Ala Ser Gln Ser Ile
                275                 280                 285
Asn Asn Val Leu Ala Trp Tyr Gln Gln Lys Pro Gly Lys Ala Pro Lys
                290                 295                 300
Leu Leu Ile Tyr Arg Ala Ser Thr Leu Ala Ser Gly Val Pro Ser Arg
305                 310                 315                 320
Phe Ser Gly Ser Gly Ser Gly Thr Asp Phe Thr Leu Thr Ile Ser Ser
                325                 330                 335
Leu Gln Pro Glu Asp Phe Ala Thr Tyr Tyr Cys Gln Ser Tyr Gly
                340                 345                 350
Asn Tyr Gly Asp Phe Gly Thr Gly Thr Lys Val Thr Val Leu Gly Gly
                355                 360                 365
Gly Gly Gly Ser Glu Val Gln Leu Val Glu Ser Gly Gly Gly Leu Val
                370                 375                 380
Gln Pro Gly Gly Ser Leu Arg Leu Ser Cys Ala Ala Ser Gly Phe Ser
385                 390                 395                 400
Phe Ser Ser Gly Tyr Asp Met Cys Trp Val Arg Gln Ala Pro Gly Lys
                405                 410                 415
Gly Leu Glu Trp Val Gly Cys Val Val Ala Gly Ser Val Asp Ile Thr
                420                 425                 430
Tyr Tyr Ala Ser Trp Ala Lys Gly Arg Phe Thr Ile Ser Arg Asp Asn
                435                 440                 445
Ser Lys Asn Thr Val Tyr Leu Gln Met Asn Ser Leu Arg Ala Glu Asp
                450                 455                 460
Thr Ala Thr Tyr Tyr Cys Ala Arg Lys Asp Ala Tyr Ser Asp Ala Phe
465                 470                 475                 480
Asn Leu Trp Gly Pro Gly Thr Leu Val Thr Val Ser Ser
                485                 490

<210> SEQ ID NO 78
<211> LENGTH: 755
<212> TYPE: PRT
<213> ORGANISM: Artificial Sequence
<220> FEATURE:
<223> OTHER INFORMATION: sequence of recombinant antibody or functional
      part thereof

<400> SEQUENCE: 78

Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Ser Ile Asn Asp Tyr
            20                  25                  30
Leu Ala Trp Tyr Gln Gln Lys Pro Gly Lys Ala Pro Lys Leu Leu Ile
                35                  40                  45
Tyr Lys Ala Ser Thr Leu Ala Ser Gly Val Pro Ser Arg Phe Ser Gly
            50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Tyr Ile Ile Thr Asp
                85                  90                  95
```

-continued

```
Ile Asp Asn Val Phe Gly Thr Gly Thr Lys Val Thr Val Leu Gly Gly
                100                 105                 110

Gly Gly Gly Ser Gln Val Gln Leu Gln Glu Ser Gly Pro Gly Leu Val
            115                 120                 125

Lys Pro Ser Glu Thr Leu Ser Leu Thr Cys Lys Val Ser Gly Phe Ser
130                 135                 140

Phe Ser Asn Ser Tyr Trp Ile Cys Trp Ile Arg Gln Pro Pro Gly Lys
145                 150                 155                 160

Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Val Asp Ser
                180                 185                 190

Ser Lys Asn Gln Phe Ser Leu Lys Leu Ser Ser Val Thr Ala Ala Asp
            195                 200                 205

Thr Ala Val Tyr Tyr Cys Ala Arg His Pro Ser Asp Ala Val Tyr Gly
        210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Ser Gly Gly Gly Gly Ser Gly
                245                 250                 255

Gly Gly Gly Ser Ile Gln Met Thr Gln Ser Pro Ser Ser Leu Ser Ala
            260                 265                 270

Ser Val Gly Asp Arg Val Thr Ile Thr Cys Gln Ala Ser Gln Ser Ile
        275                 280                 285

Asn Asn Val Leu Ala Trp Tyr Gln Gln Lys Pro Gly Lys Ala Pro Lys
290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
            340                 345                 350

Asn Tyr Gly Asp Phe Gly Thr Gly Thr Lys Val Thr Val Leu Gly Gly
        355                 360                 365

Gly Gly Gly Ser Gln Val Gln Leu Gln Glu Ser Gly Pro Gly Leu Val
    370                 375                 380

Lys Pro Ser Glu Thr Leu Ser Leu Thr Cys Lys Val Ser Gly Phe Ser
385                 390                 395                 400

Phe Ser Ser Gly Tyr Asp Met Cys Trp Ile Arg Gln Pro Pro Gly Lys
                405                 410                 415

Gly Leu Glu Trp Ile Gly Cys Val Val Ala Gly Ser Val Asp Ile Thr
            420                 425                 430

Tyr Tyr Ala Ser Trp Ala Lys Gly Arg Val Thr Ile Ser Val Asp Ser
        435                 440                 445

Ser Lys Asn Gln Phe Ser Leu Lys Leu Ser Ser Val Thr Ala Ala Asp
    450                 455                 460

Thr Ala Val Tyr Tyr Cys Ala Arg Lys Asp Ala Tyr Ser Asp Ala Phe
465                 470                 475                 480

Asn Leu Trp Gly Gln Gly Thr Leu Val Thr Val Ser Ser Gly Gly Gly
                485                 490                 495

Gly Ser Gly Gly Gly Gly Ser Ile Gln Met Thr Gln Ser Pro Ser Ser
            500                 505                 510

Leu Ser Ala Ser Val Gly Asp Arg Val Thr Ile Thr Cys Gln Ser Ser
```

```
                515                 520                 525
Glu Ser Val Tyr Ser Asn Asn Gln Leu Ser Trp Tyr Gln Gln Lys Pro
530                 535                 540

Gly Gln Pro Pro Lys Leu Leu Ile Tyr Asp Ala Ser Asp Leu Ala Ser
545                 550                 555                 560

Gly Val Pro Ser Arg Phe Ser Gly Ser Gly Ser Gly Thr Asp Phe Thr
                565                 570                 575

Leu Thr Ile Ser Ser Leu Gln Pro Glu Asp Phe Ala Thr Tyr Tyr Cys
            580                 585                 590

Ala Gly Gly Phe Ser Ser Ser Asp Thr Ala Phe Gly Gly Gly Thr
        595                 600                 605

Lys Leu Thr Val Leu Gly Gly Gly Gly Ser Gly Gly Gly Gly Ser
610                 615                 620

Gly Gly Gly Gly Ser Gly Gly Gly Ser Glu Val Gln Leu Val Glu
625                 630                 635                 640

Ser Gly Gly Gly Leu Val Gln Pro Gly Gly Ser Leu Arg Leu Ser Cys
                645                 650                 655

Ala Ala Ser Gly Phe Ser Leu Ser Ser Asn Ala Met Gly Trp Val Arg
            660                 665                 670

Gln Ala Pro Gly Lys Gly Leu Glu Tyr Ile Gly Ile Ser Val Gly
        675                 680                 685

Gly Phe Thr Tyr Tyr Ala Ser Trp Ala Lys Gly Arg Phe Thr Ile Ser
        690                 695                 700

Arg Asp Asn Ser Lys Asn Thr Val Tyr Leu Gln Met Asn Ser Leu Arg
705                 710                 715                 720

Ala Glu Asp Thr Ala Thr Tyr Phe Cys Ala Arg Asp Arg His Gly Gly
                725                 730                 735

Asp Ser Ser Gly Ala Phe Tyr Leu Trp Gly Gln Gly Thr Leu Val Thr
            740                 745                 750

Val Ser Ser
        755

<210> SEQ ID NO 79
<211> LENGTH: 761
<212> TYPE: PRT
<213> ORGANISM: Artificial Sequence
<220> FEATURE:
<223> OTHER INFORMATION: sequence of recombinant antibody or functional
      part thereof

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110
```

```
Gly Gly Gly Ser Gln Val Gln Leu Gln Glu Ser Gly Pro Gly Leu Val
            115                 120                 125
Lys Pro Ser Glu Thr Leu Ser Leu Thr Cys Lys Val Ser Gly Phe Ser
130                 135                 140
Phe Asn Asn Asp Tyr Asp Met Cys Trp Ile Arg Gln Pro Pro Gly Lys
145                 150                 155                 160
Gly Leu Glu Trp Ile Gly Cys Ile Asp Thr Gly Asp Gly Ser Thr Tyr
                165                 170                 175
Tyr Ala Ser Trp Ala Lys Gly Arg Val Thr Ile Ser Val Asp Ser Ser
            180                 185                 190
Lys Asn Gln Phe Ser Leu Lys Leu Ser Ser Val Thr Ala Ala Asp Thr
        195                 200                 205
Ala Val Tyr Tyr Cys Ala Arg Glu Ala Ala Ser Ser Gly Tyr Gly
210                 215                 220
Met Gly Tyr Phe Asp Leu Trp Gly Gln Gly Thr Leu Val Thr Val Ser
225                 230                 235                 240
Ser Gly Gly Gly Ser Gly Gly Gly Ser Gly Gly Gly Ser
                245                 250                 255
Gly Gly Gly Gly Ser Ile Gln Met Thr Gln Ser Pro Ser Ser Leu Ser
            260                 265                 270
Ala Ser Val Gly Asp Arg Val Thr Ile Thr Cys Gln Ser Ser Gln Ser
        275                 280                 285
Val Tyr Asp Asn Asn Trp Leu Ala Trp Tyr Gln Gln Lys Pro Gly Lys
290                 295                 300
Ala Pro Lys Leu Leu Ile Tyr Arg Ala Ser Asn Leu Ala Ser Gly Val
305                 310                 315                 320
Pro Ser Arg Phe Ser Gly Ser Gly Ser Gly Thr Asp Phe Thr Leu Thr
                325                 330                 335
Ile Ser Ser Leu Gln Pro Glu Asp Phe Ala Thr Tyr Tyr Cys Gln Gly
            340                 345                 350
Thr Tyr Leu Ser Ser Asn Trp Tyr Trp Ala Phe Gly Thr Gly Thr Lys
        355                 360                 365
Val Thr Val Leu Gly Gly Gly Gly Ser Gln Val Gln Leu Gln Glu
370                 375                 380
Ser Gly Pro Gly Leu Val Lys Pro Ser Glu Thr Leu Ser Leu Thr Cys
385                 390                 395                 400
Lys Val Ser Gly Phe Ser Phe Ser Ser Gly Tyr Asp Met Cys Trp Ile
                405                 410                 415
Arg Gln Pro Pro Gly Lys Gly Leu Glu Trp Ile Gly Cys Val Val Ala
            420                 425                 430
Gly Ser Val Asp Ile Thr Tyr Tyr Ala Ser Trp Ala Lys Gly Arg Val
        435                 440                 445
Thr Ile Ser Val Asp Ser Ser Lys Asn Gln Phe Ser Leu Lys Leu Ser
450                 455                 460
Ser Val Thr Ala Ala Asp Thr Ala Val Tyr Tyr Cys Ala Arg Lys Asp
465                 470                 475                 480
Ala Tyr Ser Asp Ala Phe Asn Leu Trp Gly Gln Gly Thr Leu Val Thr
                485                 490                 495
Val Ser Ser Gly Gly Gly Ser Gly Gly Gly Ser Ile Gln Met
            500                 505                 510
Thr Gln Ser Pro Ser Ser Leu Ser Ala Ser Val Gly Asp Arg Val Thr
        515                 520                 525
Ile Thr Cys Gln Ser Ser Glu Ser Val Tyr Ser Asn Asn Gln Leu Ser
```

```
                    530             535             540
Trp Tyr Gln Gln Lys Pro Gly Gln Pro Pro Lys Leu Ile Tyr Asp
545                 550                 555                 560

Ala Ser Asp Leu Ala Ser Gly Val Pro Ser Arg Phe Ser Gly Ser
                565                 570                 575

Ser Gly Thr Asp Phe Thr Leu Thr Ile Ser Ser Leu Gln Pro Glu Asp
                580                 585                 590

Phe Ala Thr Tyr Tyr Cys Ala Gly Phe Ser Ser Ser Asp Thr
            595                 600                 605

Ala Phe Gly Gly Gly Thr Lys Leu Thr Val Leu Gly Gly Gly Gly
        610                 615                 620

Ser Gly Gly Gly Gly Ser Gly Gly Gly Gly Ser Gly Gly Gly Gly Ser
625                 630                 635                 640

Glu Val Gln Leu Val Glu Ser Gly Gly Leu Val Gln Pro Gly Gly
                645                 650                 655

Ser Leu Arg Leu Ser Cys Ala Ala Ser Gly Phe Ser Leu Ser Ser Asn
                660                 665                 670

Ala Met Gly Trp Val Arg Gln Ala Pro Gly Lys Gly Leu Glu Tyr Ile
            675                 680                 685

Gly Ile Ile Ser Val Gly Gly Phe Thr Tyr Tyr Ala Ser Trp Ala Lys
        690                 695                 700

Gly Arg Phe Thr Ile Ser Arg Asp Asn Ser Lys Asn Thr Val Tyr Leu
705                 710                 715                 720

Gln Met Asn Ser Leu Arg Ala Glu Asp Thr Ala Thr Tyr Phe Cys Ala
                725                 730                 735

Arg Asp Arg His Gly Gly Asp Ser Ser Gly Ala Phe Tyr Leu Trp Gly
                740                 745                 750

Gln Gly Thr Leu Val Thr Val Ser Ser
            755                 760

<210> SEQ ID NO 80
<211> LENGTH: 753
<212> TYPE: PRT
<213> ORGANISM: Artificial Sequence
<220> FEATURE:
<223> OTHER INFORMATION: sequence of recombinant antibody or functional
      part thereof

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
        115                 120                 125
```

```
Lys Pro Ser Glu Thr Leu Ser Leu Thr Cys Lys Val Ser Gly Phe Ser
130                 135                 140
Phe Ser Asn Ser Tyr Trp Ile Cys Trp Ile Arg Gln Pro Pro Gly Lys
145                 150                 155                 160
Gly Leu Glu Trp Ile Gly Cys Thr Phe Val Gly Ser Ser Asp Ser Thr
            165                 170                 175
Tyr Tyr Ala Asn Trp Ala Lys Gly Arg Val Thr Ile Ser Val Asp Ser
            180                 185                 190
Ser Lys Asn Gln Phe Ser Leu Lys Leu Ser Ser Val Thr Ala Ala Asp
        195                 200                 205
Thr Ala Val Tyr Tyr Cys Ala Arg His Pro Ser Asp Ala Val Tyr Gly
210                 215                 220
Tyr Ala Asn Asn Leu Trp Gly Gln Gly Thr Leu Val Thr Val Ser Ser
225                 230                 235                 240
Gly Gly Gly Gly Ser Gly Gly Gly Ser Gly Gly Gly Ser Gly
            245                 250                 255
Gly Gly Gly Ser Ile Gln Met Thr Gln Ser Pro Ser Ser Leu Ser Ala
        260                 265                 270
Ser Val Gly Asp Arg Val Thr Ile Thr Cys Gln Ala Ser Gln Ser Ile
        275                 280                 285
Asn Asn Val Leu Ala Trp Tyr Gln Gln Lys Pro Gly Lys Ala Pro Lys
290                 295                 300
Leu Leu Ile Tyr Arg Ala Ser Thr Leu Ala Ser Gly Val Pro Ser Arg
305                 310                 315                 320
Phe Ser Gly Ser Gly Ser Gly Thr Asp Phe Thr Leu Thr Ile Ser Ser
            325                 330                 335
Leu Gln Pro Glu Asp Phe Ala Thr Tyr Tyr Cys Gln Ser Ser Tyr Gly
        340                 345                 350
Asn Tyr Gly Asp Phe Gly Thr Gly Thr Lys Val Thr Val Leu Gly Gly
        355                 360                 365
Gly Gly Gly Ser Gln Val Gln Leu Gln Glu Ser Gly Pro Gly Leu Val
        370                 375                 380
Lys Pro Ser Glu Thr Leu Ser Leu Thr Cys Lys Val Ser Gly Phe Ser
385                 390                 395                 400
Phe Ser Ser Gly Tyr Asp Met Cys Trp Ile Arg Gln Pro Pro Gly Lys
            405                 410                 415
Gly Leu Glu Trp Ile Gly Cys Val Val Ala Gly Ser Val Asp Ile Thr
            420                 425                 430
Tyr Tyr Ala Ser Trp Ala Lys Gly Arg Val Thr Ile Ser Val Asp Ser
            435                 440                 445
Ser Lys Asn Gln Phe Ser Leu Lys Leu Ser Ser Val Thr Ala Ala Asp
        450                 455                 460
Thr Ala Val Tyr Tyr Cys Ala Arg Lys Asp Ala Tyr Ser Asp Ala Phe
465                 470                 475                 480
Asn Leu Trp Gly Gln Gly Thr Leu Val Thr Val Ser Ser Gly Gly Gly
            485                 490                 495
Gly Ser Gly Gly Gly Gly Ser Val Val Met Thr Gln Ser Pro Ser Ser
        500                 505                 510
Leu Ser Ala Ser Val Gly Asp Arg Val Thr Ile Thr Cys Gln Ala Ser
        515                 520                 525
Gln Ile Ile Ser Arg Ser Ala Trp Tyr Gln Gln Lys Pro Gly Gln
    530                 535                 540
Pro Pro Lys Leu Leu Ile Tyr Gln Ala Ser Lys Leu Ala Ser Gly Val
```

Pro Ser Arg Phe Ser Gly Ser Gly Ser Gly Thr Asp Phe Thr Leu Thr
545                 550                 555                 560

Ile Ser Ser Leu Gln Pro Glu Asp Phe Ala Thr Tyr Tyr Cys Gln Cys
            565                 570                 575

Thr Tyr Ile Asp Ser Asn Phe Gly Ala Phe Gly Gly Gly Thr Lys Leu
        580                 585                 590

Thr Val Leu Gly Gly Gly Gly Ser Gly Gly Gly Ser Gly Gly
    595                 600                 605

Gly Gly Ser Gly Gly Gly Ser Glu Val Gln Leu Val Glu Ser Gly
610                 615                 620

Gly Gly Leu Val Gln Pro Gly Ser Leu Arg Leu Ser Cys Ala Ala
625                 630                 635                 640

Ser Gly Phe Ser Phe Ser Ser Tyr Trp Ile Cys Trp Val Arg Gln
            645                 650                 655

Ala Pro Gly Lys Gly Leu Glu Trp Val Gly Cys Val Phe Thr Gly Asp
            660                 665                 670

Gly Thr Thr Tyr Tyr Ala Ser Trp Ala Lys Gly Arg Phe Thr Ile Ser
            675                 680                 685

Arg Asp Asn Ser Lys Asn Thr Val Tyr Leu Gln Met Asn Ser Leu Arg
690                 695                 700

Ala Glu Asp Thr Ala Thr Tyr Phe Cys Ala Arg Pro Val Ser Val Tyr
705                 710                 715                 720

Tyr Tyr Gly Met Asp Leu Trp Gly Gln Gly Thr Leu Val Thr Val Ser
            725                 730                 735

Ser
                740                 745                 750

<210> SEQ ID NO 81
<211> LENGTH: 759
<212> TYPE: PRT
<213> ORGANISM: Artificial Sequence
<220> FEATURE:
<223> OTHER INFORMATION: sequence of recombinant antibody or functional
      part thereof

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Leu Gly Gly
            100                 105                 110

Gly Gly Ser Gln Val Gln Leu Gln Glu Ser Gly Pro Gly Leu Val
        115                 120                 125

Lys Pro Ser Glu Thr Leu Ser Leu Thr Cys Lys Val Ser Gly Phe Ser
    130                 135                 140

Phe Asn Asn Asp Tyr Asp Met Cys Trp Ile Arg Gln Pro Pro Gly Lys

```
            145                 150                 155                 160
Gly Leu Glu Trp Ile Gly Cys Ile Asp Thr Gly Asp Gly Ser Thr Tyr
                165                 170                 175
Tyr Ala Ser Trp Ala Lys Gly Arg Val Thr Ile Ser Val Asp Ser Ser
                180                 185                 190
Lys Asn Gln Phe Ser Leu Lys Leu Ser Ser Val Thr Ala Ala Asp Thr
                195                 200                 205
Ala Val Tyr Tyr Cys Ala Arg Glu Ala Ala Ser Ser Gly Tyr Gly
    210                 215                 220
Met Gly Tyr Phe Asp Leu Trp Gly Gln Gly Thr Leu Val Thr Val Ser
225                 230                 235                 240
Ser Gly Gly Gly Gly Ser Gly Gly Gly Ser Gly Gly Gly Gly Ser
                245                 250                 255
Gly Gly Gly Gly Ser Ile Gln Met Thr Gln Ser Pro Ser Ser Leu Ser
                260                 265                 270
Ala Ser Val Gly Asp Arg Val Thr Ile Thr Cys Gln Ser Ser Gln Ser
                275                 280                 285
Val Tyr Asp Asn Asn Trp Leu Ala Trp Tyr Gln Gln Lys Pro Gly Lys
    290                 295                 300
Ala Pro Lys Leu Leu Ile Tyr Arg Ala Ser Asn Leu Ala Ser Gly Val
305                 310                 315                 320
Pro Ser Arg Phe Ser Gly Ser Gly Ser Gly Thr Asp Phe Thr Leu Thr
                325                 330                 335
Ile Ser Ser Leu Gln Pro Glu Asp Phe Ala Thr Tyr Tyr Cys Gln Gly
                340                 345                 350
Thr Tyr Leu Ser Ser Asn Trp Tyr Trp Ala Phe Gly Thr Gly Thr Lys
                355                 360                 365
Val Thr Val Leu Gly Gly Gly Gly Ser Gln Val Gln Leu Gln Glu
                370                 375                 380
Ser Gly Pro Gly Leu Val Lys Pro Ser Glu Thr Leu Ser Leu Thr Cys
385                 390                 395                 400
Lys Val Ser Gly Phe Ser Phe Ser Ser Gly Tyr Asp Met Cys Trp Ile
                405                 410                 415
Arg Gln Pro Pro Gly Lys Gly Leu Glu Trp Ile Gly Cys Val Val Ala
                420                 425                 430
Gly Ser Val Asp Ile Thr Tyr Tyr Ala Ser Trp Ala Lys Gly Arg Val
                435                 440                 445
Thr Ile Ser Val Asp Ser Ser Lys Asn Gln Phe Ser Leu Lys Leu Ser
    450                 455                 460
Ser Val Thr Ala Ala Asp Thr Ala Val Tyr Tyr Cys Ala Arg Lys Asp
465                 470                 475                 480
Ala Tyr Ser Asp Ala Phe Asn Leu Trp Gly Gln Gly Thr Leu Val Thr
                485                 490                 495
Val Ser Ser Gly Gly Gly Gly Ser Gly Gly Gly Gly Ser Val Val Met
                500                 505                 510
Thr Gln Ser Pro Ser Ser Leu Ser Ala Ser Val Gly Asp Arg Val Thr
                515                 520                 525
Ile Thr Cys Gln Ala Ser Gln Ile Ile Ser Ser Arg Ser Ala Trp Tyr
                530                 535                 540
Gln Gln Lys Pro Gly Gln Pro Pro Lys Leu Leu Ile Tyr Gln Ala Ser
545                 550                 555                 560
Lys Leu Ala Ser Gly Val Pro Ser Arg Phe Ser Gly Ser Gly Ser Gly
                565                 570                 575
```

```
Thr Asp Phe Thr Leu Thr Ile Ser Ser Leu Gln Pro Glu Asp Phe Ala
            580                 585                 590

Thr Tyr Tyr Cys Gln Cys Thr Tyr Ile Asp Ser Asn Phe Gly Ala Phe
        595                 600                 605

Gly Gly Gly Thr Lys Leu Thr Val Leu Gly Gly Gly Gly Ser Gly
    610                 615                 620

Gly Gly Gly Ser Gly Gly Gly Ser Gly Gly Gly Ser Glu Val
625                 630                 635                 640

Gln Leu Val Glu Ser Gly Gly Leu Val Gln Pro Gly Gly Ser Leu
                645                 650                 655

Arg Leu Ser Cys Ala Ala Ser Gly Phe Ser Phe Ser Ser Tyr Trp
            660                 665                 670

Ile Cys Trp Val Arg Gln Ala Pro Gly Lys Gly Leu Glu Trp Val Gly
            675                 680                 685

Cys Val Phe Thr Gly Asp Gly Thr Thr Tyr Tyr Ala Ser Trp Ala Lys
            690                 695                 700

Gly Arg Phe Thr Ile Ser Arg Asp Asn Ser Lys Asn Thr Val Tyr Leu
705                 710                 715                 720

Gln Met Asn Ser Leu Arg Ala Glu Asp Thr Ala Thr Tyr Phe Cys Ala
                725                 730                 735

Arg Pro Val Ser Val Tyr Tyr Gly Met Asp Leu Trp Gly Gln Gly
            740                 745                 750

Thr Leu Val Thr Val Ser Ser
        755

<210> SEQ ID NO 82
<211> LENGTH: 478
<212> TYPE: PRT
<213> ORGANISM: Artificial Sequence
<220> FEATURE:
<223> OTHER INFORMATION: sequence of recombinant antibody or functional
      part thereof

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
```

```
            165                 170                 175
Ser Leu Ser Ser Thr Leu Thr Leu Ser Lys Ala Asp Tyr Glu Lys His
        180                 185                 190

Lys Val Tyr Ala Cys Glu Val Thr His Gln Gly Leu Ser Ser Pro Val
    195                 200                 205

Thr Lys Ser Phe Asn Arg Gly Glu Cys Gly Gly Gly Ser Gly Gly
    210                 215                 220

Gly Gly Ser Ile Gln Met Thr Gln Ser Pro Ser Ser Leu Ser Ala Ser
225                 230                 235                 240

Val Gly Asp Arg Val Thr Ile Thr Cys Gln Ala Ser Gln Ser Ile Asn
            245                 250                 255

Asn Val Leu Ala Trp Tyr Gln Gln Lys Pro Gly Lys Ala Pro Lys Leu
            260                 265                 270

Leu Ile Tyr Arg Ala Ser Thr Leu Ala Ser Gly Val Pro Ser Arg Phe
            275                 280                 285

Ser Gly Ser Gly Ser Gly Thr Asp Phe Thr Leu Thr Ile Ser Ser Leu
        290                 295                 300

Gln Pro Glu Asp Phe Ala Thr Tyr Tyr Cys Gln Ser Ser Tyr Gly Asn
305                 310                 315                 320

Tyr Gly Asp Phe Gly Thr Gly Thr Lys Val Thr Val Leu Gly Gly Gly
                325                 330                 335

Gly Gly Ser Gly Gly Gly Gly Ser Gly Gly Gly Gly Ser Gly Gly Gly
            340                 345                 350

Gly Ser Gln Val Gln Leu Gln Glu Ser Gly Pro Gly Leu Val Lys Pro
        355                 360                 365

Ser Glu Thr Leu Ser Leu Thr Cys Lys Val Ser Gly Phe Ser Phe Ser
    370                 375                 380

Asn Ser Tyr Trp Ile Cys Trp Ile Arg Gln Pro Pro Gly Lys Gly Leu
385                 390                 395                 400

Glu Trp Ile Gly Cys Thr Phe Val Gly Ser Ser Asp Ser Thr Tyr Tyr
                405                 410                 415

Ala Asn Trp Ala Lys Gly Arg Val Thr Ile Ser Val Asp Ser Ser Lys
            420                 425                 430

Asn Gln Phe Ser Leu Lys Leu Ser Ser Val Thr Ala Ala Asp Thr Ala
            435                 440                 445

Val Tyr Tyr Cys Ala Arg His Pro Ser Asp Ala Val Tyr Gly Tyr Ala
        450                 455                 460

Asn Asn Leu Trp Gly Gln Gly Thr Leu Val Thr Val Ser Ser
465                 470                 475

<210> SEQ ID NO 83
<211> LENGTH: 451
<212> TYPE: PRT
<213> ORGANISM: Artificial Sequence
<220> FEATURE:
<223> OTHER INFORMATION: sequence of recombinant antibody or functional
      part thereof

<400> SEQUENCE: 83

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
            20                  25                  30

Tyr Asp Met Cys Trp Ile Arg Gln Pro Pro Gly Lys Gly Leu Glu Trp
        35                  40                  45
```

```
Ile Gly Cys Val Val Ala Gly Ser Val Asp Ile Thr Tyr Tyr Ala Ser
     50                  55                  60

Trp Ala Lys Gly Arg Val Thr Ile Ser Val Asp Ser Ser Lys Asn Gln
 65                  70                  75                  80

Phe Ser Leu Lys Leu Ser Ser Val Thr Ala Ala Asp Thr Ala Val Tyr
                 85                  90                  95

Tyr Cys Ala Arg Lys Asp Ala Tyr Ser Asp Ala Phe Asn Leu Trp Gly
            100                 105                 110

Gln Gly Thr Leu Val Thr Val Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
450
```

-continued

```
<210> SEQ ID NO 84
<211> LENGTH: 217
<212> TYPE: PRT
<213> ORGANISM: Artificial Sequence
<220> FEATURE:
<223> OTHER INFORMATION: sequence of recombinant antibody or functional
      part thereof

<400> SEQUENCE: 84

Asp Ile Gln Met Thr Gln Ser Pro Ser Leu Ser Ala Ser Val Gly
1               5                   10                  15

Asp Arg Val Thr Ile Thr Cys Gln Ala Ser Gln Ser Ile Asn Asp Tyr
                20                  25                  30

Leu Ala Trp Tyr Gln Gln Lys Pro Gly Lys Ala Pro Lys Leu Leu Ile
            35                  40                  45

Tyr Lys Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 85
<211> LENGTH: 712
<212> TYPE: PRT
<213> ORGANISM: Artificial Sequence
<220> FEATURE:
<223> OTHER INFORMATION: sequence of recombinant antibody or functional
      part thereof

<400> SEQUENCE: 85

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
                20                  25                  30

Tyr Asp Met Cys Trp Ile Arg Gln Pro Pro Gly Lys Gly Leu Glu Trp
            35                  40                  45

Ile Gly Cys Val Val Ala Gly Ser Val Asp Ile Thr Tyr Tyr Ala Ser
50                  55                  60

Trp Ala Lys Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
```

```
                    85                  90                  95
Tyr Cys Ala Arg Lys Asp Ala Tyr Ser Asp Ala Phe Asn Leu Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Ser Ile Gln Met
    450                 455                 460

Thr Gln Ser Pro Ser Ser Leu Ser Ala Ser Val Gly Asp Arg Val Thr
465                 470                 475                 480

Ile Thr Cys Gln Ala Ser Gln Ser Ile Asn Asn Val Leu Ala Trp Tyr
                485                 490                 495

Gln Gln Lys Pro Gly Lys Ala Pro Lys Leu Leu Ile Tyr Arg Ala Ser
            500                 505                 510
```

```
Thr Leu Ala Ser Gly Val Pro Ser Arg Phe Ser Gly Ser Gly
        515                 520                 525

Thr Asp Phe Thr Leu Thr Ile Ser Ser Leu Gln Pro Glu Asp Phe Ala
        530                 535                 540

Thr Tyr Tyr Cys Gln Ser Ser Tyr Gly Asn Tyr Gly Asp Phe Gly Thr
545                 550                 555                 560

Gly Thr Lys Val Thr Val Leu Gly Gly Gly Gly Ser Gly Gly Gly
            565                 570                 575

Gly Ser Gly Gly Gly Ser Gly Gly Gly Ser Gln Val Gln Leu
            580                 585                 590

Gln Glu Ser Gly Pro Gly Leu Val Lys Pro Ser Glu Thr Leu Ser Leu
        595                 600                 605

Thr Cys Lys Val Ser Gly Phe Ser Phe Ser Asn Ser Tyr Trp Ile Cys
        610                 615                 620

Trp Ile Arg Gln Pro Pro Gly Lys Gly Leu Glu Trp Ile Gly Cys Thr
625                 630                 635                 640

Phe Val Gly Ser Ser Asp Ser Thr Tyr Tyr Ala Asn Trp Ala Lys Gly
                645                 650                 655

Arg Val Thr Ile Ser Val Asp Ser Ser Lys Asn Gln Phe Ser Leu Lys
            660                 665                 670

Leu Ser Ser Val Thr Ala Ala Asp Thr Ala Val Tyr Tyr Cys Ala Arg
        675                 680                 685

His Pro Ser Asp Ala Val Tyr Gly Tyr Ala Asn Asn Leu Trp Gly Gln
        690                 695                 700

Gly Thr Leu Val Thr Val Ser Ser
705                 710

<210> SEQ ID NO 86
<211> LENGTH: 478
<212> TYPE: PRT
<213> ORGANISM: Artificial Sequence
<220> FEATURE:
<223> OTHER INFORMATION: sequence of recombinant antibody or functional
      part thereof

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
```

```
            145                 150                 155                 160
Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Gly Gly Gly Ser Gly Gly
210                 215                 220

Gly Gly Ser Ile Gln Met Thr Gln Ser Pro Ser Ser Leu Ser Ala Ser
225                 230                 235                 240

Val Gly Asp Arg Val Thr Ile Thr Cys Gln Ala Ser Gln Ser Ile Asn
                245                 250                 255

Asn Val Leu Ala Trp Tyr Gln Gln Lys Pro Gly Lys Ala Pro Lys Leu
            260                 265                 270

Leu Ile Tyr Arg Ala Ser Thr Leu Ala Ser Gly Val Pro Ser Arg Phe
        275                 280                 285

Ser Gly Ser Gly Ser Gly Thr Asp Phe Thr Leu Thr Ile Ser Ser Leu
    290                 295                 300

Gln Pro Glu Asp Phe Ala Thr Tyr Tyr Cys Gln Ser Ser Tyr Gly Asn
305                 310                 315                 320

Tyr Gly Asp Phe Gly Thr Gly Thr Lys Val Thr Val Leu Gly Gly Gly
                325                 330                 335

Gly Gly Ser Gly Gly Gly Gly Ser Gly Gly Gly Ser Gly Gly Gly
            340                 345                 350

Gly Ser Gln Val Gln Leu Gln Glu Ser Gly Pro Gly Leu Val Lys Pro
        355                 360                 365

Ser Glu Thr Leu Ser Leu Thr Cys Lys Val Ser Gly Phe Ser Phe Ser
    370                 375                 380

Asn Ser Tyr Trp Ile Cys Trp Ile Arg Gln Pro Pro Gly Lys Gly Leu
385                 390                 395                 400

Glu Trp Ile Gly Cys Thr Phe Val Gly Ser Ser Asp Ser Thr Tyr Tyr
                405                 410                 415

Ala Asn Trp Ala Lys Gly Arg Val Thr Ile Ser Val Asp Ser Ser Lys
            420                 425                 430

Asn Gln Phe Ser Leu Lys Leu Ser Ser Val Thr Ala Ala Asp Thr Ala
        435                 440                 445

Val Tyr Tyr Cys Ala Arg His Pro Ser Asp Ala Val Tyr Gly Tyr Ala
    450                 455                 460

Asn Asn Leu Trp Gly Gln Gly Thr Leu Val Thr Val Ser Ser
465                 470                 475

<210> SEQ ID NO 87
<211> LENGTH: 451
<212> TYPE: PRT
<213> ORGANISM: Artificial Sequence
<220> FEATURE:
<223> OTHER INFORMATION: sequence of recombinant antibody or functional
      part thereof

<400> SEQUENCE: 87

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
            20                  25                  30
```

-continued

```
Tyr Asp Met Cys Trp Ile Arg Gln Pro Pro Gly Lys Gly Leu Glu Trp
             35                  40                  45

Ile Gly Cys Val Val Ala Gly Ser Val Asp Ile Thr Tyr Tyr Ala Ser
 50                  55                  60

Trp Ala Lys Gly Arg Val Thr Ile Ser Val Asp Ser Ser Lys Asn Gln
 65                  70                  75                  80

Phe Ser Leu Lys Leu Ser Ser Val Thr Ala Ala Asp Thr Ala Val Tyr
                 85                  90                  95

Tyr Cys Ala Arg Lys Asp Ala Tyr Ser Asp Ala Phe Asn Leu Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
```

<210> SEQ ID NO 88
<211> LENGTH: 217
<212> TYPE: PRT
<213> ORGANISM: Artificial Sequence
<220> FEATURE:
<223> OTHER INFORMATION: sequence of recombinant antibody or functional
      part thereof

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 89
<211> LENGTH: 712
<212> TYPE: PRT
<213> ORGANISM: Artificial Sequence
<220> FEATURE:
<223> OTHER INFORMATION: sequence of recombinant antibody or functional
      part thereof

<400> SEQUENCE: 89

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
            20                  25                  30

Tyr Asp Met Cys Trp Ile Arg Gln Pro Pro Gly Lys Gly Leu Glu Trp
        35                  40                  45

Ile Gly Cys Val Val Ala Gly Ser Val Asp Ile Thr Tyr Tyr Ala Ser
50                  55                  60

Trp Ala Lys Gly Arg Val Thr Ile Ser Val Asp Ser Ser Lys Asn Gln

```
                65                  70                  75                  80
            Phe Ser Leu Lys Leu Ser Ser Val Thr Ala Ala Asp Thr Ala Val Tyr
                            85                  90                  95

Tyr Cys Ala Arg Lys Asp Ala Tyr Ser Asp Ala Phe Asn Leu Trp Gly
                           100                 105                 110

Gln Gly Thr Leu Val Thr Val Ser Ser Ala Ser Thr Lys Gly Pro Ser
                           115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
            145                 150                 155                 160

Ser Trp Asn Ser Gly Ala Leu Thr Ser Gly Val His Thr Phe Pro Ala
                           165                 170                 175

Val Leu Gln Ser Ser Gly Leu Tyr Ser Leu Ser Ser Val Val Thr Val
                           180                 185                 190

Pro Ser Ser Ser Leu Gly Thr Gln Thr Tyr Ile Cys Asn Val Asn His
                           195                 200                 205

Lys Pro Ser Asn Thr Lys Val Asp Lys Arg Val Glu Pro Lys Ser Cys
            210                 215                 220

Asp Lys Thr His Thr Cys Pro Pro Cys Pro Ala Pro Glu Ala Ala Gly
            225                 230                 235                 240

Gly Pro Ser Val Phe Leu Phe Pro Pro Lys Pro Lys Asp Thr Leu Met
                           245                 250                 255

Ile Ser Arg Thr Pro Glu Val Thr Cys Val Val Val Asp Val Ser His
                           260                 265                 270

Glu Asp Pro Glu Val Lys Phe Asn Trp Tyr Val Asp Gly Val Glu Val
                           275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
            305                 310                 315                 320

Lys Glu Tyr Lys Cys Lys Val Ser Asn Lys Ala Leu Gly Ala Pro Ile
                           325                 330                 335

Glu Lys Thr Ile Ser Lys Ala Lys Gly Gln Pro Arg Glu Pro Gln Val
                           340                 345                 350

Tyr Thr Leu Pro Pro Ser Arg Glu Glu Met Thr Lys Asn Gln Val Ser
                           355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
            385                 390                 395                 400

Val Leu Asp Ser Asp Gly Ser Phe Phe Leu Tyr Ser Lys Leu Thr Val
                           405                 410                 415

Asp Lys Ser Arg Trp Gln Gln Gly Asn Val Phe Ser Cys Ser Val Met
                           420                 425                 430

His Glu Ala Leu His Asn His Tyr Thr Gln Lys Ser Leu Ser Leu Ser
                           435                 440                 445

Pro Gly Lys Gly Gly Gly Ser Gly Gly Gly Ser Ile Gln Met
            450                 455                 460

Thr Gln Ser Pro Ser Ser Leu Ser Ala Ser Val Gly Asp Arg Val Thr
            465                 470                 475                 480

Ile Thr Cys Gln Ala Ser Gln Ser Ile Asn Asn Val Leu Ala Trp Tyr
                           485                 490                 495
```

```
Gln Gln Lys Pro Gly Lys Ala Pro Lys Leu Leu Ile Tyr Arg Ala Ser
            500                 505                 510

Thr Leu Ala Ser Gly Val Pro Ser Arg Phe Ser Gly Ser Gly
            515                 520                 525

Thr Asp Phe Thr Leu Thr Ile Ser Ser Leu Gln Pro Glu Asp Phe Ala
            530                 535                 540

Thr Tyr Tyr Cys Gln Ser Ser Tyr Gly Asn Tyr Gly Asp Phe Gly Thr
545                 550                 555                 560

Gly Thr Lys Val Thr Val Leu Gly Gly Gly Gly Ser Gly Gly
                565                 570                 575

Gly Ser Gly Gly Gly Ser Gly Gly Gly Ser Gln Val Gln Leu
            580                 585                 590

Gln Glu Ser Gly Pro Gly Leu Val Lys Pro Ser Glu Thr Leu Ser Leu
            595                 600                 605

Thr Cys Lys Val Ser Gly Phe Ser Phe Ser Asn Ser Tyr Trp Ile Cys
            610                 615                 620

Trp Ile Arg Gln Pro Pro Gly Lys Gly Leu Glu Trp Ile Gly Cys Thr
625                 630                 635                 640

Phe Val Gly Ser Ser Asp Ser Thr Tyr Tyr Ala Asn Trp Ala Lys Gly
                645                 650                 655

Arg Val Thr Ile Ser Val Asp Ser Ser Lys Asn Gln Phe Ser Leu Lys
                660                 665                 670

Leu Ser Ser Val Thr Ala Ala Asp Thr Ala Val Tyr Tyr Cys Ala Arg
            675                 680                 685

His Pro Ser Asp Ala Val Tyr Gly Tyr Ala Asn Asn Leu Trp Gly Gln
            690                 695                 700

Gly Thr Leu Val Thr Val Ser Ser
705                 710

<210> SEQ ID NO 90
<211> LENGTH: 217
<212> TYPE: PRT
<213> ORGANISM: Artificial Sequence
<220> FEATURE:
<223> OTHER INFORMATION: sequence of recombinant antibody or functional
      part thereof

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
            35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
```

```
                130                 135                 140
Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 91
<211> LENGTH: 451
<212> TYPE: PRT
<213> ORGANISM: Artificial Sequence
<220> FEATURE:
<223> OTHER INFORMATION: sequence of recombinant antibody or functional
      part thereof

<400> SEQUENCE: 91

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
            20                  25                  30

Tyr Asp Met Cys Trp Ile Arg Gln Pro Pro Gly Lys Gly Leu Glu Trp
        35                  40                  45

Ile Gly Cys Val Val Ala Gly Ser Val Asp Ile Thr Tyr Tyr Ala Ser
    50                  55                  60

Trp Ala Lys Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Lys Asp Ala Tyr Ser Asp Ala Phe Asn Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

```
Glu Asp Pro Glu Val Lys Phe Asn Trp Tyr Val Asp Gly Val Glu Val
            275                 280                 285

His Asn Ala Lys Thr Lys Pro Arg Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 92
<211> LENGTH: 220
<212> TYPE: PRT
<213> ORGANISM: Artificial Sequence
<220> FEATURE:
<223> OTHER INFORMATION: sequence of recombinant antibody or functional
      part thereof

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Ala Pro Lys Leu Leu Ile
        35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175
```

```
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 93
<211> LENGTH: 452
<212> TYPE: PRT
<213> ORGANISM: Artificial Sequence
<220> FEATURE:
<223> OTHER INFORMATION: sequence of recombinant antibody or functional
      part thereof

<400> SEQUENCE: 93

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Asn Ser Asp
            20                  25                  30

Tyr Trp Ile Tyr Trp Ile Arg Gln Pro Pro Gly Lys Gly Leu Glu Trp
        35                  40                  45

Ile Gly Ser Ile Tyr Gly Gly Ser Gly Asn Thr Gln Tyr Ala Ser
    50                  55                  60

Trp Ala Gln Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
            85                  90                  95

Tyr Cys Ala Arg Gly Tyr Val Asp Tyr Gly Gly Ala Thr Asp Leu Trp
        100                 105                 110

Gly Gln Gly Thr Leu Val Thr Val Ser Ser Ala Ser Thr Lys Gly Pro
    115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
```

```
                305                 310                 315                 320
Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
    450

<210> SEQ ID NO 94
<211> LENGTH: 5
<212> TYPE: PRT
<213> ORGANISM: Artificial sequence
<220> FEATURE:
<223> OTHER INFORMATION: artificial linker
<220> FEATURE:
<221> NAME/KEY: Repeat
<222> LOCATION: (1)..(5)
<223> OTHER INFORMATION: (GGGGS)n linker, wherein n is a integer
      selected from 1 and 2

<400> SEQUENCE: 94

Gly Gly Gly Gly Ser
1               5

<210> SEQ ID NO 95
<211> LENGTH: 5
<212> TYPE: PRT
<213> ORGANISM: Artificial sequence
<220> FEATURE:
<223> OTHER INFORMATION: artificial linker
<220> FEATURE:
<221> NAME/KEY: Repeat
<222> LOCATION: (1)..(5)
<223> OTHER INFORMATION: (GGGGS)n linker, wherein n is a integer
      selected from 1 to 8

<400> SEQUENCE: 95

Gly Gly Gly Gly Ser
1               5
```